US012151988B2

(12) United States Patent
Tamsir et al.

(10) Patent No.: US 12,151,988 B2
(45) Date of Patent: Nov. 26, 2024

(54) GENE TARGETS FOR NITROGEN FIXATION TARGETING FOR IMPROVING PLANT TRAITS

(71) Applicant: Pivot Bio, Inc., Berkeley, CA (US)

(72) Inventors: Alvin Tamsir, Berkeley, CA (US); Sarah Bloch, Berkeley, CA (US); Neal Shah, Berkeley, CA (US)

(73) Assignee: Pivot Bio, Inc., Berkeley, CA (US)

( * ) Notice: Subject to any disclaimer, the term of this patent is extended or adjusted under 35 U.S.C. 154(b) by 810 days.

(21) Appl. No.: 16/759,231

(22) PCT Filed: Oct. 25, 2018

(86) PCT No.: PCT/US2018/057613
§ 371 (c)(1),
(2) Date: Apr. 24, 2020

(87) PCT Pub. No.: WO2019/084342
PCT Pub. Date: May 2, 2019

(65) Prior Publication Data
US 2020/0331820 A1     Oct. 22, 2020

Related U.S. Application Data

(60) Provisional application No. 62/577,149, filed on Oct. 25, 2017.

(51) Int. Cl.
| | | |
|---|---|---|
| *C12N 1/20* | (2006.01) |
| *C05F 11/08* | (2006.01) |
| *C07K 14/195* | (2006.01) |
| *C12N 15/52* | (2006.01) |
| *C12N 15/67* | (2006.01) |
| *C12N 15/74* | (2006.01) |
| *C12Q 1/02* | (2006.01) |

(52) U.S. Cl.
CPC ............ *C05F 11/08* (2013.01); *C07K 14/195* (2013.01); *C12N 1/20* (2013.01); *C12N 15/52* (2013.01); *C12N 15/67* (2013.01); *C12N 15/74* (2013.01); *C12Q 1/02* (2013.01)

(58) Field of Classification Search
CPC ........... C05F 11/08; C12N 1/20; C12N 15/74; C12N 9/0095; C12Y 118/06001
See application file for complete search history.

(56) References Cited

U.S. PATENT DOCUMENTS

| | | |
|---|---|---|
| 1,520,545 A | 12/1924 | Murphy |
| 4,782,022 A | 11/1988 | Puhler et al. |
| 4,832,728 A | 5/1989 | Allan et al. |
| 5,071,743 A | 12/1991 | Slilaty et al. |
| 5,116,506 A | 5/1992 | Williamson et al. |
| 5,188,960 A | 2/1993 | Payne et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,610,044 A | 3/1997 | Lam et al. |
| 5,780,270 A | 7/1998 | Lesley |
| 5,789,166 A | 8/1998 | Bauer et al. |
| 5,877,012 A | 3/1999 | Estruch et al. |
| 5,880,275 A | 3/1999 | Fischhoff et al. |
| 5,916,029 A | 6/1999 | Smith et al. |
| 6,033,861 A | 3/2000 | Schafer et al. |
| 6,033,874 A | 3/2000 | Baum et al. |
| 6,083,499 A | 7/2000 | Narva et al. |
| 6,107,279 A | 8/2000 | Estruch et al. |
| 6,114,148 A | 9/2000 | Seed et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 | 7/2003 | Bauer |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |

(Continued)

FOREIGN PATENT DOCUMENTS

| | | |
|---|---|---|
| AU | 636565 | 5/1993 |
| CA | 2051071 | 3/1993 |

(Continued)

OTHER PUBLICATIONS

US 8,476,226 B2, 07/2013, Lira (withdrawn)
Leang et al BMC genomics 2009, 10, pp. 1-19.*
Associative and Endophytic Nitrogen-fixing Bacteria and Cyanobacterial Association, C. Elmerich and W. E. Newton (eds.), 2007, Chapter 3, 31 pages.
Doroshchuk et al., "Regulation of nitrogen metabolism in gram-positive bacteria," Molecular Biology, 2006, 40(5):829-836.
Leigh et al., "Nitrogen Regulation in Bacteria and Archaea," Annual Review of Microbiology, 2007, 61(10):349-377.
Terpolilli et al., "What Determines the Efficiency of $N_2$-Fixing Rhizobium-Legume Symbioses?," Advances in Microbial Physiology, 2012, 60:325-389.

(Continued)

*Primary Examiner* — Robert B Mondesi
*Assistant Examiner* — Mohammad Y Meah
(74) *Attorney, Agent, or Firm* — Fish & Richardson P.C.

(57) ABSTRACT

Methods and systems are provided for generating and utilizing a genetically engineered bacterium comprising a modification in glnD, wherein said modification is selected from the group consisting of: deletion of the entire gene, deletion of substantially the entire gene, deletion of an ACT domain, deletion of more than 50% of an ACT domain, deactivation of an ACT domain, and deactivation of an UTase domain.

21 Claims, 40 Drawing Sheets

Specification includes a Sequence Listing.

(56) References Cited

U.S. PATENT DOCUMENTS

| | | |
|---|---|---|
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheyns et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,888,552 B2 | 2/2011 | Ye et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Harwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zhang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 11,479,516 B2 | 10/2022 | Voigt et al. |
| 11,565,979 B2 | 1/2023 | Temme et al. |
| 11,739,032 B2 | 8/2023 | Temme et al. |
| 11,946,162 B2 | 4/2024 | Zhao et al. |
| 2002/0061579 A1 | 5/2002 | Farrand et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum |
| 2006/0243011 A1 | 11/2006 | Someus |
| 2007/0249018 A1 | 10/2007 | Vemuri et al. |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015409 A1 | 1/2012 | Tabata et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener |
| 2012/0220006 A1 | 8/2012 | Hardwood et al. |
| 2012/0266332 A1 | 10/2012 | Kuykendall |
| 2012/0278954 A1 | 11/2012 | Bowen et al. |
| 2012/0284813 A1 | 11/2012 | Olivier et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswara et al. |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0301990 A1 | 10/2014 | Gregory et al. |
| 2014/0329326 A1 | 11/2014 | Mirsky et al. |
| 2014/0336050 A1 | 11/2014 | Soto, Sr. et al. |
| 2015/0080261 A1 | 3/2015 | Wigley et al. |
| 2015/0101373 A1 | 4/2015 | Munusamy et al. |
| 2015/0128670 A1 | 5/2015 | Das et al. |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2016/0304842 A1 | 10/2016 | Donovan et al. |
| 2017/0035900 A1 | 2/2017 | Kowarik et al. |
| 2017/0086402 A1 | 3/2017 | Meadows-Smith et al. |
| 2017/0107160 A1 | 4/2017 | Newman et al. |
| 2017/0119690 A1 | 5/2017 | Hansen et al. |
| 2017/0152519 A1 | 6/2017 | Mirsky |
| 2017/0267997 A1 | 9/2017 | Nicol et al. |
| 2017/0367349 A1 | 12/2017 | Gruver et al. |
| 2018/0002243 A1 | 1/2018 | Temme et al. |

(56) References Cited

U.S. PATENT DOCUMENTS

| | | |
|---|---|---|
| 2018/0020671 A1 | 1/2018 | Bioconsortia |
| 2018/0065896 A1 | 3/2018 | Ibema et al. |
| 2018/0073028 A1 | 3/2018 | Mirsky |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2021/0009483 A1 | 1/2021 | Temme et al. |
| 2021/0163374 A1 | 6/2021 | Bioch et al. |
| 2021/0214282 A1 | 7/2021 | Temme et al. |
| 2021/0284995 A1 | 9/2021 | Zhao et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |
| 2022/0127627 A1 | 4/2022 | Bloch et al. |
| 2022/0211048 A1 | 7/2022 | Temme et al. |
| 2022/0282340 A1 | 9/2022 | Ryu et al. |
| 2022/0411344 A1 | 12/2022 | Voigt et al. |
| 2023/0257317 A1 | 8/2023 | Temme et al. |
| 2023/0295559 A1 | 9/2023 | Eskiyenenturk et al. |
| 2024/0010576 A1 | 1/2024 | Temme et al. |

FOREIGN PATENT DOCUMENTS

| | | |
|---|---|---|
| CA | 2991776 | 1/2017 |
| CN | 1289852 A | 4/2001 |
| CN | 1355293 | 6/2002 |
| CN | 1355294 | 6/2002 |
| CN | 1421527 | 6/2003 |
| CN | 1500801 | 6/2004 |
| CN | 1552846 | 12/2004 |
| CN | 1746304 | 3/2006 |
| CN | 101328477 | 12/2008 |
| CN | 101880676 | 11/2010 |
| CN | 101899430 | 12/2010 |
| CN | 102041241 | 5/2011 |
| CN | 102417882 | 4/2012 |
| CN | 102690808 | 9/2012 |
| CN | 103451130 | 12/2013 |
| CN | 103917657 | 7/2014 |
| CN | 104136599 | 11/2014 |
| CN | 104204211 | 12/2014 |
| CN | 106086042 | 11/2016 |
| EA | 002757 | 8/2002 |
| EP | 0256889 | 2/1988 |
| EP | 0292984 | 11/1988 |
| EP | 1535913 | 6/2005 |
| EP | 2186890 | 5/2010 |
| EP | 3231874 | 10/2017 |
| EP | 3322679 | 5/2018 |
| FR | 2910230 | 6/2008 |
| JP | H01-225483 | 9/1989 |
| JP | 02-131581 | 5/1990 |
| JP | 2009-232721 | 10/2009 |
| JP | 2014096996 | 5/2014 |
| JP | 2015037385 | 2/2015 |
| JP | 2015042633 | 3/2015 |
| JP | 2015113274 | 6/2015 |
| JP | 2015518023 | 6/2015 |
| JP | 2015519352 | 7/2015 |
| JP | 2015-173652 | 10/2015 |
| JP | 2017-513480 | 6/2017 |
| WO | WO 1987/004182 | 7/1987 |
| WO | WO 1993/005154 | 3/1993 |
| WO | WO 1998/010088 | 3/1998 |
| WO | WO 1999/009834 | 3/1999 |
| WO | WO 2000/057183 | 9/2000 |
| WO | WO 2001/007567 | 2/2001 |
| WO | WO 2004/074462 | 9/2004 |
| WO | WO 2005/021585 | 3/2005 |
| WO | WO 2005/038032 | 4/2005 |
| WO | WO 2006/005100 | 1/2006 |
| WO | WO 2006/083891 | 8/2006 |
| WO | WO 2006/098225 | 9/2006 |
| WO | WO 2006/119457 | 11/2006 |
| WO | WO 2007/027776 | 3/2007 |
| WO | WO 2009/060012 | 5/2009 |
| WO | WO 2009/091557 | 7/2009 |
| WO | WO 2010/080184 | 7/2010 |
| WO | WO 2011/099019 | 8/2011 |
| WO | WO 2011/099024 | 8/2011 |
| WO | WO 2011/103247 | 8/2011 |
| WO | WO 2011/103248 | 8/2011 |
| WO | WO 2011/154960 | 12/2011 |
| WO | WO 2012/139004 | 10/2012 |
| WO | WO 2012/154651 | 11/2012 |
| WO | WO 2012/174271 | 12/2012 |
| WO | WO 2012/174646 | 12/2012 |
| WO | WO 2013/076687 | 5/2013 |
| WO | WO 2013/132518 | 9/2013 |
| WO | WO 2014/042517 | 3/2014 |
| WO | WO 2014/071182 | 5/2014 |
| WO | WO 2014/201044 | 12/2014 |
| WO | WO 2016/016629 | 2/2016 |
| WO | WO 2016/016630 | 2/2016 |
| WO | WO 2016/048587 | 3/2016 |
| WO | WO 2016/100727 | 6/2016 |
| WO | WO 2016/146955 | 9/2016 |
| WO | WO 2016/178580 | 11/2016 |
| WO | WO 2016/179046 | 11/2016 |
| WO | WO 2016/181228 | 11/2016 |
| WO | WO 2016/191828 | 12/2016 |
| WO | WO 2017/011602 | 1/2017 |
| WO | WO 2017/042833 | 3/2017 |
| WO | WO 2017/062412 | 4/2017 |
| WO | WO 2017/069717 | 4/2017 |
| WO | WO 2017/112827 | 6/2017 |
| WO | WO 2017/203440 | 11/2017 |
| WO | WO 2018/081543 | 5/2018 |
| WO | WO 2018/132774 | 7/2018 |
| WO | WO 2018/133774 | 7/2018 |
| WO | WO 2019/032926 | 2/2019 |
| WO | WO 2019/084059 | 5/2019 |
| WO | WO 2019/084342 | 5/2019 |
| WO | WO 2019/140125 | 7/2019 |
| WO | WO 2020/006064 | 1/2020 |
| WO | WO 2020/006246 | 1/2020 |
| WO | WO 2020/014498 | 1/2020 |
| WO | WO 2020/023630 | 1/2020 |
| WO | WO 2020/061363 | 3/2020 |
| WO | WO 2020/092940 | 5/2020 |
| WO | WO 2020/118111 | 6/2020 |
| WO | WO 2020/146372 | 7/2020 |
| WO | WO 2020/163251 | 8/2020 |
| WO | WO 2020/190363 | 9/2020 |
| WO | WO 2020/191201 | 9/2020 |
| WO | WO 2020/219893 | 10/2020 |
| WO | WO 2020/219932 | 10/2020 |
| WO | WO 2021/113352 | 6/2021 |
| WO | WO 2021/146209 | 7/2021 |

OTHER PUBLICATIONS

Travis et al., "Molecular dissection of the glutamine synthetase-GlnR nitrogen regulatory circuitry in Gram-positive bacteria," Nature Communications, Jul. 2022, 13(3793), 15 pages.

Bittner et al., "RpoS and RpoN are involved in the growth-dependent regulation of rfaH transcription and O antigen expression in *Salmonella enterica* serovar typhi," Microbial Pathogenesis, Jan. 2004, 36(1):19-24.

Extended European Search Report in European Appln. No. 18870036.3, dated Dec. 14, 2021, 28 pages.

Katsnelson, "Engineered bacteria could boost corn yields: Gene-edited microbe offer continuous nitrogen fixation," Chemical & Engineering News, Dec. 28, 2021, retrieved from URL <https://cen.acs.org/food/agriculture/Engineered-bacteria-boost-corn-yields/99/web/2021/12>, 3 pages.

(56) References Cited

OTHER PUBLICATIONS

Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.

Liu et al., "Phenazine-1-carboxylic acid biosynthesis in Pseudomonas Chlororaphis GP72 is positively regulated by the sigma factor RpoN," World Journal of Microbiology and Biotechnology, Jan. 2008, 24(9):1961-1966.

Wen et al., "Enabling Biological Nitrogen Fixation for Cereal Crops in Fertilized Fields," ACS Synth. Biol., Dec. 2021, 10(12):3264-3277.

Wu et al., "Effects of biofertilizer containing N-fixer, P and K solubilizers and AM fungi on maize growth: a greenhouse trial," Geodernna, Mar. 2005, 125(1-2):155-166.

Yan et al., "Global transcriptional analysis of nitrogen fixation and ammonium repression in root-associated Pseudomonas stutzeri A1501," BMC Genomics, Jan. 2010, 11(11):1-13.

Yao et al., "Complementation analysis of heterologous nifA genes to nifA mutants of Sinorhizobium pallida," Chinese Science Bulletin, Oct. 2006, 51(19):2258-2264, 2 pages (English abstract only).

Zhang et al., "Mutagenesis and Functional Characterization of the glnB, glnA, and nifA Genes from the Photosynthetic Bacterium *Rhodospirillum rubrum*," Journal of Bacteriology, Feb. 2000, 182(4):983-992.

EP Partial Supplementary European Search Report in European Appln. No. 18870036.3, dated Aug. 19, 2021, 19 pages.

Zhang et al., "Mutagenesis and functional characterization of the four domains of GlnD, a bifunctional nitrogen sensor protein," Journal of Bacteriology, Jun. 2010, 192(11):2711-2721.

Extended European Search Report in European Appln. No. 19833252.0, dated Mar. 14, 2022, 7 pages.

EP Extended European Search Report in European Appln. No. 18843845.1, dated Jul. 22, 2021, 20 pages.

EP Extended European Search Report in European Appln. No. 18870346.6, dated Jul. 22, 2021, 5 pages.

Kim et al., "A 20 nucleotide upstream element is essential for the nopaline synthase (nos) promoter activity," Plant Mol Biol., Jan. 1994, 24(1):105-17.

Li et al., "Human Enhancers Are Fragile and Prone to Deactivating Mutations," Mol Biol Evol., Aug. 2015, 32(8):2161-80.

Pakula et al., "Genetic analysis of protein stability and function," Annu Rev Genet, 1989, 23:289-310.

PCT International Preliminary Report on Patentability in International Appln. No. PCT/US2019/068152, mailed Jul. 1, 2021, 12 pages.

Singer et al., "Genes and Genomes," Moscow: Mir, 1998, 1:33, 4 pages (with machine translation).

Wang et al., "Roles of poly-3-hydroxybutyrate (PHB) and glycogen in symbiosis of Sinorhizobium meliloti with *Medicago* sp.," Microbiology, Feb. 2007, 153(2):388-398.

Witkowski et al., "Conversion of a β-Ketoacyl synthase to a malonyl decarboxylase by replacement of the active-site cysteine with glutamine," Biochemistry, Sep. 1999, 38(36):11643-50.

"New Plant Breeding Techniques," Science Council of Japan, retrieved from URL <http://www.scj.go.jp/ja/info/kohyo/pdf/kohyo-22-h140826.pdf>, Aug. 26, 2014, 82 pages (partial English translation).

"T7 RNA Polymerase Expression System for Bacillus megaterium"; T7 Rnap Expression System Handbook, Jan. 2010, © MoBiTec GmbH, 18 pages.

40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010).

Aita, T., Husimi, Y. Adaptive walks by the fittest among finite random mutants on a Mt. Fugi-type fitness landscape. J. Theor. Biol. 193:383-405 (1998).

Alper et al., "Tuning genetic control through promoter engineering," Proc Natl Acad Sci U SA, 2005, 102(36):12678-12683.

Altschul et al. "Basic local alignment search tool," J Mol Biol., 1990, 215(3):403-441.

Altschul et al., "Gapped BLAST and PSI-BLAST: a new generation of protein database search programs," Nucleic Acids Res., 1997, 25:3389-3402.

An et al., "Constitutive expression of the nifA gene activates associative nitrogen fixation of Enterobacter gergoviae 57-7, an opportunistic endophytic diazotroph," Journal of Applied Microbiology, 2007, 103(3):613-620.

Andersen et al. "Herpesvirus-mediated gene delivery into the rat brain: specificity and efficiency of the neuron-specific enolase promoter," Cell. Mol. Neurobiol., 1993, 13:503-515.

Andersen, et al. Energetics of biological nitrogen fixation: determination of the ratio of formation of H2 to NH4+ catalysed by nitrogenase of Klebsiella pneumoniae in vivo. J Gen Microbial. Nov. 1977, 103(1):107-22.

Anderson, J.C., et al. "BglBricks: A flexible standard for biological part assembly," Journal of Biological Engineering, 2010, 4:1, 12 pages.

Andrews et al. Use of Nitrogen Fixing Bacteria Inoculants as a Substitute for Nitrogen Fertiliser for Dryland Graminaceous Crops: Progress Made, Mechanisms of Action and Future Potential. Symbiosis 34 (2003). 21 pages.

Andrianantoandro E, et al., "Synthetic biology: new engineering rules for an emerging discipline," Mol Syst Biol 2:2006.0028 (2006).

Arbuthnot et al. "In vitro and in vivo hepatoma cell-specific expression of a gene transferred with an adenoviral vector," Hum Gene Ther., 1996, 7(13):1503-1514.

Arnold et al., (1988) Nucleotide sequence of a 24,206-base-pair DNA fragment carrying the entire nitrogen fixation gene cluster of Klebsiella pneumoniae. J Mol Biol 203(3):715-738.

Arsene et al., "Modulation of NifA activity by PII in Azospirillum brasilense: Evidence for a Regulatory role of the NifA N-Terminal Domain," Journal of Bacteriology, Aug. 1996, 178(16):4830-4838.

Austin et al. "Characterisation of the Klebsiella pneumoniae nitrogen-fixation regulatory proteins NIFA and NIFL in vitro," Eur J Biochem., 1990, 187(2):353-360.

Bageshwar, et al. An Environmentally Friendly Engineered Azotobacter Strain That Replaces a Substantial Amount of Urea Fertilizer while Sustaining the Same Wheat Yield. Appl Environ Microbial. Aug. 1, 2017; 83(15): e00590-17.

Bali et al., "Excretion of Ammonium by a nifL Mutant of Azotobacter vinelandii fixing Nitrogen." Applied and Environmental Microbiology, May 1992, 58(5):1711-1718.

Barney et al., "Gene deletions resulting in increased nitrogen release by azotobacter vinelandii: application of a novel nitrogen biosensor." Appl. Environ. Microbial. Jul. 2015, 81(13):4316-4328.

Barney et al., "Transcriptional analysis of an Ammonium-excreting stain of azotobacter vinelandii deregulated for nitrogen fixation." Appl. Environ. Microbial. Jul. 2017, 83(20):1-22.

Barrangou et al., "Exploiting CRISPR-Cas immune systems for genome editing in bacteria." Curr. Opin. Biotechnol. Nov. 2016, 37:61-68.

Batista et al. "Manipulating nitrogen regulation in diazotrophic bacteria for agronomic benefit," Biochem Soc Trans., 2019, 47(2):603-614.

Batzer et al., "Enhanced evolutionary PCR using oligonucleotides with inosine at the 3'-termins," Nucleic Acid Res. 19: 5081 (1991).

Bayer TS, et al. (2009) Synthesis of Methyl Halides from Biomass Using Engineered Microbes. J Am Chem Soc 131 (18):6508-6515.

Beringer et al., "Genetic engineering and nitrogen fixation." Biotech. Gen. Eng. Rev. Feb. 1984, 1(1):65-88.

Beynon J, Cannon M, Buchanan-Wollaston V, & Cannon F (1983) The nifpromoters of Klebsiella pneumoniae have a characteristic primary structure. Cell 34(2):665-671.

Biggins JB, Liu, X., Feng, Z., Brady, S.F. (2011) Metabolites from the induced expression of cryptic single operons found in the genome of Burkholderia pseudomallei. JACS 133:1638-1641.

Bikard et al., "The synthetic integron: an in vivo genetic shuffling device," Nucleic Acids Res., 2010, 38(15):e153.

(56) References Cited

OTHER PUBLICATIONS

Bilitchenko et al., Eugene—a domain specific language for specifying and constraining synthetic biological parts, devices, and systems. PLoS One. Apr. 29, 2011;6(4):e18882.
Blanco et al., "Sequence and molecular analysis of the nifL gene of Azotobacter vine landii." Mol Microbial. Aug. 1993, 9(4):869-79.
BLAST. Basic local alignment search tool. Available at http://blast.ncbi.nlm.nih.gov/Blast.cgi. Accessed on Oct. 10, 2016.
Bonde et al., "MODEST: a web-based design tool for oligonucleotide-mediated genome engineering and recombineering," Nucleic Acids Res., 2014, 42(W1):W408-W415.
Boshart et al. "A very strong enhancer is located upstream of an immediate early gene of human cytomegalovirus," Cell, 1985, 41(2):521-30.
Bosworth, et al. "Alfalfa yield response to inoculation with recombinant strains of Rhizobium meliloti with an extra copy of dctABD and/or modified nifA expression." Appl Environ Microbial. Oct. 1994, 60(10):3815-32.
Boyle et al. "Tools for genome-wide strain design and construction," Curr Opin Biotechnol., 2012, 23(5):666-671. doi: 10.1016/j.copbio.2012.01.012.
Brandl et al., "*Salmonella* interactions with plants and their associated microbiota," Phytopathology, 2013, 103:316-325.
Brewin et al., "The Basis of Ammonium release in nifL Mutants of Azotobacter vinelandii." Journal of Bacteriology, Dec. 1999, 181(23):7356-7362.
Buchanan-Wollaston, et al. Role of the nifA gene product in the regulation of nif expression in Klebsiella pneumoniae. Nature. Dec. 24, 1981;294(5843):776-8.
Buck M & Cannon W (1987) Frameshifts close to the Klebsiella pneumoniae nifH promoter prevent multicopy inhibition by hybrid nifH plasmids. Mal Gen Genet 207(2-3):492-498.
Buckley Lab NifH database, retrieved via WayBack Machine from URL <http://www.css.cornell.edu/faculty/buckley/nifh.htm>, available on or before Jan. 10, 2018, 2 pages.
Buddrus-Schiemann et al., "Root colonization by *Pseudomonas* sp. DSMZ 13134 and impact on the indigenous rhizosphere bacterial community of barley." Microb Ecol. Aug. 2010, 60(2):381-393.
Burris et al., "Nitrogenases," J Biol Chem., 266(15):9339-9342.
Cardinale, S., & Arkin, A.P. Contextualizing context for synthetic biology identifying causes of failure of synthetic biological systems. Biotechnol. J. 7:856-866 (2012).
Carr et al., "Enhanced multiplex genome engineering through co-operative oligonucleotide coselection," Nucleic Acids Res., 2012, 40(17):e132.
cerestrust.org [online]. "Year-end Final Report" Young et al., Ceres Trust, retreieved from URL <https://cerestrust.org/wpcontent/uploads/NitrogenFixingBacteriaCorn.pdf>. 2012, 9 pages.
Chan et al., "Refactoring bacteriophage T7," Molecular Systems Biology, 2005, 1(1):E1-E10.
Chen et al., "Complete genome sequence of Kosakonia sacchari type strain SPIT." Stand Genomic Sci., Jun. 15, 2014, 9(3):1311-1318.
Chen, et al. "Expression of rat bone sialoprotein promoter in transgenic mice." J Bone Miner Res., May 1996, 11(5):654-64.
Chen, Y.J., et al. Characterization of 582 natural and synthetic terminators and quantification of their design constraints. Nat. Methods, 2013, 10:659-664.
Chiang et al., "Mutagenic Oligonucleotide-directed PCR Amplification (Mod-PCR): An Efficient Method for Generating Random Base Substitution Mutations in a DNA sequence element." PCR methods and applications. 1993, 2:210-217.
Chin JW "Programming and engineering biological networks," Curr Opin Struct Biol 16: 551-556 (2006).
Choi, et al. A Tn7-based broad-range bacterial cloning and expression system. Nat Methods. Jun. 2005;2(6):443-8.
Choudhary, et al. Interactions of *Bacillus* spp. and Plants—With Special Reference to Induced Systemic Resistance (ISR). Microbiological Research. 2009, vol. 164, No. 5; pp. 493-513.
Clancy et al., "The domains carrying the opposing activities in adenylyltransferase are separated by a central regulatory domain," FEBS Journal, 2007, 274(11):2865-2877.
Cobb et al., Directed evolution: an evolving and enabling synthetic biology tool. Curr Opin Chem Biol. Aug. 2012;16(3-4):285-91.
Cohen, "In vitro Tomato Fruit Cultures Demonstrate a Role for Indole-3-acetic Acid in Regulating Fruit Ripening." J. Amer. Soc. Hort. Sci. 1996 121 (3):520-524.
Colebatch et al. "Symbiotic nitrogen fixation research in the postgenomics era," New Phytologist., 2002, 153(1):37-42 doi:10.1046/j.0028-646X.2001.00304.x.
Colnaghi et al., "Strategies for increased ammonium production in free-living or plant associated nitrogen fixing bacteria." Plant and Soil, Nov. 1997, 194:145-154.
Colnaghi, et al. Lethality of glnD null mutations in Azotobacter vinelandii is suppressible by prevention of glutamine synthetase adenylylation. Microbiology. May 2001;147(Pt 5):1267-76.
Conniff, "Microbes Help Grow Better Crops." (Sep. 1, 2013) Scientific American. Reteived from URL <https://www.scientificamerican.com/article/microbes-helpgrow-better-crops/>. (Year: 2013).
Contreras et al., "The product of the nitrogen fixation regulatory gene nfrX of Azotobacter vinelandii is functionally and structurally homologous to the uridylyltransferase encoded by glnD in enteric bacteria." J Bacterial. Dec. 1991, 173(24):7741-7749.
Cornelis et al., "The type III secretion injectisome," Nature Reviews Mocrobilogy, 2006, 4(11):811-825.
Crameri, A., Dawes, G., Rodriguez Jr., E., Silver, S., & Stemmer, W.P.C. Molecular evolution of an arsenate detoxification pathway by DNA shuffling. Nat. Biotechnol. 15:436-438 (1997).
Crook, N.C., Freeman, E.S., & Alper, H.S. Re-engineering multicloning sites for function and convenience. Nucl. Acids Res. 39:e92, 2011.
Curatti et al., "Genes required for rapid expression of nitrogenase activity in Azotobacter vinelandii." PNAS May 2005; 102(18):6291-6296.
Czar MJ, Anderson JC, Bader JS, & Peccoud J (2009) Gene synthesis demystified. Trends Biotechnol 27(2):63-72.
Dandekar, T., Snel, B., Huynen, M., & Bork, P. Conservation of gene order: a fingerprint of proteins that physically interact. Trends Biochem. Sci. 23:324-328 (1998).
Datsenko et al., "One-step inactivation of chromosomal genes in *Escherichia coli* K-12 using PCR products." PNAS, Jun. 2000, 97(12):6640-6645.
De Raad, M., Kooijmans, S.A.A., Teunissen, E.A., & Mastrobattista, E. A solid-phase platform for combinatorial and scarless multipart gene assembly. ACS Synth. Biol. 2:316-326 (2013).
DeBruijn et al., "The Cloning and characterization of the glnF (ntrA) Gene of Klebsiella pneumoniae: Role of glnF (ntrA) in the Regulation of Nitrogen Fixation (nif) and other Nitrogen assimilation genes." Mol. Genet. Aug. 1983; 192:342-353.
Delaux et al., "Tracing the evolutionary path to nitrogen-fixing crops." Curr. Opin. Plant Biol. Jun. 2015, 26:95-99.
Dent et al., "Establishing symbiotic nitrogen fixation in cereals and other non-legume crops: The greener nitrogen revolution." Agric & Food Secur, Dec. 2017, 6(7):1-9.
Desnoues et al., "Nitrogen fixation genetics and regulation in a Pseudomonas stutzeri strain associated with rice." Microbiology, May 2003; 149:2251-2262.
Dixon et al., Genetic regulation of biological nitrogen fixation. Nature Reviews, Aug. 2004, 2:621-631.
Dixon RA & Postgate JR (1972) Genetic transfer of nitrogen fixation from Klebsiella pneumoniae to *Escherichia coli*. Nature 237(5350):102-103.
Dong, et al. Kinetics and Strain Specificity of Rhizosphere and Endophytic Colonization by Enteric Bacteria on Seedlings of *Medicago sativa* and Medicago truncatula. Appl Environ Microbial. Mar. 2003; 69(3): 1783-1790.
Dos Santos, et al., "Distribution of nitrogen fixation and nitrogenase-like sequences amongst microbial genomes," BMC Genomics, Dec. 2012, 13(1):162, 12 pages.

(56) References Cited

OTHER PUBLICATIONS

Du et al., Customized optimization of metabolic pathways by combinatorial transcriptional engineering. Nucleic Acids Res. Oct. 2012;40(18):e142.
Dykxhoorn et al., (1996) A set of compatible tac promoter expression vectors. Gene 177(1-2):133-136.
Easter, et al., "Role of the parCBA Operon of the Broad-Host-Range Plasmid RK2 in Stable Plasmid Maintenance," Journal Of Bacteriology, 1998, 180(22):6023-6030.
Egener et al., "Identification of NifL-like protein in a diazotroph of the b-subgroup of the proteobacteria, *azoarcus* sp. strain BH72," Microbiology, Oct. 2002, 148(10):3203-3212.
EMBOSS. EMBOSS Needle: Pairwise Sequence Alignment (Nucleotide). Available at http://www.ebi.ac.uk/Tools/psa/emboss_needle/nucleotide.html. Accessed on Oct. 10, 2016.
EMBOSS. EMBOSS Water: Pairwise Sequence Alignment (Nucleotide). Available at http://www.ebi.ac.uk/Tools/psa/emboss_water/nucleotide.html. Accessed on Oct. 10, 2016.
Endy et al., "Foundations for engineering biology," Nature, 2005, 438:449-453.
Engler, et al. "A one pot, one step, precision cloning method with high throughput capability," PLoS One, 2008;3(11):e3647.
Engler, et al. "Golden gate shuffling: a one-pot DNA shuffling method based on type lls restriction enzymes," PLoS One. 2009;4(5):e5553.
Enkh-Amgalan, et al., "Molecular evolution of the nif gene cluster carrying nifl1 and nif12 genes in the Gram-positive phototrophic bacterium *Heliobacterium chlorum*," International Journal of Systematic and Evolutionary Microbiology, 2006, 56:65-74.
EP Extended European Search Report in European Appln. No. 12800054.4, mailed Dec. 19, 2014, 8 pages.
EP Extended European Search Report in European Appln. No. 16825147.8, dated Jun. 6, 2019, 19 pages.
EP Extended European Search Report in European Appln. No. 16854192.8, dated Feb. 20, 2019, 11 pages.
EP Extended European Search Report in European Appln. No. 19186353.9, dated Nov. 13, 2019, 9 pages.
EP Partial Supplementary European Search Report Appln. No. 16825147.8 dated Mar. 4, 2019, 21 pages.
Estrem, et al., "Identification of an UP element consensus sequence for bacterial promoters," PNAS, 95 (11): 9761-9766 (1998).
Fani et al., "Molecular evolution of nitrogen fixation: the evolutionary history of the nilD, nifK, nifE, and nifN gene," J Mo/ Evol., 2000, 51 ( 1 ): 1-11.
Feher, et al. In the fast lane: large-scale bacterial genome engineering. J Biotechnol. Jul. 31, 2012;160(1-2):72-9.
Ferrieres, et al. The yjbEFGH locus in *Escherichia coli* K-12 is an operon encoding proteins involved in exopolysaccharide production. Microbiology. Apr. 2007;153(Pt 4):1070-80.
Fischbach et al., "Prokaryotic gene clusters: A rich toolbox for synthetic biology," Biotechnology Journal, 2010, 15(12):1277-1296.
Fischbach, et al., The evolution of gene collectives: how natural selection drives chemical innovation. Proc. Natl. Acad. Sci. USA 105:4601-4608 (2008).
Fontana, et al., RNA folding and combinatory landscapes. Phys. Rev. E. 47:2083-2099 (1993).
Fox et al., "Major cereal crops benefit from biological nitrogen fixation when inoculated with the nitrogen-fixing bacterium *Pseudomonas protegens* Pf-5 X940." Environmental Microbiology, 2016, 18(10):3522-3534.
Frasch et al., Design-based re-engineering of biosynthetic gene clusters: plug-and-play in practice. Curr Opin Biotechnol. Dec. 2013;24(6):1144-50.
Gaby and Buckley, "A comprehensive aligned nifH gene database: a multipurpose tool for studies of nitrogen-fixing bacteria." Database 2014 (2014): bau001.
Gamer, et al. A T7 Rna polymerase-dependent gene expression system for Bacillus megaterium. Appl Micro biol Biotechnol. Apr. 2009;82(6):1195-203.
Gebeyehu, G., et al., "Novel biotinylated nucleotide-analogs for labeling and colorimetric detection of DNA," Nucl. Acids Res. 15:4513 (1987).
Geddes et al., "Use of plant colonizing bacteria as chassis for transfer of N2-fixation to cereals." Curr. Opin. Biotechnol. 2015, 32:216-222.
Georg J & Hess WR (2011) cis-antisense RNA, another level of gene regulation in bacteria. Microbiol Mol Biol Rev 75(2):286-300.
Gibson DG, et al. (2009) Enzymatic assembly of DNA molecules up to several hundred kilobases. Nat Methods 6(5):343-345.
Gibson, "Physical Environment and Symbiotic Nitrogen Fixation." Australian Journal of Biological Sciences. 1963, 16(1):28-42.
Gibson, et al., Chemical synthesis of the mouse mitochondrial genome. Nat. Methods 7, 901-903 (2010).
Gosink, Franklin and Roberts, The product of the Klebsiella pneumoniae nifX gene is a negative regulator of the nitrogen fixation (nit) regulon, J Bacteriology, 1990, 172(3):1441-1447.
Gossen et al. Tight control of gene expression in mammalian cells by tetracycline-responsive promoters. PNAS USA89.12 (1992): 5547-5551.
Gossen et al. Transcriptional activation by tetracyclines in mammalian cells. Science 268(5218):1766-1769 (1995).
Gottelt et al., (2010) Deletion of a regulatory gene within the cpk gene cluster reveals novel antibacterial activity in Streptomyces coelicolor A3(2). Microbiology 156:2343-2353.
Govantes et al., "Mechanism of coordinated synthesis of the antagonistic regulatory proteins NifL and NifA of Klebsiella pneumoniae." J Bacterial. Dec. 1996, 178(23):6817-6823.
Guell et al., (2011) Bacterial transcriptomics: what is beyond the RNA horiz-ome? Nature reviews. Microbiology 9(9):658-669.
Guell, M., et al. Transcriptome complexity in a genome-reduced bacterium. Science 326: 1268-1271 (2009).
Guo et al., Discovery of Reactive Microbiota-Derived Metabolites that Inhibit Host Proteases. Cell. Jan. 26, 2017;168(3):517-526.e18.
Haapalainen, et al., Soluble plant cell signals induce the expression of the type Ill secretion system of Pseudomonas syringae and upregulate the production of pilus protein HrpA. Mol. Plant Microbe Interact. 22, 282-290 (2009).
Hale et al., "An efficient stress-free strategy to displace stable bacterial plasmids." Bio Techniques, Mar. 2010, 48:223-228.
Hansal, et al. Cutting Edge: Induction of antigen-specific hyporesponsiveness by transplantation of hemopoietic cells containing an MHC class I transgene regulated by a lymphocyte-specific promoter. J Immunol. Aug. 1, 1998 ;161(3):1063-8.
Harvey, et al. Inducible control of gene expression: prospects for gene therapy. Curr Opin Chem Biol. Aug. 1998;2(4):512-8.
Herlache, et al. Characterization of the Agrobacterium vitis pehA gene and comparison of the encoded polygalacturonase with the homologous enzymes from Erwinia carotovora and Ralstonia solanacearum. Appl Environ Microbial. Jan. 1997; 63(1): 338-346.
Hernandez, J.A., et al. "Biochemical analysis of the recombinant Fur (ferric uptake regulator) protein from Anabaena PCC 7119: factors affecting its oligomerization state," Biochem J., 2002, 366:315-322.
Hidaka, et al. Promotion of the Growth of Rice by Inoculation of Nitrogen-Fixing-Activity-Enhanced Bacteria to the Rhizosphere. In Nitrogen Fixation: From Molecules to Crop Productivity (Part of the Current Plant Science and Biotechnology in Agriculture book series (PSBA, vol. 38)), pp. 445; 2002.
Holden, et al. Colonization outwith the colon: plants as an alternative environmental reservoir for human pathogenic enterobacteria. FEMS Microbiol. Rev. 33, 689-703 (2009).
Hu et al., (2008) Assembly of nitrogenase MoFe protein. Biochemistry 47(13):3973-3981.
Hunter, "'Genetically Modified Lite' placates public but not activists." EMBO Reports, Jan. 2014, 15(2):138-141.
Huynen, et al., Smoothness within ruggedness: the role of neutrality in adaptation. Proc. Natl. Acad. Sci. USA 93:397-401 (1996).
Iber, D. A quantitative study of the benefits of co-regulation using the spoIIA operon as an example. Mol. Sys. Biol. 2, 1-6 (2006).

(56) References Cited

OTHER PUBLICATIONS

Idalia and Bernardo, "*Escherichia coli* as a model organism and its application in biotechnology," Recent Advances on Physiology, Pathogenesis, and Biotechnological Applications, Chapter 13, 2017, pp. 253-274.
Iniguez et al., "Nitrogen Fixation in Wheat Provided by Klebsiella pneumoniae 342." MPMI, 2004, 17(10):1078-1085.
International Preliminary Report on Patentability dated Jul. 16, 2019 in connection with Application No. PCT/US2018/013671, 6 pages.
International Preliminary Report on Patentability dated May 14, 2015 in connection with Application No. PCT/US2013/068055.
International Preliminary Report on Patentability in International Appln. No. PCT/US2018/046148, dated Feb. 11, 2020, 12 pages.
International Preliminary Report on Patentability in International Appln. No. PCT/US2018/057174, dated Apr. 28, 2020, 5 pages.
International Preliminary Report on Patentability in International Appln. No. PCT/US2018/057613, dated Apr. 28, 2020, 8 pages.
International Preliminary Report on Patentability in PCT Appln. No. PCT/US2012/042502, dated Dec. 17, 2013, 8 pages.
International Preliminary Report on Patentability in PCT Appln. No. PCT/US2016/042170, dated Jan. 16, 2018, 19 pages.
International Preliminary Report on Patentability mailed Apr. 19, 2018 for Application No. PCT/US2016/055429.
International Search Report and Written Opinion in International Appln. No. PCT/US2012/042502, dated Jan. 31, 2013, 11 pages.
International Search Report and Written Opinion in International Appln. No. PCT/US2013/068055, dated Feb. 18, 2014, 15 pages.
International Search Report and Written Opinion in International Appln. No. PCT/US2016/042170, dated Dec. 2, 2016, 26 pages.
International Search Report and Written Opinion in International Appln. No. PCT/US2016/055429, dated Dec. 30, 2016, 16 pages.
International Search Report and Written Opinion in International Appln. No. PCT/US2018/0013671, dated Mar. 22, 2018, 8 pages.
International Search Report and Written Opinion in International Appln. No. PCT/US2018/046148, dated Dec. 3, 2018, 6 pages.
International Search Report and Written Opinion in International Appln. No. PCT/US2018/057613, dated Mar. 5, 2019.
International Search Report and Written Opinion in International Appln. No. PCT/US2019/068152, dated Jun. 25, 2020.
Ishihama A (2010) Prokaryotic genome regulation: multifactor promoters, multitarget regulators and hierarchic networks. FEMS Microbial Rev 34(5):628-645.
Ivanova et al. "Artificial Regulation of Genes, Of the coding proteins of the nitrogenase complex Rhizobial bacteria," Natural Sciences, 2014, 13(174):36-39 (Machine Translation).
Izquierdo et al., "Distribution of Extensive nifH Gene Diversity Across Physical Soil Microenvironments," Microbial Ecology, 2006, 51(4):441-452.
Jacob et al., (1987) Solid-state NMR studies of Klebsiella pneumoniae grown under nitrogen-fixing conditions. J Biol Chem 262(1):254-259.
Jacoby et al., "The Role of Soil Microorganisms in Plant Mineral Nutrition-Current Knowledge and Future Directions," Frontiers in Plant Scients, 2017, 8(19):1-19.
Jaschke, et al. A fully decompressed synthetic bacteriophage 0X174 genome assembled and archived in yeast. Virology 434, 278-284 (2012).
Jensen, K.F. The *Escherichia coli* K-12 "wild types" W3110 and MG1655 have an rph frameshift mutation that leads to pyrimidine starvation due to low pyre expression levels. J. Bacteriol. 175:3401-3407 (1993).
Johnson ZI & Chisholm SW (2004) Properties of overlapping genes are conserved across microbial genomes. Genome Res 14(11):2268-2272.
Kalir S, et al. (2001) Ordering genes in a flagella pathway by analysis of expression kinetics from living bacteria. Science 292(5524):2080-2083.
Kaneko, T., et al. Complete genomic structure of the cultivated rice endophyte *Azospirillum* sp. B510. DNA Res. 17:37-50 (2010).

Kant et al., "Understanding plant response to nitrogen limitation for the improvement of crop nitrogen use efficiency." Journal of Experimental Botany, 2011, 62(4):1499-1509.
Karlin, et al. Applications and statistics for multiple high-scoring segments in molecular sequences. Proc Natl Acad Sci USA. Jun. 15, 1993;90(12):5873-7.
Karlin, et al. Methods for assessing the statistical significance of molecular sequence features by using general scoring schemes. Proc Natl Acad Sci USA. Mar. 1990;87(6):2264-8.
Kececiglu, J., et al. "Of mice and men: Algorithms for evolutionary distances between genomes with translocation," SODA: Proceedings of the sixth annual ACM-SIA< symposium on Discrete algorithms, 1995, 10 pages.
Kelly JR, et al. (2009) Measuring the activity of BioBrick promoters using an in vivo reference standard. J Biol Eng 3 :4.
Kent et al., "A Transposable Partitioning Locus Used To Stabilize Plasmid-Borne Hydrogen Oxidation and Trifolitoxin Production Genes in a Sinorhizobium Strain," Appl. Environ. Microbiol., 1998, 64(5):1657-1662.
Kerby et al., "Photoproduction of ammonium by immobilized mutant strains of Anabaena variabilis." Applied Microbiology and Biotechnology. Apr. 1986, 24(1):42-46.
Kim et al., "Constitutive expression of nitrogenase system in Klebsiella oxytoca by gene targeting mutation to the chromosomal nifLA operon." Journal of Biotechnology. Jun. 1989, 10(3-4):293-301.
Kingsford et al., "Rapid, accurate, computational discovery of Rho-independent transcription terminators illuminates their relationship to DNA uptake," Genome Bio. 2007, 8(2):R22.
Kitano H (2002) Systems biology: a brief overview. Science 295(5560): 1662-1664.
Knight, T., "Idempotent Vector Design for Standard Assembly of Biobricks," MIT Artificial Intelligence Laboratory, The TTL Data Book for Design Engineers, 2003, 11 pages.
Kovacs et al., (2009) Stochasticity in protein levels drives colinearity of gene order in metabolic operons of *Escherichia coli*. PLoS Biol 7(5):e1000115.
Kurzweil, "Plant Bacteria breakthrough enables crops worldwide to take nitrogen from the air." Plant Bacteria Breakthrough Enables Crops Worldwide Take Nitrogen From Air. Aug. 1, 2013. http://www.kurzweilai.neUplant-bacteria-breakthrough-enables-cropsworldwide-to-take-nitrogen-from- the-air. 4 pages.
Kutter, et al. Colonization of barley (*Hordeum vulgare*) with *Salmonella enterica* and *Listeria* spp. FEMS Microbial. Ecol. 56, 262-271 (2006).
Lauritsen et al., "A versatile one-step CRISPR-Cas9 based approach to plasmid-curing." Microb Cell Fact, 2017, 16(135):1-10.
Leang, et al. Genome-wide analysis of the RpoN regulon in Geobacter sulfurreducens. BMC Genomics. Jul. 22, 2009;10:331.
Lee et al., "The class IId bacteriocin thuricin-17 increases plant growth," Planta, 2009, 229:747-755.
Levin-Karp, A., et al. Quantifying translational coupling in *E. coli* synthetic operons using RBS modulation and fluorescent reporters. ACS Synth. Biol. 2:327-336 (2013).
Liang et al., Minimal effect of gene clustering on expression in *Escherichia coli*. Genetics. Feb. 2013;193(2):453-65.
Lim, et al. Fundamental relationship between operon organization and gene expression. Proc Natl Acad Sci US =A. Jun. 28, 2011;108(26):10626-31.
Liu, et al. Whole genome analysis of halotolerant and alkalotolerant plant growth-promoting rhizobacterium *Klebsiella* sp. D5A. Sci Rep. May 24, 2016; 6: 1-10.
Lombo et al., (1999) The mithramycin gene cluster of Streptomyces argillaceus contains a positive regulatory gene and two repeated DNA sequences that are located at both ends of the cluster. J. Bacterial. 181:642-647.
Lucks et al., Toward scalable parts families for predictable design of biological circuits. Curr. Opin. Microbiol. 11, 567-573 (2008).
Ma et al., "Effect of nicotine from tobacco root exudates on chemotaxis, growth, biocontrol efficiency, and colonization byPseudomonas aeruginosaNXHG29," Antonie van Leeuwenhoek, 2018, 111(7):1237-1257.

(56) References Cited

OTHER PUBLICATIONS

MacNeil et al., "Fine-structure mapping and complementation analysis of nif (nitrogen fixation) genes in Klebsiella pneumoniae." J Bacteriol. Oct. 1978, 136(1):253-266.
MacNeil et al., "Mutations in nif genes that cause Klebsiella pneumoniae to be derepressed for nitrogenase synthesis in the presence of ammonium." J Bacteriol. Nov. 1980, 144(2):744-751.
Maduro M (2011) Random DNA Generator, retrieved from URL <http://www.faculty.ucr.edu/~mmaduro/random.htm>, 1 page.
Magari, et al. Pharmacologic control of a humanized gene therapy system implanted into nude mice. J Clin Invest. Dec. 1, 1997; 100(11): 2865-2872.
Mandal M & Breaker RR (2004) Gene regulation by riboswitches. Nat Rev Mol Cell Biol 5(6):451-463.
Marroqui et al. "Enhanced Symbiotic Performance by Rhizobium tropici Glycogen Synthase 17, 18 Mutants," Journal of Bacteriology, Feb. 1, 2001, vol. 183, No. 3, pp. 854-864.
Martinez-Noel et al., NifB and NifEN protein levels are regulated by ClpX2 under nitrogen fixation conditions in Azotobacter vinelandii. Mol Microbiol. Mar. 2011;79(5):1182-93.
Marx, et al. Broad-host-range ere-lox system for antibiotic marker recycling in gram-negative bacteria. Biotechniques. Nov. 2002;33(5):1062-7.
Masepohl et al., "Organization and regulation of genes encoding the molybdenum nitrogenase and the alternative nitrogenase in Rhodobacter capsulatus." Arch. Microbial. Sep. 1996;165:80-90.
Mason CA & Hamer G (1987) Cryptic Growth in Klebsiella-Pneumoniae. Appl Microbiol Biot 25(6):577-584.
Matsubayashi, et al. Peptide hormones in plants. Annu Rev Plant Biol. 2006;57:649-74.
Medema et al., (2011) Synthetic biology in Streptomyces bacteria. Methods Enzymol 497:485-502.
Medema et al., Computational tools for the synthetic design of biochemical pathways. Nat Rev Microbiol. Jan. 23, 2012;10(3):191-202.
Medema, et al., Exploiting plug-and-play synthetic biology for drug discovery and production in microorganisms. Nat. Rev. Microbiol. 9:131-137 (2011).
Mengel, "Roots, growth and nutrient uptake." Dept. of Agronomy publication #AGRY-95-08 (Rev. May 1995), 8 pages.
Merriam-Webster "originate" accessed Jul. 7, 2020 (Year: 2020).
Mirsky, Ethan M., Refactoring the *Salmonella* Type Ill Secretion System. (Doctoral Dissertation) Apr. 12, 2012, 60 pages.
Mirzahoseini, et al., "Heterologous Proteins Production in *Escherichia coli*: An Investigation on the Effect of Codon Usage and Expression Host Optimization," Cell Journal (Yakhteh) 12(4):453 Winter 2011.
Mitra, Ranjana. Regulation of nifLA operon in Azotobacter vinelandii. Thesis submitted to the Jawaharlal Nehru University, New Delhi, for the degree of doctor of philosophy. 2000.
Miyazaki K (2003) Creating random mutagenesis libraries by megaprimer PCR of whole plasmid (Mega Whop). Methods Mol Biol 231 :23-28.
Moon et al., Genetic programs constructedfrom layered logic gates in single cells. Nature. Nov. 8, 2012;491(7423):249-53.
Mueller, et al. Closing yield gaps through nutrient and water management. Nature 490, 254-257 (2012).
Mus et al., "Symbiotic Nitrogen Fixation and the Challenges to Its Extension to Nonlegumes." Appl Environ Microbial. Jul. 2016, 82(13):3698-3710.
Mutalik, V.K., et al. Quantitative estimation of activity and quality for collections of functional genetic elements. Nat. Methods 10:347-353 (2013).
Nassar et al.. "Promotion of plant growth by an auxin-producing isolate of the yeast *Williopsis saturnus* endophytic in maize (*Zea mays* L.) roots." Biology and Fertility of Soils, 2005, 42:97-108.
Nelissen et al., Translational research:from pot to plot. Plant Biotechnology Journal, Jan. 2014 12:277-285.
Nestmann, "Mutagenesis by nitrosoguanidine, ethyl methanesulfonate, and mutator gene mutH in continuous cultures of *Escherichia coli*." Science Direct. Jun. 1975, 28(3):323-330.

Nichkawade, Anuradha. Studies on upstream regulatory sequence of the nifLA promoter of Klebsiella pnuemoniae. Thesis submitted to the Jawaharlal Nehru University, New Delhi, for the degree of doctor of philosophy. 1996.
Nielsen, "Transgenic organisms—time for conceptual diversification?" Nature Biotechnology 2003; 21:227-228.
No, et al., "Ecdysone-inducible gene expression in mammalian cells and transgenic mice" Proc. Natl. Acad. Sci. USA vol. 93, Issue 8, pp. 3346-3351, Apr. 1996.
Noskov, V.N., et al. Assembly of large, high G+C bacterial DNA fragments in yeast. ACS Synth. Biol. 1:267-273 (2012).
Oh, et al., "Organization of nif gene cluster in *Frankia* sp. EuIK1 strain, a symbiont of Elaeagnus umbellata," Arch. Microbiol., 2012, 194:29-34.
Ohtsuka et al., "An alternative approach to deoxyoligonucleotides as hybridization probes by insertion of deoxyinosine at ambiguous codon positions," J. Biol. Chem. 260:2605-2608 (1985).
Okubo et al., "Effects of Elevated Carbon Dioxide, Elevated Temperature, and Rice Growth Stage on the Community Structure of Rice Root-Associated Bacteria." Microbes Environ. Jun. 2014, 29(2):184-190 Published online May 31, 2014.doi: 10.1264/jsme2. ME14011.
Orme-Johnson WH (1985) Molecular basis of biological nitrogen fixation. Annu Rev Biophys Biophys Chem 14:419-459.
Ortiz-Marquez et al., "Association with an Ammonium-excreting bacterium allows diazotrophic culture of oil-rich Eukaryotic microalagae." Appl. Microbial. 2012; 78(7):2345-2352.
Pfleger et al., "Combinatorial engineering of intergenic regions in operons tunes expression of multiple genes"; Nature Biotechnology; 24(8):1027-1031 (2006).
Philippe et al., (2004) Improvement of pCVD442, a suicide plasmid for gene allele exchange in bacteria. Plasmid 51(3):246-255.
Piccioli, et al. Neuroantibodies: ectopic expression of a recombinant anti-substance P antibody in the central nervous system of transgenic mice. Neuron. Aug. 1995;15(2):373-84.
Piccioli, et al. Neuroantibodies: molecular cloning of a monoclonal antibody against substance P for expression in the central nervous system. Proc Natl Acad Sci U SA. Jul. 1, 1991; 88(13): 5611-5615.
Pickens LB, Tang, Y., Chooi, Y-H. (2011) Metabolic engineering for the production of natural products. Annu. Rev. Chem. Biomol. Eng. 2:211-236.
Plotnikova, et a. Pathogenesis of the human opportunistic pathogen Pseudomonas aeruginosa PA14 in *Arabidopsis*. Plant Physiol. 124, 1766-1774 (2000).
Price, M.N., Arkin, A.P., & Alm, E.J. The life-cycle of operons. PLoS Genet. 2, e96. (2006).
Price, M.N., Huang, K.H., Arkin, A.P., & Alm, E.J. Operon formation is driven by coregulation and not by horizontal gene transfer. Genome Res. 15, 809-819 (2005).
Purnick PE & Weiss R (2009) The second wave of synthetic biology: from modules to systems. Nat Rev Mol Cell Biol 10(6):410-422.
Qiu, et al. Construction of genetically engineered strains of Enterobacter cloacae (nifL~(-)A~(c)). Acta Phytophysiologica Sinica. [Jan. 1, 1999, 25(3):269-273].
Ramon, A., & Smith, H.O. Single-step linker-based combinatorial assembly of promoter and gene cassettes for pathway engineering. Biotechnol. Lett. 33:549-555 (2011).
Ran et al., Genome erosion in a nitrogen-fixing vertically transmitted endosymbiotic multicellular cyanobacterium. PLoS One. Jul. 8, 2010;5(7):e11486.
Resendis-Antonio, et al. Systems biology of bacterial nitrogen fixation: High-throughput technology and its integrative description with constraint-based modeling. BMC Syst Biol. 2011; 5: 120.
Riedel et al., (1983) Nitrogen fixation by Klebsiella pneumoniae is inhibited by certain multicopy hybrid nif plasmids. J Bacterial 153(1):45-56.
Roberts, et al. Regulation and characterization of protein products coded by the nif (nitrogen fixation) genes of Klebsiella pneumoniae. J Bacterial. Oct. 1978; 136(1): 267-279.
Rogers, et al., Synthetic biology approaches to engineering the nitrogen symbiosis in cereals. Journal of Experimental Botany, 2014; 65(8):1939-1946.

(56) References Cited

OTHER PUBLICATIONS

Rommens, et al. Intergeneric transfer and functional expression of the tomato disease resistance gene Pto. Plant Cell. Oct. 1995; 7(10):1537-1544.
Roncato-Maccari, et al., Endophytic Herbaspirillum seropedicae expresses nif genes in gramineous plants. FEMS Microbiology Ecology. 2003; 45: 39-47.
Rong et al., "Promoter specificity determinants of T7 RNA polymerase," Proc. Natl. Acad. Sci. USA, 95(2):515-519 (1998).
Rosenblueth et al. Nitrogen Fixation in Cereals. Frontiers in Microbiology, vol. 9, Article 1794. (Aug. 9, 2018). 13 pages.
Rosenblueth, et al. Bacterial endophytes and their interactions with hosts. Mol Plant Microbe Interact. Aug. 2006 ;19(8):827-37.
Rossolini et al., "Use of Deoxyinosine-Containing Primers vs Degenerate Primers for Polymerase Chain Reaction Based on Ambiguous Sequence Information" Mol. Cell. Probes 8:91-98 (1994).
Rubio and Ludden, Maturation of Nitrogenase: a Biochemical Puzzle, J. Bacteriology, 2005, 187(2):405-414.
Saikia et al., "Biological nitrogen fixation with non-legumes: An achievable target or a dogma?" Curr. Sci. Feb. 2007, 92(3): 317-322.
Salis et al., (2009) Automated design of synthetic ribosome binding sites to control protein expression. Nat Biotechnol 27(10):946-950.
Sandoval, et al. Strategy for directing combinatorial genome engineering in Escherichia coli. Proc Natl Acad Sci USA. Jun. 26, 2012;109(26):10540-5.
Sanjuan and Olivares, "Multicopy plasmids carrying the Klebsiella pneumoniae nifA gene enhance Rhizobium meliloti nodulation competitiveness on alfalfa," Molecular Plant-Microbe Interactions, 1991, 4(4):365-369.
Santi et al., Biological nitrogen fixation in non-legume plants. Annals of Botany, Jan. 2013, 111:743-767.
Schmidt-Dannert, et al., Molecular breeding of carotenoid biosynthetic pathways. Nat. Biotechnol. 18:750-753 (2000).
Schmitz, et al. "Iron is required to relieve inhibitory effects on NifL on transcriptional activation by NifA in Klebsiella pneumoniae." J Bacterial. Aug. 1996, 178(15):4679-4687.
Schouten et al., "Do cisgenic plants warrant less stringent oversight?" Nature Biotechnology, Jul. 2006, 24(7):753.
Service, R. Genetically engineered microbes make their own fertilizer, could feed the world's poorest. Science Apr. 2017: doi:I0.1126/science.aal1000.
Setten, et al., Engineering Pseudomonas protegens Pf-5 for Nitrogen Fixation and its application to improve plant growth under nitrogen-deficient conditions, PLOS One 2013; 8(5):1-14.
Shamseldin, "The role of different genes involoved in symbiotic nitrogen fixation—review." Global Journal of Biotechnology & Biochemistry, 2013, 8(4):84-94.
Shetty et al., (2008) Engineering BioBrick vectors from BioBrick parts. J Biol Eng 2:5.
Sibold et al., "A nif mutant of Klebsiella pneumoniae fixing nitrogen in the presence of ammonia." FEMS Microbiology Letters 10(1):37-41 (Jan. 1, 1981).
Sibold et al., "Constitutive expression of nitrogen fixation (nif) genes of Klebsiella pneumoniae due to a DNA duplication." EMBO J. 1982, 1(12):1551-8.
Siddavattam et al., "Regulation of nif Gene expression in Enterobacter agglomerans: Nucleotide sequence of the nifLA operon and influence of temperature and ammonium on its transcription." Molecular and general genetics. Dec. 1995, 249(6):629-636.
Simon et al., (1996) Perturbation of niff expression in Klebsiella pneumoniae has limited effect on nitrogen fixation. J Bacteriol 178(10):2975-2977.
Singh et al., "An L-methionine-D,L-sulfoximine-resistant mutant of the cyanobacterium Nostoc muscorum showing inhibitor-resistant y-glutamyl-transferase, defective glutamine synthetase and producing extracellular ammonia during N2 fixation." FESS Letters. Apr. 5, 1983, 154(1):10-14.
Sivaraman et al., "Codon choice in genes depends on flanking sequence information-implications for theoretical reverse translation," Nucleic Acids Res. 36:e16 (2008).
Sleight et al., Designing and engineering evolutionary robust genetic circuits. J Biol Engin. 2010;4(12):1-20.
Sleight, S.C., & Sauro, H.M. Randomized BioBrick assembly: a novel DNA assembly method for randomizing and optimizing genetic circuits and metabolic pathways. ACS Synth. Biol., 2013, 2(9):506-518.
Smanski et al., "Engineered Streptomyces platensis strains that overproduce antibiotics platensimycin and platencin," Antimicrob. Agents Chemother., 2009, 53:1299-12304.
Smanski et al., Synthetic biology to access and expand nature's chemical diversity. Nat Rev Microbial. Mar. 2016;14(3):135-49.
Smanski, et al. "Functional optimization of gene clusters by combinatorial design and assembly," Nat Biotechnol., 2014, 32(12):1241-1249.
Sorek and Cossart, Prokaryotic transcriptomics: a new view on regulation, physiology, and pathogenicity. Nat. Rev. Genet. 11:9-16 (2010).
Souza et al., "The N-Terminus of the NIFA protein of herbaspirillum seropedicae is probably involved in sensing of ammonia." In Tikhonovich et al. (Eds.) Proceedings of the 10th International Congress on Nitrogen Fixation, St. Petersburg, Russia, May 28-Jun. 3, 1995 (p. 260) Dordrecht: Kluwer.
Spiller, et al. Isolation and characterization of nitrogenase-derepressed mutant strains of cyanobacterium Anabaena variabilis. J Bacterial. Feb. 1986, 165(2):412-419.
Staron et al., "The Third Pillar of Bacterial Signal Transduction: Classification of the Extracytoplasmic Function (ECF) Sigma Factor Protein Family," Mol Microbiol 14(3): 557-81 (2009).
Steenhoudt et al., "Azospirillum, a free-living nitrogen-fixing bacterium closely associated with grasses: genetic, biochemical and ecological aspects." FEMS Microbial. Rev. 2000; 24:487-506.
Stein, et al. The osteocalcin gene: a model for multiple parameters of skeletal-specific transcriptional control. Mol Biol Rep. Aug. 1997;24(3):185-96.
Stemmer, "DNA shuffling by random fragmentation and reassembly: In vitro recombination for molecular evolution" Oct. 1994, Proc. Natl. Acad. Sci. USA 91:10747-10751.
Stemple, "Tilling—a high-throughput harvest for functional genomics." Nature Reviews Genetics 5, 1-7 (Feb. 2004), doi: 10.1038/nrg1273.
Stephanopoulos. Challenges in engineering microbes for biofuels production. Science. Feb. 9, 2007;315(5813):801-4.
Stewart et al., (1967) In situ studies on nitrogen fixation with the acetylene reduction technique. Science 158(3800):536.
Stucken, K., et al. The smallest known genomes of multicellular and toxic cyanobacteria: comparison, minimal gene sets for linked traits and the evolutionary implications. PLoS One 5:e9235 (2010).
Subtil, et al. Secretion of Predicted Inc Proteins of Chlamydia pneumoniae by a Heterologous Type Ill Machinery. Molecular Microbiology. Feb. 2001, vol. 39, No. 3; pp. 792-800.
Suh, et al., Functional expression of the FeMo-cofactor-specific biosynthetic genes nifEN as a NifE-N fusion protein synthesizing unit in Azotobacter vinelandii. Biochem. Biophys. Res. Comm. 299:233-240 (2002).
Swain et al., "Nitrogen fixation and its improvement through genetic engineering." J. Global Biosciences, 2013, 2(5): 98-112.
Tamsir et al., (2011) Robust multicellular computing using genetically encoded NOR gates and chemical 'wires'. Nature 469(7329):212-215.
Tan C, "A synthetic biology challenge: making cells compute," Mol Biosyst 3: 343-353 (2007).
Temme et al., "Designing and Engineering Complex Behavior in Living Machines." (Doctoral Dissertation) Oct. 1, 2011. Retrieved from URL <escholarship.org/uc/item/1r41x99s>, 75 pages.
Temme et al., "Refactoring the nitrogen fixation gene cluster from Klebsiella oxytoca," Proc. Natl. Acad. Sci. USA, 2012, 109(18):7085-7090.
Temme et al., Modular control of multiple pathways using engineered orthogonal T7 polymerases. Nucleic Acids Res. Sep. 1, 2012 ;40(17):8773-81.
Temme K, et al. (2008) Induction and relaxation dynamics of the regulatory network controlling the type III secretion system encoded within Salmonella pathogenicity island 1. J Mol Biol 377(1):47-61.

(56) References Cited

OTHER PUBLICATIONS

Thiel, T., Lyons, E.M., & Erker, J.C., Characterization of genes for a second Modependent nitrogenase in the cyanobacterium *Anabaena variabilis*. J. Bact. 179:5222-5225 (1997).
Thomas et al., "Ammonium Excretion by an I-Methionine-dl-Sulfoximine-Resistant Mutant of the Rice Field Cyanobacterium *Anabaena siamensis*." Appl Environ Microbial. Nov. 1990, 56(11):3499-3504.
Tilman et al. "Global food demand and the sustainable intensification of agriculture." PNAS 108:20260-20264 (2011).
Triplett, "Diazotrophic endophytes: progress and prospects for nitrogen fixation in monocots." Plant and Soil 1996; 186:29-38.
Tritt et al., "An Integrated Pipeline for de Novo Assembly of Microbial Genomes."Sep. 13, 2012. PLOS one. https://doi.org/10.1371/journal.pone.0042304, 9 pages.
Ueda, et al., Remarkable N2-Fixing Bacterial Diversity Detected in Rice Roots by Molecular Evolutionary Analysis of nifH Gene Sequences. Journal of Bacteriology, Mar. 1995, p. 177:1414-1417.
Van Dongen, S.A., "Performance criteria for graph clustering and Markov cluster experiments," CWI, 2000, 36 pages.
Vernon et al., Analysis of 16S rRNA gene sequences and circulating cell-free DNA from plasma of chronic fatigue syndrome and non-fatigued subjects. BMC Microbiology 2002; 2:39.
Villa et al., "Azotobacter vinelandii siderophore can provide nitrogen to support the culture of the green algae *Neochloris oleoabundans* and *scenedesmus*." FEMS Microbial. Lett. 2014, 351(1):70-77.
Villalobos et al., (2006) Gene Designer: a synthetic biology tool for constructing artificial ONA segments. BMC Bioinformatics 7:285.
Voigt, "Genetic parts to program bacteria," Current Opinion in Biotechnology, 2006, 17(5):548-557.
Voigt, C., "Gaining Access: Rebuilding Genetics from the Ground Up". Institute of Medicine Board on Global Health Forum on Microbial Threats. Mar. 14, 2011. Retrieved from the web at iom.edu/-/media/Files/ActivityFiles/PublicHealth/MicrobialThreats/2011-MAR- 14Noigt.pdf.
Wang et al., Positive and negative regulation of gene expression in eukaryotic cells with an inducible transcriptional regulator. Gene Ther., 4.5 (May 1997): 432-441.
Wang et al., Using Synthetic biology to distinguish and overcome regulatory and functional barriers related to nitrogen fixation. PLoS One. 2013;8(7):e68677. 11 pages.
Wang, et al. Ligand-inducible and liver-specific target gene expression in transgenic mice. Nat Biotechnol. Mar. 1997;15(3):239-43.
Wang, et al. Programming cells by multiplex genome engineering and accelerated evolution. Nature. Aug. 13, 2009;460(7257):894-8.
Wang, et al., "A minimal nitrogen fixation gene cluster from *paenibacillus* sp. WLY78 enables expression of active nitrogenase in *Escheichia coli*." Plos Genetics, 2013, 9(10):1-11.
Watanabe et al., (2006) Total biosynthesis of antitumor nonribosomal peptides in *Escherichia coli*. Nature Chemical Biology, 2:423-428.
Watanabe et al., Chapter 15. Plasmid-borne gene cluster assemblage and heterologous biosynthesis of nonribosomal peptides in *Escherichia coli*. Methods Enzymol. 2009; 458:379-99.
Weber, et al. A modular cloning system for standardized assembly of multigene constructs. PLoS One. Feb. 18, 2011;6(2):e16765.
Wei et al., "Endophytic nitrogen-fixing Klebsiella variicola strain DX120E promotes sugarcane growth", Biology and fertility of soils 50: 657-666, 2014.
Welch et al. (2009) "Design Parameters to Control Synthetic Gene Expression in *Escherichia coli*" PLoS One 4(9):e7002.
Wells, J.A. Additivity of mutational effects in proteins. Biochemistry 29:8509-8517 (1990).
Wenzel SC & Muller R (2005) Recent developments towards the heterologous expression of complex bacterial natural product biosynthetic pathways. Curr Opin Biotechnol 16(6):594-606.
Werner et al., Fast track assembly of multigene constructs using Golden Gate cloning and the MoClo system. Bioeng Bugs. Jan. 1, 2012 ;3(1):38-43.
Widmaier, et al. Engineering the *Salmonella* type III secretion system to export spider silk monomers. Mol. Syst. Biol. 5, 309 (2009).
Wootton, et al. Statistics of local complexity in amino acid sequences and sequence databases. Computers & Chemistry. vol. 17, Issue 2, Jun. 1993, pp. 149-163.
Wu et al., "Root exudates from two tobacco cultivars affect colonization of Ralstonia solanacearum and the disease index," European Journal of Plant Pathology, 2014, 141(4):667-677.
Wu, J., et al. Multivariate modular metabolic engineering of *Escherichia coli* to produce resveratrol from L-tyrosine. J. Biotechnol. (2013), 167:404-411.
Xu, et al., ePathBrick: a synthetic biology platform for engineering metabolic pathways in *E. coli*. ACS Synth. Biol., 1:256-266 (2012).
Yarza, et al., "Uniting the classification of cultured and uncultured bacteria and archaea using 16S rRNA gene sequences," Nature Rev. Micro., 2014 12:635-345.
Ye et al., "Primer-BLAST: a tool to design target-specific primers for polymerase chain reaction," BMC Bioinformatics., Jun. 2012, 13(134), 1-11.
Yokobayashi et al, (2002) Directed evolution of a genetic circuit. Proc Natl Acad Sci USA 99(26):16587-16591.
Yoshida et al., Atmospheric dinitrogen fixation in the flooded rice rhizosphere as determined by the N-15 isotope technique. Soil Science and Plant Nutrition, Dec. 1980, 26(4):551-559.
Zaslaver et al., (2006) Optimal gene partition into operons correlates with gene functional order. Phys Biol 3(3): 183-189.
Zazopoulos E, et al. (2003) A genomics-guided approach for discovering and expressing cryptic metabolic pathways. Nat Biotechnol 21 (2): 187-190.
Zehr et al., New Nitrogen-Fixing Microorganisms Detected in Oligotrophic Oceans by Amplification of Nitrogenase (nifH) Genes. Appl Environ Microbial. Sep. 1998, 64(9):3444-3450.
Zehr lab NifH database, retrieved from URL <https://wwwzehr.pmc.ucsc.edu/nifH_Database_Public/>, Apr. 4, 2014, 1 page.
Zhang et al., "Influence of different factors on the nitrogenase activity of the engineered *Escherichia coli* 78-7," World J Microbiol Biotechnol. Jun. 2015, 31(6):921-7.
Zhang et al., "Involvement of the ammonium transporter AmtB in nitrogenase regulation and ammonium excretion in Pseudomonas stutzeri A 1501." Res. Microbial, Jun. 2012, 163(5):332-339.
Zhang, et al. "GlnD Is Essential for NifA Activation, NtrB/NtrC-Regulated Gene Expression, and Posttranslational Regulation of Nitrogenase Activity in the Photosynthetic, Nitrogen-Fixing Bacterium *Rhodospirillum rubrum*," J. Bacteriol., Feb. 2005, 187(4): 1254-1265.
Zhao et al., "Evidence for nifU and nifS participation in the biosynthesis of the iron-molybdenum cofactor of nitrogenase," J. Biol. Chem., 2007, 282(51):37016-37025.
Zomer AL (2011) PPP: Perform Promoter Prediction, retireved from URL <http://bioinformatics.biol.rug.nl/websoftware/ppp/ppp_start.php>, 2 pages.
Ohta et al., "Associative N2-fixation of Rice with Soil and Microorganisms", 1985, 27:17-27 (Abstract Only).
Muse et al., "The nac (Nitrogen Assimilation Control) Gene from *Escherichia coli*," Journal of Bacteriology, Mar. 1998, 180(5):1166-1173.
PCT International Preliminary Report on Patentability in International Appln. No. PCT/US2020/029894, dated Nov. 4, 2021, 13 pages.
PCT International Search Report and Written Opinion in International Appln. No. PCT/US2020/029894, mailed Aug. 31, 2020, 19 pages.
Robson et al., "Azotobacter Genomes: The Genome of Azotobacter chroococcum NCIMB 8003 (ATCC 4412)," PLOS One, Jun. 2015, 35 pages.
Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.
Das et al. "Microbial assay of N2 fixation rate, a simple alternate for acetylene reduction assay" MethodsX, 2018, 5: 909-914.

(56) References Cited

OTHER PUBLICATIONS

Davin-Regli et al. "Enterobacter aerogenes and Enterobacter cloacae; versatile bacterial 1-3, 7, 12, 17-24, 26-32, pathogens confronting antibiotic treatment," Front Microbiol, 2015, 6, 35, 41-45, 49, 54, 56-66, 392:1-10.

De Freitas J R Ed-Eisenhauer Nico et al: "Yield and N assimilation of winter wheat (*Triticum aestivum* L., var. *norstar*) inoculated with rhizobacteria", Pedobiologia, Elsevier, Amsterdam, NL, vol. 44, No. 2, Jan. 1, 2000 (Jan. 1, 2000), pp. 97-104, XP004633526, ISSN: 0031-4056, DOI: 10.1078/S0031-4056(04)70031-1.

GenBank CP007215 "Kosakonia sacchari SP1 chromosome, complete genome" 19 Sep. 43-46, 2017 [online]. [Retrieved Oct. 28, 2019]. Retrieved from the internet (URL:https://www.ncbi.nlm.nih.gov/nuccore/CP007215).

Joseph et al., "Recent developments of the synthetic biology toolkit for Clostridum." Frontiers in microbology, 2018, 9(154):1-13.

Levican et al. "Comparative genomic analysis of carbon and nitrogen assimilation mechanisms in three indigenous bioleaching bacteria: predictions and validations" BMC Genomics 2008, 9:581, 19 pages (Year: 2008).

Mabrouk et al. "Chapter 6: Potential of Rhizobia in Improving Nitrogen Fixation and Yields of Legumes," Symbiosis, May 30, 2018 (May 30, 2018), IntechOpen, pp. 1-16. Retrieved from the Internet:<https://www.intechopen.com/books/symbiosis/potential-of-rhizobia-in-improving-B35lnitrogen-fixation-and-yields-of-legumes> on Nov. 18, 2019 (Nov. 18, 2019).

Magasanik "Genetic Control of Nitrogen Assimilation in Bacteria" Ann. Rev. Genet 1982. 16:135-68 (Year: 1982).

PCT International Search Report in International Appl. No. PCT/US2019/041429, Dec. 3, 2019, 18 pages.

PCT International Search Report in International Appl. No. PCT/US2019/059450, Mar. 10, 2020, 6 pages.

PCT International Search Report in International Appl. No. PCT/US2019/39217, Nov. 19, 2019, 5 pages.

PCT International Search Report in International Appl. No. PCT/US2019/39528, Nov. 6, 2019, 6 pages.

PCT Supplementary Partial European Search Report in International Appln. No. PCT/US2018013671, dated Oct. 27, 2020, 18 pages.

Takeshi Uozumi et al: "Cloning and Expression of the nit A Gene of Klebsiella oxytoca in K. pneumoniae and Azospirillum lipoferum", Agricultural and Biological Chemistry, 1986, 50(6):1539-1544.

Van Heeswijk et al. "Nitrogen Assimilation in *Escherichia coli*: Putting Molecular Data into a Systems Perspective" Microbiology and Molecular Biology Reviews p. 628-695 Dec. 2013 vol. 77 No. 4 (Year: 2013).

Duca et al., "Indole-3-acetic acid in plant-microbe interactions," Antonie van Leeuwenhoek, Jan. 2014, 106(1):85-125, 41 pages.

Extended European Search Report in European Appln. No. 19826654.6, dated Jul. 4, 2022, 16 pages.

Schluter et al., "Global mapping of transcription start sites and promoter motifs in the symbiotic α-proteobacterium *Sinorhizobium meliloti*," BMC Genomics, Mar. 2013, 14(1):156, 21 pages.

Aquino et al., "Effect of point mutations on *Herbaspirillum seropedicae* NifA activity," Brazilian Journal of Medical and Biological Research, Aug. 2015, 48(8):683-690.

Dunican et al., "Genetic transfer of nitrogen fixation from Rhizobium Trifolii to Klebsiella Aerogenes," Biochemical and Biophysical Research Communications, Mar. 1974, 57(1):62-72.

Invitation to Pay Additional Fees in International Appln. No. PCT/US2022/035873, mailed Sep. 30, 2022, 19 pages.

Paschen et al., "*Rhodobacter capsulatus* nifA mutants mediating nif gene expression in the presence of ammonium," FEMS Microbiology Letters, Jan. 2001, 207-213.

Rey et al., "Redirection of Metabolism for Biological Hydrogen Production," Applied and Enviornmental Microbiology, Mar. 2007, 73(5):1665-1671.

Zou et al., "Identification and functional characterization of NifA variants that are independent of GlnB activiation in the photosynthetic bacterium *Rhodospirillum rubrum*," Microbiology, Sep. 2008, 154(9):2689-2699.

Adhikary et al., "Artificial citrate operon confers mineral phosphate solubilization ability to diverse fluorescent pseudomonads," PLoS One, Sep. 2014, 9(9):e107554, 12 pages.

Ambrosio et al., "Metabolic engineering of a diazotrophic bacterium improves ammonium release and biofertilization of plants and microalgae," Metab Eng., Mar. 2017, 40:59-68.

Blast.ncbi.nlm.nih.gov, [online], "BLAST. Basic local alignment search tool," 2021, retrieved on Apr. 8, 2021, retrieved from URL<https://blast.ncbi.nlm.nih.gov/Blast.cgi>, 3 pages.

Dash et al., "Functionalities of Phosphate-Solubilizing Bacteria of Rice Rhizosphere: Techniques and Perspectives," Recent Advances in Applied Microbiology, 2017, 151-163.

EP Extended European Search Report in European Appln. No. 18739050.5, dated Feb. 1, 2021, 22 pages.

Intechopen.com, [online], "*Escherichia coli* as a Model Organism and Its Application in Biotechnology, IntechOpen," 2020, retrieved on Mar. 31, 2020, retrieved from URL<https://www.intechopen.com/books/-i-escherichia-coli-i-recent-advances-on-physiology-pathogenesis-and-biotechnological-applications/-i-escherichi%E2%80%A6>, 15 pages.

Jayaraman et al., "Strain Improvement of Phosphate Solubilizing Fungal Strains," Journal of Ecobiotechnology, Dec. 2010, 2(5):65-70.

Kumar et al., "Establishment of phosphate-solubilizing strains of *Azotobacter chroococcum* in the rhizosphere and their effect on wheat cultivars under green house conditions," Microbiol Res., 2001, 156(1):87-93.

Lenski et al., "Effects of Segregation and Selection on Instability of Plasmid pACYC184 in *Escherichia coli* B," Journal of Bacteriology, Nov. 1987, 169(11):5314-5316.

Liu et al., "Development of an engineered soil bacterium enabling to convert both insoluble inorganic and organic phosphate into plant available phosphate and its use as a biofertilizer," Mol Biotechnol., May 2015, 57(5):419-29.

Miller et al., "Biochemical and genomic comparison of inorganic phosphate solubilization in *Pseudomonas* species," Environ Microbiol Rep., Jun. 2010, 2(3):403-11.

Murphy et al., "A modified single solution method for the determination of phosphate in natural waters," Analytica Chimica Acta, 1962, 27:31-36.

Parts.igem.org, [online], "Registry of Standard Biological Parts," 2017, retrieved on Apr. 8, 2021, retrieved from URL<parts.igem.org/Catalog>, 4 pages.

PCT International Preliminary Report on Patentability in International Appln. No. PCT/US2019/052003, dated Mar. 23, 2021, 10 pages.

PCT International Search Report and Written Opinion in International Appln. No. PCT/US2019/052003, dated Dec. 19, 2019, 15 pages.

Poliner et al., "Nontransgenic Marker-Free Gene Disruption by an Episomal CRISPR System in the Oleaginous Microalga, *Nannochloropsis oceanica* CCMP1779," Acs Synth. Biol., 2018, 7(4):962-968.

Pyne et al., "Coupling the CRISPR/Cas9 System with Lambda Red Recombineering Enables Simplified Chromosomal Gene Replacement in *Escherichia coli*," Applied and Environmental Microbiology, Aug. 2015, 81(15):5103-5144.

Rajput et al., "Derepression of Mineral Phosphate Solubilization Phenotype by Insertional Inactivation of icIR in Klebsiella pneumoniae," PLoS One, Sep. 2015, 10(9):e0138235, 15 pages.

Ramirez et al., "*Burkholderia* and *Paraburkholderia* are Predominant Soybean Rhizobial Genera in Venezuelan Soils in Different Climatic and Topographical Regions," Microbes and Environments, Mar. 2019, 34(1):43-58.

Reyes et al., "Characteristics of phosphate solubilization by an isolate of a tropical Penicillium rugulosum and two UV-induced mutants," FEMS Microbiology Ecology, Mar. 1999, 28(3):291-295.

(56) References Cited

OTHER PUBLICATIONS

Rodriguez et al., "Genetics of phosphate solubilization and its potential applications for improving plant growth-promoting bacteria," Plant and Soil, Sep. 2006, 287(1-2):15-21.
Shulse et al., "Engineered Root Bacteria Release Plant-Available Phosphate from Phytate," Appl Environ Microbiol., Aug. 2019, 85(18):e01210-19.
Suzuki et al., "Immune-mediated motor polyneuropathy after hematopoietic stem cell transplantation," Bone Marrow Transplant., Aug. 2007, 40(3):289-91.
Vick et al., "Optimized compatible set of BioBrick™ vectors for metabolic pathway engineering," Appl Microbiol Biotechnol., Dec. 2011, 92(6):1275-86.
Wagh et al., "Heterologous expression of pyrroloquinoline quinone (pqq) gene cluster confers mineral phosphate solubilization ability to Herbaspirillum seropedicae Z67," Appl. Microbiol Biotechnol., Jun. 2014, 98(11):5117-29.
Werra et al., "Role of gluconic acid production in the regulation of biocontrol traits of Pseudomonas fluorescens CHAo," Appl Environ Microbiol., Jun. 2009, 75(12):4162-74.
Xie et al., "Interaction between NifL and NifA in the nitrogen-fixing Pseudomonas stutzeri A1501," Microbiology (Reading), Dec. 2006, 152(Pt 12):3535-3542.
Amalraj et al., "Effect of Polymeric Additives, Adjuvants, Surfactants on Survival, Stability and Plant Growth Promoting Ability of Liquid Bioinoculants," J. Plant Physiol Pathol, 2013, 1:2, 6 pages.
Arriel-Elias et al., "Shelf life enhancement of plant growth promoting rhizobacteria using a simple formulation screening method," African Journal of Microbiology Research, Feb. 2018, 12(5):115-126.
Berninger et al., "Maintenance and assessment of cell viability in formulation of non-sporulating bacterial inoculants," Microb. Biotechnol., Mar. 2018, 11(2):277-301 (2018); doi: 10.1111/1751-7915.12880.
Bloch et al., "Biological nitrogen fixation in maize: optimizing nitrogenase expression in a root-associated diazotroph," Journal of Experimental Botany, Jul. 2020, 71(15):4591-4603.
cera-gmc.org [online], "GM Crop Database," Center for Environmental Risk Assessment (CERA), 2010, retrieved from URL <http://ucbiotech.org/biotech_info/PDFs/Center for Environmental Risk Assessment CERA_2011_GM_Crop_Database.pdf>, 1 page.
Colby, "Calculating Synergistic and Antagonistic Responses of Herbicide Combinations," Weeds, Jan. 1967, 15(1):20-22, 4 pages.
Costerton et al., "Microbial Biofilms," Annu. Rev. Microbial., Oct. 1995, 49:711-745.
Da Silva et al., "Survival of endophytic bacteria in polymer-based inoculants and efficiency of their application to sugarcane," Plant Soil, May 2012, 356:231-243.
EP Partial Supplementary European Search Report Appln. No. 19826654.6 dated Mar. 17, 2022, 11 pages.
GenBank Accession No. CP016337.1 "Kosakonia sacchari strain BO-1 chromosome, complete genome," Jul. 11, 2016, 1119 pages.
Hoeschle-Zeledon et al., "Regulatory challenges for biological control," The CGIAR Systemwide Program on Integrated Pest Management, Jan. 2013, SP-IPM Secretariat, International Institute of Tropical Agriculture (IITA), Ibadan, Nigeria, 53 pages.
International Preliminary Report on Patentability in International Appln. No. PCT/US2019/039528, mailed Jan. 7, 2021, 15 pages.
International Preliminary Report on Patentability in International Appln. No. PCT/US2020/029831, mailed Nov. 4, 2021, 8 pages.
International Search Report and Written Opinion in International Appln. No. PCT/US2019/064782, mailed Apr. 16, 2020, 14 pages.
International Search Report and Written Opinion in International Appln. No. PCT/US2020/014083, mailed Jul. 20, 2020, 24 pages.
International Search Report and Written Opinion in International Appln. No. PCT/US2021/029993, mailed Sep. 15, 2021, 12 pages.
International Search Report and Written Opinion in International Appln. No. PCT/US2021/055858, dated Mar. 25, 2022, 12 pages.
Invitation to Pay Additional Fees in International Appln. No. PCT/US2020/014083, mailed May 28, 2020, 20 pages.

Jahn et al., "Extraction of Extracellular Polymeric Substances (EPS) from Biofilms Using a Cation Exchange Resin," Wat. Sci. Tech., 1995, 32(8):157-164.
Kabaluk et al., "The use and regulation of microbial pesticides in representative jurisdictions worldwide," IOBC Global, 2010, 99 pages.
Lowman et al., "Strategies for enhancement of switchgrass (*Panicum virgatum* L.) performance under limited nitrogen supply based on utilization of N-fixing bacterial endophytes," Plant and Soil, Aug. 2016, 405(1):47-63, 17 pages.
Mao et al., "Silencing a cotton bollworm P450 monooxygenase gene by plant-mediated RNAi impairs larval tolerance of gossypol," Nature Biotechnology, Nov. 2007, 25(11): 1307-1313.
Nagy et al., "Nanofibrous solid dosage form of living bacteria prepared by electrospinning," eXPRESS Polymer Letters, 2014, 8(5):352-361.
Nielsen et al., "Conceptual model for production and composition of exopolymers in biofilms," Wat. Sci. Tech., 1997, 36(1): 11-19.
Nielsen et al., "Extraction of EPS," Wingender et al. (eds.), Microbial Extracellular Polymeric Substances, 1999, 24 pages.
Patil et al., "Liquid formulations of Acetobacter diazotrophicus L 1 and Herbaspirillum seropedicae J24 and their field trials on wheat," International Journal of Environmental Science, 2012, 3(3):1116-1129, 4 pages (Abstract Only).
Rakhee et al., "Extracellular polymeric substances of the marine fouling diatom amphora rostrata Wm.Sm," Biofouling, 2001, 17(2):117-127, 12 pages.
Rojas-Tapias et al., "Preservation of Azotobacter chroococcum vegetative cells in dry polymers," Univ. Sci., 2015, 20(2):201-207.
Ryu et al., "Control of nitrogen fixation in bacteria that associate with cereals," Nat. Microbiol., Feb. 2020, 5(2):314-330, 31 pages.
Schuler et al., "Potential side effects of insect-resistant transgenic plants on arthropod natural enemies," Trends Biotechnol., May 1999, 17(5):210-216.
Search Report in AP Appln. No. AP/P/2020/012401, dated Feb. 8, 2022, 4 pages.
Search Report in AP Appln. No. AP/P/2020/012402, dated Feb. 15, 2022, 5 pages.
Wang et al., "Biofilm formation enables free-living nitrogen-fixing rhizobacteria to fix nitrogen under aerobic conditions," The ISME Journal, Jul. 2017, 11:1602-1613.
Wimpenny et al., "Community structure and co-operation in biofilms," 59th Symposium of the Society for General Microbiology, Allison et al. (eds.), Sep. 2000, 23 pages.
Yu et al., "Recombineering Pseudomonas protegens CHA0: An innovative approach that improves nitrogen fixation with impressive bactericidal potency," Microbiological Research, Jan. 2019, 218:58-65.
Baum et al., "Control of coleopteran insect pests through RNA interference," Nature Biotechnology, Nov. 2007, 25(11):1322-1326.
Bosmans et al., "Sea anemone venom as a source of insecticidal peptides acting on voltage-gated Na+ channels," Toxicon, Mar. 2007, 49(4):550-560.
Chakroun et al., "Bacterial Vegetative Insecticidal Proteins (Vip) from Entomopathogenic Bacteria," Microbiol Mol Biol Rev., Mar. 2016, 80(2):329-50.
Compant et al., "A review on the plant microbiome: Ecology, functions, and emerging trends in microbial application," Journal of Advanced Research, Sep. 2019, 19:29-37.
Crickmore et al., "Revision of the Nomenclature for the Bacillus thuringiensis Pesticidal Crystal Proteins," Microbiol Mol Biol Rev., Sep. 1998, 62(3):807-813.
EP Partial Supplementary European Search Report in European Appln. No. 18843845.1, dated Apr. 12, 2021, 17 pages.
Eyraud et al., "Expression and Biological Activity of the Cystine Knot Bioinsecticide PAlb (Pea Albumin 1 Subunit b)," PLOS One, Dec. 2013, 8(12):e81619, 9 pages.
Forner et al., "Treatment of hepatocellular carcinoma," Crit Rev Oncol Hematol., Nov. 2006, 60(2):89-98.
Janczarek et al., "Multiple copies of rosR and pssA genes enhance exopolysaccharide production, symbiotic competitiveness and clover nodulation in Rhizobium leguminosarum bv. trifolii," Antonie Van Leeuwenhoek, Nov. 2009, 96(4):471-86.

(56) References Cited

OTHER PUBLICATIONS

King et al., "Spider-Venom Peptides: Structure, Pharmacology, and Potential for Control of Insect Pests," Annu. Rev. Entomol., 2013, 58:475-96.
Lifesci.sussex.ac.uk, [online], "Bacillus thuringiensis Toxin Nomenclature," 2016, retrieved on Mar. 25, 2021, retrieved from URL<www.lifesci.sussex.ac.uk/home/Neil_Crickmore/Bt/> 1 page.
Lin et al., "PC, a Novel Oral Insecticidal Toxin from Bacillus bombysepticus Involved in Host Lethality via APN and BIR-175," Scientific Reports, Jun. 2015, 5:11101, 14 pages.
Martinelli et al., "Structure-function studies on jaburetox, a recombinant insecticidal peptide derived from jack bean (*Canavalia ensiformis*) urease," Biochimica et Biophysica Acta, Mar. 2014, 1840(3):935-44.
Naimov et al., "Solubilization, Activation, and Insecticidal Activity of Bacillus thuringiensis Serovar thompsoni HDS42 Crystal Proteins," Applied and Environmental Microbiology, Dec. 2008, 74(23):7145-7151.
Nature.com, [online], "Transcription Unit," 2005, retrieved on Apr. 15, 2021, retrieved from URL<https://www.nature.com/scitable/definition/transcription-unit-260>, 2 pages.
Parker et al., "Pore-forming protein toxins: from structure to function," Progress in Biophysics & Molecular Biology, 2005, 88:91-142.
PCT International Preliminary Report on Patentability in International Appln. No. PCT/US2019/041429, dated Jan. 12, 2021, 11 pages.
PCT International Search Report and Written Opinion in International Appl. No. PCT/US2019/039528, dated Nov. 6, 2019, 19 pages.
PCT International Search Report and Written Opinion in International Appln. No. PCT/US2018/057613, dated March 5. 2019, 11 pages.
PCT Written Opinion in International Appln. No. PCT/US2018/057174, dated Jan. 4, 2019, 3 pages.
Purcell et al., "Cholesterol oxidase: a potent insecticidal protein active against boll weevil larvae," Biochem Biophys Res Commun, Nov. 1993, 196(3):1406-13.
Qaim et al., "Yield Effects of Genetically Modified Crops in Developing Countries," Science, Feb. 2003, 299(5608):900-2.
Robledo et al., "Rhizobium cellulase CelC2 is essential for primary symbiotic infection of legume host roots," Proc Natl Acad Sci USA, May 2008, 105(19):7064-9.
Robledo et al., "Role of Rhizobium endoglucanase CelC2 in cellulose biosynthesis and biofilm formation on plant roots and abiotic surfaces," Microb Cell Fact., Sep. 2012, 11:125, 12 pages.
Sanahuja et al., "Bacillus thuringiensis: a century of research, development and commercial applications," Plant Biotechnology Journal, Apr. 2011, 9(3):283-300.
Sanyal et al., "The etiology of hepatocellular carcinoma and consequences for treatment," Oncologist, 2010, 15(Suppl 4):14-22.
Schuler et al., "Insect-resistant transgenic plants," Trends in Biotechnology, Apr. 1998, 16(4):168-175.
Tijssen, "Laboratory Techniques In Biochemistry And Molecular Biology," Elsevier, 1993, 24:65 pages.
Woolbright et al., "Novel insight into mechanisms of cholestatic liver injury," World J Gastroenterol., Sep. 2012, 18(36):4985-93.
Lugtenberg et al., "Molecular Determinants of Rhizosphere Colonization by *Pseudomonas*," Annu. Rev. Phytopathol., Sep. 2001, 39(1):461-490, 31 pages.
Machado et al., "Excretion of ammonium by *Azospirillum brasilense* mutants resistant to ethylenediamine," Can. J. Microbiol., Jul. 1991, 37(7): 549-553, 2 pages (Abstract Only).
Pankievicz et al., "Robust biological nitrogen fixation in a model grass-bacterial association," The Plant Journal, 81(6), Mar. 2015, 907-919.
Klose et al., "Glutamate at the site of phosphorylation of nitrogen-regulatory protein NTRC mimics aspartyl-phosphate and activates the protein," J Mol Biol., Jul. 1993, 232(1):67-78.

Kranz et al., "Ammonia-constitutive nitrogen fixation mutants of Rhodobacter capsulatus," Gene, Nov. 1988, 71(1):65-74.
Mus et al., "Diazotrophic Growth Allows Azotobacter vinelandii To Overcome the Deleterious Effects of a glnE Deletion," Appl Environ Microbiol., Jun. 2017, 83(13):e00808-17.
PCT International Search Report and Written Opinion in International Appln. No. PCT/US2020/031201, dated Mar. 9, 2021, 28 pages.
Search Report in Russian Appln. No. 2020116764, dated Apr. 28, 2022, 15 pages (with English translation).
Brady et al., "Taxonomic evaluation of the genus *Enterobacter* based on multilocus sequence analysis (MLSA): Proposal to reclassify *E. nimipressuralis* and *E. amnigenus* into *Lelliottia* gen. nov. as *Lelliottia nimipressuralis* comb. nov. and *Lelliottia amnigena* comb. nov., respectively, *E. gergovie* and *E. pyrinus* into *Pluralibacter* gen. nov. as *Pluralibacter gergoviae* comb. nov. and *Pluralibacter pyrinus* comb. nov., respectively, *E. cowanii*, *E. radicincitans*, *E. oryzae* and *E. arachidis* into *Kosakonia* gen. nov. as *Kosakonia cowanii* comb. nov., *Kosakonia radicincitans* comb. nov., *Kosakonia oryzae* comb. nov. and *Kosakonia arachidis* comb. nov., respectively, and *E. turicensis*, *E. helveticus* and *E. pulveris* into *Cronobacter* as *Cronobacter zurichensis* nom. nov., *Cronobacter helveticus* comb. nov. and *Cronobacter pulveris* comb. nov., respectively, and emended description of the genera *Enterobacter* and *Cronobacter*," Syst. Appl. Microbiol., Jul. 2013, 36(5):309-319.
Giri, "The First Report of Indigenous Free-Living Diazotroph *Kosakonia sacchari* Isolated from Himalayan Alder-Based Shifting Cultivation System in Nagaland, India," Journal of Soil Science and Plant Nutrition, Apr. 2019, 19:574-579.
Hosseini-Abari et al., "LC/MS detection of oligogalacturonic acids obtained from tragacanth degradation by pectinase producing bacteria," J Basic Microbiol., Dec. 2018, 59(3):249-255.
Hu et al., "Application of bryophyte rhizoid-associated bacteria increases silicon accumulation and growth in maize (*Zea mays* L.) seedlings," App. Ecol. Env. Res., Oct. 2019, 17(6):13423-13433.
PreNewsWire.com [online], "Global Agricultural Inoculants Market Research Report—Industry Analysis, Size, Share, Growth, Trends and Forecast 2015-2022," Dec. 2016, retrieved on Mar. 24, 2023, retrieved from URL <https://www.prnewswire.com/news-releases/global-agricultural-inoculants-market-research-report---industry-analysis-size-share-growth-trends-and-forecast-2015---2022-300375864.html>, 4 pages.
Shahid et al., "Colonization of *Vigna radiata* by a halotolerant bacterium *Kosakonia sacchari* improves the ionic balance, stressor metabolites, antioxidant status and yield under NaCl stress," Appl. Soil Ecol., Feb. 2021, 158:1-14.
Tian et al., "Six New Families of Aerobic Arsenate Reducing Bacteria: Leclercia, Raoultella, Kosakonia, Lelliottia, Yokenella, and Kluyvera," Geomicrobiology Journal, Feb. 2019, 36(4):339-347.
Tyler et al., "Plants as a Habitat for Beneficial and/or Human Pathogenic Bacteria," Annu. Rev. Phytopathol., 2008, 46:53-73.
Wang et al., "High throughput sequencing analysis of bacterial communities in soils of a typical Poyang Lake wetland," Acta Ecologica Sinica, 2017, 37(5), 9 pages, English Abstract.
Wu et al., "Effects of different amendments on contents of phenolic acids and specific microbes in rhizosphere of *Pseudostellaria heterophylla*," Ying Yong Sheng Tai Xue Bao, Nov. 2016, 18(27):3623-3630, English Abstract.
Yan et al., "Influence of salinity and water content on soil microorganisms," Int. Soil Water Conserv. Res., 2015, 3:316-323.
Berge et al., "*Rahnella aquatilis*, a nitrogen-fixing enteric bacterium associated with the rhizosphere of wheat and maize," Canadian Journal of Microbiology, 1991, 37(3):195-203.
Bhattacharjee et al., "Use of nitrogen-fixing bacteria as biofertiliser for non-legumes: prospects and challenges," Applied Microbiology and Biotechnology, Jul. 2008, 80:199-209.
Iniguez et al., "Regulation of Enteric Endophytic Bacterial Colonization by Plant Defense," MPMI, 2005, 18(2):169-178.
Zhang et al., "Expression of the $N_2$ fixation gene operon of *Paenibacillus* sp. WLY78 under the control of the T7 promoter in *Escherichia coli* BL21," Biotechnol. Lett., Oct. 2015, 37(10):1999-2004.

(56) References Cited

OTHER PUBLICATIONS

Bashor, "Understanding biological regulation through synthetic biology," Annu. Rev. Biophys., May 2018, 47:399-423, 52 pages.
Dessaux et al., "Engineering the Rhizosphere," Trends in Plant Science, Mar. 2016, 21(3):266-278.
Drummond et al., "Expression from the nifB promoter of *Azotobacter vinelandii* Can Be Activated by NifA, VnfA, or AnfA Transcriptional Activators," Journal of Bacteriology, Feb. 1996, 178(3):788-792.
Fernandes et al., "Glutamine synthetase stabilizes the binding of GlnR to nitrogen fixation gene operators," The FEBS Journal, Feb. 2017, 284(6):903-918.
Fisher et al., "Mutations in the *Bacillus subtilis* glnRA Operon that Cause Nitrogen Source-Dependent Defects in Regulation of TnrA Activity," Journal of Bacteriology, Aug. 2002, 184(16):4636-4639.
Fisher et al., "Novel trans-Acting *Bacillus subtilis* glnA Mutations that Depress glnRA Expression," Journal of Bacteriology, Apr. 2009, 191(8):2485-2492.
International Preliminary Report on Patentability in International Application No. PCT/US2020/031201, mailed on Nov. 10, 2022, 17 pages.
International Preliminary Report on Patentability in International Application No. PCT/US2021/029895, mailed on Nov. 10, 2022, 14 pages.
International Preliminary Report on Patentability in International Application No. PCT/US2021/031808, mailed on Nov. 24, 2022, 17 pages.
International Search Report and Written Opinion in International Application No. PCT/US2021/031808, mailed on Mar. 9, 2022, 29 pages.
International Search Report and Written Opinion in International Application. No. PCT/US2022/035873, mailed on Dec. 21, 2022, 31 pages.
Noindorf et al., "Role of PII proteins in nitrogen fixation control of *Herbaspirillum seropedicae* strain SmR1," BMC Microbiology, Jan. 2011, 11(1), 8 pages.
Schreier et al., "*Bacillus subtilis* glnR mutants defective in regulation," Gene., Aug. 1995, 161(1):51-56.
Venkateshwaran, "Exploring the Feasibility of Transferring Nitrogen Fixation to Cereal Crops," Principles of Plant-microbe Interactions, 2015, 403-410.
Yurgel et al., "A Mutant GlnD Nitrogen Sensor Protein Leads to a Nitrogen-fixing but Ineffective *Sinorhizobium meliloti* Symbiosis with Alfalfa," PNAS, Dec. 2008, 105(48):18958-18963.
Bennett, "Engineering Nitrogenases for Synthetic Nitrogen Fixation: From Pathway Engineering to Directed Evolution," BioDesign Research, Feb. 7, 2023, 5(0005):1-12.
Bush et al., "The role of bacterial enhancer binding proteins as specialized activators of $\sigma^{54}$-dependent transcription," Microbiology and Molecular Biology Reviews, Sep. 2012, 76(3):497-529.
Chen et al., "Engagement of Arginine Finger to ATP Triggers Large Conformational Changes in NtrC1 AAA+ ATPase for Remodeling Bacterial RNA Polymerase," Structure, Nov. 10, 2010, 18(11):1420-1430.
Chen et al., "Functional analysis of the GAF domain of NifA in *Azospirillum brasilense*: effects of Tyr→Phe mutations on NifA and its interaction with GlnB," Mol Genet Genomics, Jun. 2005, 5:415-422.
Chen et al., "Plant Physiology and Molecular Biology," Editor-in-Chief, Higher Education Publishing House, Jun. 30, 2007, 3rd edition, pp. 261-269, 18 pages (with Machine Translation).
De Castro et al., "ScanProsite: detection of PROSITE signature matches and ProRule-associated functional and structural residues in proteins," Nucleic Acids Res., Jul. 2006, 34:W362-365.
Iltis et al., "*Zea diploperennis* (Gramineae): A New Teosinte from Mexico," Science, Jan. 1979, 203(4376):186-188.
Inaba et al., "Mutational analysis of GlnB residues critical for NifA activation in *Azospirillum brasilense*," Microbiological Research, Feb. 2015, 171:65-72.
Jumper et al., "Highly accurate protein structure prediction with AlphaFold," Nature, Aug. 2021, 596(7873):583-589.
Letunic et al., "20 years of the SMART protein domain annotation resource," Nucleic Acids Res., Jan. 4, 2018, 46(D1):D493-496.
Lim et al., "Methionine in Proteins: It's Not Just for Protein Initiation Anymore," Neurochemical Research, Jan. 15, 2019, 44(1):247-257.
Mckinlay et al., "Carbon dioxide fixation as a central redox cofactor recycling mechanism in bacteria," Proceedings of the National Academy of Sciences, Jun. 29, 2010, 107(26):11669-11675.
Monteiro et al., "In-trans regulation of the N-truncated-NIFA protein of *Herbaspirillum seropedicae* by the N-terminal domain," FEMS Microbiol Lett., 1999, 180(2):157-161.
Monteiro et al., "Expression and functional analysis of an N-truncated NifA protein of *Herbaspirillum seropedicae*," FEBS Lett., 1999, 447(2-3):283-286.
Nagy et al., "Structural Characterization of Arginine Fingers: Identification of an Arginine Finger for the Pyrophosphatase dUTPases," J Am Chem Soc., Nov. 16, 2016, 138(45):15035-15045.
Oliveira et al., "Interaction of GlnK with the GAF domain of *Herbaspirillum seropedicae* NifA mediates $NH_4^+$-regulation," Biochimie, 2012, 94(4):1041-1047.
Oliveira et al., "Role of conserved cysteine residues in *Herbaspirillum seropedicae* NifA activity," Res Microbiol., Jul. 2009, 160:389-395.
Sotomaior et al., "Effect of ATP and 2-oxoglutarate on the in vitro interaction between the NifA GAF domain and the GlnB protein of *Azospirillum brasilense*," Braz J Med Biol Res., Dec. 2012, 45(12):1135-40.
Souza et al., "Expression of the nifA gene of *Herbaspirillum seropedicae*: role of the NtrC and NifA binding sites and of the-24/-12 promoter element," Microbiology, 2000, 146:1407-1418.
Yousuf et al., "The AAA+ superfamily: a review of the structural and mechanistic principles of these molecular machines," Crit. Rev. Biochem. Mol. Biol., Apr. 2022, 57(2):156-187.
Gruber et al., "Versatile plasmid-based expression systems for Gram-negative bacteria-General essentials exemplified with the bacterium *Ralstonia eutropha* H16," New Biotechnology, Dec. 25, 2015, 32(6):552-558.
Montañez et al., "Biological nitrogen fixation in maize (*Zea mays* L.) by $^{15}N$ isotope-dilution and identification of associated culturable diazotrophs," Biology and Fertility of Soils, Feb. 2009, 45:253-263.
Riggs et al., "Enhanced maize productivity by inoculation with diazotrophic bacteria," Australian Journal of Plant Physiology, Sep. 3, 2001, 28(9):829-836 (Abstract only).
Biswas et al., "Rhizobia Inoculation Improves Nutrient Uptake and Growth of Lowland Rice," Soil Science Society of America Journal, Sep. 2000, 64(5):1644-1650.
Biswas et al., "Rhizobial Inoculation Influences Seedling Vigor and Yield of Rice," Agronomy Journal, Sep. 2000, 92(5):880-886.
Brophy et al., "Engineered integrative and conjugative elements for efficient and inducible DNA transfer to undomesticated bacteria.," Nat. Microbio., Sep. 2018, 3(9):1043-1053.
Burén et al., "Formation of Nitrogenase NifDK Tetramers in the Mitochondria of *Saccharomyces cerevisiae*," ACS Synthetic Biology, Jun. 16, 2017, 6(6):1043-1055.
Cannon et al., "Chromosomal Integration of Klebsiella Nitrogen Fixation Genes in *Escherichia coli*," Journal of General Microbiology, Jan. 1974, 80(1):227-239.
Cannon et al., "Plasmids Formed in Nitrogen-fixing *Escherichia coli-Klebsiella pneumoniae* Hybrids," Journal of General Microbiology, Jan. 1974, 80(1):241-251.
Delmotte et al., "An integrated proteomics and transcriptomics reference data set provides new insights into the *Bradyrhizobium japonicum* bacteroid metabolism in soybean root nodules," Proteomics, Apr. 8, 2010, 10(7):1391-1400.
Edgar, "MUSCLE: multiple sequence alignment with high accuracy and high throughput," Nucleic Acids Res., Mar. 19, 2004, 32(5):1792-1797.
Ferri et al., "Plasmid electroporation of *Sinorhizobium* strains: The role of the restriction gene hsdR in type strain Rm1021," Plasmid, May 2010, 63(3):128-135.

(56) References Cited

OTHER PUBLICATIONS

Gorochowski et al., "Genetic circuit characterization and debugging using RNA-seq," Mol Syst Biol., Nov. 9, 2017, 13(11):952, 16 pages.
Gutiérrez-Zamora et al., "Natural endophytic association between *Rhizobium etli* and maize (*Zea mays* L.)," J Biotechnol., Oct. 4, 2001, 91(2-3):117-126.
Haskett et al., "Engineered plant control of associative nitrogen fixation," PNAS, Apr. 19, 2022, 119(16):e2117465119, 9 pages.
Hoover et al., "Homocitrate is a Component of the Iron-Molybdenum Cofactor of Nitrogenase," Biochemistry, Apr. 4, 1989, 28(7):2768-2771.
Igiehon et al., "Rhizosphere Microbiome Modulators: Contributions of Nitrogen Fixing Bacteria towards Sustainable Agriculture," Int J Environ Res Public Health, Mar. 23, 2018, 15(4):574, 25 pages.
International Preliminary Report on Patentability in International Application No. PCT/US2022/035873, mailed on Jan. 11, 2024, 18 pages.
Jones et al., "Soil microbial community analysis using two-dimensional polyacrylamide gel electrophoresis of the bacterial ribosomal internal transcribed spacer regions," J Microbiol Methods, May 200769(2):256-267.
Kechris et al., "Quantitative exploration of the occurrence of lateral gene transfer by using nitrogen fixation genes as a case study," Proc Natl Acad Sci U S A., Jun. 20, 2006, 103(25):9584-9589.
Kornberg, "DNA Replication," W. H. Freeman & Co., San Francisco, 1980, Section 2-12:75-77.
Li et al., "The anti-Shine-Dalgarno sequence drives translational pausing and codon choice in bacteria," Nature, Mar. 28, 2012, 484(7395):538-541.
Li et al., "Using synthetic biology to increase nitrogenase activity," Microb Cell Fact., 2016, 15(43):1-11.
Mahmood et al., "Seed biopriming with plant growth promoting rhizobacteria: a review," FEMS Microbiol Ecol., Aug. 2016, 92(8): fiw112, 14 pages.
Malik et al., "Association of nitrogen-fixing, plant-growth-promoting rhizobacteria (PGPR) with kallar grass and rice," Plant and Soil, Oct. 1997, 194:37-44.
Martinez-Argudo et al., "The NifL-NifA System: a Multidomain Transcriptional Regulatory Complex That Integrates Environmental Signals," Journal of Bacteriology, Feb. 9, 2004, 186(3):601-10.
Pascuan et al., "Exploring the Ancestral Mechanisms of Regulation of Horizontally Acquired Nitrogenases," J Mol Evol., Oct. 2015, 81(3-4):84-89.
Perrine-Walker et al., "Infection process and the interaction of rice roots with rhizobia," Journal of Experimental Botany, Sep. 2007, 58(12):3343-3350.
Sandig et al., "HBV-derived promoters direct liver-specific expression of an adenovirally transduced LDL receptor gene," Gene Therapy, Nov. 1996, 3(11):1002-1009.
Shanks et al., "*Saccharomyces cerevisiae*-based molecular tool kit for manipulation of genes from gram-negative bacteria," Applied and Environmental Microbiology, Jul. 2006, 72(7):5027-5036.
Tang et al., "Biology of Nitrogen Fixers" (Chinese), Northeast Forestry University Press, First Edition, Jun. 30, 2009, pp. 172-183 (with English Translation).
Thöny, et al., "Dual Control of the *Bradyrhizobium japonicum* Symbiotic Nitrogen Fixation Regulatory Operon fixR nifA: Analysis of cis- and trans-Acting Elements," J Bacteriol., Aug. 1989, 171(8):4162-4169.

Tsukada et al., "Comparative Genome-Wide Transcriptional Profiling of *Azorhizobium caulinodans* ORS571 Grown under Free-Living and Symbiotic Conditions," Appl Environ Microbiol., Aug. 2009, 75(15):5037-5046.
Woodruff et al., "Registry in a tube: multiplexed pools of retrievable parts for genetic design space exploration," Nucleic Acids Research, Feb. 17, 2017, 45(3):1553-1565.
Xu et al., "Advance of Study on Nitrogenase" (Chinese), Journal of Biology, Aug. 31, 2011, 8(4):61-64 (English Abstract).
Yan et al., "Nitrogen fixation island and rhizosphere competence traits in the genome of root-associated *Pseudomonas stutzeri* A1501," Proc Natl Acad Sci U S A, May 27, 2008, 105(21):7564-7569.
Berrada et al., "Taxonomy of the Rhizobia: Current Perspectives," British Microbiology Research Journal, Jan. 2014, 4(6):616-639.
Merrick et al., "Repressor properties of the nifL gene product in *Klebsiella pneumoniae*," Mol. Gen. Genet., Mar. 1982, 185:75-81.
European Search Report in European Application No. EP 20795673.1, dated May 22, 2023, 9 pages.
Merrick et al., "Nitrogen control of the nif regulon in *Klebsiella pneumoniae*: involvement of the ntrA gene and analogies between ntrC and nifA," The EMBO Journal, Jan. 1, 1983, 2:39-44.
Schreier et al., "Altered Regulation of the glnA Gene in Glutamine Synthetase Mutants of *Bacillus subtilis*," Jul. 1, 1986, 167(1):35-43.
Streicher et al., "Genetic Control of Glutamine Synthetase in *Klebsiella aerogens*," Journal of Bacteriology, Jan. 1, 1975, 121(1):320-331.
Willardson et al., "Development and Testing of a Bacterial Biosensor for Toluene-Based Environmental Contaminants," Applied and Environmental Microbiology, Mar. 1, 1998, 64(3):1006-1012.
Xiao et al., "Developing a Genetically Encoded, Cross-Species Biosensor for Detecting Ammonium and Regulating Biosynthesis of Cyanophycin," ACS Synthetic Biology, Jul. 13, 2017, 6(10):1807-1815.
AddGene.org [online], "Plasmids 101: Inducible Promoters," Jan. 2018, retrieved on Oct. 23, 2023, retrieved from URL<https://blog.addgene.org/plasmids-101-inducible-promoters>, 8 pages.
Bürgmann et al., "Effects of model root exudates on structure and activity of a soil diazotroph community," Environmental Microbiology, Nov. 2005, 7(11):1711-1724.
Eberhart et al., "A methodology for markerless genetic modifications in *Azotobacter vinelandii*," Journal of Applied Microbiology, Jun. 2016, 120(6):1595-1604.
Galvão et al., "Adaptation of the Yeast URA3 Selection System to Gram-Negative Bacteria and Generation of a ΔbetCDE *Pseudomonas putida* Strain," Applied and Environmental Microbiology, Feb. 2005, 71(2): 883-892.
Genbank Accession No. AGN85586.1, "cellulose synthase [*Enterobacter* sp. R4-368]," Jun. 29, 2015, 2 pages.
GenBank Accession No. AHJ75701.1, "hypothetical protein C813_13915 [Kosakonia sacchari SP1]," Sep. 19, 2017, 2 pages.
GenBank Accession No. AHJ76132.1, "hypothetical protein C813_16530 [Kosakonia sacchari SP1]," Sep. 19, 2017, 2 pages.
Martinez et al., "Symbiotic Autoregulation of nifA Expression in *Rhizobium leguminosarum* bv. viciae," J. Bacteriol., Oct. 2004, 186(19):6586-6594.
Parsons, "Physiological regulation of nitrogen fixation in soybean root nodules," Thesis for the degree of Doctor of Philosophy, Australian National University, Sep. 1989, pp. 3-4.
Priyanka et al., "Diversity Study of Nitrate Reducing Bacteria from Soil Samples—A Metagenomics Approach," Journal of Computer Science and Systems Biology, Jul. 2015, 8(4): 191-198.
Steyert et al., "Development of a Novel Genetic System To Create Markerless Deletion Mutants of *Bdellovibrio bacteriovorus*," Applied and Environmental Microbiology, Aug. 2007, 73(15):4717-4724.

* cited by examiner

| | no glutamine | 1mM glutamine | 10 mM glutamine | |
|---|---|---|---|---|
| amtB | 716462 | 175150 | 1045 | |
| galK | 15 | 405 | 814 | |
| glnB | 8025 | 10275 | 7493 | |
| glnK | 752360 | 183994 | 320 | |
| nifA | 306663 | 92963 | 194 | 0% air |
| nifH | 12387186 | 3599183 | 161 | |
| nifL | 226368 | 42825 | 123 | |
| ntrB | 50439 | 25236 | 1081 | |
| ntrC | 78056 | 35760 | 1216 | |
| amtB | 241247 | 139599 | 1207 | |
| galK | 404 | 770 | 1012 | |
| glnB | 8296 | 6899 | 9376 | |
| glnK | 241645 | 158973 | 288 | |
| nifA | 237483 | 115545 | 197 | 10% air |
| nifH | 4702957 | 2448758 | 108 | |
| nifL | 173765 | 66818 | 75 | |
| ntrB | 25676 | 19630 | 1118 | |
| ntrC | 40312 | 30703 | 1295 | |
| amtB | 160293 | 167736 | 1353 | |
| galK | 1311 | 976 | 1200 | |
| glnB | 8522 | 8185 | 9445 | |
| glnK | 166653 | 191992 | 366 | |
| nifA | 200774 | 164973 | 198 | 20% air |
| nifH | 862984 | 2337297 | 80 | |
| nifL | 129054 | 99096 | 80 | |
| ntrB | 17326 | 21370 | 1146 | |
| ntrC | 24115 | 31446 | 1370 | |

FIG. 5

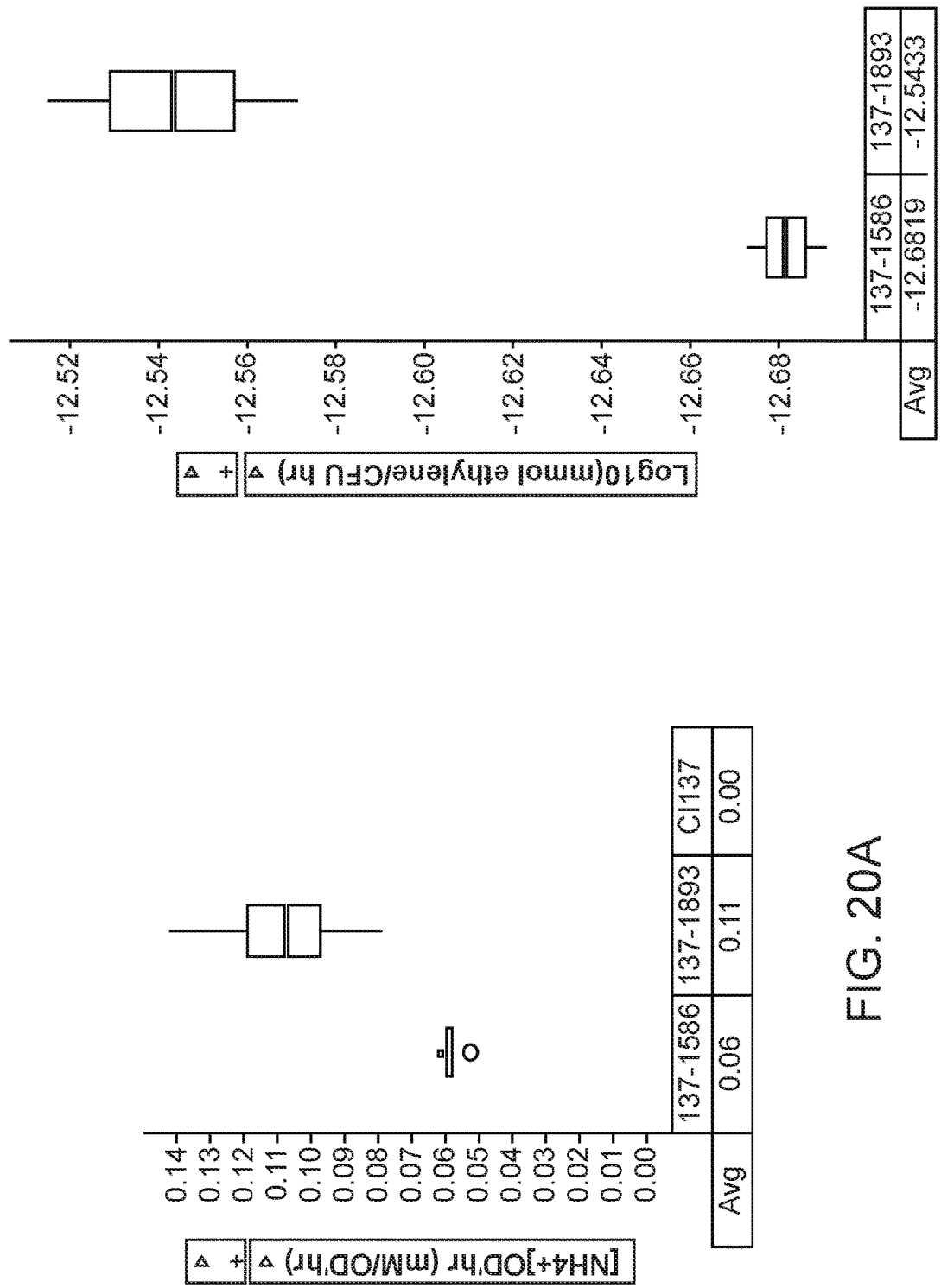

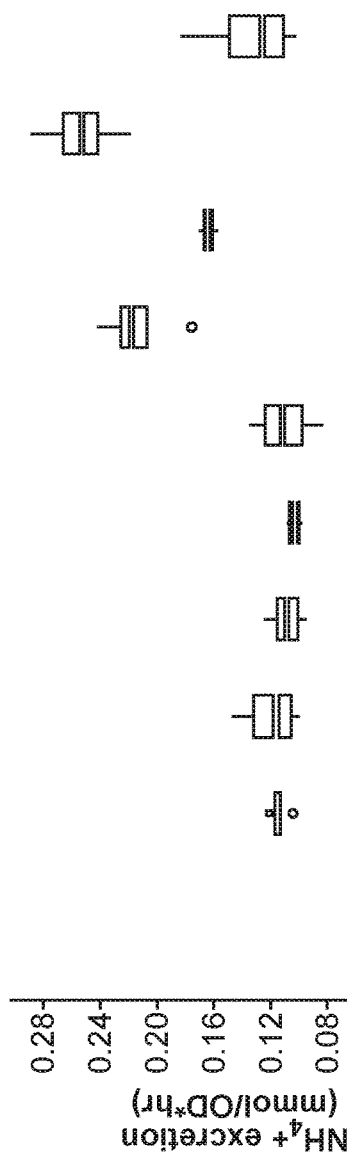

| parent strain | 137-1036 | | | | | 137-2084 | | | | Cl137 |
|---|---|---|---|---|---|---|---|---|---|---|
| strain ID | 137-1036 | 137-2227 | 137-2229 | 137-2253 | 137-2283 | 137-2084 | 137-2219 | 137-2221 | 137-2223 | 137-2245 | Cl137 |
| Avg | 0.003 | 0.116 | 0.120 | 0.109 | 0.103 | 0.110 | 0.214 | 0.164 | 0.253 | 0.134 | 0.000 |

| Strain ID | Genotype | glnD modification |
|---|---|---|
| 137-2084 | ΔnifL::Prm1.2, ΔglnE_KO2 | none |
| 137-2219 | ΔnifL::Prm1.2, ΔglnE_KO2, ΔglnD-ACT1/2 | C-terminal glutamine sensing ACT1 and ACT2 domains deleted |
| 137-2221 | ΔnifL::Prm1.2, ΔglnE_KO2, ΔglnD-UTase | N-terminal uridylyl-transferase domain deleted |
| 137-2223 | ΔnifL::Prm1.2, ΔglnE_KO2, ΔglnD | entire gene deleted |
| 137-2245 | ΔnifL::Prm1.2, ΔglnE_KO2, ΔglnD-HD | uridylyl-removing HD domain deleted |
| 137-1036 | ΔnifL::PinfC | none |
| 137-2227 | ΔnifL::PinfC, ΔglnD-ACT1/2 | C-terminal glutamine sensing ACT1 and ACT2 domains deleted |
| 137-2229 | ΔnifL::PinfC, ΔglnD | entire gene deleted |
| 137-2253 | ΔnifL::PinfC, ΔglnD-Utase | N-terminal uridylyl-transferase domain deleted |
| 137-2283 | ΔnifL::PinfC, ΔglnD-UTase-deact | N-terminal uridylyl-transferase domain deactivated by site directed mutagenesis: G90L, G91D, D104A |

FIG. 22

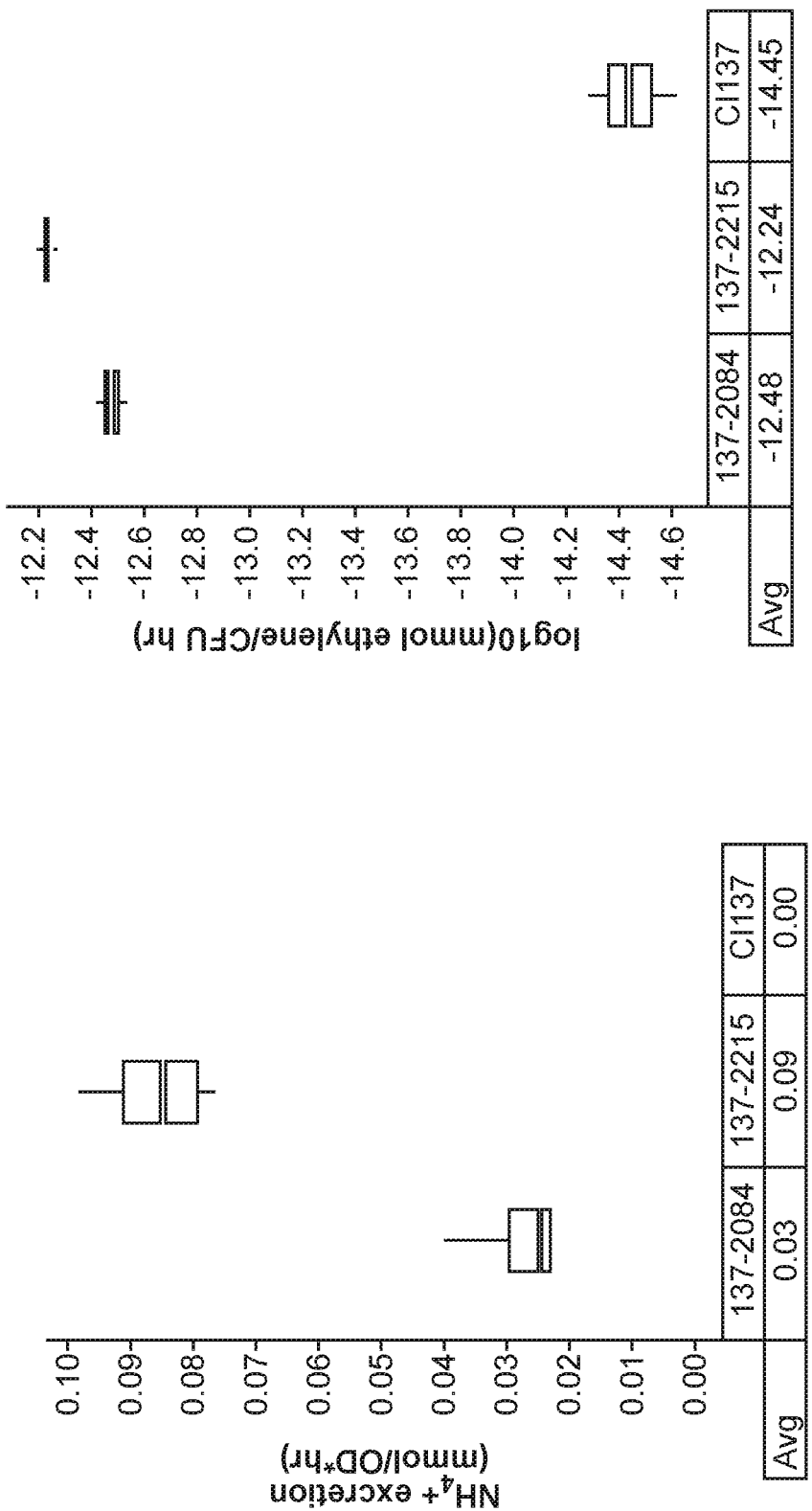

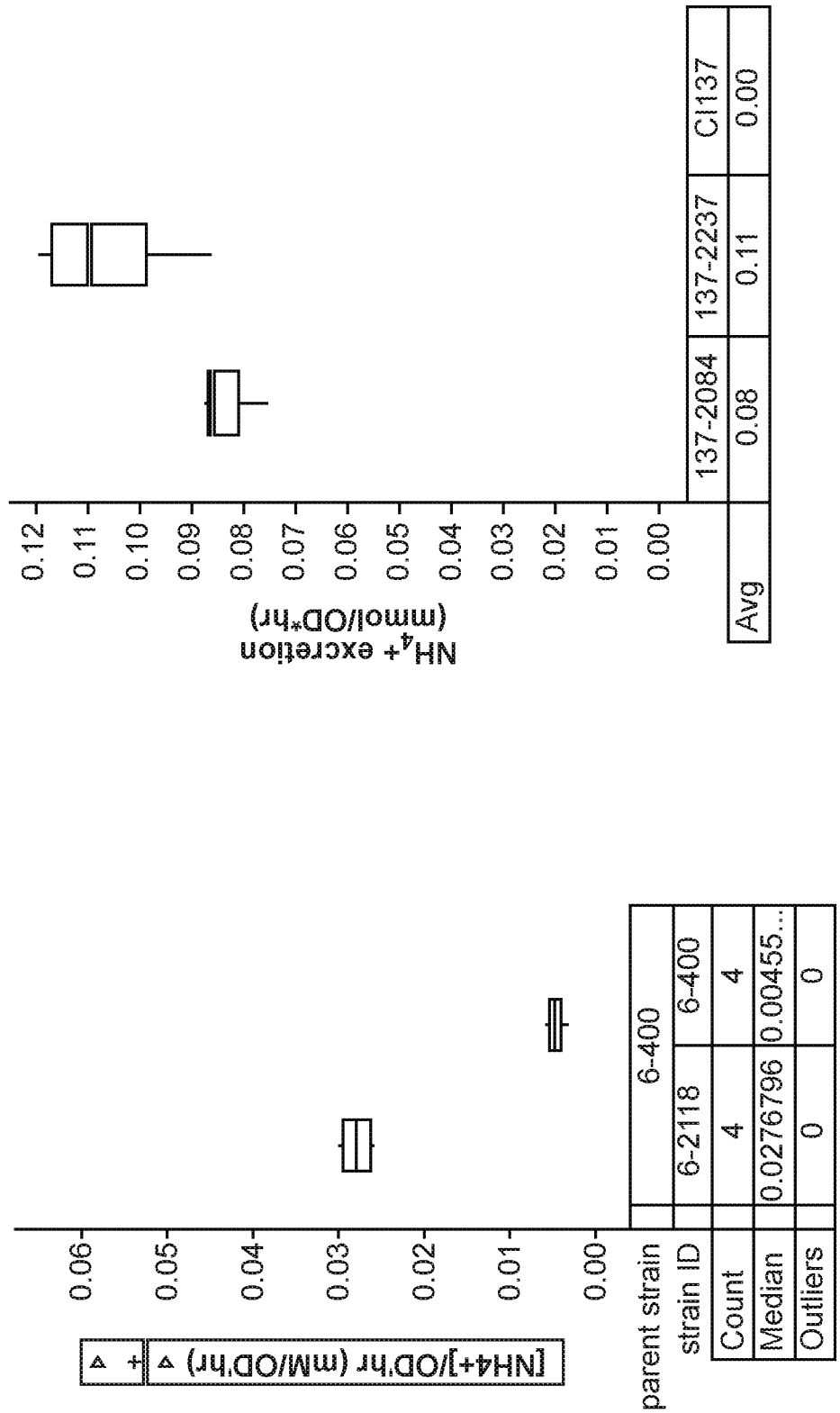

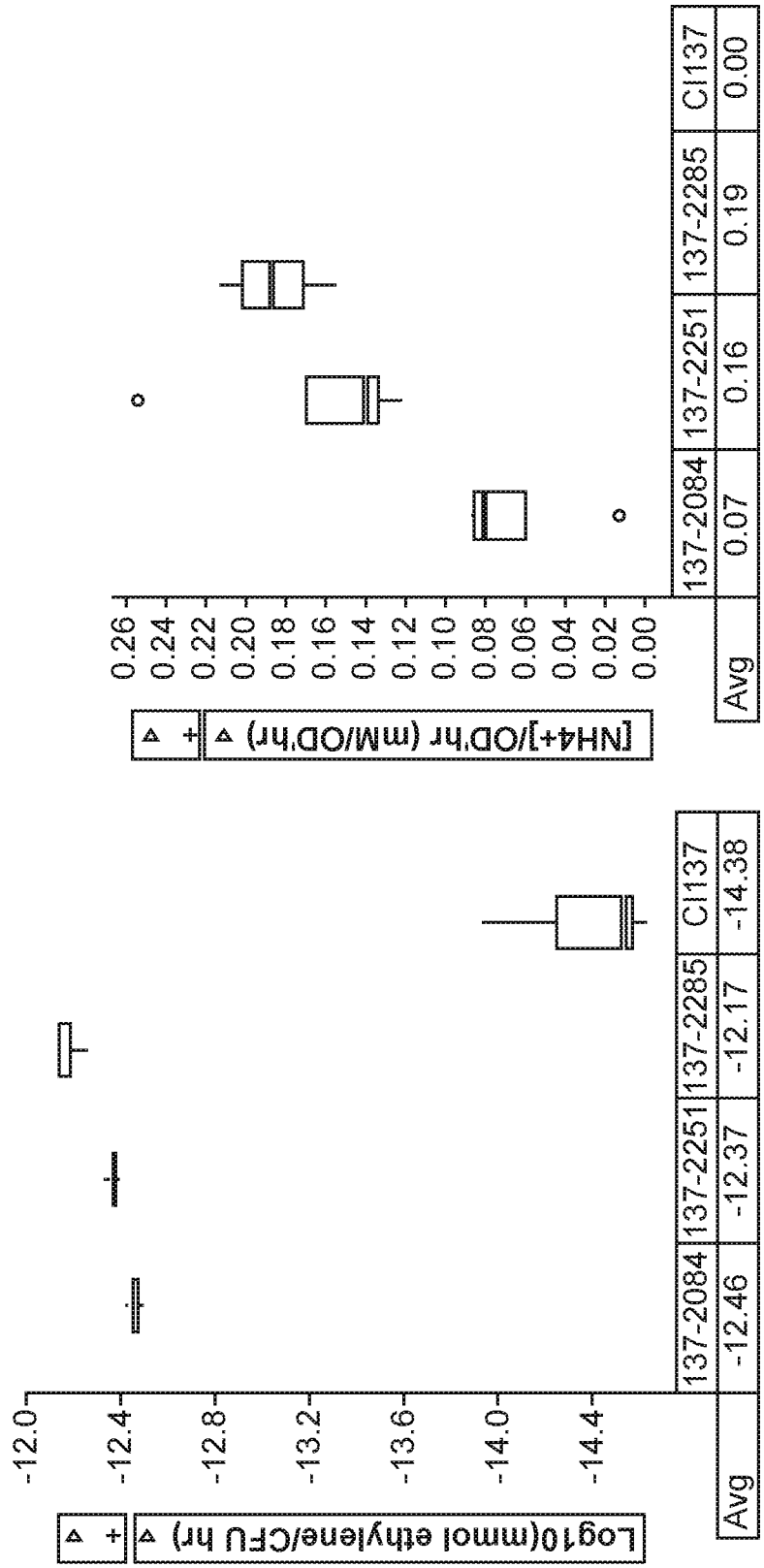

SEQUENCE LISTING

```
<160> NUMBER OF SEQ ID NOS: 2

<210> SEQ ID NO 1
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 1

Leu Ala Gly Leu Ile Asp Ala Asp Gly
1               5

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttgatcaga ccgatgttcg gaccttccaa ggtttcgatc ggacatacgc gaccgtagtg    60
ggtcgggtgt acgtctcgaa cttcaaagcc                                     90
```

GENE TARGETS FOR NITROGEN FIXATION TARGETING FOR IMPROVING PLANT TRAITS

CROSS-REFERENCE

This application is a National Stage application under 35 U.S.C. § 371 of International Application No. PCT/US2018/057613 having an International Filing Date of Oct. 25, 2018, which claims priority to U.S. Provisional Patent Application No. 62/577,149, filed Oct. 25, 2017, each of which is entirely incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: 48624-0012WO1_Sequence_Listing.txt, date created, Apr. 24, 2020, file size≈1 kilobyte.

BACKGROUND OF THE INVENTION

Plants are linked to the microbiome via a shared metabolome. A multidimensional relationship between a particular crop trait and the underlying metabolome is characterized by a landscape with numerous local maxima. Optimizing from an inferior local maximum to another representing a better trait by altering the influence of the microbiome on the metabolome may be desirable for a variety of reasons, such as for crop optimization. Economically-, environmentally-, and socially-sustainable approaches to agriculture and food production are required to meet the needs of a growing global population. By 2050 the United Nations' Food and Agriculture Organization projects that total food production must increase by 70% to meet the needs of the growing population, a challenge that is exacerbated by numerous factors, including diminishing freshwater resources, increasing competition for arable land, rising energy prices, increasing input costs, and the likely need for crops to adapt to the pressures of a drier, hotter, and more extreme global climate.

One area of interest is in the improvement of nitrogen fixation. Nitrogen gas ($N_2$) is a major component of the atmosphere of Earth. In addition, elemental nitrogen (N) is an important component of many chemical compounds which make up living organisms. However, many organisms cannot use $N_2$ directly to synthesize the chemicals used in physiological processes, such as growth and reproduction. In order to utilize the $N_2$, the $N_2$ must be combined with hydrogen. The combining of hydrogen with $N_2$ is referred to as nitrogen fixation. Nitrogen fixation, whether accomplished chemically or biologically, requires an investment of large amounts of energy. In biological systems, an enzyme known as nitrogenase catalyzes the reaction which results in nitrogen fixation. An important goal of nitrogen fixation research is the extension of this phenotype to non-leguminous plants, particularly to important agronomic grasses such as wheat, rice, and maize. Despite enormous progress in understanding the development of the nitrogen-fixing symbiosis between *Rhizobia* and legumes, the path to use that knowledge to induce nitrogen-fixing nodules on non-leguminous crops is still not clear. Meanwhile, the challenge of providing sufficient supplemental sources of nitrogen, such as in fertilizer, will continue to increase with the growing need for increased food production.

SUMMARY OF THE INVENTION

The present disclosure provides a genetically engineered bacterium comprising a modification in glnD, wherein said modification is selected from the group consisting of: deletion of the entire gene, deletion of substantially the entire gene, deletion of an ACT domain, deletion of more than 50% of an ACT domain, deactivation of an ACT domain, and deactivation of an UTase domain. In some embodiments, the genetically engineered bacterium comprising a modification in glnA which results in altered expression or activity of glnA. In some embodiments, the modification results in decreased expression of glnA. In some embodiments, the modification comprises replacing the native promoter of glnA with a promoter with lower activity. In some embodiments, the modification comprises replacing the native promoter of glnA with a promoter selected from the group consisting of: a glnB promoter, a glnD promoter, and a glnE promoter. In some embodiments, the genetically engineered bacterium comprising a modification in glnA which results in decreased expression or activity of glnA.

The present disclosure provides a genetically engineered bacterium comprising altered expression of rpoN. In some embodiments, the genetically engineered bacterium has increased expression of rpoN. In some embodiments, the genetically engineered bacterium has increased expression of rpoN. In some embodiments, the genetically engineered bacterium of any one of claims 1-9, wherein said genetically engineered bacterium is a genetically engineered diazotrophic bacterium. In some embodiments, rpoN expression is increased by deleting the native rpoN promoter and replacing with a strong constitutive promoter. In some embodiments, the genetically engineered bacterium is intergeneric. In some embodiments, the genetically engineered bacterium is able to fix atmospheric nitrogen in the presence of exogenous nitrogen. In some embodiments, the genetically engineered bacterium comprises a modification in a nitrogen fixation genetic network. In some embodiments, the genetically engineered bacterium comprises a modification in NifA. In some embodiments, the genetically engineered bacterium comprises a modification which results in increased expression of NifA. In some embodiments, the genetically engineered bacterium comprises a modification in NifL. In some embodiments, the genetically engineered bacterium comprises a modification which results in decreased expression of NifL. In some embodiments, the genetically engineered bacterium comprises a modification in NifH. In some embodiments, the genetically engineered bacterium comprises a modification which results in increased expression of NifH. In some embodiments, the said genetically engineered bacterium comprises a modification which results in increased expression of Nif cluster genes. In some embodiments, the genetically engineered bacterium comprises a modification in a nitrogen assimilation genetic network. In some embodiments, the genetically engineered bacterium comprises a modification in GlnE. In some embodiments, the genetically engineered bacterium comprises a modification which results in decreased activity of GlnE. In some embodiments, the genetically engineered bacterium comprises a modification which results in decreased activity of amtB.

The present disclosure provides a method of increasing the amount of atmospheric derived nitrogen in a plant, comprising contacting said plant with a plurality of said genetically engineered bacterium described herein. In some embodiments, the genetically engineered bacterium is applied to a seed of said plant. In some embodiments, the genetically engineered bacterium is applied to a seedling of said plant. In some embodiments, the genetically engineered bacterium is applied to said plant in a liquid formulation. In some embodiments, the genetically engineered bacterium is applied to said plant after planting but before harvest of said plant. In some embodiments, the genetically engineered bacterium is applied to said plant as a side dressing. In some embodiments, the genetically engineered bacterium is applied to said plant between one month and eight months after germination. In some embodiments, the genetically engineered bacterium is applied to said plant between two months and eight months after germination. In some embodiments, the genetically engineered bacterium is applied to said plant between one month and three months after germination. In some embodiments, the genetically engineered bacterium is applied to said plant between three months and six months after germination. In some embodiments, the plant is a cereal plant. In some embodiments, the plant is a corn plant. In some embodiments, the plant is a rice plant. In some embodiments, the plant is a wheat plant. In some embodiments, the plant is a soy plant.

The present disclosure provides a composition comprising a seed, and a seed coating; wherein the seed coating comprises a plurality of said genetically engineered bacteria as described herein. In some embodiments, the seed is a cereal seed. In some embodiments, the seed is selected from the group consisting of: a corn seed, a wheat seed, a rice seed, a soy seed, a rye seed and a *sorghum* seed. The present disclosure provides a composition comprising a plant and a plurality of said genetically engineered bacterium described herein. In some embodiments, the plant is a seedling. In some embodiments, the seed is a cereal seed. In some embodiments, the seed is selected from the group consisting corn, rice, wheat, soy, rye, and *sorghum*.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 depicts in culture expression profile of 9 different genes in strains CI006 involved in diazaotrophic nitrogen fixation. Numbers represent counts of each transcript. Various conditions (0, 1, 10 mM Glutamine and 0%, 10%, 20% atmospheric air in N2) are indicated.

FIGS. 20A and 20B depict, increased nitrogenase activity and ammonium excretion in mutants of K. variicola strain CI137 with modifications in the glycogen synthesis gene glgA over parent strains with identical genotypes but lacking the glgA modification.

FIG. 22 depicts increased ammonium excretion in minimal nitrogen-free media in mutants of K. variicola strain CI137 with modifications in the glnD gene.

FIG. 27 depicts increased ammonium excretion in mutants of K. variicola strain CI137 with modifications in an operon encoding GOGAT (glnBD) created by inserting the glnD promoter upstream of the operon over the parent strain 137-2084.

FIG. 28 depicts, in mutants of K. variicola strain CI137 with modifications in an operon encoding GOGAT (glnBD) created by inserting the glnD promoter upstream of the operon, increased nitrogenase activity as measured by ARA over the parent strain 137-2084.

FIG. 29 depicts increased ammonium excretion in mutants of K. sacchari strain CI006 with modifications in glutaminase enzyme glsA2 expression created by inserting a strong promoter upstream of the glsA2 gene compared with the parent control.

FIG. 30 depicts increased ammonium excretion in mutants of K. variicola strain CI137 with modifications in glutaminase enzyme glsA2 expression created by inserting a strong promoter upstream of the glsA2 gene compared with the parent control.

FIG. 32 depicts increased nitrogenase activity in mutants of K. variicola strain CI137 with rpoN modifications compared with the parental control.

FIG. 33 depicts increased nitrogen excretion in mutants of K. variicola strain CI137 with rpoN modifications compared with the parental control.

DETAILED DESCRIPTION OF THE INVENTION

Figure 1A:
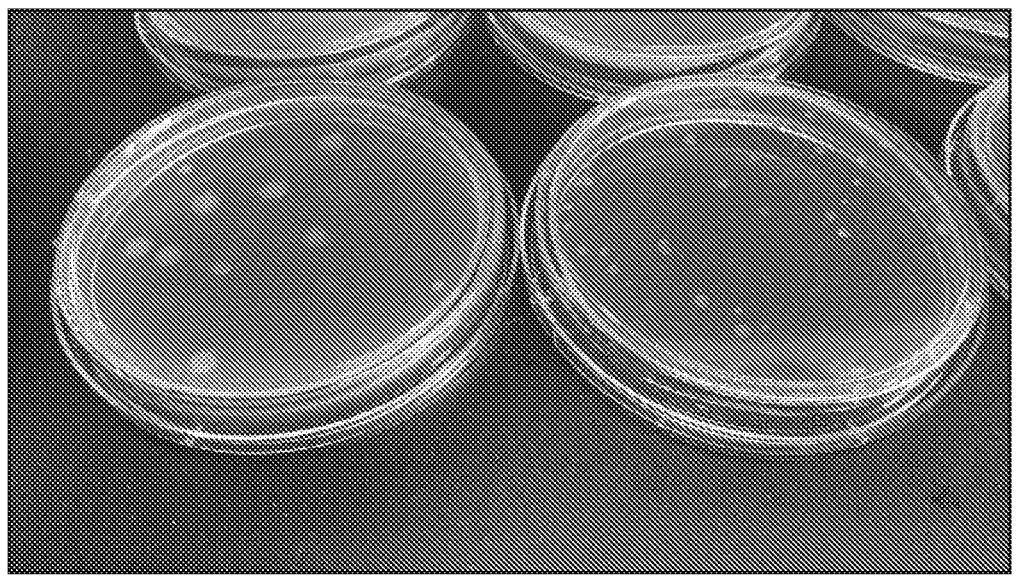
FIG. 1A-B depicts enrichment and isolation of nitrogen fixing bacteria. (A) Nfb agar plate was used to isolate single colonies of nitrogen fixing bacteria. (B) Semi-solid Nfb agar casted in Balch tube. The arrow points to pellicle of enriched nitrogen fixing bacteria.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, Whether nucleic acid or amino acid sequences, may be calculated as the number of exact matches between two aligned sequences divided by the length of the shorter sequences and multiplied by 100. In some cases, the percent identity of a test sequence and a reference sequence, whether nucleic acid or amino acid sequences, may be calculated as the number of exact matches between two aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403410 (1990), Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identifies between a disclosed sequence and a claimed sequence are at least 80%, at least 85%, at least 90%, at least 95%, at least 98% or at least 99%.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

"Plant productivity" refers generally to any aspect of growth or development of a plant that is a reason for which the plant is grown. For food crops, such as grains or vegetables, "plant productivity" can refer to the yield of grain or fruit harvested from a particular crop. As used herein, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, reducing $NO_2$ emission due to reduced nitrogen fertilizer usage and similar improvements of the growth and development of plants.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

As used herein, a "control sequence" refers to an operator, promoter, silencer, or terminator.

In some embodiments, native or endogenous control sequences of genes of the present disclosure are replaced with one or more intrageneric control sequences.

As used herein, "introduced" refers to the introduction by means of modern biotechnology, and not a naturally occurring introduction.

In some embodiments, the bacteria of the present disclosure have been modified such that they are not naturally occurring bacteria.

In some embodiments, the bacteria of the present disclosure are present in the plant in an amount of at least $10^3$ cfu, $10^4$ cfu, $10^5$ cfu, $10^6$ cfu, $10^7$ cfu, $10^8$ cfu, $10^9$ cfu, $10^{10}$ cfu, $10^{11}$ cfu, or $10^{12}$ cfu per gram of fresh or dry weight of the plant. In some embodiments, the bacteria of the present disclosure are present in the plant in an amount of at least about $10^3$ cfu, about $10^4$ cfu, about $10^5$ cfu, about $10^6$ cfu, about $10^7$ cfu, about $10^8$ cfu, about $10^9$ cfu, about $10^{10}$ cfu, about $10^{11}$ cfu, or about $10^{12}$ cfu per gram of fresh or dry weight of the plant.

In some embodiments, the bacteria of the present disclosure are present in the plant in an amount of at least $10^3$ to $10^9$, $10^3$ to $10^7$, $10^3$ to $10^5$, $10^5$ to $10^9$, $10^5$ to $10^7$, $10^6$ to $10^{10}$, $10^6$ to $10^7$ cfu per gram of fresh or dry weight of the plant.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

As used herein, "non-nitrogen limiting conditions" refers to non-atmospheric nitrogen available in the soil, field, media at concentrations greater than about 4 mM nitrogen, as disclosed by Kant et al. (2010. J. Exp. Biol. 62(4):1499-1509), which is incorporated herein by reference.

As used herein, "introduced genetic material" means genetic material that is added to, and remains as a component of, the genome of the recipient.

In some embodiments, the nitrogen fixation and assimilation genetic regulatory network comprises polynucleotides encoding genes and non-coding sequences that direct, modulate, and/or regulate microbial nitrogen fixation and/or assimilation and can comprise polynucleotide sequences of the nif cluster (e.g., nifA, nifB, nifC, . . . nifZ), polynucleotides encoding nitrogen regulatory protein C, polynucleotides encoding nitrogen regulatory protein B, polynucleotide sequences of the gln cluster (e.g. glnA and glnD), draT, and ammonia transporters/permeases. In some cases, the Nif cluster may comprise NifB, NifH, NifD, NifK, NifE, NifN, NifX, hesa, and NifV. In some cases, the Nif cluster may comprise a subset of NifB, NifH, NifD, NifK, NifE, NifN, NifX, hesa, and NifV.

In some embodiments, fertilizer of the present disclosure comprises at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% nitrogen by weight.

In some embodiments, fertilizer of the present disclosure comprises at least about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% nitrogen by weight.

In some embodiments, fertilizer of the present disclosure comprises about 5% to 50%, about 5% to 75%, about 10% to 50%, about 10% to 75%, about 15% to 50%, about 15% to 75%, about 20% to 50%, about 20% to 75%, about 25% to 50%, about 25% to 75%, about 30% to 50%, about 30% to 75%, about 35% to 50%, about 35% to 75%, about 40% to 50%, about 40% to 75%, about 45% to 50%, about 45% to 75%, or about 50% to 75% nitrogen by weight.

In some embodiments, the increase of nitrogen fixation and/or the production of 1% or more of the nitrogen in the plant are measured relative to control plants, which have not been exposed to the bacteria of the present disclosure. All increases or decreases in bacteria are measured relative to control bacteria. All increases or decreases in plants are measured relative to control plants.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

Regulation of Nitrogen Fixation

One trait that may be targeted for regulation by the methods described herein is nitrogen fixation. Nitrogen fertilizer is the largest operational expense on a farm and the biggest driver of higher yields in row crops like corn and wheat. Described herein are microbial products that can deliver renewable forms of nitrogen in non-leguminous crops. While some endophytes have the genetics necessary for fixing nitrogen in pure culture, the fundamental technical challenge is that wild-type endophytes of cereals and grasses stop fixing nitrogen in fertilized fields. The application of chemical fertilizers and residual nitrogen levels in field soils signal the microbe to shut down the biochemical pathway for nitrogen fixation.

Changes to the transcriptional and post-translational levels of nitrogen fixation regulatory network are required to develop a microbe capable of fixing and transferring nitrogen to corn in the presence of fertilizer. To that end, described herein is Host-Microbe Evolution (HoME) technology to precisely evolve regulatory networks and elicit novel phenotypes. Also described herein are unique, proprietary libraries of nitrogen-fixing endophytes isolated from corn, paired with extensive omics data surrounding the interaction of microbes and host plant under different environmental conditions like nitrogen stress and excess. This technology enables precision evolution of the genetic regulatory network of endophytes to produce microbes that actively fix nitrogen even in the presence of fertilizer in the field. Also described herein are evaluations of the technical potential of evolving microbes that colonize corn root tissues and produce nitrogen for fertilized plants and evaluations of the compatibility of endophytes with standard formulation practices and diverse soils to determine feasibility of integrating the microbes into modern nitrogen management strategies.

In order to utilize elemental nitrogen (N) for chemical synthesis, life forms combine nitrogen gas ($N_2$) available in the atmosphere with hydrogen in a process known as nitrogen fixation. Because of the energy-intensive nature of biological nitrogen fixation, diazotrophs (bacteria and archaea that fix atmospheric nitrogen gas) have evolved sophisticated and tight regulation of the nif gene cluster in response to environmental oxygen and available nitrogen. Nif genes encode enzymes involved in nitrogen fixation (such as the nitrogenase complex) and proteins that regulate nitrogen fixation. Shamseldin (2013. Global J. Biotechnol. Biochem. 8(4):84-94) discloses detailed descriptions of nif genes and their products, and is incorporated herein by reference. Described herein are methods of producing a plant with an improved trait comprising isolating bacteria from a first plant, introducing a genetic variation into a nif gene of the isolated bacteria, exposing a second plant to the variant bacteria, isolating bacteria from the second plant having an improved trait relative to the first plant, and repeating the steps with bacteria isolated from the second plant.

In Proteobacteria, regulation of nitrogen fixation centers around the $\sigma_{54}$-dependent enhancer-binding protein NifA, the positive transcriptional regulator of the nif cluster. Intracellular levels of active NifA are controlled by two key factors: transcription of the nifLA operon, and inhibition of NifA activity by protein-protein interaction with NifL. Both of these processes are responsive to intraceullar glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine.

Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another $\sigma_{54}$-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein. These processes may also be responsive to intracellular levels of ammonia, urea or nitrates.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifA interaction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. In some bacteria the Nif cluster may be regulated by glnR, and further in some cases this may comprise negative regulation. Regardless of the mechanism, post-translational inhibition of NifA is an important regulator of the nif cluster in most known diazotrophs. Additionally, nifL, amtB, glnK, and glnR are genes that can be mutated in the methods described herein.

In addition to regulating the transcription of the nif gene cluster, many diazotrophs have evolved a mechanism for the direct post-translational modification and inhibition of the nitrogenase enzyme itself, known as nitrogenase shutoff. This is mediated by ADP-ribosylation of the Fe protein (NifH) under nitrogen-excess conditions, which disrupts its interaction with the MoFe protein complex (NifDK) and abolishes nitrogenase activity. DraT catalyzes the ADP-ribosylation of the Fe protein and shutoff of nitrogenase, while DraG catalyzes the removal of ADP-ribose and reactivation of nitrogenase. As with nifLA transcription and NifA inhibition, nitrogenase shutoff is also regulated via the PII protein signaling cascade. Under nitrogen-excess conditions, deuridylylated GlnB interacts with and activates DraT, while deuridylylated GlnK interacts with both DraG and AmtB to form a complex, sequestering DraG to the membrane. Under nitrogen-limiting conditions, the uridylylated forms of GlnB and GlnK do not interact with DraT and DraG, respectively, leading to the inactivation of DraT and the diffusion of DraG to the Fe protein, where it removes the ADP-ribose and activates nitrogenase. The methods described herein also contemplate introducing genetic variation into the nifH, nifD, nifK, and draT genes.

Although some endophytes have the ability to fix nitrogen in vitro, often the genetics are silenced in the field by high levels of exogenous chemical fertilizers. One can decouple the sensing of exogenous nitrogen from expression of the nitrogenase enzyme to facilitate field-based nitrogen fixation. Improving the integral of nitrogenase activity across time further serves to augment the production of nitrogen for utilization by the crop. Specific targets for genetic variation to facilitate field-based nitrogen fixation using the methods described herein include one or more genes selected from the group consisting of nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

An additional target for genetic variation to facilitate field-based nitrogen fixation using the methods described herein is the NifA protein. The NifA protein is typically the activator for expression of nitrogen fixation genes. Increasing the production of NifA (either constitutively or during high ammonia condition) circumvents the native ammonia-sensing pathway. In addition, reducing the production of NifL proteins, a known inhibitor of NifA, also leads to an increased level of freely active NifA. In addition, increasing the transcription level of the nifAL operon (either constitutively or during high ammonia condition) also leads to an overall higher level of NifA proteins. Elevated level of nifAL expression is achieved by altering the promoter itself or by reducing the expression of NtrB (part of ntrB and ntrC signaling cascade that originally would result in the shutoff of nifAL operon during high nitrogen condition). High level of NifA achieved by these or any other methods described herein increases the nitrogen fixation activity of the endophytes.

Another target for genetic variation to facilitate field-based nitrogen fixation using the methods described herein is the GlnD/GlnB/GlnK PII signaling cascade. The intracellular glutamine level is sensed through the GlnD/GlnB/GlnK PII signaling cascade. Active site mutations in GlnD that abolish the uridylyl-removing activity of GlnD disrupt the nitrogen-sensing cascade. In addition, reduction of the GlnB concentration short circuits the glutamine-sensing cascade. These mutations "trick" the cells into perceiving a nitrogen-limited state, thereby increasing the nitrogen fixation level activity. These processes may also be responsive to intracellular, or extracellular, levels of ammonia, urea or nitrates.

The amtB protein is also a target for genetic variation to facilitate field-based nitrogen fixation using the methods described herein. Ammonia uptake from the environment can be reduced by decreasing the expression level of amtB protein. Without intracellular ammonia, the endophyte is not able to sense the high level of ammonia, preventing the down-regulation of nitrogen fixation genes. Any ammonia that manages to get into the intracellular compartment is converted into glutamine. Intracellular glutamine level is the major currency of nitrogen sensing. Decreasing the intracellular glutamine level prevents the cells from sensing high ammonium levels in the environment. This effect can be achieved by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation may enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and de-adenylylation of GS through activity of its adenylyl-transferase (AT) and adenylyl-removing (AR) domains, respectively. Under nitrogen limiting conditions, glnA is expressed, and GlnE's AR domain de-adynylylates GS, allowing it to be active. Under conditions of nitrogen excess, glnA expression is turned off, and GlnE's AT domain is activated allosterically by glutamine, causing the adenylylation and deactivation of GS.

Furthermore, the draT gene may also be a target for genetic variation to facilitate field-based nitrogen fixation using the methods described herein. Once nitrogen fixing enzymes are produced by the cell, nitrogenase shut-off represents another level in which cell downregulates fixation activity in high nitrogen condition. This shut-off could be removed by decreasing the expression level of DraT.

Methods for imparting new microbial phenotypes can be performed at the transcriptional, translational, and post-translational levels. The transcriptional level includes changes at the promoter (such as changing sigma factor affinity or binding sites for transcription factors, including deletion of all or a portion of the promoter) or changing transcription terminators and attenuators. The translational level includes changes at the ribosome binding sites and changing mRNA degradation signals. The post-translational level includes mutating an enzyme's active site and changing protein-protein interactions. These changes can be achieved in a multitude of ways. Reduction of expression level (or complete abolishment) can be achieved by swapping the native ribosome binding site (RBS) or promoter with another with lower strength/efficiency. ATG start sites can be swapped to a GTG, TTG, or CTG start codon, which results in reduction in translational activity of the coding region. Complete abolishment of expression can be done by knocking out (deleting) the coding region of a gene. Frameshifting the open reading frame (ORF) likely will result in a premature stop codon along the ORF, thereby creating a non-functional truncated product. Insertion of in-frame stop codons will also similarly create a non-functional truncated product. Addition of a degradation tag at the N or C terminal can also be done to reduce the effective concentration of a particular gene.

Conversely, expression level of the genes described herein can be achieved by using a stronger promoter. To ensure high promoter activity during high nitrogen level condition (or any other condition), a transcription profile of the whole genome in a high nitrogen level condition could be obtained and active promoters with a desired transcription level can be chosen from that dataset to replace the weak promoter. Weak start codons can be swapped out with an ATG start codon for better translation initiation efficiency. Weak ribosomal binding sites (RBS) can also be swapped out with a different RBS with higher translation initiation efficiency. In addition, site specific mutagenesis can also be performed to alter the activity of an enzyme.

Increasing the level of nitrogen fixation that occurs in a plant can lead to a reduction in the amount of chemical fertilizer needed for crop production and reduce greenhouse gas emissions (e.g., nitrous oxide).

Increasing the Activity of Nitrogen Fixation

Nitrogenases are enzymes responsible for catalyzing nitrogen fixation. There are three types of nitrogenase found in various nitrogen-fixing bacteria: molybdenum (Mo) nitrogenase, vanadium (V) nitrogenase, and iron-only (Fe) nitrogenase. Nitrogenases are two-component systems made up of Component I (also known as dinitrogenase) and Component II (also known as dinitrogenase reductase). Component I is a MoFe protein in molybdenum nitrogenase, a VFe protein in vanadium nitrogenase, and a Fe protein in iron-only nitrogenase. Component II is a Fe protein that contains an iron-sulfur (Fe—S) cluster.

In some cases, varying the supply of cofactors may result in an increase of nitrogen fixation. For example, increasing sulfur uptake may provide a larger pool of cofactors for nitrogenase enzymes, thus increasing the number of functional nitrogenase complexes. In some cases, sulfur uptake may be increased by upregulating sulfate transport genes. Some examples of sulfate transport genes may be, but are not limited to, cysPTWA, sbp, sbp, cysZK.

In some cases, varying the supply of cofactors may result in an increase in nitrogen fixation. For example, increasing molybdenum (Mo) uptake may increase the number of functional nitrogenase complexes. In some cases, Mo uptake may be increased by upregulating Mo transport genes. Some examples of Mo transport genes may be, but are not limited to, modEBA, modEB and modA.

In some cases, cofactor supply may be affected by iron uptake. Iron uptake may be influenced by the tonB transport system. In some cases, influencing iron uptake may be achieved by upregulating tonB transport system genes. Some examples of tonB transport system genes may be, but are not limited to, tonB, and exbAB. In some cases, iron uptake may be influenced by siderophores which increase iron uptake in microbes and plants. In some cases, influencing iron uptake may be achieved by upregulating siderophore biosynthesis genes. Some examples of siderophore biosynthesis genes may be, but are not limited to, yhfA, yusV, sbnA, fiu, yfiZ, and fur.

Varying the metabolic flux to ATP may result in an increase of nitrogen fixation. For example, the metabolic flux to ATP may be increased by targeting glycogen biosynthesis. Glycogen biosynthesis may be influenced by shunting carbon to glycolysis, the TCA cycle and/or oxidative phosphorylation rather than glycogen synthesis. In some cases, glycogen biosynthesis may be influenced by deleting or downregulating the relevant gene for glycogen synthase. An example of a glycogen synthase gene may be, but is not limited to, glgA.

Varying the number of nitrogenase enzymes per cell may result in an increase in nitrogen fixation. For example, the number of nitrogenase enzymes per cell may be affected by nif derepression. Nif derepression may be achieved by constitutively signaling nitrogen starvation. In some cases, nif derepression may be achieved by deleting the UR-domain of relevant genes. An example of a gene which may be targeted to derepress nif genes may be, but is not limited to, glnD. In some cases, the transcription of the nif cluster(s) may be increased by inserting strong promoters upstream of a nifHDK or nifDK operon.

Another way to increase nitrogen fixation may be to increase the number of nitrogenase enzymes per cell by increasing nif cluster transcription. Nif cluster transcription may be increased by increasing nifA transcription. In some cases, nif cluster transcription may be influenced by increasing the copy number of a nifA gene in the genome.

Nif cluster transcription may also be increased by increasing NifA translation. In some cases, NifA translation may be increased by increasing the strength of the ribosome binding site in the nifA gene.

Altering the oxygen sensitivity of nitrogenase may result in an increase of nitrogen fixation. Oxygen sensitivity may be influenced by reducing oxygen sensing. In some cases, reducing oxygen sensing may be by disrupting oxygen-sensing genes. Some examples of oxygen-sensing genes may be, but are not limited to, nifT/fixU, fixJ and fixL.

In some cases, oxygen sensitivity may be influenced by keeping cytosolic oxygen levels low by promoting cytochrome bd-mediated respiration. In some cases, oxygen sensitivity may be influenced by upregulating genes encoding cytochrome bd oxidase and/or knocking out alternative cytochrome systems. Some examples of genes encoding cytochrome bd genes may be, but are not limited to, cyd-ABX, cydAB, and cydX. In some cases, nitrogenase may be protected from oxidation by altering redox balance in the cell. Redox balance may be altered through ROS scavenging. One strategy for accomplishing ROS scavenging would be to upregulate relevant genes. Some examples of ROS scavenging genes may be, but are not limited, to grxABCD, trxA, trxC, and tpx.

In some cases, oxygen sensitivity may be influenced by scavenging free oxygen. In some cases, scavenging free oxygen may be achieved by upregulating bacterial hemoglobin genes.

An example of a hemoglobin gene may be, but is not limited to, glbN. In some cases, scavenging free oxygen may be achieved by upregulating fixNOPQ genes which code for a high-affinity heme-copper cbb3-type oxidase.

Modifying IHFa may result in an increase of nitrogenase expression. In some cases, nitrogenase expression may be increased by facilitating interaction between nifA and σ54 at the upstream activation sequence upstream of certain genes. In particular, upregulation of IHF may increase nitrogenase transcription. In some cases, upregulation of IHF in combination with nifA and σ54 may increase transcription of nitrogenase operon. In some cases, strains that may be utilized in this process of increasing nitrogen expression may include, but is not limited to, *Rahnella aquatilis, Kosakonia sacchari,* and/or *Klebsiella variicola* strains. In some cases, the upregulation of a nitrogenase operon may be more effective when stacked with mutation in a gene encoding σ54.

Modifying a gene encoding σ54 may result in an increase of nitrogenase expression. In some cases, upregulation of a gene for σ54 may increase nitrogenase transcription. An example of a gene encoding σ54 includes, but is not limited to, rpoN. In some cases, strains that may be utilized in this process of increasing nitrogen expression may include, but are not limited to, *Rahnella aquatilis, Kosakonia sacchari,* and/or *Klebsiella variicola* strains. In some cases, upregulation of σ54 in combination with nifA and IHF may increase transcription of a nitrogenase operon. In some cases, the transcription of the nitrogenase operon may be further improved by stacking the upregulation of σ54 with an IHF mutation.

In some cases, deleting a protein such as DraT in a strain, such as a *kosakonia* strain, may increase nitrogenase activity. In some cases, DraT may post-translationally modify a nitrogenase enzyme to inhibit its activity. In some cases, strains that may be utilized in this process of increasing nitrogenase activity may include, but are not limited to, *kosakonia* strains.

In some cases, modification of an asnB gene may increase ammonium excretion. In particular, truncation and upregulation of an asnB gene may convert glutamine back to ammonium. The AsnB enzymes contain two domains; one can deaminate glutamine to release ammonium, and the other uses the ammonium to generate asparagine. Truncating AsnB to delete the asparagine synthase domain and/or upregulating the glutamine deaminase domain may help to convert back cellular glutamine to ammonium, thereby increasing ammonium excretion. In some cases, strains that may be utilized in this process of increasing ammoniumexcretion may include, but are not limited to, *Rahnella aquatilis, Kosakonia sacchari,* and *Klebsiella variicola* strains.

In some cases, modification of an asnB gene may increase ammonium excretion. In particular, deletion of an asnB gene may reduce ammonium sinks in a cell. asnB is able to use cytosolic ammonium instead of glutamine as an N donor. In some cases, deleting, truncating, or upregulating asnB may increase the amount of ammonium excreted from a cell. In some cases, strains that may be utilized in this process of increasing ammonium excretion may include, but are not limited to, *Rahnella aquatilis, Kosakonia sacchari,* and *Klebsiella variicola* strains.

In some cases, modification of glnD may be beneficial in modifying regulation of nitrogen assimilation. In particular, modifications of glnD may be used to optimize regulation of nitrogen assimilation pathways through the PII protein signaling pathway. The enzyme encoded by glnD modifies the PII proteins GlnK and GlnB. The GlnD enzyme reversibly uridylylates and de-uridylylates the PII proteins in conditions of nitrogen limitation and excess, respectively. The PII proteins confer signaling cascades to nitrogen metabolic pathways. Examples of nitrogen metabolism genes influenced by PII protein signaling include but are not limited to, glnA encoding glutamine synthetase, ntrB/glnL encoding sensory histidine kinase/phosphatase ntrB, glnG/ntrC DNA-binding transcriptional regulator ntrC and the niflA operon. In some cases, glnD may be deleted so as to decrease the transcription of nitrogen assimilation genes and the amount of nitrogen assimilated within a cell. In some cases, glnD may be modified by deleting the ACT12 region, deleting the UR region and/or by deactivating the UR region by mutating specific amino acid residues (for example residues 90, 91 and/or 104). In some cases, strains that may be utilized in this process of decreasing nitrogen assimilation may include, but are not limited to, *Rahnella aquatilis, Kosakonia sacchari,* and *Klebsiella variicola* strains.

In some cases, modification of glnD may be beneficial in increasing nitrogenase activity, ammonium excretion and/or plant growth. In particular, removal of a nitrogen sensing region may increase nitrogenase activity and/or plant growth. In some cases, an ACT domain of glnD may be deleted. In some cases, ACT domain is involved in sensing nitrogen status via allosteric regulation by glutamine. Removing an ACT domain may decrease uridylyl-transferase activity, thereby signaling nitrogen excess and down-regulating nitrogen assimilation genes, leading to an increase in ammonium excretion. In some cases, strains that may be utilized in this process of increasing nitrogenase activity, ammonium excretion and/or plant growth may include, but are not limited to, *Kosakonia sacchari* and *Klebsiella variicola* strains.

In some cases, modification of glnD may be beneficial in increasing nitrogenase activity, ammonium excretion and/or plant growth. In particular, removal or deactivation of a uridylyl-transferase (UT) region within a domain of glnD may increase nitrogenase activity, ammonium excretion and/or plant growth. Removing or deactivating a UT domain may decrease uridylyl-transferase activity, thereby signaling nitrogen excess and downregulating nitrogen assimilation genes, leading to an increase in ammonium excretion In some cases, strains that may be utilized in this process of increasing nitrogenase activity, ammonium excretion and/or plant growth may include, but are not limited to, *Rahnella aquatilis, Kosakonia sacchari*, and *Klebsiella variicola* strains.

In some cases, modification of GlnB may be beneficial in increasing nitrogen compound excretion. In some cases, the uridylyl transferase (UTase) domain of GlnD modifies GlnB at tyrosine-51. In some cases, by modifying the UTase domain of GlnD, GlnB-UMP production may be decreased. In some cases, by removing the UTase domain of GlnD, GlnB-UMP production may be decreased. In some cases, by changing the UTase domain of GlnD, GlnB-UMP production may be prevented. In some cases, by removing the UTase domain of GlnD, GlnB-UMP production may be prevented. In some cases, GlnB may be modified by deleting tyrosine-51. In some cases, GlnB may be modified by modifying GlnB at tyrosine-51. In some cases, strains that may be utilized in this process of increasing ammonium excretion may include, but are not limited to, *Rahnella aquatilis, Kosakonia sacchari*, and *Klebsiella variicola* strains.

In some cases, modification of GlnK may be beneficial in increasing ammonium excretion. In some cases, GlnK may behave within a strain as a GlnB analogue based on a similarity of structure between GlnK and GlnB. In some cases, modifying GlnK may increase ammonium excretion by removing inhibitory effects that may be based on GlnK. In some cases, by changing GlnK, inhibitory effects on ammonium excretion may be decreased. In some cases, by removing GlnK, inhibitory effects on ammonium excretion may be decreased. In some cases, by changing GlnK, inhibitory effects on ammonium excretion based on GlnK may be prevented. In some cases, by removing the glnK gene, inhibitory effects on ammonium excretion based on GlnK may be prevented. In some cases, strains that may be utilized in this process of increasing ammonium excretion may include, but are not limited to, *Rahnella aquatilis, Kosakonia sacchari*, and *Klebsiella variicola* strains.

In some cases, modification of glnK may be beneficial in increasing ammonium excretion. In some cases, the UTase domain of GlnD modifies glnK at tyrosine-51. In some cases, by modifying the UTase domain of GlnD, glnK-UMP production may be decreased. In some cases, by removing the UTase domain of GlnD, glnK-UMP production may be decreased. In some cases, by changing the UTase domain of GlnD, glnK-UMP production may be prevented. In some cases, by removing the UTase domain of GlnD, glnK-UMP production may be prevented. In some cases, GlnK may be modified by deleting tyrosine-51. In some cases, GlnK may be modified by modifying GlnK at tyrosine-51. In some cases, strains that may be utilized in this process of increasing ammonium excretion may include, but are not limited to, *Rahnella aquatilis, Kosakonia sacchari*, and *Klebsiella variicola* strains.

In some cases, modification of the glnL encoding the NtrB protein may be beneficial in increasing ammonium excretion. In particular, modification of NtrB may be beneficial in controlling glnA transcription independent of nitrogen status. In some cases, modification of ntrB may be achieved by deleting specific resides to titrate activity. In some cases, strains that may be utilized in this process of increasing ammonium excretion may include, but are not limited to, *Rahnella aquatilis, Kosakonia sacchari*, and *Klebsiella variicola* strains.

In some cases, modification of glnA may be beneficial in increasing ammonium excretion. In some cases, modification of NtrC may be beneficial in modifying the level of GlnA protein in the cell. In particular, modification of NtrC may be beneficial by preventing the phosphorylization of NtrC. Phosphorylated NtrC may lead to transcriptional activation of glnA. As such, modification of ntrC so as to prevent the phosphorylization of ntrC may be beneficial in decreasing transcription of glnA. In some cases, modification of NtrC may be achieved by replacing asparate 54. In some cases, strains that may be utilized in this process of increasing ammonium excretion may include, but are not limited to, *Rahnella aquatilis, Kosakonia sacchari*, and *Klebsiella variicola* strains.

In some cases, modification of Glutaminase B may be beneficial in increasing ammonium excretion. In particular, in some cases the conversion of glutamine back to glutamate and ammonia by Glutaminase B may be upregulated so as to increase ammonium excretion. In some cases, strains that may be utilized in this process of increasing nitrogen excretion may include, but are not limited to, *Rahnella aquatilis, Kosakonia sacchari*, and *Klebsiella variicola* strains.

In some cases, modification of nifA may be beneficial in increasing nitrogenase expression. In some cases, it may be beneficial to modify nifA so as to increase nifA gene copy numbers in a cell. nifA gene copy numbers may be increased by insert multiple copies of a nifA gene in front of constitutively expressing promoters. In some cases, attaching a nifA gene copy to one or more housekeeping operons may increase an overall number of nifA genes in a cell. In some cases, strains that may be utilized in this process of increasing nitrogenase expression may include, but are not limited to, *Rahnella aquatilis* and *Klebsiella variicola* strains.

In some cases, modification of a nitrogenase operon may be beneficial in increasing nitrogenase expression. In some cases, it may be beneficial to upregulate nitrogenase operons so as to increase nitrogenase transcription. In some cases, promoters from within the bacterium that are active when the bacterium is colonizing the rhizosphere may be inserted in front of nitrogenase operons to upregulate nitrogenase operons. In some cases, nifL may be deleted within nitrogenase operons to upregulate nitrogenase operons. In some cases, nifA may be deleted within nitrogenase operons to upregulate nitrogenase operons. In some cases, nifA and nifL may be deleted within nitrogenase operons to upregulate nitrogenase operons. In some cases, multiple promoters may be placed directly in front of nifHDK genes so as to circumvent nifA transcription control. In some cases, strains that may be utilized in this process of increasing nitrogenase expression may include, but are not limited to, *Rahnella aquatilis* and *Klebsiella variicola* strains.

In some cases, modification of glnE may be beneficial in increasing ammonium excretion. In some cases, a conserved aspartate-amino acid-aspartate (DXD) motif on AR domain of glnE may be changed. In some cases, changing a conserved DXD residue on AR domain of glnE may be used to remove de-adenylylation activity from glnE. In some cases, a D residue may be replaced on a DXD motif in the AR region of glnE. In some cases, the replacement of a D residue on a DXD motif in the AR region of glnE may leave the GlnB binding site intact so as to allow for regulation of adenylation activity while decreasing or preventing AR activity. In some cases, strains that may be utilized in this process of increasing ammonium excretion may include, but are not limited to, *Rahnella aquatilis, Kosakonia sacchari*, and *Klebsiella variicola* strains.

In some cases, modification of glnA may be beneficial in increasing AMM excretion. In some cases, glnA may be downregulated by inserting the promoters of glnB, glnD, and/or glnE upstream of the glnA gene. In some cases, modification of glnA may decouple glnA expression from an N-status signaling cascade and decrease expression to a basal level so that more fixed nitrogen remains unassimilated. In some cases, strains that may be utilized in this process of increasing ammonium excretion may include, but are not limited to, *Rahnella aquatilis, Kosakonia sacchari*, and *Klebsiella variicola* strains.

In some cases, modification of GOGAT may be beneficial in increasing ammonium excretion. In some cases, GOGAT may be downregulated by inserting upstream of the GOGAT genes a promoter that controls glnB, glnD, and/or glnE. Downregulation of GOGAT may, in turn, lead to lowering glutamine oxyglutarate aminotransferase expression. In some cases, modification of GOGAT may decouple GOGAT expression from an N-status signaling cascade and decrease expression to a basal level so that more fixed nitrogen remains unassimilated. In some cases, strains that may be utilized in this process of increasing ammonium excretion may include, but are not limited to, *Rahnella aquatilis, Kosakonia sacchari*, and *Klebsiella variicola* strains.

In some cases, modification of GDH may be beneficial in increasing ammonium excretion. In some cases, GDH may be downregulated by inserting upstream of the GDH gene a promoter that controls glnB, glnD, and/or glnE. Downregulation of GDH may, in turn, lead to lowering NAD-specific glutamate dehydrogenase expression. In some cases, modification of GDH may decouple GDH expression from an N-status signaling cascade and decrease expression to a basal level so that more fixed nitrogen remains unassimilated. In some cases, strains that may be utilized in this process of increasing ammonium excretion may include, but are not limited to, *Rahnella aquatilis, Kosakonia sacchari*, and *Klebsiella variicola* strains.

Increasing Nitrogen Fixation Through Assimilation

The amount of nitrogen provided to a microbe-associated plant may be increased by decreasing the nitrogen assimilation in the microbe. Here, the assimilation may be influenced by the excretion rate of ammonia. By targeting the assimilation of ammonia, nitrogen availability may be increased. In some cases influencing ammonia assimilation may be by decreasing the rate of ammonia reuptake after excretion. To decrease the rate of ammonia reuptake after excretion, any relevant gene may be knocked out. An example of a ammonia reuptake genes may be, but is not limited to, amtB.

In some cases, the assimilation may be influenced by the plant uptake rate. By targeting the plant nitrogen assimilation genes and pathways, nitrogen availability may be increased. In some cases, ammonia assimilation by a plant may be altered through inoculation with N-fixing plant growth promoting microbes. A screen may be carried out to identify microbes which induce ammonia assimilation in plants.

Increasing Nitrogen Fixation Through Colonization

Increasing the colonization capacity of the microbes may increase the amount of fixed nitrogen provided to a plant. The colonization may be influenced by altering carrying capacity (the abundance of microbes on the root surface) and/or microbe fitness. In some cases, influencing carrying capacity and microbe fitness may be achieved through altering organic acid transport. Organic acid transport may be improved by upregulating relevant genes. An example of an organic acid transport gene may be, but is not limited to, dctA.

For example, the colonization capacity may be affected by expression of agglutinins. Increased expression of agglutinins may help the microbes stick to plant roots. Examples of agglutinin genes may include, but are not limited to, fhaB and fhaC.

The colonization capacity may be affected by an increase in endophytic entry. For example, endophytic entry may be affected by plant cell wall-degrading enzymes (CDWE). Increasing CDWE expression and/or secretion may increase the colonization and endophytic entry of the microbes. Some examples of CDWEs are, but are not limited to, polygalacturonases and cellulases. An example of a polygalacturonases gene is pehA. In some cases, export of polygalacturonases and cellulases may be increased by providing an export signal with the enzymes.

Varying the carrying capacity may result in an increased amount of nitrogen being provided to an associated plant. Carrying capacity may be affected by biofilm formation. In some cases, carrying capacity may be affected by small RNA rsmZ. Small RNA rsmZ is a negative regulator of biofilm formation. In some cases, biofilm formation may be promoted by deleting or downregulating rsmZ, leading to increased translation of rsmA (a positive regulator of secondary metabolism) and biofilm formation.

In some cases, biofilm formation may be influenced by enhancing the ability of strains to adhere to the root surface. In some cases, biofilm formation may be promoted by upregulating large adhesion proteins. An example of a large adhesion protein may be, but is not limited to, lapA.

In some cases, carrying capacity may be affected by quorum sensing. In some cases, quorum sensing may be enhanced by increasing the copy number of AHL biosynthesis genes.

In some cases, the colonization of the rhizosphere may be influenced by root mass. For example, root mass may be affected by microbial IAA biosynthesis. Increased IAA biosynthesis by the microbe may stimulate root biomass formation. In some cases, influencing IAA biosynthesis may be achieved through upregulation (at a range of levels) of IAA biosynthesis genes. An example of an IAA biosynthesis gene may be, but is not limited to, ipdC.

In some cases ethylene signaling can induce systemic resistance in the plant and affect the colonization capacity of the microbe. Ethylene is a plant signaling molecule that elicits a wide range of responses based on plant tissue and ethylene level. The prevailing model for root ethylene response is that plants that are exposed to stress quickly respond by producing a small peak of ethylene that initiates a protective response by the plant, for example, transcription of genes encoding defensive proteins. If the stress persists or is intense, a second much larger peak of ethylene occurs, often several days later. This second ethylene peak induces processes such as senescence, chlorosis, and abscission that may lead to a significant inhibition of plant growth and survival. In some cases, plant growth promoting bacteria may stimulate root growth by producing the auxin IAA, which stimulates a small ethylene response in the roots. At the same time, the bacteria may prevent the second large ethylene peak by producing an enzyme (ACC deaminase) that slows ethylene production in the plant, thus maintaining an ethylene level that's conducive to stimulating root growth. Induction of systemic resistance in the plant may be influenced by bacterial IAAs. In some cases, stimulating IAA biosynthesis may be achieved through upregulation (at a range of levels) of IAA biosynthesis genes. An example of a biosynthesis gene may be, but is not limited to, ipdC.

In some cases, colonization may be affected by ACC Deaminase. ACC Deaminase may be decrease ethylene production in the root by shunting ACC to a side product. In some cases, influencing ACC Deaminase may be achieved through upregulation of ACC Deaminase genes. Some examples of ACC Deaminase genes may be, but are not limited to, dcyD.

In some cases, the colonization may be influenced by carrying capacity and/or microbe fitness. For example, carrying capacity and/or microbe fitness may be affected by trehalose overproduction. Trehalose overproduction may increase of drought tolerance. In some cases, influencing trehalose overproduction may be achieved through upregulation (at a range of levels) of trehalose biosynthesis genes. Some examples of trehalose biosynthesis genes may be, but are not limited to, otsA, otsB, treZ and treY. In some cases, upregulation of otsB may also increase nitrogen fixation activity.

In some cases, carrying capacity may be affected by root attachment. Root attachment may be influenced by exopolysaccharide secretion. In some cases, influencing exopolysaccharide secretion may be achieved through upregulation of exopolysaccharide production proteins. Some examples of exopolysaccharide production proteins may be, but are not limited to, yjbE and pssM. In some cases, influencing exopolysaccharide secretion may be achieved through upregulation of cellulose biosynthesis. Some examples of cellulose biosynthesis genes may be, but are not limited to, acs genes, and bcs gene clusters.

In some cases, carrying capacity and/or the microbe's fitness may be affected by fungal inhibition. Fungal inhibition may be influenced by chitinases which can break down fungal cell walls and may lead to biocontrol of rhizosphere fungi. In some cases, influencing fungal inhibition may be achieved through upregulation of chitinase genes. Some examples of chitinase genes may be, but are not limited to, chitinase class 1 and chiA.

In some cases, efficient iron uptake can help microbes to survive in the rhizosphere where they have to compete with other soil microbes and the plant for iron uptake. In some cases, high-affinity chelation (siderophores) and transport systems can help with rhizosphere competency by 1) ensuring the microbes obtains enough iron and 2) reducing the iron pool for competing species. Increasing the microbe's ability to do this could increase its competitive fitness in the rhizosphere. In some cases, influencing iron uptake may be by upregulating siderophore genes. Some examples of siderophore genes may be, but are not limited to, yhfA, yusV, sbnA, fiu, yfiZ, and fur. In some cases iron uptake may be influenced by the tonB transport system. In some cases, influencing iron uptake may be by upregulating tonB transport system genes. Some examples of tonB transport system genes may be, but are not limited to, tonB, and exbAB.

In some cases, carrying capacity and/or microbe fitness may be affected by redox balance and/or ROS scavenging. Redox balance and/or ROS scavenging may be influenced by bacterial glutathione (GSH) biosynthesis. In some cases, influencing bacterial glutathione (GSH) biosynthesis may be through upregulation of bacterial glutathione biosynthesis genes. Some examples of bacterial glutathione biosynthesis genes may be, but are not limited to, gshA, gshAB, and gshB.

In some cases, Redox balance may be influenced by ROS scavenging. In some cases, influencing ROS scavenging may be through upregulation of catalases. Some examples of catalases genes may be, but are not limited to, katEG, and Mn catalase.

In some cases, biofilm formation may be influenced by phosphorus signaling. In some cases, influencing phosphorus signaling may be by altering the expression of phosphorous signaling genes. Some examples of phosphorous signaling genes may be, but are not limited to, phoR and phoB.

In some cases, carrying capacity may be affected by root attachment. Root attachment may be influenced by surfactin biosynthesis. In some cases, influencing surfactin biosynthesis may be achieved by upregulating surfactin biosynthesis to improve biofilm formation. An example of surfactin biosynthesis genes may be, but is not limited to, srfAA.

In some cases, the colonization and/or microbe fitness may be influenced by carrying capacity, competition with other microbes and/or crop protection from other microbes. In some cases, competition with other microbes and/or crop protection from other microbes may be influenced by quorum sensing and/or quorum quenching. Quorum quenching may influence colonization by inhibiting quorum-sensing of potential pathogenic/competing bacteria. In some cases, influencing quorum quenching may be achieved by inserting and/or upregulating genes encoding quorum quenching enzymes. Some examples of quorum quenching genes may be, but are not limited to, ahlD, Y2-aiiA, aiiA, ytnP and attM. In some cases, modification of enzymes involved in quorum quenching, such as Y2-aiiA and/or ytnP may be beneficial for colonization. In some cases, upregulation of Y2-aiiA and/or ytnP may result in hydrolysis of extracellular acyl-homoserine lactone (AHL). aiiA is an N-acyl homoserine lactonase that is an enzyme that breaks down homoserine lactone. Breaking down AHL may stop or slow the quorum signaling ability of competing gram negative bacteria. In some cases, strains that may be utilized in this process of increasing colonization may include, but are not limited to, *Rahnella aquatilis, Kosakonia sacchari*, and *Klebsiella variicola* strains.

In some cases, carrying capacity and/or microbes fitness may be affected by rhizobitoxine biosynthesis. Rhizobitoxine biosynthesis may decrease ethylene production in the root by inhibiting ACC synthase. In some cases, influencing rhizobitoxine biosynthesis may be achieved by upregulating rhizobitoxine biosynthesis genes.

In some cases, carrying capacity may be affected by root attachment. Root attachment may be influenced by exopolysaccharide secretion. In some cases, influencing exopolysaccharide secretion may be achieved by generating hypermucoid mutants by deleting mucA.

In some cases, root attachment may be influenced by phenazine biosynthesis. In some cases, influencing phenazine biosynthesis may be achieved by upregulating phenazine biosynthesis genes to improve biofilm formation.

In some cases, root attachment may be influenced by cyclic lipopeptide (CLP) biosynthesis. In some cases, influencing cyclic lipopeptide (CLP) biosynthesis may be achieved by upregulating CLP biosynthesis to improve biofilm formation.

In some cases, carrying capacity and/or competition may be affected by antibiotic synthesis. Antibiotic synthesis may increase antibiotic production to kill competing microbes. In some cases, increasing antibiotic production may be achieved by mining genomes for antibiotic biosynthesis pathways and upregulation.

In some cases, colonization may be affected by desiccation tolerance. In some cases, modification of rpoE may be beneficial for colonization. In some cases, upregulation of rpoE may result in increasing expression of stress tolerance genes and pathways. In some cases, rpoE may be upregulated using a unique switchable promoter. In some cases, rpoE may be upregulated using an arabinose promoter. rpoE is a sigma factor similar to phyR. When expressed, rpoE may cause upregulation of multiple stress tolerance genes. As stress tolerance enzymes may not be useful during a colonization cycle, a switchable promoter may be used. In some cases, the promoter may be active during biomass growth and/or during seed coating. In some cases, a switchable promoter may be used where the sugar or chemical can be spiked in during the log phase of biomass growth but may also have the promoter not turned on during one or more other applications of the microbe. In some cases, rpoE may be upregulated while also downregulating rseA. In some cases, strains that may be utilized in this process of increasing colonization may include, but are not limited to, *Rahnella aquatilis, Kosakonia sacchari*, and *Klebsiella variicola* strains.

In some cases, colonization may be affected by desiccation tolerance. In some cases, modification of rseA may be beneficial for colonization. In some cases, rseA may be downregulated using an unique switchable promoter. In some cases, rseA may be downregulated using an arabinose promoter. rseA is an anti-sigma factor coexpressed with rpoE. In some cases, the enzymes remain bound to each other, which may decrease or disable rpoE's ability to act as a transcription factor. However, during stress conditions, resA may be cleaved and rpoE may be free to up/down regulate stress tolerance genes. By breaking co-transcription with rpoE, levels of rpoE and resA may be titered independently, which may be beneficial in optimizing colonization of engineered strains. In some cases, strains that may be utilized in this process of increasing colonization may include, but are not limited to, *Rahnella aquatilis, Kosakonia sacchari*, and *Klebsiella variicola* strains.

Generation of Bacterial Populations

Isolation of Bacteria

Microbes useful in methods and compositions disclosed herein can be obtained by extracting microbes from surfaces or tissues of native plants. Microbes can be obtained by grinding seeds to isolate microbes. Microbes can be obtained by planting seeds in diverse soil samples and recovering microbes from tissues. Additionally, microbes can be obtained by inoculating plants with exogenous microbes and determining which microbes appear in plant tissues. Non-limiting examples of plant tissues may include a seed, seedling, leaf, cutting, plant, bulb, or tuber.

A method of obtaining microbes may be through the isolation of bacteria from soils. Bacteria may be collected from various soil types. In some example, the soil can be characterized by traits such as high or low fertility, levels of moisture, levels of minerals, and various cropping practices. For example, the soil may be involved in a crop rotation where different crops are planted in the same soil in successive planting seasons. The sequential growth of different crops on the same soil may prevent disproportionate depletion of certain minerals. The bacteria can be isolated from the plants growing in the selected soils. The seedling plants can be harvested at 2-6 weeks of growth. For example, at least 400 isolates can be collected in a round of harvest. Soil and plant types reveal the plant phenotype as well as the conditions, which allow for the downstream enrichment of certain phenotypes.

Microbes can be isolated from plant tissues to assess microbial traits. The parameters for processing tissue samples may be varied to isolate different types of associative microbes, such as rhizopheric bacteria, epiphytes, or endophytes. The isolates can be cultured in nitrogen-free media to enrich for bacteria that perform nitrogen fixation. Alternatively, microbes can be obtained from global strain banks.

In planta analytics are performed to assess microbial traits. In some embodiments, the plant tissue can be processed for screening by high throughput processing for DNA and RNA. Additionally, non-invasive measurements can be used to assess plant characteristics, such as colonization. Measurements on wild microbes can be obtained on a plant-by-plant basis. Measurements on wild microbes can also be obtained in the field using medium throughput methods. Measurements can be done successively over time. Model plant system can be used including, but not limited to, *Setaria*.

Microbes in a plant system can be screened via transcriptional profiling of a microbe in a plant system. Examples of screening through transcriptional profiling are using methods of quantitative polymerase chain reaction (qPCR), molecular barcodes for transcript detection, Next Generation Sequencing, and microbe tagging with fluorescent markers. Impact factors can be measured to assess colonization in the greenhouse including, but not limited to, microbiome, abiotic factors, soil conditions, oxygen, moisture, temperature, inoculum conditions, and root localization. Nitrogen fixation can be assessed in bacteria by measuring 15N gas/fertilizer (dilution) with IRMS or NanoSIMS as described herein NanoSIMS is high-resolution secondary ion mass spectrometry. The NanoSIMS technique is a way to investigate chemical activity from biological samples. The catalysis of reduction of oxidation reactions that drive the metabolism of microorganisms can be investigated at the cellular, subcellular, molecular and elemental level. NanoSIMS can provide high spatial resolution of greater than 0.1 µm. NanoSIMS can detect the use of isotope tracers such as $^{13}C$, $^{15}N$, and $^{18}O$. Therefore, NanoSIMS can be used to the chemical activity nitrogen in the cell.

Automated greenhouses can be used for planta analytics. Plant metrics in response to microbial exposure include, but are not limited to, biomass, chloroplast analysis, CCD camera, volumetric tomography measurements.

One way of enriching a microbe population is according to genotype. For example, a polymerase chain reaction (PCR) assay with a targeted primer or specific primer. Primers designed for the nifH gene can be used to identity diazotrophs because diazotrophs express the nifH gene in the process of nitrogen fixation. A microbial population can also be enriched via single-cell culture-independent approaches and chemotaxis-guided isolation approaches. Alternatively, targeted isolation of microbes can be performed by culturing the microbes on selection media. Premeditated approaches to enriching microbial populations for desired traits can be guided by bioinformatics data and are described herein.

Enriching for Microbes with Nitrogen Fixation Capabilities Using Bioinformatics

Bioinformatic tools can be used to identify and isolate plant growth promoting rhizobacteria (PGPRs), which are selected based on their ability to perform nitrogen fixation. Microbes with high nitrogen fixing ability can promote favorable traits in plants. Bioinformatic modes of analysis for the identification of PGPRs include, but are not limited to, genomics, metagenomics, targeted isolation, gene sequencing, transcriptome sequencing, and modeling.

Genomics analysis can be used to identify PGPRs and confirm the presence of mutations with methods of Next Generation Sequencing as described herein and microbe version control.

Metagenomics can be used to identify and isolate PGPR using a prediction algorithm for colonization. Metadata can also be used to identify the presence of an engineered strain in environmental and greenhouse samples.

Transcriptomic sequencing can be used to predict genotypes leading to PGPR phenotypes. Additionally, transcriptomic data is used to identify promoters for altering gene expression. Transcriptomic data can be analyzed in conjunction with the Whole Genome Sequence (WGS) to generate models of metabolism and gene regulatory networks.

Domestication of Microbes

Microbes isolated from nature can undergo a domestication process wherein the microbes are converted to a form that is genetically trackable and identifiable. One way to domesticate a microbe is to engineer it with antibiotic resistance. The process of engineering antibiotic resistance can begin by determining the antibiotic sensitivity in the wild type microbial strain. If the bacteria are sensitive to the antibiotic, then the antibiotic can be a good candidate for antibiotic resistance engineering. Subsequently, an antibiotic resistant gene or a counterselectable suicide vector can be incorporated into the genome of a microbe using recombineering methods. A counterselectable suicide vector may consist of a deletion of the gene of interest, a selectable marker, and the counterselectable marker sacB. Counterselection can be used to exchange native microbial DNA sequences with antibiotic resistant genes. A medium throughput method can be used to evaluate multiple microbes simultaneously allowing for parallel domestication. Alternative methods of domestication include the use of homing nucleases to prevent the suicide vector sequences from looping out or from obtaining intervening vector sequences.

DNA vectors can be introduced into bacteria via several methods including electroporation and chemical transformations. A standard library of vectors can be used for transformations. An example of a method of gene editing is CRISPR preceded by Cas9 testing to ensure activity of Cas9 in the microbes.

Non-Transgenic Engineering of Microbes

A microbial population with favorable traits can be obtained via directed evolution. Direct evolution is an approach wherein the process of natural selection is mimicked to evolve proteins or nucleic acids towards a user-defined goal. An example of direct evolution is when random mutations are introduced into a microbial population, the microbes with the most favorable traits are selected, and the growth of the selected microbes is continued. The most favorable traits in growth promoting rhizobacteria (PGPRs) may be in nitrogen fixation. The method of directed evolution may be iterative and adaptive based on the selection process after each iteration.

Plant growth promoting rhizobacteria (PGPRs) with high capability of nitrogen fixation can be generated. The evolution of PGPRs can be carried out via the introduction of genetic variation. Genetic variation can be introduced via polymerase chain reaction mutagenesis, oligonucleotide-directed mutagenesis, saturation mutagenesis, fragment shuffling mutagenesis, homologous recombination, CRISPR/Cas9 systems, chemical mutagenesis, and combinations thereof. These approaches can introduce random mutations into the microbial population. For example, mutants can be generated using synthetic DNA or RNA via oligonucleotide-directed mutagenesis. Mutants can be generated using tools contained on plasmids, which are later cured. Genes of interest can be identified using libraries from other species with improved traits including, but not limited to, improved PGPR properties, improved colonization of cereals, increased oxygen sensitivity, increased nitrogen fixation, and increased ammonia excretion. Intrageneric genes can be designed based on these libraries using software such as Geneious or Platypus design software. Mutations can be designed with the aid of machine learning. Mutations can be designed with the aid of a metabolic model. Automated design of the mutation can be done using a la Platypus and will guide RNAs for Cas-directed mutagenesis.

The intra-generic genes can be transferred into the host microbe. Additionally, reporter systems can also be transferred to the microbe. The reporter systems characterize promoters, determine the transformation success, screen mutants, and act as negative screening tools.

The microbes carrying the mutation can be cultured via serial passaging. A microbial colony contains a single variant of the microbe. Microbial colonies are screened with the aid of an automated colony picker and liquid handler. Mutants with gene duplication and increased copy number express a higher genotype of the desired trait.

Selection of Plant Growth Promoting Microbess Based on Nitrogen Fixation

The microbial colonies can be screened using various assays to assess nitrogen fixation. One way to measure nitrogen fixation is via a single fermentative assay, which measures nitrogen excretion. An alternative method is the acetylene reduction assay (ARA) with in-line sampling over time. ARA can be performed in high throughput plates of microtube arrays. ARA can be performed with live plants and plant tissues. The media formulation and media oxygen concentration can be varied in ARA assays. Another method of screening microbial variants is by using biosensors. The use of NanoSIMS and Raman microspectroscopy can be used to investigate the activity of the microbes. In some cases, bacteria can also be cultured and expanded using methods of fermentation in bioreactors. The bioreactors are designed to improve robustness of bacteria growth and to decrease the sensitivity of bacteria to oxygen. Medium to high TP plate-based microfermentors are used to evaluate oxygen sensitivity, nutritional needs, nitrogen fixation, and nitrogen excretion. The bacteria can also be co-cultured with competitive or beneficial microbes to elucidate cryptic pathways. Flow cytometry can be used to screen for bacteria that produce high levels of nitrogen using chemical, colorimetric, or fluorescent indicators. The bacteria may be cultured in the presence or absence of a nitrogen source. For example, the bacteria may be cultured with glutamine, ammonia, urea or nitrates.

Microbe Breeding

Microbe breeding is a method to systematically identify and improve the role of species within the crop microbiome.

The method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets breeding and improve the frequency of selecting improvements in microbiome-encoded traits of agronomic relevance.

Production of bacteria to improve plant traits (e.g., nitrogen fixation) can be achieved through serial passage. The production of this bacteria can be done by selecting plants, which have a particular improved trait that is influenced by the microbial flora, in addition to identifying bacteria and/or compositions that are capable of imparting one or more improved traits to one or more plants. One method of producing a bacteria to improve a plant trait includes the steps of: (a) isolating bacteria from tissue or soil of a first plant; (b) introducing a genetic variation into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated from the plant with an improved trait (step (d)). Steps (b) to (d) can be repeated any number of times (e.g., once, twice, three times, four times, five times, ten times, or more) until the improved trait in a plant reaches a desired level. Further, the plurality of plants can be more than two plants, such as 10 to 20 plants, or 20 or more, 50 or more, 100 or more, 300 or more, 500 or more, or 1000 or more plants.

In addition to obtaining a plant with an improved trait, a bacterial population comprising bacteria comprising one or more genetic variations introduced into one or more genes (e.g., genes regulating nitrogen fixation) is obtained. By repeating the steps described above, a population of bacteria can be obtained that include the most appropriate members of the population that correlate with a plant trait of interest. The bacteria in this population can be identified and their beneficial properties determined, such as by genetic and/or phenotypic analysis. Genetic analysis may occur of isolated bacteria in step (a). Phenotypic and/or genotypic information may be obtained using techniques including: high through-put screening of chemical components of plant origin, sequencing techniques including high throughput sequencing of genetic material, differential display techniques (including DDRT-PCR, and DD-PCR), nucleic acid microarray techniques, RNA-sequencing (Whole Transcriptome Shotgun Sequencing), and qRT-PCR (quantitative real time PCR). Information gained can be used to obtain community profiling information on the identity and activity of bacteria present, such as phylogenetic analysis or microarray-based screening of nucleic acids coding for components of rRNA operons or other taxonomically informative loci. Examples of taxonomically informative loci include 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene, nifD gene. Example processes of taxonomic profiling to determine taxa present in a population are described in US20140155283. Bacterial identification may comprise characterizing activity of one or more genes or one or more signaling pathways, such as genes associated with the nitrogen fixation pathway. Synergistic interactions (where two components, by virtue of their combination, increase a desired effect by more than an additive amount) between different bacterial species may also be present in the bacterial populations.

The genetic variation may be a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ. The genetic variation may be a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, or NAD+-dinitrogen-reductase aDP-D-ribosyltransferase. The genetic variation may be a mutation that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD. Introducing a genetic variation may comprise insertion and/or deletion of one or more nucleotides at a target site, such as 1, 2, 3, 4, 5, 10, 25, 50, 100, 250, 500, or more nucleotides. The genetic variation introduced into one or more bacteria of the methods disclosed herein may be a knock-out mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a bacterial species or genus corresponding to the bacteria into which the genetic variation is introduced. Moreover, regulatory sequences may be selected based on the expression level of a gene in a bacterial culture or within a plant tissue. The genetic variation may be a pre-determined genetic variation that is specifically introduced to a target site. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria before exposing the bacteria to plants for assessing trait improvement. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of genetic variations in bacteria imparting progressively improved traits on the associated plants.

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

Genetic variation may be introduced into numerous metabolic pathways within microbes to elicit improvements in the traits described above. Representative pathways include sulfur uptake pathways, glycogen biosynthesis, the glutamine regulation pathway, the molybdenum uptake pathway, the nitrogen fixation pathway, ammonia assimilation, ammonia excretion or secretion, Nitrogen uptake, glutamine biosynthesis, annamox, phosphate solubilization, organic acid transport, organic acid production, agglutinins production, reactive oxygen radical scavenging genes, Indole Acetic Acid biosynthesis, trehalose biosynthesis, plant cell wall degrading enzymes or pathways, root attachment genes, exopolysaccharide secretion, glutamate synthase pathway, iron uptake pathways, siderophore pathway, chitinase pathway, ACC deaminase, glutathione biosynthesis, phosphorous signaling genes, quorum quenching pathway, cytochrome pathways, hemoglobin pathway, bacterial hemoglobin-like pathway, small RNA rsmZ, rhizobitoxine biosynthesis, lapA adhesion protein, AHL quorum sensing pathway, phenazine biosynthesis, cyclic lipopeptide biosynthesis, and antibiotic production.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme Dpnl which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US20100267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Saturation mutagenesis is another form of random mutagenesis, in which one tries to generate all or nearly all possible mutations at a specific site, or narrow region of a gene. In a general sense, saturation mutagenesis is comprised of mutagenizing a complete set of mutagenic cassettes (wherein each cassette is, for example, 1-500 bases in length) in defined polynucleotide sequence to be mutagenized (wherein the sequence to be mutagenized is, for example, from 15 to 100,000 bases in length). Therefore, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuffling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US20050266541.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Mutagens that create primarily point mutations and short deletions, insertions, transversions, and/or transitions, including chemical mutagens or radiation, may be used to create genetic variations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for use in exposing to plants for assessing conferral of an improved trait.

A CRISPR nuclease may be used as the site-specific nuclease to direct cleavage to a target site. An improved selection of mutated microbes can be obtained by using Cas9 to kill non-mutated cells. Plants are then inoculated with the mutated microbes to re-confirm symbiosis and create evolutionary pressure to select for efficient symbionts. Microbes can then be re-isolated from plant tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions.

A preferred trait to be introduced or improved is nitrogen fixation, as described herein. In some cases, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil. In additional examples, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under similar conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress). The trait improved by methods and compositions of the present disclosure may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic variation. In some cases, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with glutamine, ammonia, or other chemical source of nitrogen. Methods for assessing degree of nitrogen fixation are known, examples of which are described herein.

Microbe breeding is a method to systematically identify and improve the role of species within the crop microbiome. The method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets breeding and improve the frequency of selecting improvements in microbiome-encoded traits of agronomic relevance.

Nitrogen Fixation

Described herein are methods of increasing nitrogen fixation in a plant, comprising exposing the plant to bacteria comprising one or more genetic variations introduced into one or more genes regulating nitrogen fixation, wherein the bacteria produce 1% or more of nitrogen in the plant (e.g. 2%, 5%, 10%, or more), which may represent a nitrogen-fixation capability of at least 2-fold as compared to the plant in the absence of the bacteria. The bacteria may produce the nitrogen in the presence of fertilizer supplemented with glutamine, urea, nitrates or ammonia. Genetic variations can be any genetic variation described herein, including examples provided above, in any number and any combination. The genetic variation may be introduced into a gene selected from the group consisting of nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic variation may be a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; or decreased uridylyl-removing activity of GlnD. The genetic variation introduced into one or more bacteria of the methods disclosed herein may be a knock-out mutation or it may abolish a regulatory sequence of a target gene, or it may comprise insertion of a heterologous regulatory sequence, for example, insertion of a regulatory sequence found within the genome of the same bacterial species or genus. The regulatory sequence can be chosen based on the expression level of a gene in a bacterial culture or within plant tissue. The genetic variation may be produced by chemical mutagenesis. The plants grown in step (c) may be exposed to biotic or abiotic stressors.

The amount of nitrogen fixation that occurs in the plants described herein may be measured in several ways, for example by an acetylene-reduction (AR) assay. An acetylene-reduction assay can be performed in vitro or in vivo. Evidence that a particular bacterium is providing fixed nitrogen to a plant can include: 1) total plant N significantly increases upon inoculation, preferably with a concomitant increase in N concentration in the plant; 2) nitrogen deficiency symptoms are relieved under N-limiting conditions upon inoculation (which should include an increase in dry matter); 3) $N_2$ fixation is documented through the use of an $^{15}N$ approach (which can be isotope dilution experiments, $^{15}N_2$ reduction assays, or $^{15}N$ natural abundance assays); 4) fixed N is incorporated into a plant protein or metabolite; and 5) all of these effects are not be seen in non-inoculated plants or in plants inoculated with a mutant of the inoculum strain.

The wild-type nitrogen fixation regulatory cascade can be represented as a digital logic circuit where the inputs $O_2$ and $NH_4^+$ pass through a NOR gate, the output of which enters an AND gate in addition to ATP. In some embodiments, the methods disclosed herein disrupt the influence of $NH_4^+$ on this circuit, at multiple points in the regulatory cascade, so that microbes can produce nitrogen even in fertilized fields. However, the methods disclosed herein also envision altering the impact of ATP or $O_2$ on the circuitry, or replacing the circuitry with other regulatory cascades in the cell, or altering genetic circuits other than nitrogen fixation. Gene clusters can be re-engineered to generate functional products under the control of a heterologous regulatory system. By eliminating native regulatory elements outside of, and within, coding sequences of gene clusters, and replacing them with alternative regulatory systems, the functional products of complex genetic operons and other gene clusters can be controlled and/or moved to heterologous cells, including cells of different species other than the species from which the native genes were derived. Once re-engineered, the synthetic gene clusters can be controlled by genetic circuits or other inducible regulatory systems, thereby controlling the products' expression as desired. The expression cassettes can be designed to act as logic gates, pulse generators, oscillators, switches, or memory devices. The controlling expression cassette can be linked to a promoter such that the expression cassette functions as an environmental sensor, such as an oxygen, temperature, touch, osmotic stress, membrane stress, or redox sensor.

As an example, the nifL, nifA, nifT, and nifX genes can be eliminated from the nif gene cluster. Synthetic genes can be designed by codon randomizing the DNA encoding each amino acid sequence. Codon selection is performed, specifying that codon usage be as divergent as possible from the codon usage in the native gene. Proposed sequences are scanned for any undesired features, such as restriction enzyme recognition sites, transposon recognition sites, repetitive sequences, sigma 54 and sigma 70 promoters, cryptic ribosome binding sites, and rho independent terminators. Synthetic ribosome binding sites are chosen to match the strength of each corresponding native ribosome binding site, such as by constructing a fluorescent reporter plasmid in which the 150 bp surrounding a gene's start codon (from −60 to +90) is fused to a fluorescent gene. This chimera can be expressed under control of the Ptac promoter, and fluorescence measured via flow cytometry. To generate synthetic ribosome binding sites, a library of reporter plasmids using 150 bp (−60 to +90) of a synthetic expression cassette is generated. Briefly, a synthetic expression cassette can consist of a random DNA spacer, a degenerate sequence encoding an RBS library, and the coding sequence for each synthetic gene. Multiple clones are screened to identify the synthetic ribosome binding site that best matched the native ribosome binding site. Synthetic operons that consist of the same genes as the native operons are thus constructed and tested for functional complementation. A further exemplary description of synthetic operons is provided in US20140329326.

Bacterial Species

Microbes useful in the methods and compositions disclosed herein may be obtained from any source. In some cases, microbes may be bacteria, archaea, protozoa or fungi. The microbes of this disclosure may be nitrogen fixing microbes, for example a nitrogen fixing bacteria, nitrogen fixing archaea, nitrogen fixing fungi, nitrogen fixing yeast, or nitrogen fixing protozoa. Microbes useful in the methods and compositions disclosed herein may be spore forming microbes, for example spore forming bacteria. In some cases, bacteria useful in the methods and compositions disclosed herein may be Gram positive bacteria or Gram negative bacteria. In some cases, the bacteria may be an endospore forming bacteria of the Firmicute phylum. In some cases, the bacteria may be a diazotroph. In some cases, the bacteria may not be a diazotroph.

The methods and compositions of this disclosure may be used with an archaea, such as, for example, *Methanothermobacter thermoautotrophicus*.

In some cases, bacteria which may be useful include, but are not limited to, *Agrobacterium radiobacter, Bacillus acidocaldarius, Bacillus acidoterresiris, Bacillus agri, Bacillus aizawai, Bacillus albolactis, Bacillus alcalophilus, Bacillus alvei, Bacillus aminoglucasidicus, Bacillus aininovorans, Bacillus amylolyticus* (also known as *Paenibacillus*

*amylolyticus*) *Bacillus amyloliquefaciens, Bacillus aneurinolyticus, Bacillus atrophaeus, Bacillus azotoformans, Bacillus badius, Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus laterosporus* (also known as *Brevibacillus laterosporus*), *Bacillus lautus, Bacillus lentimorbus, Bacillus lentus, Bacillus lichenijormis, Bacillus maroccanus, Bacillus megaterium, Bacillus metiens, Bacillus mycoides, Bacillus natto, Bacillus nematocida, Bacillus nigrificans, Bacillus nigrum, Bacillus pantothenticus, Bacillus popillae, Bacillus psychrosaccharolyticus, Bacillus puinilus, Bacillus siamensis, Bacillus smithii, Bacillus sphaericus, Bacillus subtilis, Bacillus thuringiensis, Bacillus unillagellatus, Bradyrhizobium japonicum, Brevibacillus brevis Brevibacillus laterosporus* (formerly *Bacillus laterosporus*), *Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae, Serratia entomophila, Serratia marcescens, Streptomyces colombiensis, Streptomyces galbus, Streptomyces goshikiensis, Streptomyces griseoviridis, Streptomyces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRRL Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), and *Streptomyces* sp. strain NRRL Accession No. B-30145. In some cases the bacterium may be *Azotobacter chroococcum Methanosarcina barkeri, Klesiella pneumoniae, Azotobacter vinelandii, Rhodobacter spharoides, Rhodobacter capsulatus, Rhodobcter palustris, Rhodosporillum rubrum, Rhizobium leguminosarum* or *Rhizobium etli*.

In some cases the bacterium may be a species of *Clostridium*, for example *Clostridium pasteurianum, Clostridium beijerinckii, Clostridium perfringens, Clostridium tetani, Clostridium acetobutylicum*.

In some cases, bacteria used with the methods and compositions of the present disclosure may be cyanobacteria. Examples of cyanobacterial genuses include *Anabaena* (for example *Anagaena* sp. PCC7120), *Nostoc* (for example *Nostoc punctiforme*), or *Synechocystis* (for example *Synechocystis* sp. PCC6803).

In some cases, bacteria used with the methods and compositions of the present disclosure may belong to the phylum Chlorobi, for example *Chlorobium tepidum*.

In some cases, microbes used with the methods and compositions of the present disclosure may comprise a gene homologous to a known NifH gene. Sequences of known NifH genes may be found in, for example, the Zehr lab NifH database, (https://wwwzehr.pmc.ucsc.edu/nifH_Database_vPublic/, Apr. 4, 2014), or the Buckley lab NifH database (http://www.css.cornell.edu/faculty/buckley/nifh.htm, and Gaby, John Christian, and Daniel H. Buckley. "A comprehensive aligned nifH gene database: a multipurpose tool for studies of nitrogen-fixing bacteria." *Database* 2014 (2014): bau001.). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Zehr lab NifH database, (https://wwwzehr.pmc.ucsc.edu/nifH_Database_Public/, Apr. 4, 2014). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Buckley lab NifH database, (Gaby, John Christian, and Daniel H. Buckley. "A comprehensive aligned nifH gene database: a multipurpose tool for studies of nitrogen-fixing bacteria." *Database* 2014 (2014): bau001.).

Microbes useful in the methods and compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. Non-limiting examples of plant tissues include a seed, seedling, leaf, cutting, plant, bulb or tuber. In some cases, bacteria are isolated from a seed. The parameters for processing samples may be varied to isolate different types of associative microbes, such as rhizospheric, epiphytes, or endophytes. Bacteria may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

The bacteria and methods of producing bacteria described herein may apply to bacteria able to self-propagate efficiently on the leaf surface, root surface, or inside plant tissues without inducing a damaging plant defense reaction, or bacteria that are resistant to plant defense responses. The bacteria described herein may be isolated by culturing a plant tissue extract or leaf surface wash in a medium with no added nitrogen. However, the bacteria may be unculturable, that is, not known to be culturable or difficult to culture using standard methods known in the art. The bacteria described herein may be an endophyte or an epiphyte or a bacterium inhabiting the plant rhizosphere (rhizospheric bacteria). The bacteria obtained after repeating the steps of introducing genetic variation, exposure to a plurality of plants, and isolating bacteria from plants with an improved trait one or more times (e.g. 1, 2, 3, 4, 5, 10, 15, 25, or more times) may be endophytic, epiphytic, or rhizospheric. Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some cases, a seed-borne bacterial endophyte is capable of replicating within the plant tissue, for example, the interior of the seed. Also, in some cases, the seed-borne bacterial endophyte is capable of surviving desiccation.

The bacterial isolated according to methods of the disclosure, or used in methods or compositions of the disclosure, can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma*, and *Acetabacterium*), and Actinobacteria (such as *Streptomyces, Rhodacoccus, Microbacterium*, and *Curtobacterium*). The bacteria used in methods and compositions of this disclosure may include nitrogen fixing bacterial consortia of two or more species. In some cases, one or more bacterial species of the bacterial consortia may be capable of fixing nitrogen. In some cases, one or more species of the bacterial consortia may facilitate or enhance the ability of other bacteria to fix nitrogen. The bacteria which fix nitrogen and the bacteria which enhance the ability of other bacteria to fix nitrogen may be the same or different. In some examples, a bacterial strain may be able to fix nitrogen when in combination with a different bacterial strain, or in a certain bacterial consortia, but may be unable to fix nitrogen in a monoculture. Examples of bacterial genuses which may be found in a nitrogen fixing bacterial consortia include, but are not limited to, *Herbaspirillum, Azospirillum, Enterobacter*, and *Bacillus*.

Bacteria that can be produced by the methods disclosed herein include *Azotobacter* sp., *Bradyrhizobium* sp., *Klebsiella* sp., and *Sinorhizobium* sp. In some cases, the bacteria may be selected from the group consisting of: *Azotobacter vinelandii, Bradyrhizobium japonicum, Klebsiella pneumoniae*, and *Sinorhizobium meliloti*. In some cases, the bacteria may be of the genus *Enterobacter* or *Rahnella*. In some cases, the bacteria may be of the genus *Frankia*, or *Clostridium*. Examples of bacteria of the genus *Clostridium* include, but are not limited to, *Clostridium acetobutilicum, Clostridium pasteurianum, Clostridium beijerinckii, Clostridium perfringens*, and *Clostridium tetani*. In some cases, the bacteria may be of the genus *Paenibacillus*, for example *Paenibacillus azotofixans, Paenibacillus borealis, Paenibacillus durus, Paenibacillus macerans, Paenibacillus polymyxa, Paenibacillus alvei, Paenibacillus amylolyticus, Paenibacillus campinasensis, Paenibacillus chibensis, Paenibacillus glucanolyticus, Paenibacillus illinoisensis, Paenibacillus larvae* subsp. *Larvae, Paenibacillus larvae* subsp. *Pulvifaciens, Paenibacillus lautus, Paenibacillus macerans, Paenibacillus macquariensis, Paenibacillus macquariensis, Paenibacillus pabuli, Paenibacillus peoriae*, or *Paenibacillus polymyxa*.

In some examples, bacteria isolated according to methods of the disclosure can be a member of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulomonas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Enhydrobacter, Enterobacter, Enterococcus, Envinia, Escherichia, Escherichia/Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Pelomonas, Perlucidibaca, Plantibacter, Polynucleobacter, Propionibacterium, Propioniciclava, Pseudoclavibacter, Pseudomonas, Pseudonocardia, Pseudoxanthomonas, Psychrobacter, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus*, 25 *Stenotrophomonas, Strenotrophomonas, Streptococcus, Streptomyces, Stygiolobus, Sulfurisphaera, Tatumella, Tepidimonas, Thermomonas, Thiobacillus, Variovorax*, WPS-2 genera *Incertae sedis, Xanthomonas*, and *Zimmermannella*.

The bacteria may be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, and road surfaces).

The plants from which the bacteria are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria may be isolated from plant tissue. This isolation can occur from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth. Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface-dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Biologically pure cultures of *Rahnella aquatilis* and *Enterobacter sacchari* were deposited on Jul. 14, 2015 with the American Type Culture Collection (ATCC; an International Depositary Authority), Manassas, VA, USA, and assigned ATTC Patent Deposit Designation numbers PTA-122293 and PTA-122294, respectively. These deposits were made under the provisions of the Budapest Treaty on the International Recognition of the Deposit of Microorganisms for the Purpose of Patent Procedure and the Regulations (Budapest Treaty).

Compositions

Compositions comprising bacteria or bacterial populations produced according to methods described herein and/or having characteristics as described herein can be in the form of a liquid, a foam, or a dry product. In some examples, a composition comprising bacterial populations may be in the form of a dry powder, a slurry of powder and water, or a flowable seed treatment.

The composition can be fabricated in bioreactors such as continuous stirred tank reactors, batch reactors, and on the farm. In some examples, compositions can be stored in a container, such as a jug or in mini bulk. In some examples, compositions may be stored within an object selected from the group consisting of a bottle, jar, ampule, package, vessel, bag, box, bin, envelope, carton, container, silo, shipping container, truck bed, and/or case.

Compositions may also be used to improve plant traits. In some examples, one or more compositions may be coated onto a seed. In some examples, one or more compositions may be coated onto a seedling. In some examples, one or more compositions may be coated onto a surface of a seed. In some examples, one or more compositions may be coated as a layer above a surface of a seed. In some examples, a composition that is coated onto a seed may be in liquid form, in dry product form, in foam form, in a form of a slurry of powder and water, or in a flowable seed treatment. In some examples, one or more compositions may be applied to a seed and/or seedling by spraying, immersing, coating, encapsulating, and/or dusting the seed and/or seedling with the one or more compositions. In some examples, multiple bacteria or bacterial populations can be coated onto a seed and/or a seedling of the plant. In some examples, at least two, at least three, at least four, at least five, at least six, at least seven, at least eight, at least nine, at least ten, or more than ten bacteria of a bacterial combination can be selected from one of the following genera: Acidovorax, *Agrobacterium, Bacillus, Burkholderia, Chryseobacterium, Curtobacterium, Enterobacter, Escherichia, Methylobacterium, Paenibacillus, Pantoea, Pseudomonas, Ralstonia, Saccharibacillus, Sphingomonas,* and *Stenotrophomonas.*

In some examples, at least two, at least three, at least four, at least five, at least six, at least seven, at least eight, at least nine, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, *Incertae sedis,* Lasiosphaeriaceae, Netriaceae, and Pleosporaceae.

In some examples, at least two, at least three, at least four, at least five, at least six, at least seven, at least eight, at least night, at least ten, or more than ten bacteria and bacterial populations of an endophytic combination are selected from one of the following families: Bacillaceae, Burkholderiaceae, Comamonadaceae, Enterobacteriaceae, Flavobacteriaceae, Methylobacteriaceae, Microbacteriaceae, Paenibacillileae, Pseudomonnaceae, Rhizobiaceae, Sphingomonadaceae, Xanthomonadaceae, Cladosporiaceae, Gnomoniaceae, *Incertae sedis,* Lasiosphaeriaceae, Netriaceae, Pleosporaceae.

Examples of compositions may include seed coatings for commercially important agricultural crops, for example, *sorghum,* canola, tomato, strawberry, barley, rice, maize, and wheat. Examples of compositions can also include seed coatings for corn, soybean, canola, *sorghum,* potato, rice, vegetables, cereals, and oilseeds. Seeds as provided herein can be genetically modified organisms (GMO), non-GMO, organic, or conventional. In some examples, compositions may be sprayed on the plant aerial parts, or applied to the roots by inserting into furrows in which the plant seeds are planted, watering to the soil, or dipping the roots in a suspension of the composition. In some examples, compositions may be dehydrated in a suitable manner that maintains cell viability and the ability to artificially inoculate and colonize host plants. The bacterial species may be present in compositions at a concentration of between $10^8$ to $10^{10}$ CFU/ml. In some examples, compositions may be supplemented with trace metal ions, such as molybdenum ions, iron ions, manganese ions, or combinations of these ions. The concentration of ions in examples of compositions as described herein may between about 0.1 mM and about 50 mM. Some examples of compositions may also be formulated with a carrier, such as beta-glucan, carboxylmethyl cellulose (CMC), bacterial extracellular polymeric substance (EPS), sugar, animal milk, or other suitable carriers. In some examples, peat or planting materials can be used as a carrier, or biopolymers in which a composition is entrapped in the biopolymer can be used as a carrier.

The compositions comprising the bacterial populations described herein may be coated onto the surface of a seed. As such, compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a dessicant, a bactericide, a nutrient, or any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% to about 35%, or between about 20% to about 30%. In some cases, it is advantageous for the formulation to contain agents such as a fungicide, an antibacterial agent, an herbicide, a nematicide, an insecticide, a plant growth regulator, a rodenticide, bactericide, or a nutrient. In some examples, agents may include protectants that provide protection against seed surface-borne pathogens. In some examples, protectants may provide some level of control of soil-borne pathogens. In some examples, protectants may be effective predominantly on a seed surface.

In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil.

In some examples, fungicide can be a systemic fungicide, which can be absorbed into the emerging seedling and inhibit or kill the fungus inside host plant tissues. Systemic fungicides used for seed treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances which can kill or otherwise prevent the growth of fungi. Any type of fungicide, particularly ones that are commonly used on plants, can be used as a control agent in a seed composition.

In some examples, the seed coating composition comprises a control agent which has antibacterial properties. In one embodiment, the control agent with antibacterial properties is selected from the compounds described herein elsewhere. In another embodiment, the compound is Streptomycin, oxytetracycline, oxolinic acid, or gentamicin. Other examples of antibacterial compounds which can be used as part of a seed coating composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some examples, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-tri-iodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and Rhizobacteria. Particularly preferred nematode-antagonistic biocontrol agents include ARF18, *Arthrobotrys oligospora, Arthrobotrys dactyloides, Chaetomium globosum, Cylindrocarpon heteronema, Exophilia jeanselmei, Exophilia piscipila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli,* vesicular-Arbuscular mycorrhizal fungi, *Burkholderia cepacia, Pasteuria penetrans, Pasteuria thornei, Pasteuria*

*nishizawae, Pasteuria ramosa, Pastrueia usage, Brevibacillus laterosporus* strain G4, *Pseudomonas fluorescens* and Rhizobacteria.

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

Application of Bacterial Populations on Crops

The composition of the bacteria or bacterial population described herein can be applied in furrow, in talc, or as seed treatment. The composition can be applied to a seed package in bulk, mini bulk, in a bag, or in talc.

The planter can plant the treated seed and grows the crop according to conventional ways, twin row, or ways that do not require tilling. The seeds can be distributed using a control hopper or an individual hopper. Seeds can also be distributed using pressurized air or manually. Seed placement can be performed using variable rate technologies. Additionally, application of the bacteria or bacterial population described herein may be applied using variable rate technologies. In some examples, the bacteria can be applied to seeds of corn, soybean, canola, *sorghum*, potato, rice, vegetables, cereals, pseudocereals, and oilseeds. Examples of cereals may include barley, fonio, oats, palmer's grass, rye, pearl millet, *sorghum*, spelt, teff, triticale, and wheat. Examples of pseudocereals may include breadnut, buckwheat, cattail, chia, flax, grain amaranth, hanza, quinoa, and sesame. In some examples, seeds can be genetically modified organisms (GMO), non-GMO, organic or conventional.

Additives such as micro-fertilizer, PGR, herbicide, insecticide, and fungicide can be used additionally to treat the crops. Examples of additives include crop protectants such as insecticides, nematicides, fungicide, enhancement agents such as colorants, polymers, pelleting, priming, and disinfectants, and other agents such as inoculant, PGR, softener, and micronutrients. PGRs can be natural or synthetic plant hormones that affect root growth, flowering, or stem elongation. PGRs can include auxins, gibberellins, cytokinins, ethylene, and abscisic acid (ABA).

The composition can be applied in furrow in combination with liquid fertilizer. In some examples, the liquid fertilizer may be held in tanks. NPK fertilizers contain macronutrients of sodium, phosphorous, and potassium.

The composition may improve plant traits, such as promoting plant growth, maintaining high chlorophyll content in leaves, increasing fruit or seed numbers, and increasing fruit or seed unit weight. Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, tolerance to low nitrogen stress, nitrogen use efficiency, resistance to nematode stress, resistance to a fungal pathogen, resistance to a bacterial pathogen, resistance to a viral pathogen, level of a metabolite, modulation in level of a metabolite, proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under identical conditions. In some examples, the desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under similar conditions.

An agronomic trait to a host plant may include, but is not limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation In some cases, plants are inoculated with bacteria or bacterial populations that are isolated from the same species of plant as the plant element of the inoculated plant. For example, an bacteria or bacterial population that is normally found in one variety of *Zea mays* (corn) is associated with a plant element of a plant of another variety of *Zea mays* that in its natural state lacks said bacteria and bacterial populations. In one embodiment, the bacteria and bacterial populations is derived from a plant of a related species of plant as the plant element of the inoculated plant. For example, an bacteria and bacterial populations that is normally found in *Zea diploperennis* Iltis et al., (diploperennial teosinte) is applied to a *Zea mays* (corn), or vice versa. In some cases, plants are inoculated with bacteria and bacterial populations that are heterologous to the plant element of the inoculated plant. In one embodiment, the bacteria and bacterial populations is derived from a plant of another species. For example, an bacteria and bacterial populations that is normally found in dicots is applied to a monocot plant (e.g., inoculating corn with a soybean-derived bacteria and bacterial populations), or vice versa. In other cases, the bacteria and bacterial populations to be inoculated onto a plant is derived from a related species of the plant that is being inoculated. In one embodiment, the bacteria and bacterial populations is derived from a related taxon, for example, from a related species. The plant of another species can be an agricultural plant. In another embodiment, the bacteria and bacterial populations is part of a designed composition inoculated into any host plant element.

In some examples, the bacteria or bacterial population is exogenous wherein the bacteria and bacterial population is isolated from a different plant than the inoculated plant. For example, in one embodiment, the bacteria or bacterial population can be isolated from a different plant of the same species as the inoculated plant. In some cases, the bacteria or bacterial population can be isolated from a species related to the inoculated plant.

In some examples, the bacteria and bacterial populations described herein are capable of moving from one tissue type to another. For example, the present invention's detection and isolation of bacteria and bacterial populations within the mature tissues of plants after coating on the exterior of a seed demonstrates their ability to move from seed exterior into the vegetative tissues of a maturing plant. Therefore, in one embodiment, the population of bacteria and bacterial populations is capable of moving from the seed exterior into the vegetative tissues of a plant. In one embodiment, the bacteria and bacterial populations that is coated onto the seed of a plant is capable, upon germination of the seed into a vegetative state, of localizing to a different tissue of the plant. For example, bacteria and bacterial populations can be capable of localizing to any one of the tissues in the plant, including: the root, adventitious root, seminal 5 root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the bacteria and bacterial populations is capable of localizing to the root and/or the root hair of the plant. In another embodiment, the bacteria and bacterial populations is capable of localizing to the photosynthetic tissues, for example, leaves and shoots of the plant. In other cases, the bacteria and bacterial populations is localized to the vascular tissues of the plant, for example, in the xylem and phloem. In still another embodiment, the bacteria and bacterial populations is capable of localizing to the reproductive tissues (flower, pollen, pistil, ovaries, stamen, fruit) of the plant. In another embodiment, the bacteria and bacterial populations is capable of localizing to the root, shoots, leaves and reproductive tissues of the plant. In still another embodiment, the bacteria and bacterial populations colonizes a fruit or seed tissue of the plant. In still another embodiment, the bacteria and bacterial populations is able to colonize the plant such that it is present in the surface of the plant (i.e., its presence is detectably present on the plant exterior, or the episphere of the plant). In still other embodiments, the bacteria and bacterial populations is capable of localizing to substantially all, or all, tissues of the plant. In certain embodiments, the bacteria and bacterial populations is not localized to the root of a plant. In other cases, the bacteria and bacterial populations is not localized to the photosynthetic tissues of the plant.

The effectiveness of the compositions can also be assessed by measuring the relative maturity of the crop or the crop heating unit (CHU). For example, the bacterial population can be applied to corn, and corn growth can be assessed according to the relative maturity of the corn kernel or the time at which the corn kernel is at maximum weight. The crop heating unit (CHU) can also be used to predict the maturation of the corn crop. The CHU determines the amount of heat accumulation by measuring the daily maximum temperatures on crop growth.

In examples, bacterial may localize to any one of the tissues in the plant, including: the root, adventitious root, seminal root, root hair, shoot, leaf, flower, bud tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In another embodiment, the bacteria or bacterial population is capable of localizing to the photosynthetic tissues, for example, leaves and shoots of the plant. In other cases, the bacteria and bacterial populations is localized to the vascular tissues of the plant, for example, in the xylem and phloem. In another embodiment, the bacteria or bacterial population is capable of localizing to reproductive tissues (flower, pollen, pistil, ovaries, stamen, or fruit) of the plant. In another embodiment, the bacteria and bacterial populations is capable of localizing to the root, shoots, leaves and reproductive tissues of the plant. In another embodiment, the bacteria or bacterial population colonizes a fruit or seed tissue of the plant. In still another embodiment, the bacteria or bacterial population is able to colonize the plant such that it is present in the surface of the plant. In another embodiment, the bacteria or bacterial population is capable of localizing to substantially all, or all, tissues of the plant. In certain embodiments, the bacteria or bacterial population is not localized to the root of a plant. In other cases, the bacteria and bacterial populations is not localized to the photosynthetic tissues of the plant.

The effectiveness of the bacterial compositions applied to crops can be assessed by measuring various features of crop growth including, but not limited to, planting rate, seeding vigor, root strength, drought tolerance, plant height, dry down, and test weight.

Plant Species

The methods and bacteria described herein are suitable for any of a variety of plants, such as plants in the genera *Hordeum*, *Oryza*, *Zea*, and *Triticeae*. Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. In some examples, plants may be used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human-food product, a sugar, an alcohol, and/or a protein. Non-limiting examples of crop plants include maize, rice, wheat, barley, sorghum, millet, oats, rye triticale, buckwheat, sweet corn, sugar cane, onions, tomatoes, strawberries, and asparagus.

In some examples, plants that may be obtained or improved using the methods and composition disclosed herein may include plants that are important or interesting for agriculture, horticulture, biomass for the production of biofuel molecules and other chemicals, and/or forestry. Some examples of these plants may include pineapple, banana, coconut, lily, grasspeas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum bicolor* (sorghum, sudan), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp. *Sorghum* spp., *Miscanthus* spp., *Saccharum* spp., *Erianthus* spp., *Populus* spp., *Secale cereale* (rye), *Salix* spp. (willow), *Eucalyptus* spp. (*eucalyptus*), *Triticosecale* spp. (*triticum*-25 wheat X rye), Bamboo, *Carthamus tinctorius* (safflower), *Jatropha curcas* (*Jatropha*), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea*, *Manihot esculenta* (cassava), *Lycopersicon esculentum* (tomato), *Lactuca saliva* (lettuce), *Musa paradisiaca* (banana), *Solanum tuberosum* (potato), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacia oleracea* (spinach), *Citrullus lanatus* (watermelon), *Abelmoschus esculentus* (okra), *Solanum melongena* (eggplant), *Papaver somniferum* (opium poppy), *Papaver orientale*, *Taxus baccata*, *Taxus brevifolia*, *Artemisia annua*, *Cannabis saliva*, *Camptotheca acuminate*, *Catharanthus roseus*, *Vinca rosea*, *Cinchona officinalis*, *Coichicum autumnale*, *Veratrum californica*, *Digitalis lanata*, *Digitalis purpurea*, *Dioscorea* spp., *Andrographis paniculata*, *Atropa belladonna*, *Datura stomonium*, *Berberis* spp., *Cephalotaxus* spp., *Ephedra sinica*, *Ephedra* spp., *Erythroxylum coca*, *Galanthus wornorii*, *Scopolia* spp., *Lycopodium serratum* (*Huperzia serrata*), *Lycopodium* spp., *Rauwolfia serpentina*, *Rauwolfia* spp., *Sanguinaria canadensis*, *Hyoscyamus* spp., *Calendula officinalis*, *Chrysanthemum parthenium*, *Coleus forskohlii*, *Tanacetum parthenium*, *Parthenium argentatum* (guayule), *Hevea* spp. (rubber), *Mentha spicata* (mint), *Mentha piperita* (mint), *Bixa orellana*, *Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some examples, a monocotyledonous plant may be used. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales. In some examples, the monocotyledonous plant can be selected from the group consisting of a maize, rice, wheat, barley, and sugarcane.

In some examples, a dicotyledonous plant may be used, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. In some examples, the dicotyledonous plant can be selected from the group consisting of cotton, soybean, pepper, and tomato.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria*, *Brachypodium*, and *Arabidopsis*. Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

EXAMPLES

The examples provided herein describe methods of bacterial isolation, bacterial and plant analysis, and plant trait improvement. The examples are for illustrative purposes only and are not to be construed as limiting in any way.

Example 1: Isolation of Microbes from Plant Tissue

Topsoil was obtained from various agricultural areas in central California. Twenty soils with diverse texture characteristics were collected, including heavy clay, peaty clay loam, silty clay, and sandy loam. Seeds of various field corn, sweet corn, heritage corn and tomato were planted into each soil, as shown in Table 1.

TABLE 1

Crop Type and Varieties planted into soil with diverse characteristics

| Crop Type | Field Corn | Sweet Corn | Heritage Corn | Tomato |
|---|---|---|---|---|
| Varieties | Mo17 | Ferry-Morse 'Golden Cross Bantam T-51' | Victory Seeds 'Moseby Prolific' | Ferry-Morse Roma VF |
| | B73 | Ferry-Morse 'Silver Queen Hybrid' | Victory Seeds 'Reid's Yellow Dent' | Stover Roma |
| | DKC 66-40 | Ferry-Morse 'Sugar Dots' | Victory Seeds 'Hickory King' | Totally Tomatoes 'Micro Tom Hybrid' |
| | DKC 67-07 | | | Heinz 1015 |
| | DKC 70-01 | | | Heinz 2401 |
| | | | | Heinz 3402 |
| | | | | Heinz 5508 |
| | | | | Heinz 5608 |
| | | | | Heinz 8504 |

Plants were uprooted after 2-4 weeks of growth and excess soil on root surfaces was removed with deionized water. Following soil removal, plants were surface sterilized with bleach and rinsed vigorously in sterile water. A cleaned, 1 cm section of root was excised from the plant and placed in a phosphate buffered saline solution containing 3 mm steel beads. A slurry was generated by vigorous shaking of the solution with a Qiagen TissueLyser II.

Figure 1B:
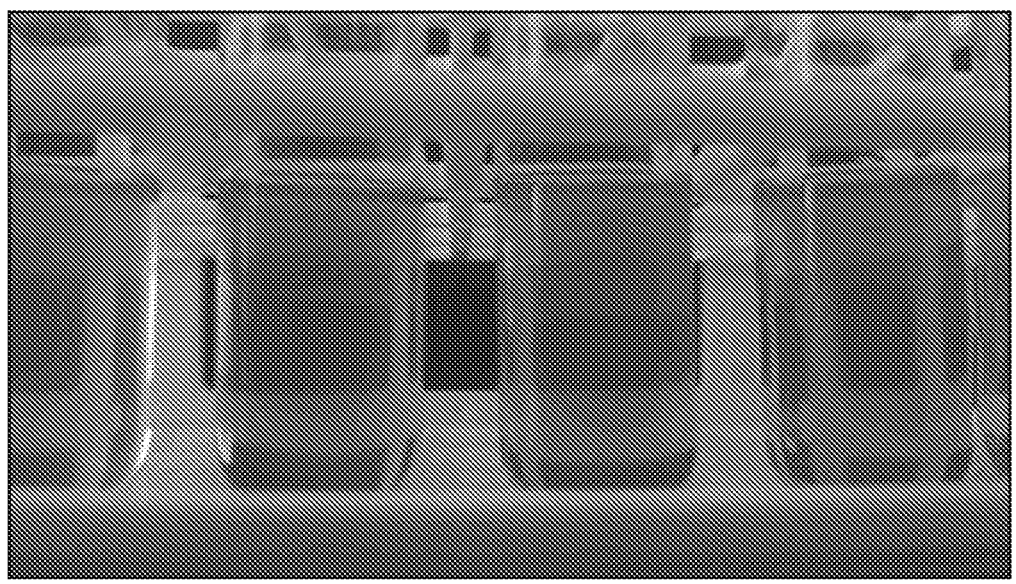

The root and saline slurry was diluted and inoculated onto various types of growth media to isolate rhizospheric, endophytic, epiphytic, and other plant-associated microbes. R2A and Nfb agar media were used to obtain single colonies, and semisolid Nfb media slants were used to obtain populations of nitrogen fixing bacteria. After 2-4 weeks incubation in semi-solid Nfb media slants, microbial populations were collected and streaked to obtain single colonies on R2A agar, as shown in FIGS. 1A-B. Single colonies were resuspended in a mixture of R2A and glycerol, subjected to PCR analysis, and frozen at −80° C. for later analysis. Approximately 1,000 single colonies were obtained and designated "isolated microbes."

Figure 2:
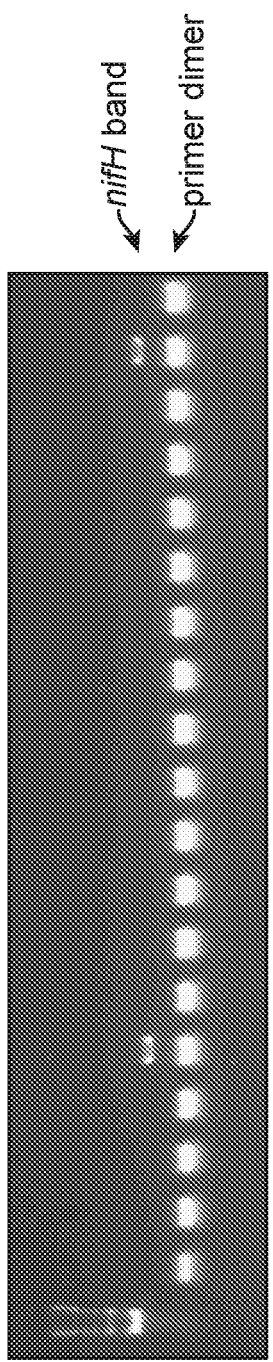
FIG. 2 depicts a representative nifH PCR screen. Positive bands were observed at ~350 bp for two colonies in this screen. Lower bands represent primer-dimers.

Isolates were then subjected to a colony PCR screen to detect the presence of the nifH gene in order to identify diazotrophs. The previously-described primer set Ueda 19F/388R, which has been shown to detect over 90% of diazotrophs in screens, was used to probe the presence of the nif cluster in each isolate (Ueda et al. 1995; J. Bacteriol. 177: 1414-1417). Single colonies of purified isolates were picked, resuspended in PBS, and used as a template for colony PCR, as shown in FIG. 2. Colonies of isolates that gave positive PCR bands were re-streaked, and the colony PCR and re-streaking process was repeated twice to prevent false positive identification of diazotrophs. Purified isolates were then designated "candidate microbes."

Example 2: Characterization of Isolated Microbes

Sequencing, Analysis and Phylogenetic Characterization

Sequencing of 16S rDNA with the 515f-806r primer set was used to generate preliminary phylogenetic identities for isolated and candidate microbes (see e.g. Vernon et al.; BMC Microbiol. 2002 Dec. 23; 2:39.). The microbes comprise diverse genera including: *Enterobacter, Burkholderia, Klebsiella, Bradyrhizobium, Rahnella, Xanthomonas, Raoultella, Pantoea, Pseudomonas, Brevundimonas, Agrobacterium,* and *Paenibacillus*, as shown in Table 2.

TABLE 2

Diversity of microbes isolated from tomato plants as determined by deep 16S rDNA sequencing.

| Genus | Isolates |
|---|---|
| *Achromobacter* | 7 |
| *Agrobacterium* | 117 |
| *Agromyces* | 1 |
| *Alicyctobacillus* | 1 |
| *Asticcacaulis* | 6 |
| *Bacillus* | 131 |
| *Bradyrhizobium* | 2 |
| *Brevibacillus* | 2 |
| *Burkholderia* | 2 |
| *Caulobacter* | 17 |
| *Chryseobacterium* | 42 |
| *Comamonas* | 1 |
| *Dyadobacter* | 2 |
| *Flavobacterium* | 46 |
| *Halomonas* | 3 |
| *Leptothrix* | 3 |
| *Lysobacter* | 2 |
| *Neisseria* | 13 |
| *Paenibacillus* | 1 |
| *Paenisporosarcina* | 3 |

TABLE 2-continued

Diversity of microbes isolated from tomato plants as determined by deep 16S rDNA sequencing.

| Genus | Isolates |
|---|---|
| Pantoea | 14 |
| Pedobacter | 16 |
| Pimelobacter | 2 |
| Pseudomonas | 212 |
| Rhizobium | 4 |
| Rhodoferax | 1 |
| Sphingobacterium | 13 |
| Sphingobium | 23 |
| Sphingomonas | 3 |
| Sphingopyxis | 1 |
| Stenotrophomonas | 59 |
| Streptococcus | 3 |
| Variovorax | 37 |
| Xylanimicrobium | 1 |
| unidentified | 75 |

Subsequently, the genomes of 39 candidate microbes were sequenced using Illumina Miseq platform. Genomic DNA from pure cultures was extracted using the QIAmp DNA mini kit (QIAGEN), and total DNA libraries for sequencing were prepared through a third party vendor (SeqMatic, Hayward). Genome assembly was then carried out via the A5 pipeline (Tritt et al. 2012; PLoS One 7(9):e42304). Genes were identified and annotated, and those related to regulation and expression of nitrogen fixation were noted as targets for mutagenesis.

Transcriptomic Profiling of Candidate Microbes

Transcriptomic profiling of strain CI010 was performed to identify promoters that are active in the presence of environmental nitrogen. Strain CI010 was cultured in a defined, nitrogen-free media supplemented with 10 mM glutamine. Total RNA was extracted from these cultures (QIAGEN RNeasy kit) and subjected to RNAseq sequencing via Illumina HiSeq (SeqMatic, Fremont CA). Sequencing reads were mapped to CI010 genome data using Geneious, and highly expressed genes under control of proximal transcriptional promoters were identified. Tables 3A-C lists genes and their relative expression level as measured through RNASeq sequencing of total RNA. Sequences of the proximal promoters were recorded for use in mutagenesis of nif pathways, nitrogen utilization related pathways, or other genes with a desired expression level.

Assessment of Genetic Tractability

Candidate microbes were characterized based on transformability and genetic tractability. First, optimal carbon source utilization was determined by growth on a small panel of relevant media as well as a growth curve in both nitrogen-free and rich media. Second, the natural antibiotic resistance of each strain was determined through spot-plating and growth in liquid culture containing a panel of antibiotics used as selective markers for mutagenesis. Third, each strain was tested for its transformability through electroporation of a collection of plasmids. The plasmid collection comprises the combinatorial expansion of seven origins of replication, i.e., p15a, pSC101, CloDF, colA, RK2, pBBR1, and pRO1600 and four antibiotic resistance markers, i.e., CmR, KmR, SpecR, and TetR. This systematic evaluation of origin and resistance marker compatibility was used to identify vectors for plasmid-based mutagenesis in candidate microbes.

Example 3: Mutagenesis of Candidate Microbes

Lambda-Red Mediated Knockouts

Several mutants of candidate microbes were generated using the plasmid pKD46 or a derivative containing a kanamycin resistance marker (Datsenko et al. 2000; PNAS 97(12): 6640-6645). Knockout cassettes were designed with 250 bp homology flanking the target gene and generated via overlap extension PCR. Candidate microbes were transformed with pKD46, cultured in the presence of arabinose to induce Lambda-Red machinery expression, prepped for electroporation, and transformed with the knockout cassettes to produce candidate mutant strains. Four candidate microbes and one laboratory strain, Klebsiella oxytoca M5A1, were used to generate thirteen candidate mutants of the nitrogen fixation regulatory genes nifL, glnB, and amtB, as shown in Table 4.

TABLE 4

List of single knockout mutants created through Lambda-red mutagenesis Oligo-Directed Mutagenesis with Cas9 Selection

| Strain | nifL | glnB | amtB |
|---|---|---|---|
| M5A1 | X | X | X |
| CI006 | X | X | X |
| CI010 | X | X | X |
| CI019 | X | X | |
| CI028 | X | X | |

Oligo-directed mutagenesis was used to target genomic changes to the rpoB gene in E. coli DH10B, and mutants were selected with a CRISPR-Cas system. A mutagenic oligo (ss1283: "G*T*T*G*ATCAGACCGATGTTCGG-ACCTTCcaagGTTTCGATCGGACATACGCGAC CGTAGTGGGTCGGGTGTACGTCTCGAACTT-CAAAGCC", where * denotes phosphorothioate bond) was designed to confer rifampicin resistance through a 4-bp mutation to the rpoB gene. Cells containing a plasmid encoding Cas9 were induced for Cas9 expression, prepped for electroporation, and then electroporated with both the mutagenic oligo and a plasmid encoding constitutive expression of a guide RNA (gRNA) that targets Cas9 cleavage of the WT rpoB sequence. Electroporated cells were recovered in nonselective media overnight to allow sufficient segregation of the resulting mutant chromosomes. After plating on selection for the gRNA-encoding plasmid, two out of ten colonies screened were shown to contain the desired mutation, while the rest were shown to be escape mutants generated through protospacer mutation in the gRNA plasmid or Cas9 plasmid loss.

Lambda-Red Mutagenesis with Cas9 Selection

Figure 3:
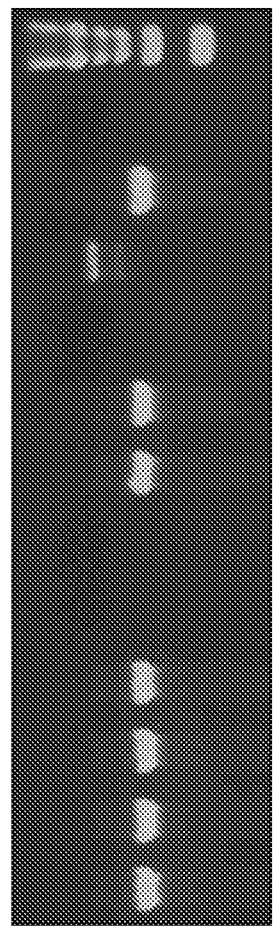
FIG. 3 depicts an example of a PCR screen of colonies from CRISPR-Cas-selected mutagenesis. CI006 colonies were screened with primers specific for the nifL locus. The wild type PCR product is expected at ~2.2 kb, whereas the mutant is expected at ~1.1 kb. Seven of ten colonies screened unambiguously show the desired deletion.

Mutants of candidate microbes CI006 and CI010 were generated via lambda-red mutagenesis with selection by CRISPR-Cas. Knockout cassettes contained an endogenous promoter identified through transcriptional profiling (as described in Example 2 and depicted in Table 3) and ~250 bp homology regions flanking the deletion target. CI006 and CI010 were transformed with plasmids encoding the Lambda-red recombination system (exo, beta, gam genes) under control of an arabinose inducible promoter and Cas9 under control of an IPTG inducible promoter. The Red recombination and Cas9 systems were induced in resulting transformants, and strains were prepared for electroporation. Knockout cassettes and a plasmid-encoded selection gRNA were subsequently transformed into the competent cells. After plating on antibiotics selective for both the Cas9 plasmid and the gRNA plasmid, 7 of the 10 colonies screened showed the intended knockout mutation, as shown in FIG. 3.

Example 4: In Vitro Phenotyping of Candidate Molecules

The impact of exogenous nitrogen on nitrogenase biosynthesis and activity in various mutants was assessed. The Acetylene Reduction Assay (ARA) (Temme et. al. 2012; 109(18): 7085-7090) was used to measure nitrogenase activity in pure culture conditions. Strains were grown in air-tight test tubes, and reduction of acetylene to ethylene was quantified with an Agilent 6890 gas chromatograph. ARA activities of candidate microbes and counterpart candidate mutants grown in nitrogen fixation media supplemented with 0 to 10 mM glutamine are shown in FIGS. 4A-B and FIGS. 10A-C.

Figure 11:
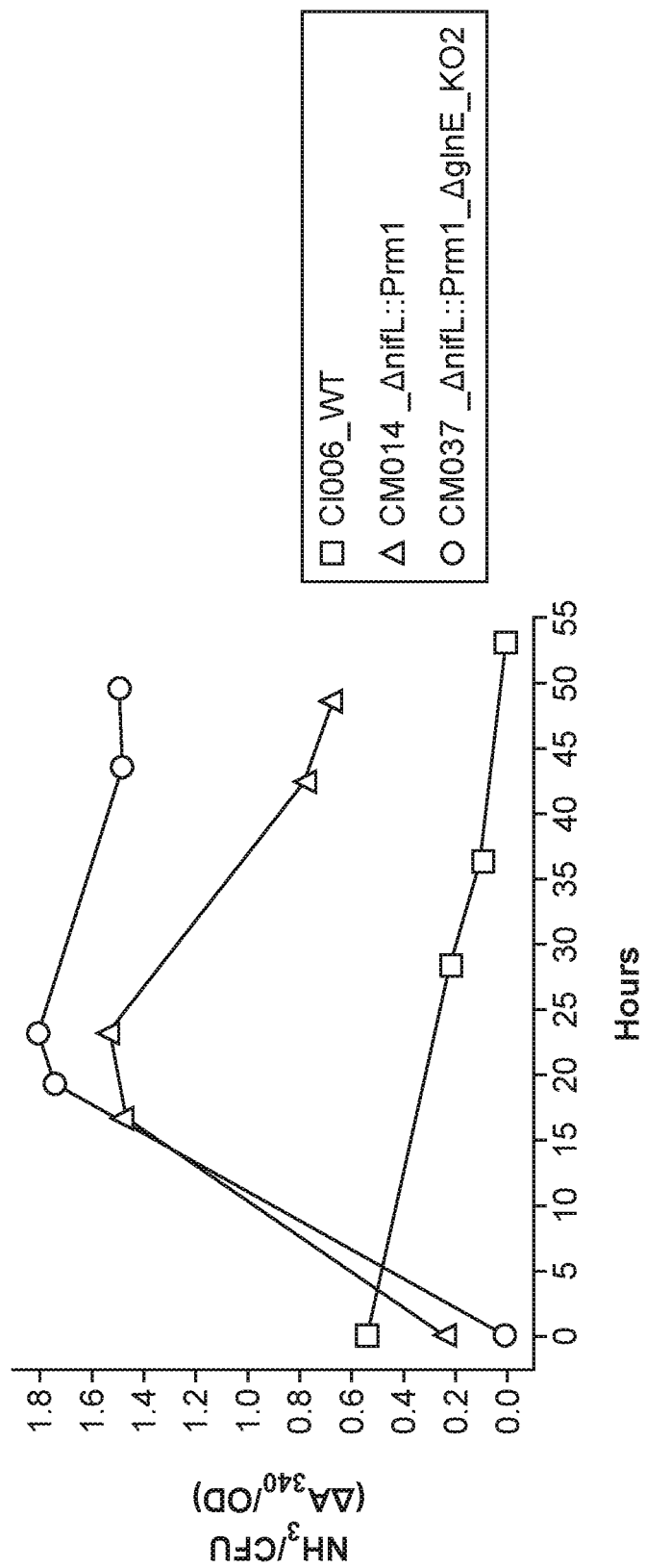
FIG. 11 depicts a double mutant that exhibits higher ammonia excretion than the single mutant from which it was derived.

Under anaerobic culture conditions, a range of glutamine and ammonia concentrations was tested to quantify impact on nitrogen fixation activity. In wild-type cells, activity quickly diminished as glutamine concentrations increased. However, in a series of initial knock-out mutations, a class of mutation was validated enabling expression of nitrogen fixation genes under concentrations of glutamine that would otherwise shut off activity in wild type. This profile was generated in four different species of diazotrophs, as seen in FIG. 4C. In addition, by rewiring the regulatory network using genetic parts that have been identified, the nitrogen fixation activity level was tuned predictably. This is seen in FIG. 4B, which illustrates strains CM023, CM021, CM015, and CI006. Strain CM023 is an evolved strain low; strain CM021 is an evolved strain high; strain CM015 is an evolved strain mid; strain CI006 is a wild-type (strain 2). Ammonia excreted into culture supernatants was tested using a enzymatic-based assay (MEGAZYME). The assay measures the amount of NADPH consumed in the absorbance of 340 nm. The assay was conducted on bacterial cultures grown in nitrogen-free, anaerobic environment with a starting density of 1E9 CFU/ml. Across a panel of six evolved strains, one strain excreted up to 100 µM of ammonia over a course of a 48 hour period, as seen in FIG. 4D. Further, a double mutant exhibited higher ammonia excretion than the single mutant from which it was derived, as seen in FIG. 11. This demonstrates a microbial capacity to produce ammonia in excess of its physiological needs.

Transcription Profiling of Pure Cultures

Transcriptional activity of CI006 was measured using the Nanostring Elements platform. Cells were grown in nitrogen-free media and 10E8 cells were collected after 4 hours incubation. Total RNA was extracted using the Qiagen RNeasy kit. Purified RNA was submitted to Core Diagnostics in Palo Alto, CA, for probe hybridization and Digital Analyzer analysis, as shown in FIG. 5.

Example 5: In Planta Phenotyping of Candidate Microbes

Colonization of Plants by Candidate Microbes

Figure 6:
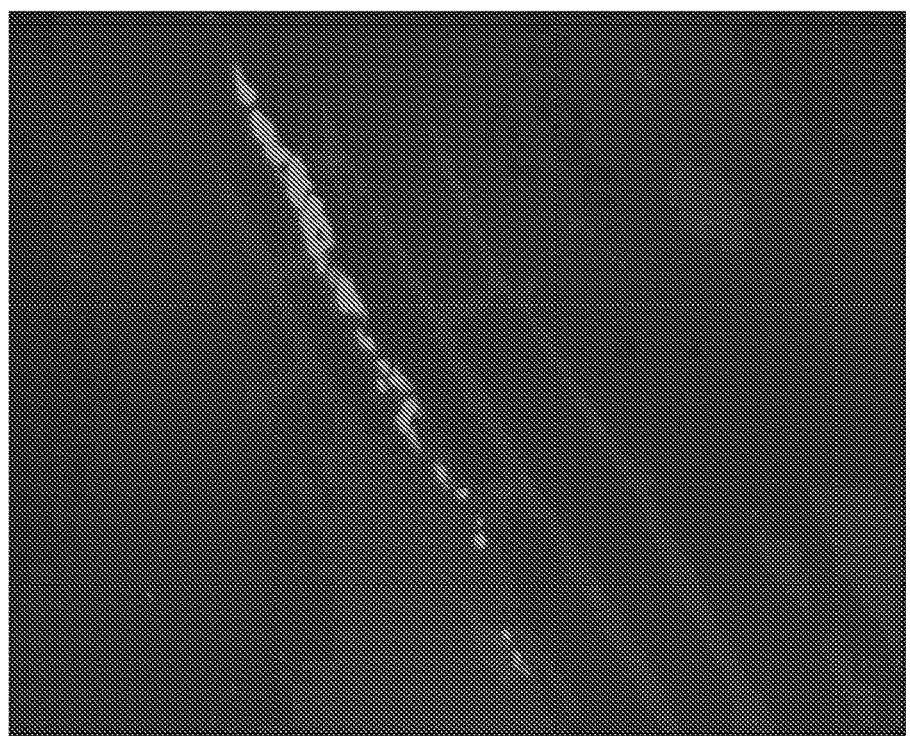
FIG. 6 depicts CI006 colonization of corn roots. Corn seedlings were inoculated with CI006 harboring an RFP expression plasmid. After two weeks of growth and plasmid maintenance through watering with the appropriate antibiotic, roots were harvested and imaged through fluorescence microscopy. Colonization of the root intercellular space is observed.

Colonization of desired host plants by a candidate microbe was quantified through short-term plant growth experiments. Corn plants were inoculated with strains expressing RFP either from a plasmid or from a Tn5-integrated RFP expression cassette. Plants were grown in both sterilized sand and nonsterile peat medium, and inoculation was performed by pipetting 1 mL of cell culture directly over the emerging plant coleoptile three days post-germination. Plasmids were maintained by watering plants with a solution containing the appropriate antibiotic. After three weeks, plant roots were collected, rinsed three times in sterile water to remove visible soil, and split into two samples. One root sample was analyzed via fluorescence microscopy to identify localization patterns of candidate microbes. Microscopy was performed on 10 mm lengths of the finest intact plant roots, as shown in FIG. 6.

A second quantitative method for assessing colonization was developed. A quantitative PCR assay was performed on whole DNA preparations from the roots of plants inoculated with the endophytes. Seeds of corn (Dekalb DKC-66-40) were germinated in previously autoclaved sand in a 2.5 inch by 2.5 inch by 10 inch pot. One day after planting, 1 ml of endophyte overnight culture (SOB media) was drenched right at the spot of where the seed was located. 1 mL of this overnight culture is roughly equivalent to about $10^9$ cfu, varying within 3-fold of each other, depending on which strain is being used. Each seedling was fertilized 3× weekly with 50 mL modified Hoagland's solution supplemented with either 2.5 mM or 0.25 mM ammonium nitrate. At four weeks after planting, root samples were collected for DNA extraction. Soil debris were washed away using pressurized water spray. These tissue samples were then homogenized using QIAGEN Tissuelyzer and the DNA was then extracted using QIAmp DNA Mini Kit (QIAGEN) according to the recommended protocol. qPCR assay was performed using Stratagene Mx3005P RT-PCR on these DNA extracts using primers that were designed (using NCBI's Primer BLAST) to be specific to a loci in each of the endophyte's genome. The presence of the genome copies of the endophytes was quantified. To further confirm the identity of the endophytes, the PCR amplification products were sequenced and are confirmed to have the correct sequence. The summary of the colonization profile of strain CI006 and CI008 from candidate microbes are presented in Table 5. Colonization rate as high as $10^7$× cfu/g fw of root was demonstrated in strain CI008.

TABLE 5

Colonization of corn as measured by qPCR

| Strain | Colonization Rate (CFU/g fw) |
|---|---|
| CI006 | $1.45 \times 10^5$ |
| CI008 | $1.24 \times 10^7$ |

In Planta RNA Profiling

Biosynthesis of nif pathway components in planta was estimated by measuring the transcription of nif genes. Total RNA was obtained from root plant tissue of CI006 inoculated plants (planting methods as described previously). RNA extraction was performed using RNEasy Mini Kit according to the recommended protocol (QIAGEN). Total RNA from these plant tissues was then assayed using Nanostring Elements kits (NanoString Technologies, Inc.) using probes that were specific to the nif genes in the genome of strain CI006. The data of nif gene expression in planta is summarized in Table 6. Expression of nifH genes was detected in plants inoculated by CM013 strains whereas nifH expression was not detectable in CI006 inoculated plants. Strain CM013 is a derivative of strain CI006 in which the nifL gene has been knocked out.

Highly expressed genes of CM011, ranked by transcripts per kilobase million (TPM), were measured in planta under fertilized condition. The promoters controlling expression of some of these highly expressed genes were used as templates for homologous recombination into targeted nitrogen fixation and assimilation loci. RNA samples from greenhouse grown CM011 inoculated plant were extracted, rRNA removed using Ribo-Zero kit, sequenced using Illumina's Truseq platform and mapped back to the genome of CM011. Highly expressed genes from CM011 are listed in Table 7.

TABLE 6

Expression of nifH in planta

| Strains | Relative Transcript Expression |
|---|---|
| CI006 | 9.4 |
| CM013 | 103.25 |

TABLE 7 highly expressed genes from CM011

| Gene Name | Gene Location | Direction | Raw Read Count | TPM (Transcripts Per Kilobase Million) |
|---|---|---|---|---|
| rpsH CDS | 18196-18588 | reverse | 4841.5 | 27206.4 |
| rplQ CDS | 11650-12039 | reverse | 4333 | 24536.2 |
| rpsJ CDS | 25013-25324 | reverse | 3423 | 24229 |
| rplV CDS | 21946-22278 | reverse | 3367.5 | 22333 |
| rpsN CDS | 18622-18927 | reverse | 2792 | 20150.1 |
| rplN CDS | 19820-20191 | reverse | 3317 | 19691.8 |
| rplF CDS | 17649-18182 | reverse | 4504.5 | 18628.9 |
| rpsD CDS | 13095-13715 | reverse | 5091.5 | 18106.6 |
| rpmF CDS | 8326-8493 | forward | 1363.5 | 17923.8 |
| rplW CDS | 23429-23731 | reverse | 2252 | 16413.8 |
| rpsM CDS | 14153-14509 | reverse | 2269 | 14036.2 |
| rplR CDS | 17286-17639 | reverse | 2243.5 | 13996.1 |
| rplC CDS | 24350-24979 | reverse | 3985 | 13969.2 |
| rplK CDS | 25526-25954 | reverse | 2648.5 | 13634.1 |
| rplP CDS | 20807-21217 | reverse | 2423 | 13019.5 |
| rplX CDS | 19495-19809 | reverse | 1824 | 12787.8 |
| rpsQ CDS | 20362-20616 | reverse | 1460.5 | 12648.7 |
| bhsA 3 CDS | 79720-79977 | reverse | 1464 | 12531.5 |
| rpmC CDS | 20616-20807 | reverse | 998.5 | 11485 |
| rpoA CDS | 12080-13069 | reverse | 4855 | 10830.2 |
| rplD CDS | 23728-24333 | reverse | 2916.5 | 10628.5 |
| bhsA 1 CDS | 78883-79140 | reverse | 1068 | 9141.9 |
| rpsS CDS | 22293-22571 | reverse | 1138.5 | 9011.8 |
| rpmA CDS | 2210-2467 | forward | 1028.5 | 8803.7 |
| rpmD CDS | 16585-16764 | reverse | 694.5 | 8520.8 |
| rplB CDS | 22586-23410 | reverse | 3132 | 8384 |
| rpsC CDS | 21230-21928 | reverse | 2574.5 | 8133.9 |
| rplE CDS | 18941-19480 | reverse | 1972.5 | 8066.9 |
| rplO CDS | 16147-16581 | reverse | 1551 | 7874.2 |
| preprotein translocase subunit SecY CDS | 14808-16139 | reverse | 4657 | 7721.2 |
| rpsE CDS | 16771-17271 | reverse | 1671.5 | 7368 |
| rpsK CDS | 13746-14135 | reverse | 1223.5 | 6928.2 |
| tufA CDS | 27318-28229 | reverse | 2850 | 6901.3 |
| rpmI CDS | 38574-38771 | forward | 615 | 6859.5 |
| rplU CDS | 1880-2191 | forward | 935.5 | 6621.7 |
| rplT CDS | 38814-39170 | forward | 1045 | 6464.4 |
| bhsA 2 CDS | 79293-79550 | reverse | 754 | 6454.1 |
| rpmB CDS | 8391-8627 | reverse | 682 | 6355.1 |
| rplJ CDS | 23983-24480 | reverse | 1408 | 6243.9 |
| fusA 2 CDS | 481-2595 | reverse | 5832 | 6089.6 |
| rpsA CDS | 25062-26771 | reverse | 4613 | 5957.6 |
| rpmJ CDS | 14658-14774 | reverse | 314 | 5926.9 |
| rpsR CDS | 52990-53217 | forward | 603 | 5840.7 |
| rpsG CDS | 2692-3162 | reverse | 1243 | 5828.2 |
| rpsI CDS | 11354-11746 | reverse | 980.5 | 5509.8 |
| cspC 1 CDS | 8091-8300 | reverse | 509 | 5352.8 |
| rpsF CDS | 52270-52662 | forward | 916 | 5147.4 |
| rpsT CDS | 55208-55471 | reverse | 602 | 5035.9 |
| infC CDS | 38128-38478 | forward | 755 | 4750.3 |
| cspG CDS | 30148-30360 | forward | 446 | 4624.2 |

$^{15}$N Assay

The primary method for demonstrating fixation uses the nitrogen isotope 15N, which is found in the atmosphere at a set rate relative to 14N. By supplementing either fertilizer or atmosphere with enriched levels of 15N, one can observe fixation either directly, in heightened amounts of 15N fixed from an atmosphere supplemented with 15N2 gas (Yoshida 1980), or inversely, through dilution of enriched fertilizer by atmospheric N2 gas in plant tissues (Iniguez 2004). The dilution method allows for the observation of cumulative fixed nitrogen over the course of plant growth, while the $15N_2$ gas method is restricted to measuring the fixation that occurs over the short interval that a plant can be grown in a contained atmosphere (rate measurement). Therefore, the gas method is superior in specificity (as any elevated $15N_2$ levels in the plant above the atmospheric rate can be attributed unambiguously to fixation) but cannot show cumulative activity.

Figure 7:
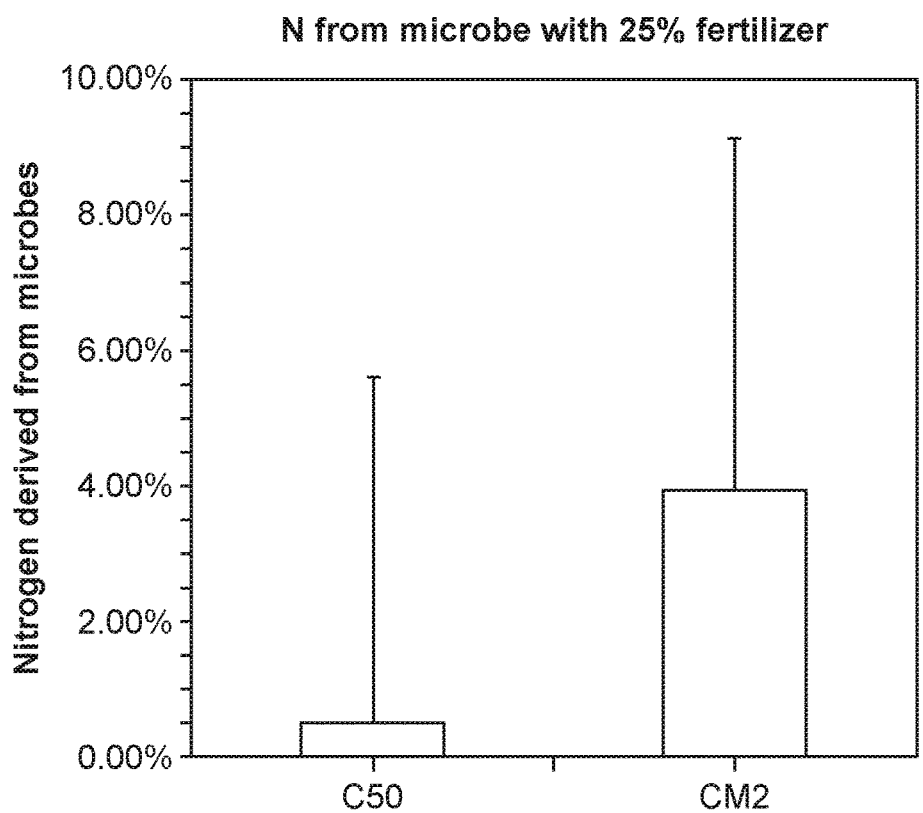
FIG. 7 depicts nitrogen derived from microbe level in WT (CI050) and optimized (CM002) strain.
Figure 12:
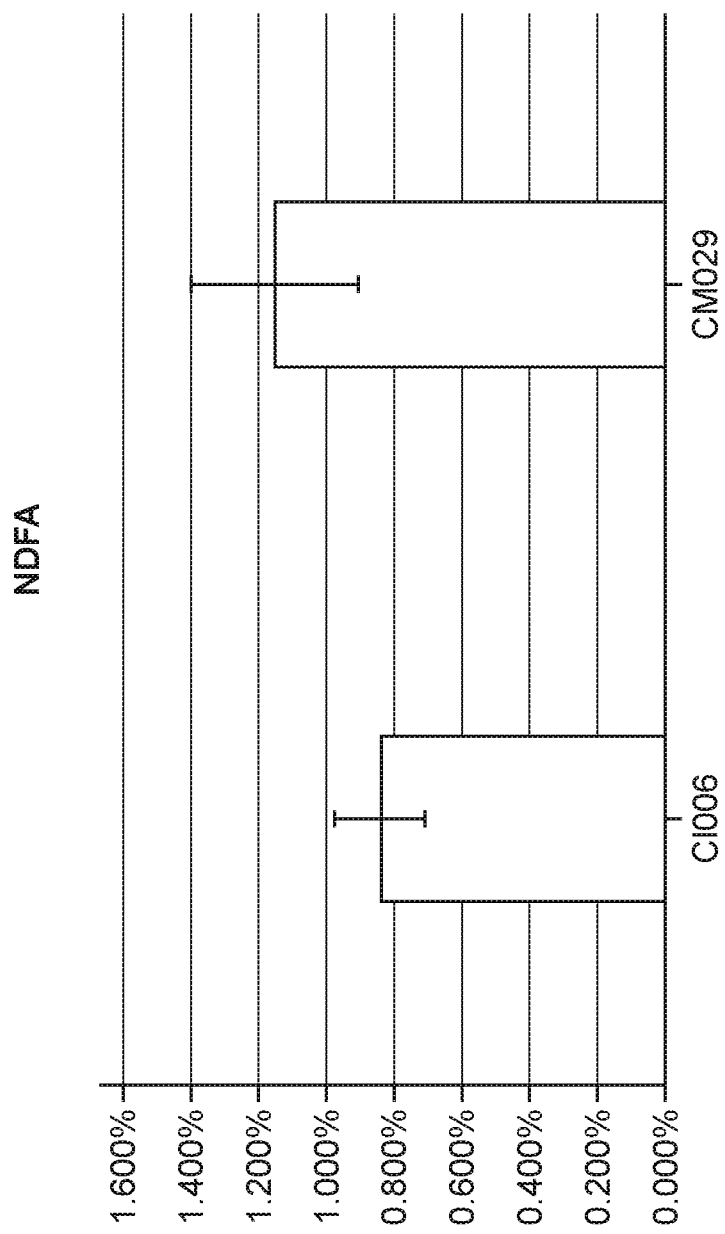
FIG. 12 depicts NDFA obtained from 15N Gas Uptake experiment (extrapolated back using days exposed) to measure NDFA in Corn plants in fertilized condition.
Figure 13:
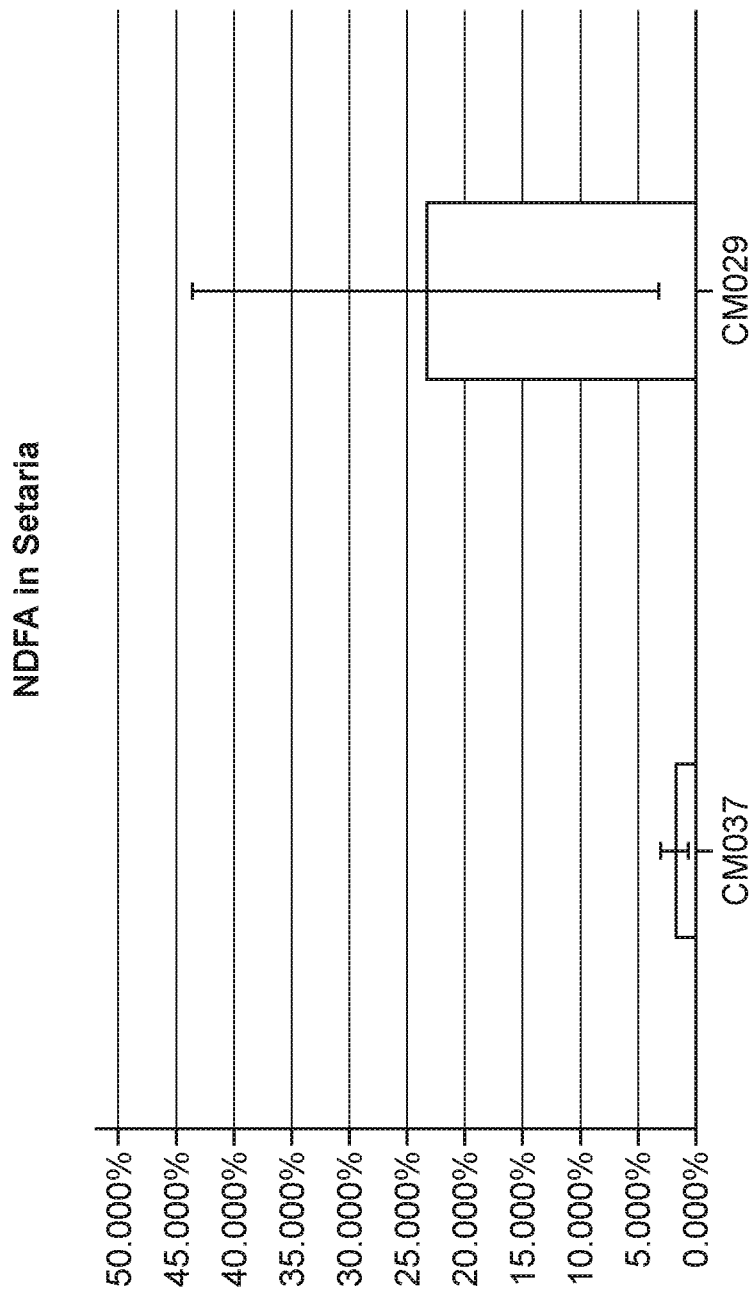
FIG. 13 depicts NDFA value obtained from 15N Gas Uptake experiment (extrapolated back using days exposed) to measure NDFA in *Setaria* plants in fertilized condition.
Figure 14A:
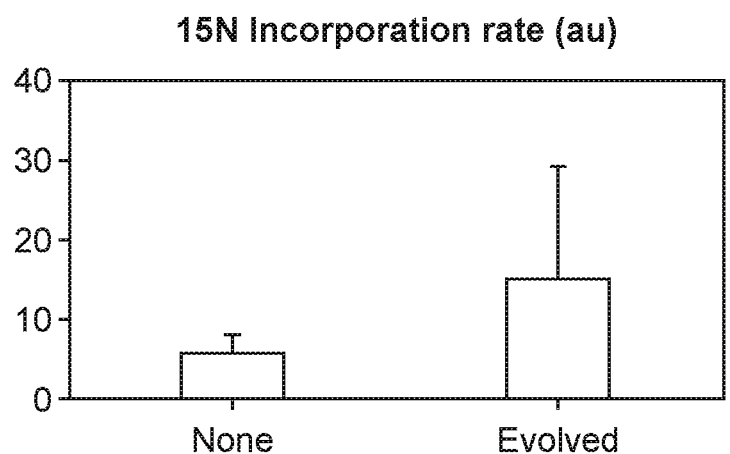
FIG. 14A depicts rate of incorporation of 15N gas. Plants inoculated with evolved strain showed increase in 15N gas incorporation compared to uninoculated plants.
Figure 14B:
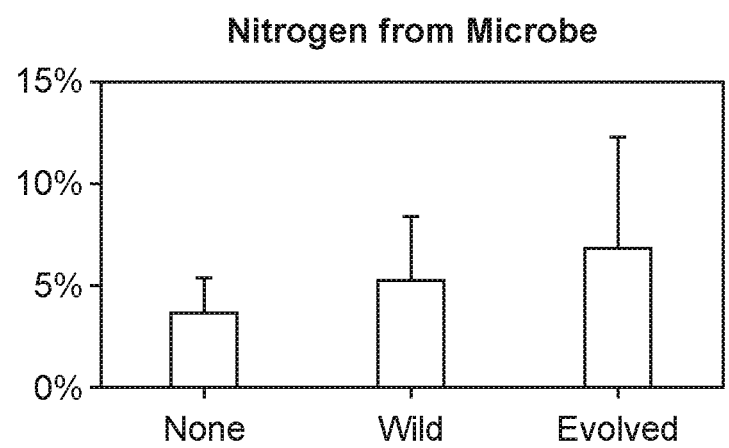
FIG. 14B depicts 4 weeks after planting, up to 7% of the nitrogen in plants inoculated with an evolved strain is derived from microbially fixed nitrogen.
Figure 14C:
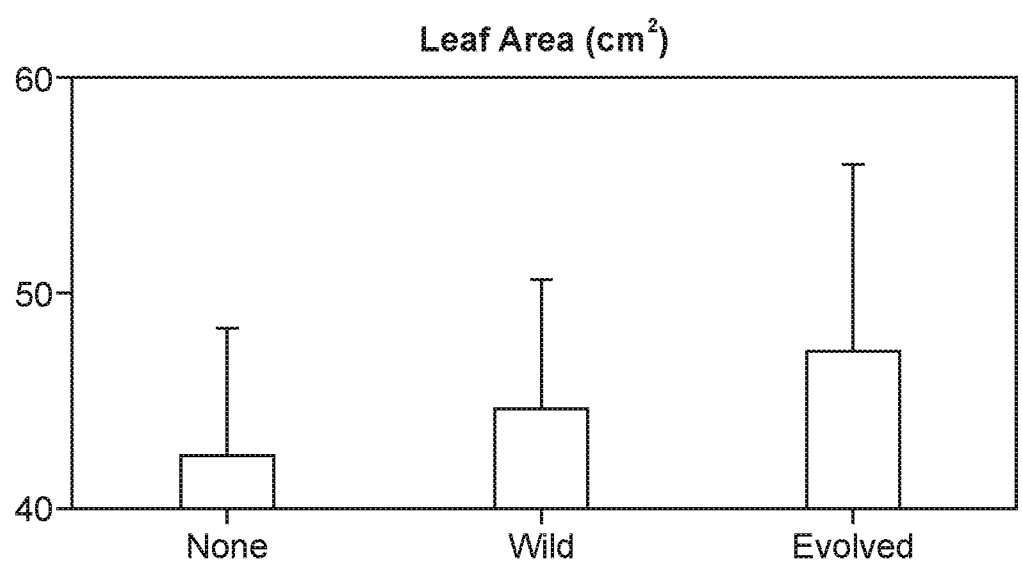
FIG. 14C depicts leaf area (and other biomass measurement, data not shown) is increased in plants inoculated with an evolved strain when compared to uninoculated or wild type inoculated plants.

Both types of assay has been performed to measure fixation activity of improved strains relative to wild-type and uninoculated corn plants, and elevated fixation rates were observed in planta for several of the improved strains (FIG. 12, FIG. 14A, and FIG. 14B). These assays are instrumental in demonstrating that the activity of the strains observed in vitro translates to in vivo results. Furthermore, these assays allow measurement of the impact of fertilizer on strain activity, suggesting suitable functionality in an agricultural setting. Similar results were observed when *setaria* plants were inoculated with wild-type and improved strains (FIG. 13). In planta fixation activity shown in FIGS. 14A-14C is further backed up by transcriptomic data. Evolved strains exhibit increased nifH transcript level relative to wild-type counterparts. Furthermore, the microbe derived nitrogen level in planta is also correlated with the colonization level on a plant by plant basis. These results (FIG. 12, FIG. 13, FIGS. 14A-14C, FIG. 15A, and FIG. 15B) support the hypothesis that the microbe, through the improved regulation of the nif gene cluster, is the likely reason for the increase in atmospheric derived nitrogen seen in the plant tissue. In addition to measuring fixation directly, the impact of inoculating plants with the improved strains in a nitrogen-stressed plant biomass assay was measured. While plant biomass may be related to many possible microbe interactions with the plant, one would expect that the addition of fixed nitrogen would impact the plant phenotype when nitrogen is limited. Inoculated plants were grown in the complete absence of nitrogen, and significant increases in leaf area, shoot fresh and dry weight, and root fresh and dry weight in inoculated plants relative to untreated controls was observed (FIG. 14C). Although these differences cannot be attributed to nitrogen fixation exclusively, they support the conclusion that the improved strains are actively providing nitrogen to the plant. Corn and *setaria* plants were grown and inoculated as described above. Fertilizer comprising 1.2% $^{15}$N was regularly supplied to plants via watering. Nitrogen fixation by microbes was quantified by measuring the $^{15}$N level in the plant tissue. Fourth leaf tissue was collected and dried at 4 weeks after planting. Dried leaf samples were homogenized using beads (QIAGEN Tissuelyzer) and aliquoted out into tin capsules for IRMS (MBL Stable Isotope Laboratory at The Ecosystems Center, Woods Hole, MA). Nitrogen derived from the atmosphere (NDFA) was calculated, and nitrogen production by CI050 and CM002 are shown in FIG. 7.

Phytohormone Production Assay

Figure 8:
FIG. 8 shows an experimental setup for a Micro-Tom fruiting mass assay.
Figure 9:
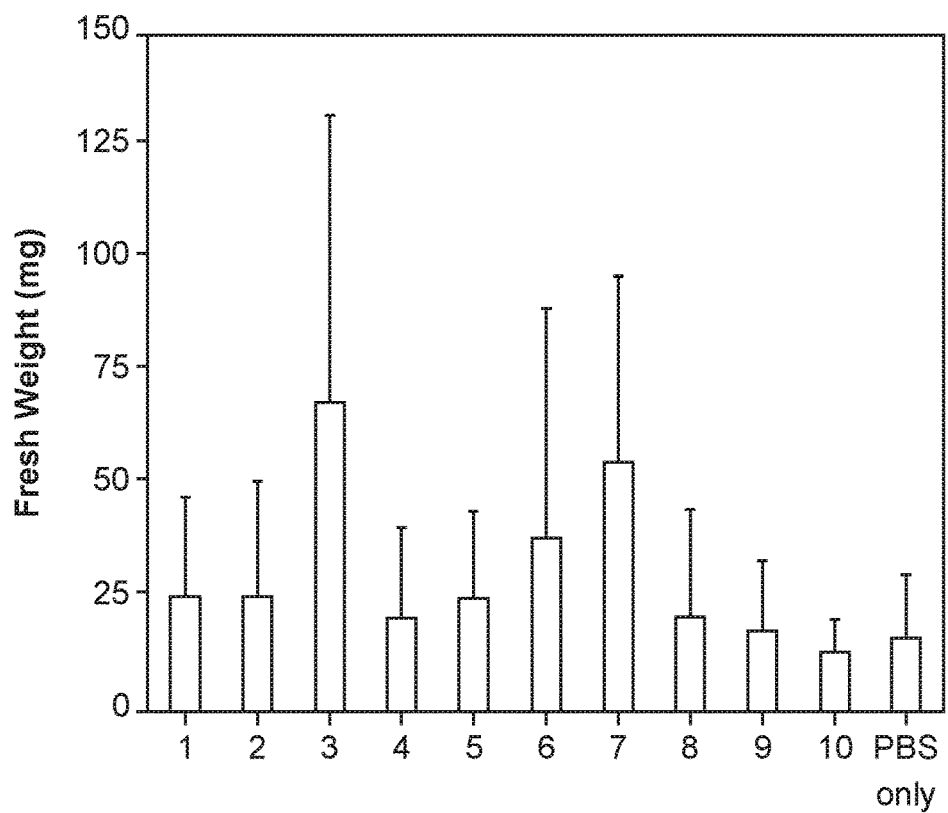
FIG. 9 shows a screen of 10 strains for increase in Micro-Tom plant fruit mass. Results for six replicates are presented. For column 3, p=0.07. For column 7, p=0.05.

The dwarf tomato (*Solanum lycopersicum*) cultivar 'Micro-Tom' has previously been used to study the influence of indole-3-acetic acid on fruit ripening through an in vitro assay (Cohen 1996; J Am Soc Hortic Sci 121: 520-524). To evaluate phytohormone production and secretion by candidate microbes, a plate-based screening assay using immature Micro-Tom fruit was developed. Twelve-well tissue culture test plates were prepared by filling wells with agar medium, allowing it to solidify, and spotting 10 uL of overnight microbial cultures onto the agar surface, as shown in FIG. 8. Wells with agar containing increasing amounts of gibberellic acid (GA) but no bacterial culture were used as a positive control and standards. Flowers one day post-anthesis abscised from growing Micro-Tom plants were inserted, stem-first, into the agar at the point of the bacterial spot culture. These flowers were monitored for 2-3 weeks, after which the fruits were harvested and weighed. An increase in plant fruit mass across several replicates indicates production of plant hormone by the inoculant microbe, as shown in FIG. 9.

Example 6: Cyclical Host-Microbe Evolution

Corn plants were inoculated with CM013 and grown 4 weeks to approximately the V5 growth stage. Those demonstrating improved nitrogen accumulation from microbial sources via $^{15}$N analysis were uprooted, and roots were washed using pressurized water to remove bulk soil. A 0.25 g section of root was cut and rinsed in PBS solution to remove fine soil particles and non-adherent microbes. Tissue samples were homogenized using 3 mm steel beads in QIAGEN TissueLyser II. The homogenate was diluted and plated on SOB agar media. Single colonies were resuspended in liquid media and subjected to PCR analysis of 16s rDNA and mutations unique to the inoculating strain. The process of microbe isolation, mutagenesis, inoculation, and re-isolation can be repeated iteratively to improve microbial traits, plant traits, and the colonization capability of the microbe.

Example 7: Compatibility Across Geography

The ability of the improved microbes to colonize an inoculated plant is critical to the success of the plant under field conditions. While the described isolation methods are designed to select from soil microbes that may have a close relationship with crop plants such as corn, many strains may not colonize effectively across a range of plant genotypes, environments, soil types, or inoculation conditions. Since colonization is a complex process requiring a range of interactions between a microbial strain and host plant, screening for colonization competence has become a central method for selecting priority strains for further development. Early efforts to assess colonization used fluorescent tagging of strains, which was effective but time-consuming and not scalable on a per-strain basis. As colonization activity is not amenable to straightforward improvement, it is imperative that potential product candidates are selected from strains that are natural colonizers.

An assay was designed to test for robust colonization of the wild-type strains in any given host plant using qPCR and primers designed to be strain-specific in a community sample. This assay is intended to rapidly measure the colonization rate of the microbes from corn tissue samples. Initial tests using strains assessed as probable colonizers using fluorescence microscopy and plate-based techniques indicated that a qPCR approach would be both quantitative and scalable.

A typical assay is performed as follows: Plants, mostly varieties of maize and wheat, are grown in a peat potting mix in the greenhouse in replicates of six per strain. At four or five days after planting, a 1 mL drench of early stationary phase cultures of bacteria diluted to an OD590 of 0.6-1.0 (approximately 5E+08 CFU/mL) is pipetted over the emerging coleoptile. The plants are watered with tap water only and allowed to grow for four weeks before sampling, at which time, the plants are uprooted and the roots washed thoroughly to remove most peat residues. Samples of clean root are excised and homogenized to create a slurry of plant cell debris and associated bacterial cells. We developed a high-throughput DNA extraction protocol that effectively produced a mixture of plant and bacterial DNA to use as template for qPCR. Based on bacterial cell spike-in experiments, this DNA extraction process provides a quantitative bacterial DNA sample relative to the fresh weight of the roots. Each strain is assessed using strain-specific primers designed using Primer BLAST (Ye 2012) and compared to background amplification from uninoculated plants. Since some primers exhibit off-target amplification in uninoculated plants, colonization is determined either by presence of amplification or elevated amplification of the correct product compared to the background level.

Figure 16B:
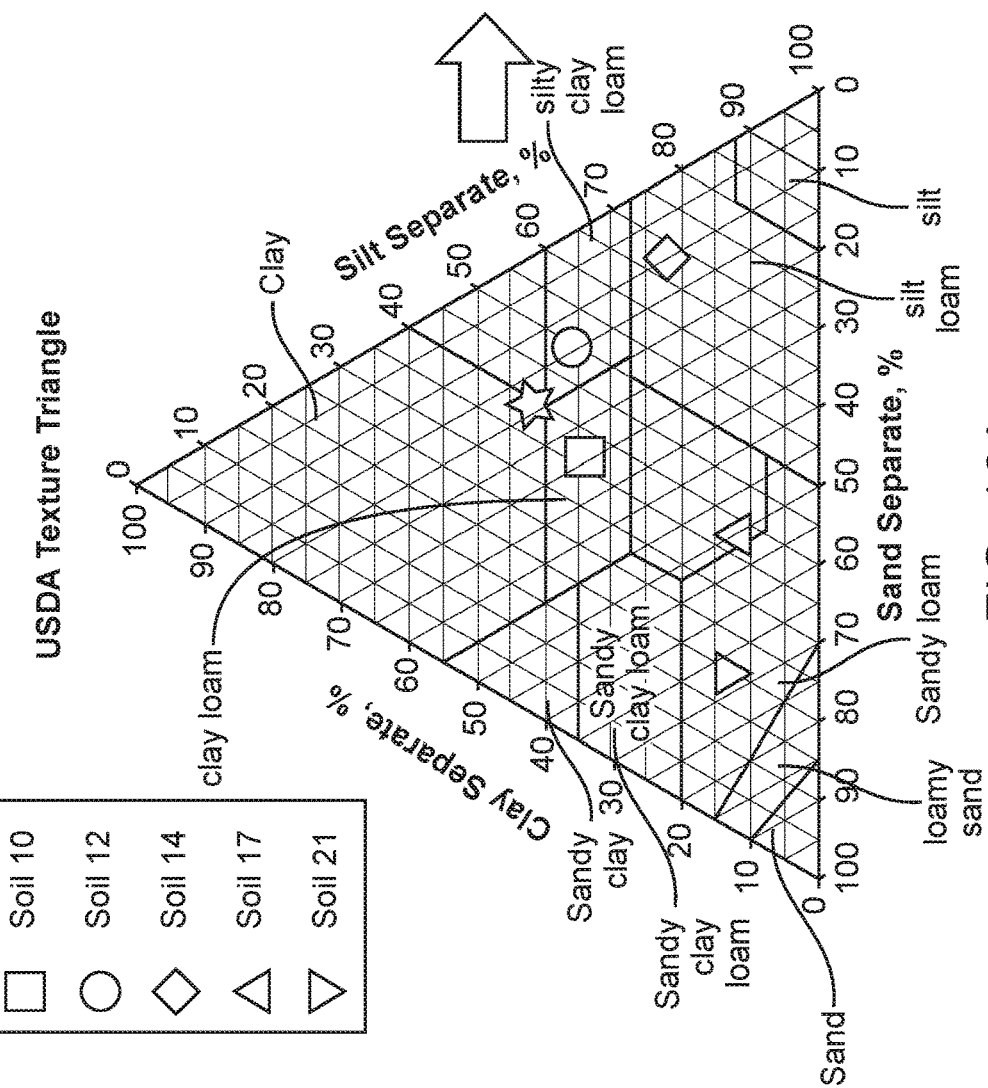
FIG. 16B depicts the colonization rate of Strain 1 and Strain 5 that are tested across four different soil types (circles). Both strains showed relatively robust colonization profile across diverse soil types.
Figure 16A:
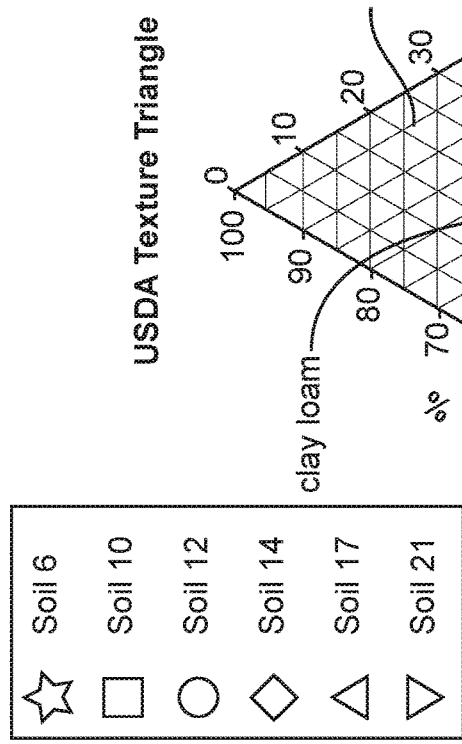
FIG. 16A depicts a soil texture map of various field soils tested for colonization. Soils in which a few microbes were originally source from are indicated as stars.

This assay was used to measure the compatibility of the microbial product across different soil geography. Field soil qualities and field conditions can have a huge influence on the effect of a microbial product. Soil pH, water retention capacity, and competitive microbes are only a few examples of factors in soil that can affect inoculum survival and colonization ability. A colonization assay was performed using three diverse soil types sampled from agricultural fields in California as the plant growth medium (FIG. 16A). An intermediate inoculation density was used to approximate realistic agricultural conditions. Within 3 weeks, Strain 5 colonized all plants at 1E+06 to 1E+07 CFU/g FW. After 7 weeks of plant growth, an evolved version of Strain 1 exhibited high colonization rates (1E+06 CFU/g FW) in all soil types. (FIG. 16B).

Figure 16C:
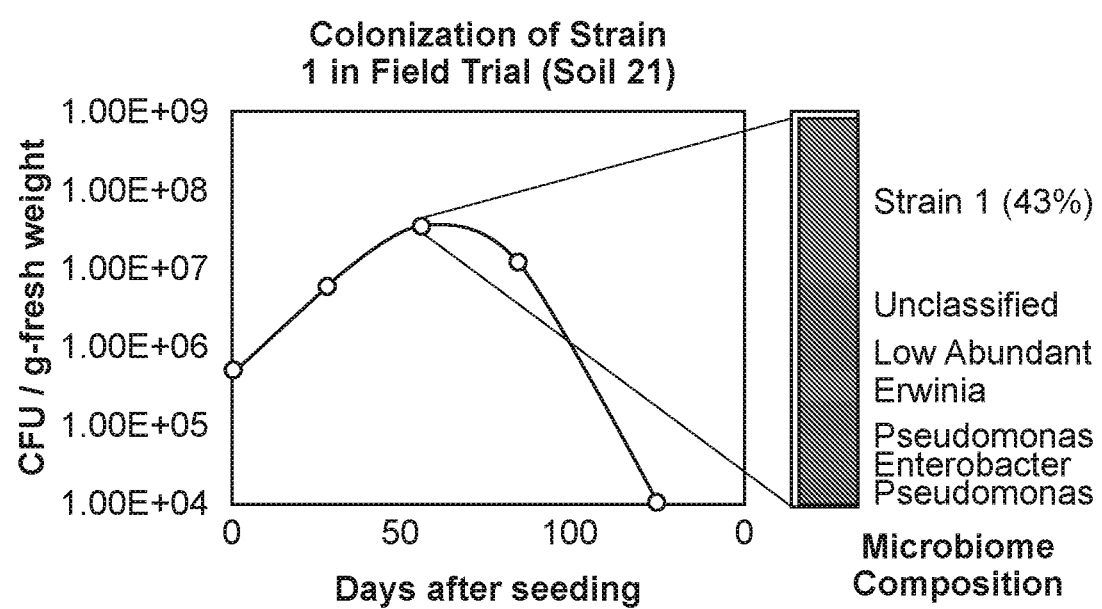
FIG. 16C depicts colonization of Strain 1 as tested in a field trial over the span of a growing season. Strain 1 persists in the corn tissue up to week 12 after planting and starts to show decline in colonization after that time.
Figure 17:
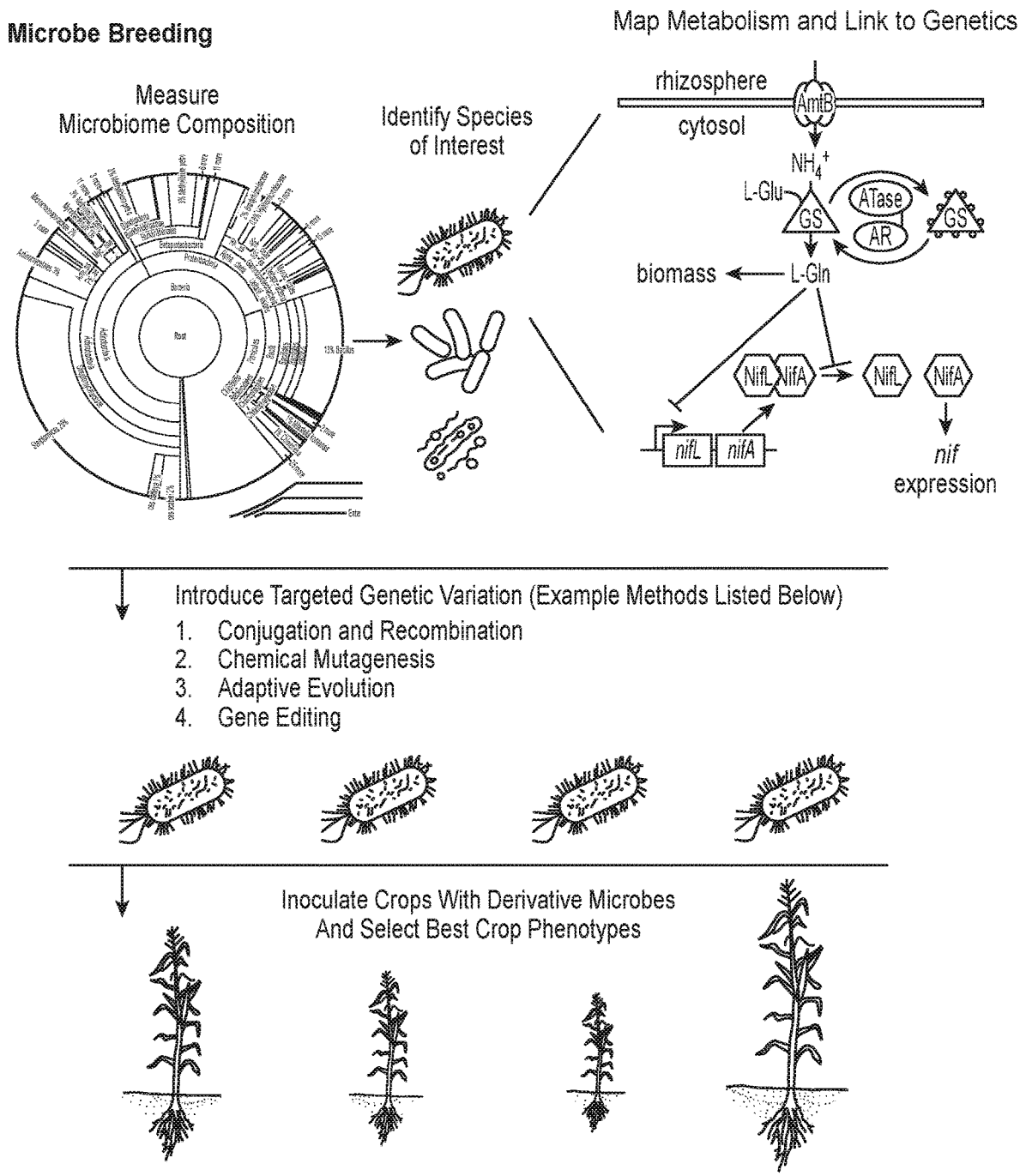
FIG. 17 depicts a schematic of microbe breeding, in accordance with embodiments.
Figure 18:
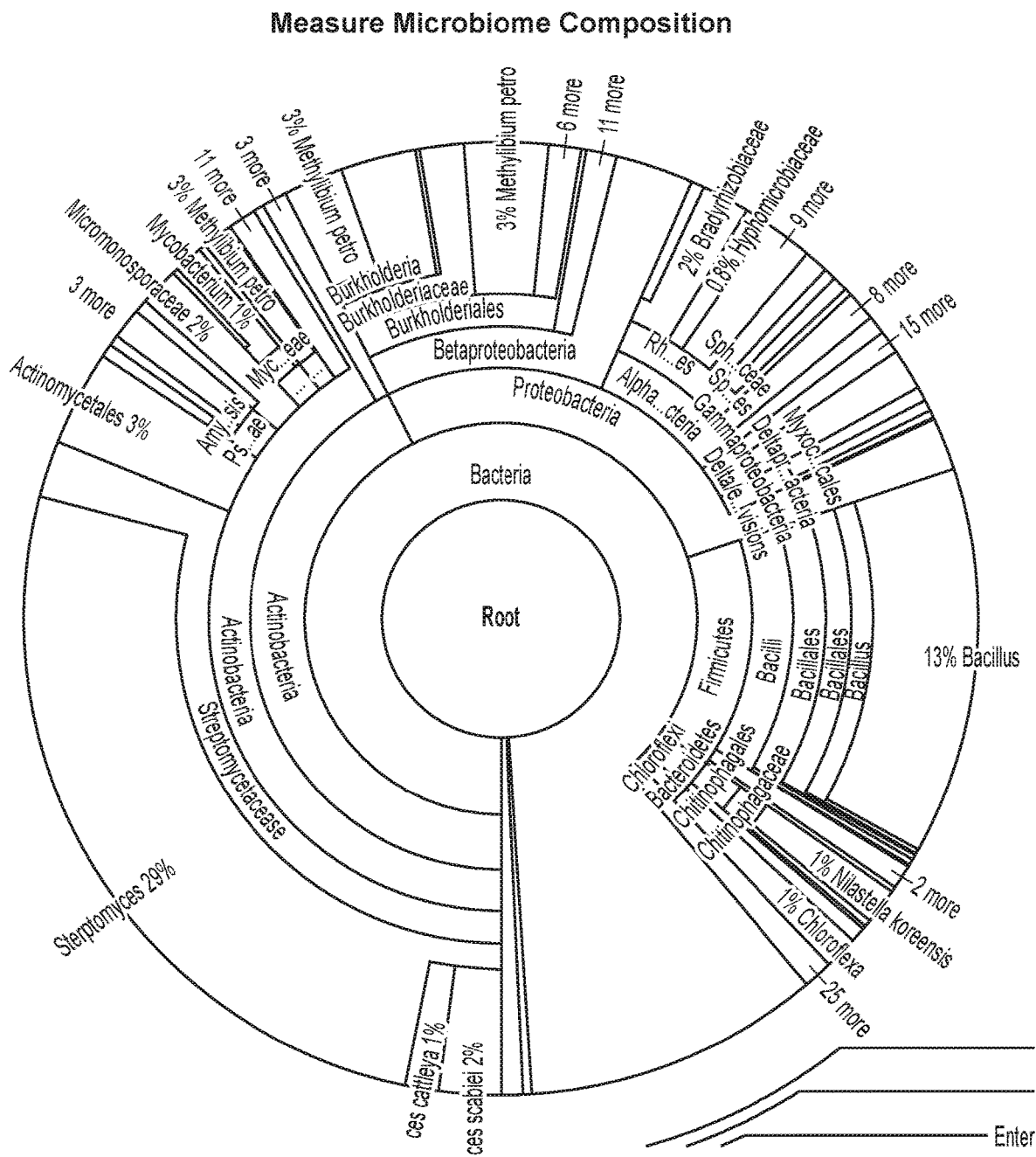
FIG. 18 depicts an expanded view of the measurement of microbiome composition as shown in FIG. 17.

Additionally, to assess colonization in the complexity of field conditions, a 1-acre field trial in in San Luis Obispo in June of 2015 was initiated to assess the impacts and colonization of seven of the wild-type strains in two varieties of field corn. Agronomic design and execution of the trial was performed by a contract field research organization, Pacific Ag Research. For inoculation, the same peat culture seed coating technique tested in the inoculation methods experiment was employed. During the course of the growing season, plant samples were collected to assess for colonization in the root and stem interior. Samples were collected from three replicate plots of each treatment at four and eight weeks after planting, and from all six reps of each treatment shortly before harvest at 16 weeks. Additional samples were collected from all six replicate plots of treatments inoculated with Strain 1 and Strain 2, as well as untreated controls, at 12 weeks. Numbers of cells per gram fresh weight of washed roots were assessed as with other colonization assays with qPCR and strain-specific primers. Two strains, Strain 1 and Strain 2, showed consistent and widespread root colonization that peaked at 12 weeks and then declined precipitously (FIG. 16C). While Strain 2 appeared to be present in numbers an order of magnitude lower than Strain 1, it was found in more consistent numbers from plant to plant. No strains appeared to effectively colonize the stem interior. In support of the qPCR colonization data, both strains were successfully re-isolated from the root samples using plating and 16S sequencing to identify isolates of matching sequence Examples of microbe breeding can be summarized in the schematic of FIG. 17 and FIG. 18. FIG. 17 depicts microbe breeding wherein the composition of the microbiome can be first measured and a species of interest is identified. The metabolism of the microbiome can be mapped and linked to genetics. Afterwards, a targeted genetic variation can be introduced using methods including, but not limited to, conjugation and recombination, chemical mutagenesis, adaptive evolution, and gene editing. Derivative microbes are used to inoculate crops. In some examples, the crops with the best phenotypes are selected.

As provided in FIG. 17, the composition of the microbiome can be first measured and a species of interest is identified. The metabolism of the microbiome can be mapped and linked to genetics. The metabolism of nitrogen can involve the entrance of ammonia ($NH_4^+$) from the rhizosphere into the cytosol of the bacteria via the AmtB transporter. Ammonia and L-glutamate (L-Glu) are catalyzed by glutamine synthetase and ATP into glutamine. Glutamine can lead to the formation of biomass (plant growth), and it can also inhibit expression of the nif operon. Afterwards, a targeted genetic variation can be introduced using methods including, but not limited to, conjugation and recombination, chemical mutagenesis, adaptive evolution, and gene editing. Derivative microbes are used to inoculate crops. The crops with the best phenotypes are selected.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 3A

| Name | Minimum | Maximum | Length | Direction |
|---|---|---|---|---|
| murein lipoprotein CDS | 2,929,898 | 2,930,134 | 237 | forward |
| membrane protein CDS | 5,217,517 | 5,217,843 | 327 | forward |
| zinc/cadmium-binding protein CDS | 3,479,979 | 3,480,626 | 648 | forward |
| acyl carrier protein CDS | 4,563,344 | 4,563,580 | 237 | reverse |
| ompX CDS | 4,251,002 | 4,251,514 | 513 | forward |
| DNA-binding protein HU-beta CDS | 375,156 | 375,428 | 273 | forward |
| sspA CDS | 629,998 | 630,636 | 639 | reverse |
| tatE CDS | 3,199,435 | 3,199,638 | 204 | reverse |
| LexA repressor CDS | 1,850,457 | 1,851,065 | 609 | forward |
| hisS CDS | <3999979 | 4,001,223 | >1245 | forward |

TABLE 3B

| Name | Differential Expression Absolute Confidence | Differential Expression Ratio | RNASeq_ nifL - Raw Read Count | RNASeq_ nifL - Raw Transcript Count | RNASeq_ WT - Raw Read Count | RNASeq_ WT - Raw Transcript Count |
|---|---|---|---|---|---|---|
| murein lipoprotein CDS | 1000 | −1.8 | 12950.5 | 10078.9 | 5151.5 | 4106.8 |
| membrane protein CDS | 1000 | −1.3 | 9522.5 | 5371.3 | 5400 | 3120 |
| zinc/cadmium-binding protein CDS | 3.3 | 1.1 | 6461 | 1839.1 | 5318 | 1550.6 |
| acyl carrier protein CDS | 25.6 | 1.6 | 1230.5 | 957.6 | 1473.5 | 1174.7 |
| ompX CDS | 1.7 | 1.1 | 2042 | 734.2 | 1687.5 | 621.5 |
| DNA-binding protein HU-beta CDS | 6.9 | −1.3 | 1305 | 881.7 | 725 | 501.8 |
| sspA CDS | 0.2 | 1 | 654 | 188.8 | 504.5 | 149.2 |
| tatE CDS | 1.4 | 1.3 | 131 | 118.4 | 125 | 115.8 |
| LexA repressor CDS | 0.1 | −1.1 | 248 | 75.1 | 164 | 50.9 |
| hisS CDS | 0 | −1.1 | 467 | 69.2 | 325 | 49.3 |

Example 8: glgA Deletion Increases Nitrogen Excretion

Glycogen synthesis shunts carbon away from glycolysis and the TCA cycle. Decreasing or abolishing glycogen synthesis may result in greater carbon flux towards glycolysis and the TCA cycle, leading to greater ATP availability in the cell. This may lead to increased nitrogenase activity, as nitrogen fixation requires 16 ATP to reduce one molecule of N2 and may be limited by ATP availability. Glycogen synthase is encoded by the gene glgA. Downregulation or deletion of glgA may lead to an increase in nitrogen fixation activity.

To this end, strains of *Kosakonia sacchari* CI006 and *Klebsiella variicola* in which glgA was deleted were constructed. Strains 6-1694, 6-1744, and 137-1893 were subjected to an ammonium excretion (AMM) assay, wherein ammonia excretion over time was measured in nitrogen fixing conditions by culturing cells in nitrogen-free media, pelleting the cells, and measuring free ammonium in the cell-free broth; higher ammonium excretion levels indicated higher nitrogen fixation and excretion. Strains 6-1681 and 137-1893 were subjected to an ARA assay as previously described, in media supplemented with 5 mM ammonium phosphate. Strains 6-1694 corresponds to parent strain 6-342. Strain 6-1744 corresponds to parent strain 6-923. Strain 6-1681 corresponds to parent strain 6-346. Strain 137-1893 corresponds to parent strain 137-1586.

Figures 19A, 19B:
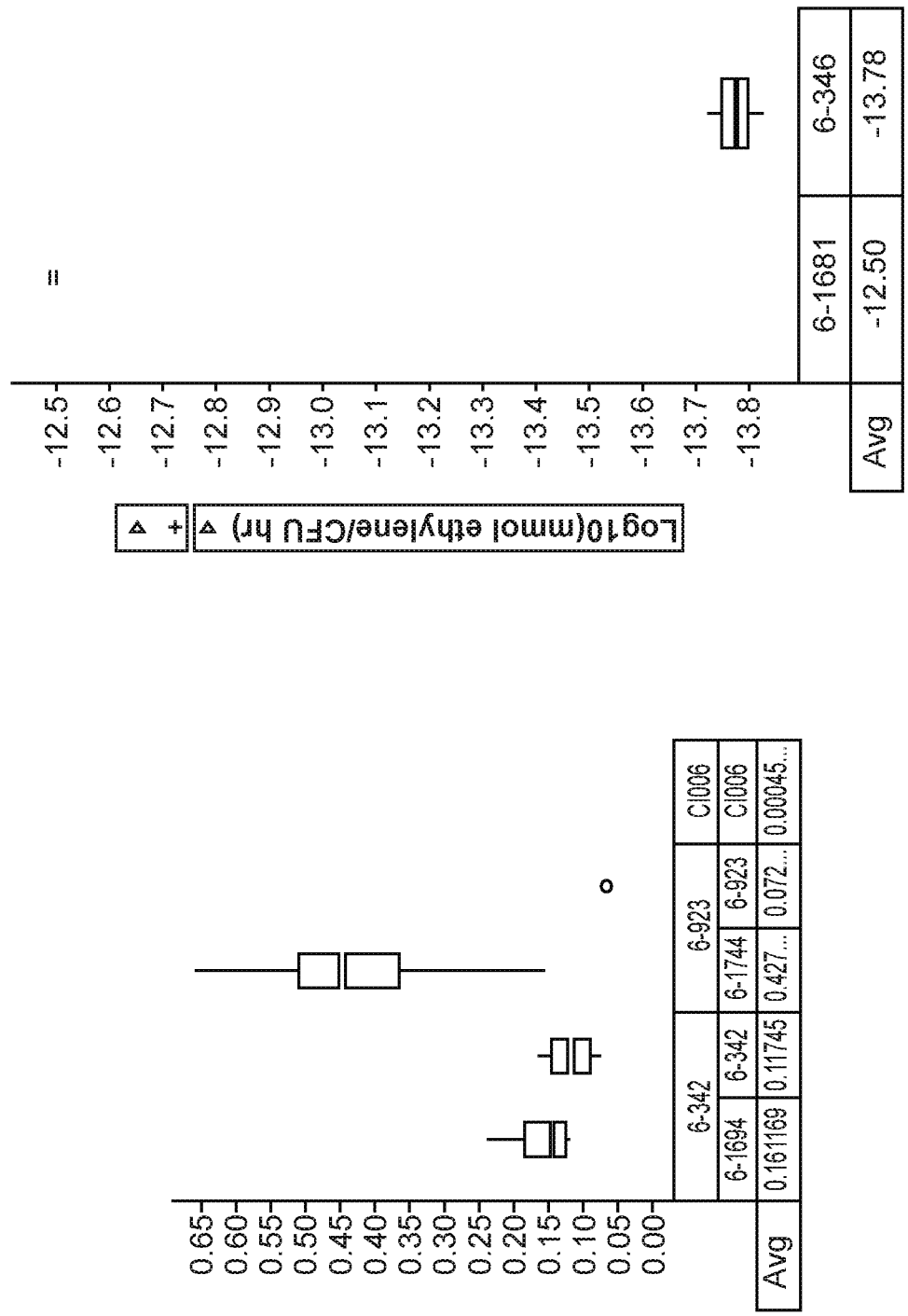
FIGS. 19A and 19B depict increased nitrogenase activity and ammonium excretion, in mutants of K. sacchari strain CI006 with modifications in the glycogen synthesis gene glgA.

Data from the AMM assay is shown in FIGS. 19A-20B. Strain 6-1694 and 6-1744 display increased nitrogen excreting ability compared with their parent strains (FIG. 19A). Strain 6-1681 exhibited increased ARA activity compared to its parent strain (FIG. 19B). Strain 137-1893 exhibited both increased ammonium excretion (FIG. 20A) and nitrogenase activity as measured by ARA (FIG. 20B). Thus, reducing or eliminating glycogen synthesis in bacteria, can increase the amount of nitrogen excreted. Details of strains described herein may be found in Tables 8 and 9.

Example 9: glnD Mutations Increase Nitrogen Excretion

Figure 21:
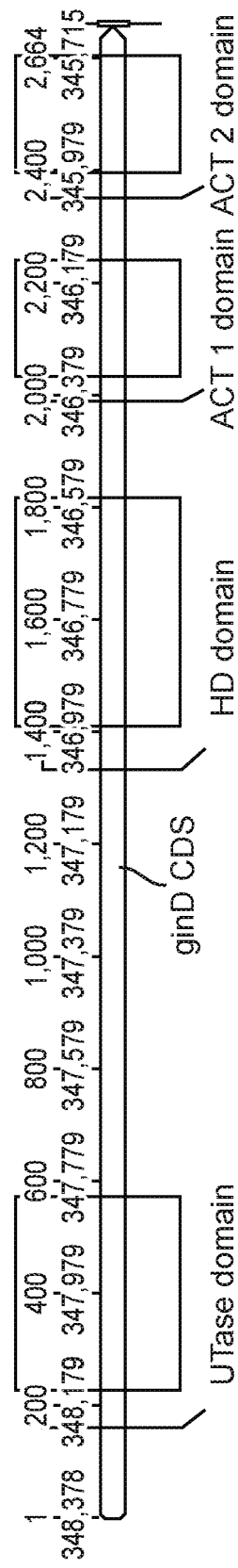
FIG. 21 illustrates a schematic of the glnE gene, showing regions corresponding to the functional domains of the GlnE protein.

GlnD is a bifunctional uridylyltransferase/uridylyl-removing enzyme which acts as the central "switch" for nitrogen sensing in the cell. It contains three distinct domains: the UTase domain, which uridylylates the PII proteins GlnB and GlnK; the uridylyl-reoving (UR) domain, also known as the HD domain, which remove the uriylyl group from the PII proteins; and two ACT domains, which regulate the activity of the other two domains in response to glutamine binding (FIG. 21). In nitrogen excess, glutamine binds the ACT domain and the UR domain is activated; in nitrogen starvation, ACT is unbound and the UTase domain is active. Subsequent PII protein signaling affects transcription of several gene clusters, including nitrogenase and nitrogen assimilation genes.

Figure 23:
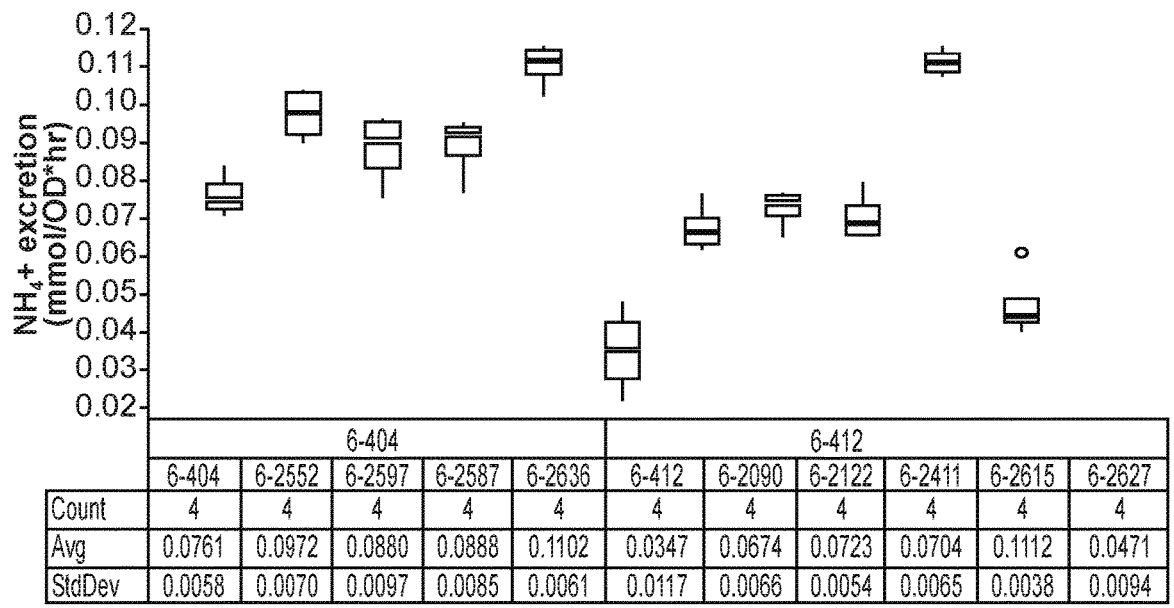
FIG. 23 depicts increased ammonium excretion in mutants of K. sacchari strain CI006 with modifications in the glnD gene.

Various truncations and deletions were performed to see how they impact fixation and excretion of nitrogen. Several glnD mutations modifying the UTase, UR and ACT1/2 (glutamine-sensing) domains lead to increases in activity as measured in ARA and ammonium excretion assays. FIG. 22 demonstrates several glnD modifications which lead to increased ammonium excretion in *K. variicola* CI137; FIG. 23 demonstrates several glnD modifications which lead to increases ammonium excretion in *K. sacchari*.

Example 10: glnK Deletion Increases Nitrogen Excretion

GlnK is the PII protein which may be a post-translational regulator, and may be involved in glutamine synthesis, which may be a competing pathway of ammonium excretion. Higher levels of GlnK may reduce the amount of NH4 excreted. Removing glnK may reduce or eliminate inhibitory effects on NH4 excretion.

Figure 24A:
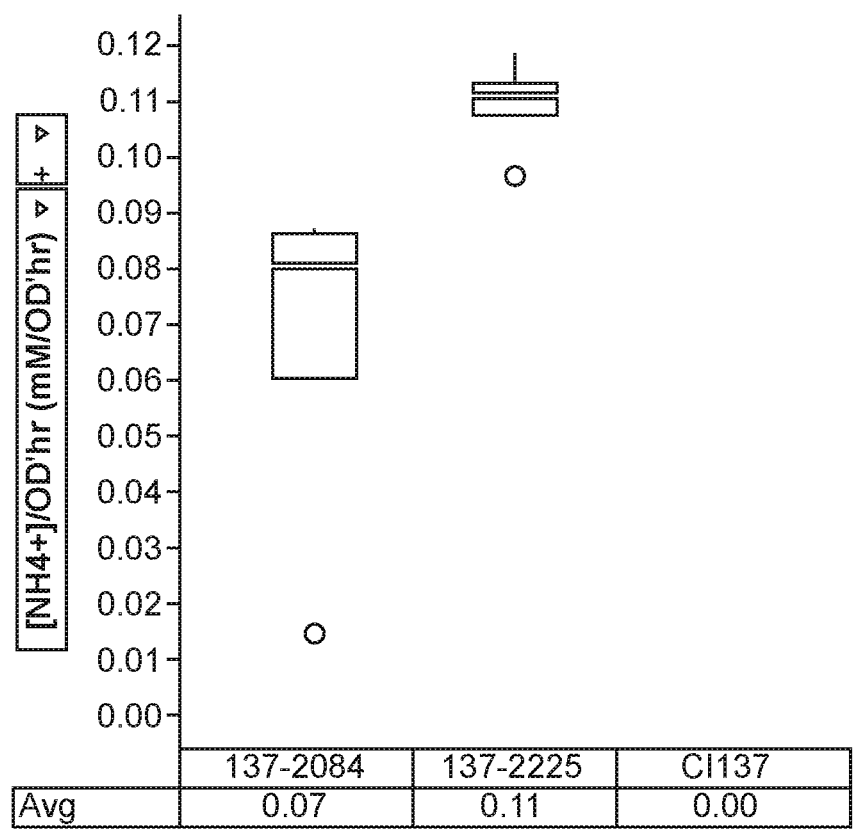
FIG. 24A depicts increased ammonium excretion in minimal nitrogen-free media in mutants of K. variicola strain CI137 with modifications in the glnK gene.

GlnK was deleted in a strain which already contained a nifL::1.2 deletion and a glnE deletion. Thus the deletion of glnK was introduced into a strain which already had an increased ability to fix nitrogen. The strain with the glnK deletion is indicated as 137-2225, and the parent strain is indicated as 137-2084 in FIG. 24A. An AMM analysis was performed on these cells, such that the amount of NH4+ excreted per OD per hour (in mM) was measured. In this assay, more NH4+ excretion may indicate higher nitrogen fixation activity. In particular, the 137-2225 strain displayed nitrogen fixation activity which was 1.32 times higher than the parent strain as measured by the AMM assay.

Example 11: Downregulation of the glnA Gene Increases Ammonium Excretion

Glutamine synthetase (GS) is encoded by the glnA gene. A reduction in GS activity may result in a decreased rate of nitrogen assimilation. In nitrogen-fixing conditions, this may lead to a buildup of intracellular ammonium and ammonium excretion.

Figure 24B:
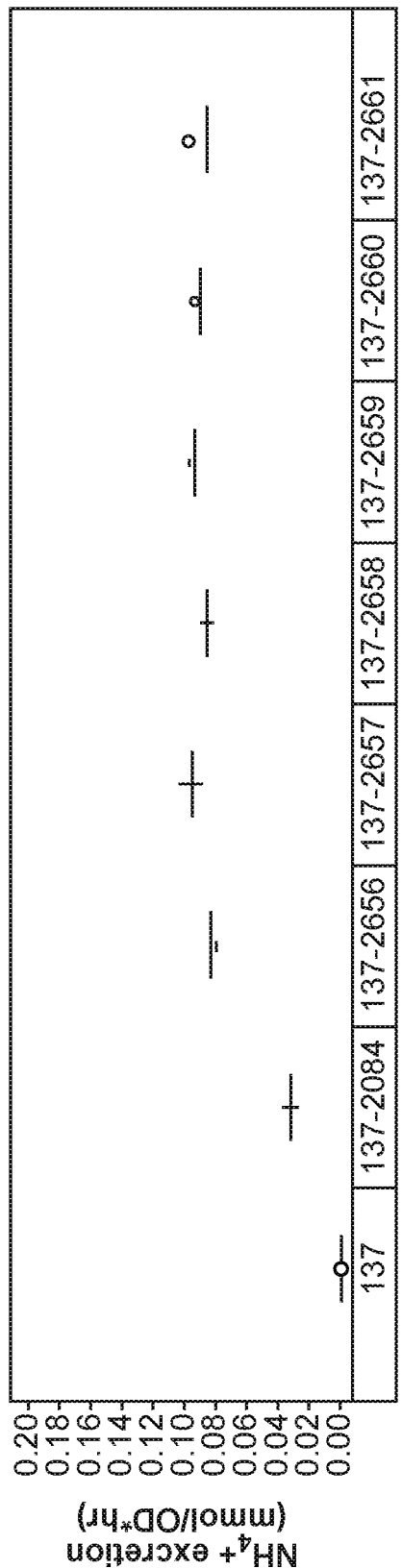
FIG. 24B depicts increased ammonium excretion in mutants of K. variicola strain CI137 with modifications in the glnA gene created by inserting a promoter from a gene expressed constitutively at a low level (glnE, glnD, or glnB) upstream and mutating the ATG start codon to GTG over a strain with a glnE_KO2 mutation in minimal media supplemented with 5 mM glutamine.
Figure 25:
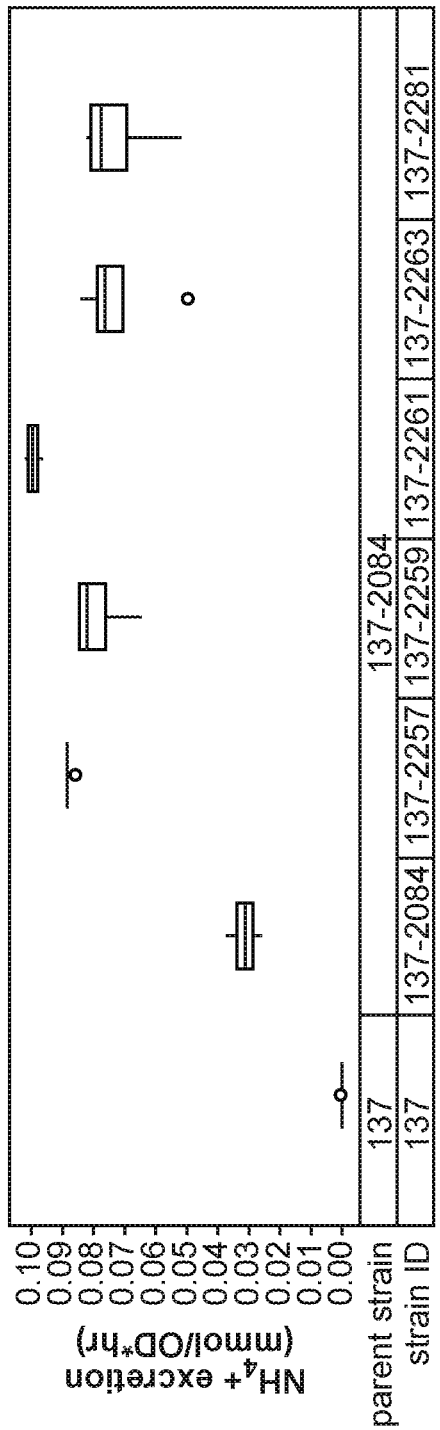
FIG. 25 depicts increased ammonium excretion in mutants of K. variicola strain CI137 with modifications in the glnA gene created by inserting a promoter from a gene expressed constitutively at a low level (glnE, glnD, or glnB) upstream and mutating the ATG start codon to GTG over a strain with a glnE_KO2 and ΔnifL::Prm1.2 mutation in minimal media supplemented with 5 mM glutamine.
Figure 26:
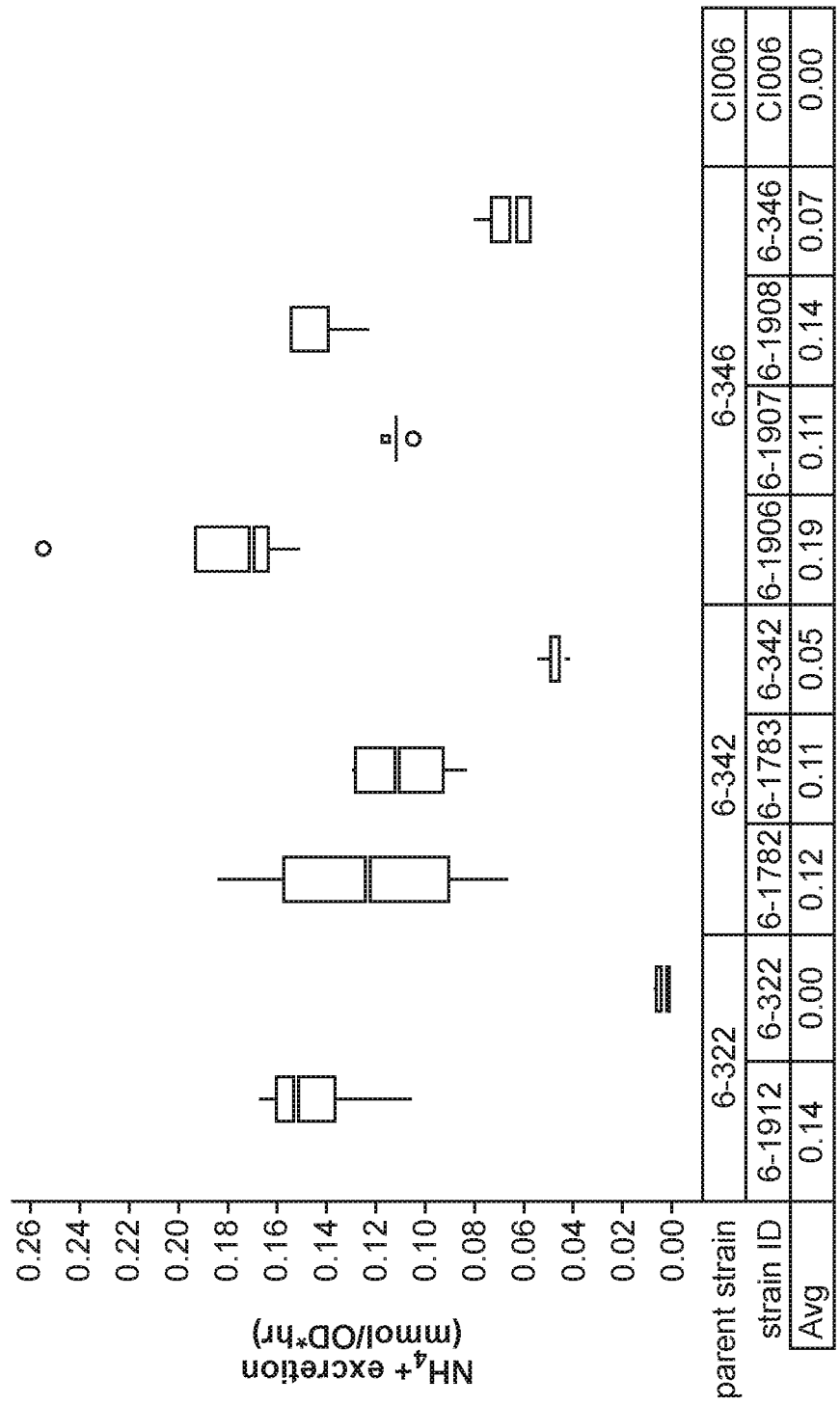
FIG. 26 depicts increased ammonium excretion in mutants of K. sacchari strain CI006 with modifications in the glnA gene created by inserting a promoter from a gene expressed constitutively at a low level (glnE, glnD, or glnB) upstream and mutating the ATG start codon to GTG over a strain with a glnE_KO2 and ΔnifL::Prm1.2 mutation in minimal nitrogen-free media

Several strains were constructed in which the native promoter for glnA was replaced by a promoter known to be constitutively expressed at a low level: the promoter of either the glnB, glnD or glnE genes. This is expected to lead to a decrease in glnA transcription. In some cases, the ATG start codon of the glnA gene was also mutated to GTG to decrease the rate of translation initiation of the GS protein. FIG. 24B, FIG. 25 and FIG. 26 describe several mutants of CI137 and CI006 in which downregulation of the glnA gene led to increased ammonium excretion.

Example 12: Downregulation of Glutamate Synthase Leads to Increased Ammonium Excretion Glutamate serves as the main pool for nitrogen in the cell, and the GS-GOGAT pathway is the main pathway for nitrogen assimilation. The gltBD operon encodes GOGAT. A strain (137-2215) was constructed in which the native promoter for the gltBD operon was deleted and replaced with a strong constitutive promoter. FIG. 27 demonstrates how 137-2215 exhibits increased ammonium excretion compared to the parent control; FIG. 28 demonstrates that 137-2215 exhibited increased nitrogen fixation activity as measured by ARA.

Example 13: Upregulation of Glutaminase Gene glsA2 Leads to Increased Ammonium Excretion Glutaminase enzymes cleave a C—N bond in glutamine, releasing ammonium and glutamate. Increasing glutaminase activity in a cell may lead to increased ammonium release from glutamine and ammonium excretion. The glsA2 gene encodes a glutaminase. Strains were constructed in which the native promoter of the glsA2 gene was deleted and replaced with a strong promoter sequence. FIG. 29 and FIG. 30 demonstrate increased ammonium excretion by these strains compared to parent strain controls.

Figure 31:
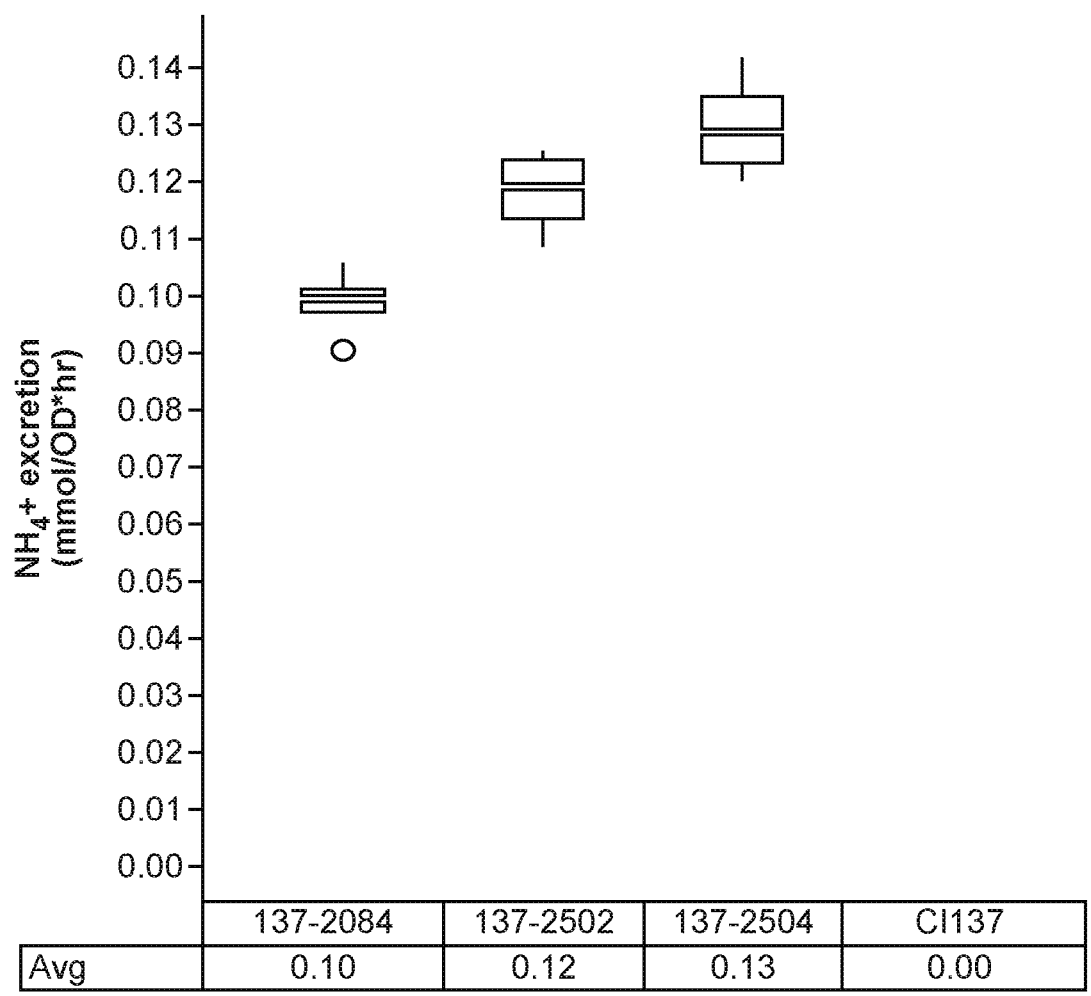
FIG. 31 depicts increased ammonium excretion in mutants of K. variicola strain CI137 with modifications in the asnB gene compared with the parent control strain.

Example 14: Upregulation of Glutaminase Domain of asnB Leads to Increased Ammonium Excretion The asnB gene encodes a transaminase enzyme which has two domains: a glutaminase domain and an asparagine synthase domain. FIG. 31 demonstrates how deletion of the asparagine synthase domain or upregulation of the asnB gene may lead to increased ammonium excretion.

Example 15: rpoN Upregulation Increases Nitrogen Fixation rpoN (sigma54) is an initiation factor used to promote RNA polymerase attachment to specific initiation sites. Along with nifA and ihfA/B, it transcribes nifH. Upregulating rpoN may allow for increased nifH levels, which may result in increased nitrogen fixation.

Two strains of *K. variicola* CI137 were constructed in which rpoN was upregulated by deleting its native promoter and replacing with a strong constitutive promoter. Data is shown in FIG. 32 and FIG. 33. Strains with the rpoN modification are indicated as 137-2251 and 137-2285, and the parent strain is indicated as 137-2084

In FIG. 32, Data is shown as the base 10 logarithm of the amount of ethylene formed per colony forming unit per hour, such that a higher amount of ethylene formation indicates more nitrogen fixation. The assay was performed with 5 mM ammonium phosphate provided as a nitrogen source. The 137-2251 strain fixed nitrogen 1.23 times better than the parent strain (p=0.028), while the 137-2285 strain fixed nitrogen 1.95 times better than the parent strain (p=0.031).

These results suggest that nitrogen fixation can be enhanced by increasing the amount of polymerase responsible for transcribing the RNA which codes for the enzyme nifH.

Example 16: Upregulation of otsB Leads to Increase Nitrogen Fixation Activity otsB is involved in the biosynthesis of trehalose in the cell, and modifications of otsB may improve robustness of a strain. Here, modifications of otsB were created and tested to determine if these modifications negatively impacted nitrogen fixing in the cells.

Figure 34:
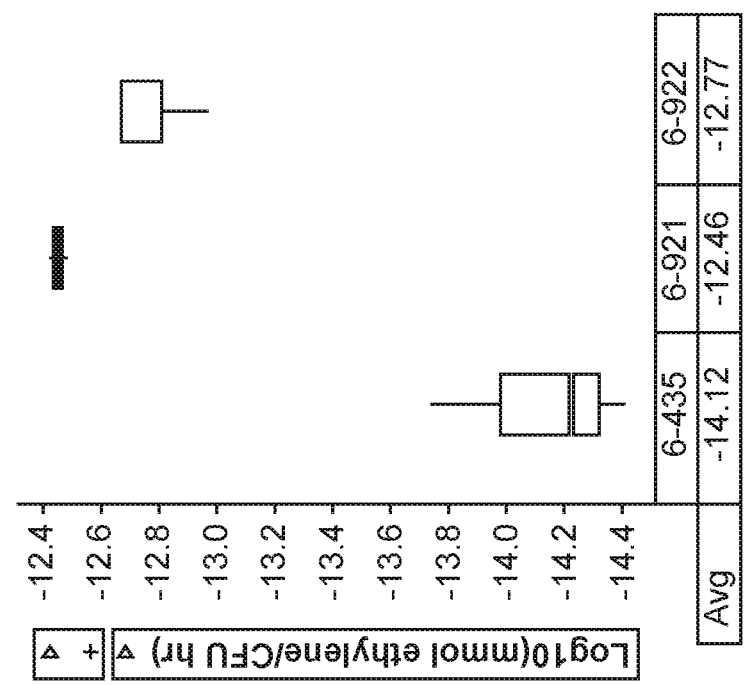
FIG. 34 depicts increased nitrogenase activity in mutants of K. sacchari strain CI006 with altered expression of the otsB gene compared with the parent control.

Three strains of nitrogen fixing bacteria were modified to increase expression of the otsB gene. The native promoter of the otsB gene was deleted and replaced with a strong constitutive promoter. The modified strains are 6-921 and 6-922 (parent strain 6-435) and 6-1697 (parent strain 6-923). An ARA assay was performed on the modified strains 6-921 and 6-922 (FIG. 34). Data is shown as the base 10 logarithm of the amount of ethylene formed per colony forming unit per hour, such that a higher amount of ethylene formation indicates more nitrogen fixation. The assay was performed 5 mM ammonium phosphate provided as the nitrogen source. CI006 was used as a negative control. Surprisingly, nitrogen fixing activity of the modified strain is increased compared with the parent.

Figure 35:
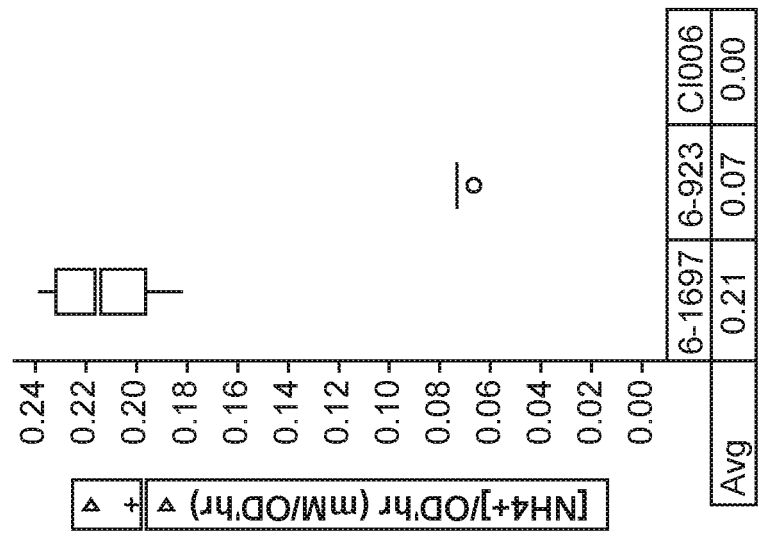
FIG. 35 depicts increased nitrogen excretion in mutants of K. sacchari strain CI006 with altered expression of the otsB gene compared with the parent control.

An ammonium excretion assay was performed on strain 6-1697. Data is shown as the amount of NH4+ excreted (mM/OD) per hour, such that a higher value indicates greater nitrogen excretion. The data represents experiments conducted on different days. Data is shown in FIG. 35. Nitrogen excreting activity was increased compared with the parent. Surprisingly, ammonium excretion activity of the modified strain is increased compared with the parent.

Example 17: phoB May be Modified to Increase Colonization of the Rhizosphere

Colonization of some strains may be associated with biofilm formation, which may be influenced by phosphorus signaling, which in some cases may be influenced by altering the expression of phosphorus signaling genes, such as phoB. Thus, alterations in phoB may affect colonization of some strains of bacteria.

A modification to phoB (strain 137-1901) was created in a bacterial strain with high nitrogen excretion as measured by an AMM assay. The parent strain was indicated as 137-1586.

Figure 36A:
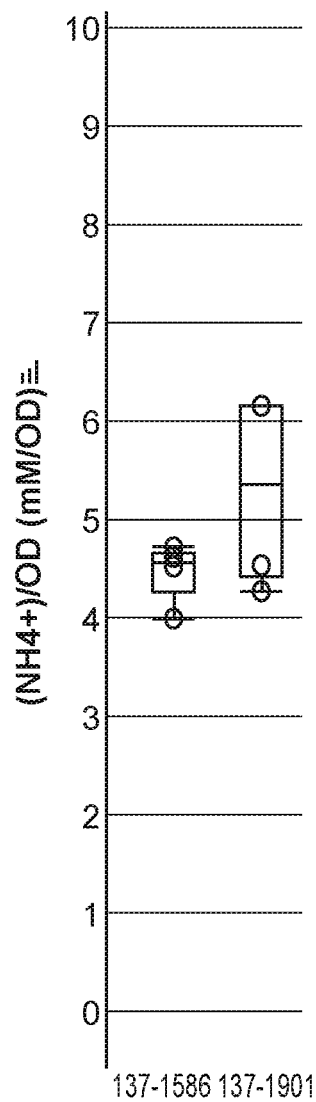
FIGS. 36A and 36B depicts unaltered nitrogen excretion and increased colonization in mutants of K. variicola strain CI137 with modifications in phoB compared with the parent control.

An AMM assay was performed on the cells to determine whether the modifications negatively affected the nitrogen excretion activity of the cells. The modifications did not reduce the nitrogen excretion activity of the cells (FIG. 36A). Thus phoB can be modified without reducing nitrogen excretion.

Figure 36B:
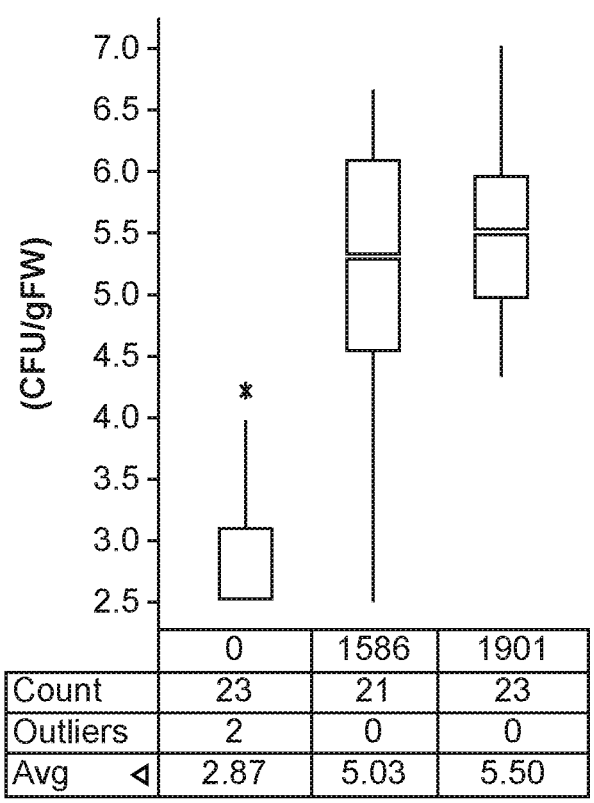

A corn root colonization assay was performed to determine whether the modifications affected the strain's ability to colonize plant roots. Briefly, plants were inoculated with about 109 cells after germination, and allowed to grow for 4 weeks, at which point they were harvested. Samples of combined seminal root and first node were taken from about 1-2 inches below the crown of the plant. After collection, samples were lysed and qPCR was performed to determine number of cells present per gram of root tissue (CFU/gfw). Strain 137-1901 displayed increased colonization compared to the parent strain 137-1586, as seen in FIG. 36B. Thus modifications of phoB can increase the colonization of cells on the root colonization of the mutant strain was higher than that of the parent strain in this case.

Example 18: yjbE2 May be Modified to Increase Colonization of the Rhizosphere yjbE genes can promote exopolysaccharide secretion, which may increase root attachment of certain strains.

Figure 37:
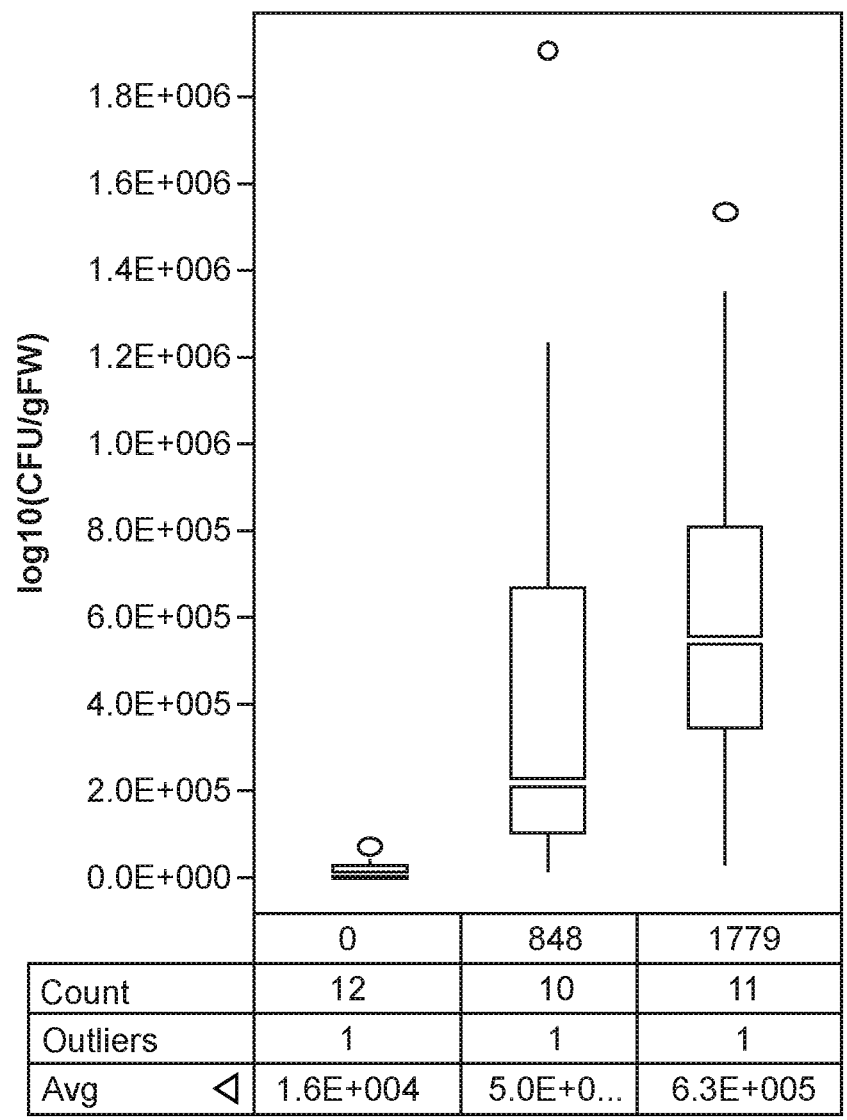
FIG. 37 depicts increased colonization in mutants of K. sacchari strain CI006 with modifications in yjbE compared with the parent control.

A corn root colonization assay was performed to determine whether the modification of yjbE affected the strain's ability to colonize plant roots. Briefly, plants were inoculated with about $10^9$ cells after germination, and allowed to grow for 4 weeks, at which point they were harvested. Samples of combined seminal root and first node were taken from about 1-2 inches below the crown of the plant. After collection, samples were lysed and qPCR was performed to determine number of cells present per gram of root tissue (CFU/gfw). Strain 6-1779 displayed increased colonization compared to the parent strain 6-848, as seen in FIG. 37.

Example 19: otsB otsB is involved in the biosynthesis of trehalose in the cell, and modifications of otsB may improve robustness of a strain. Here, modifications of otsB were created and tested to determine if these modifications negatively impacted nitrogen fixing in the cells.

Figures 38A, 38B:
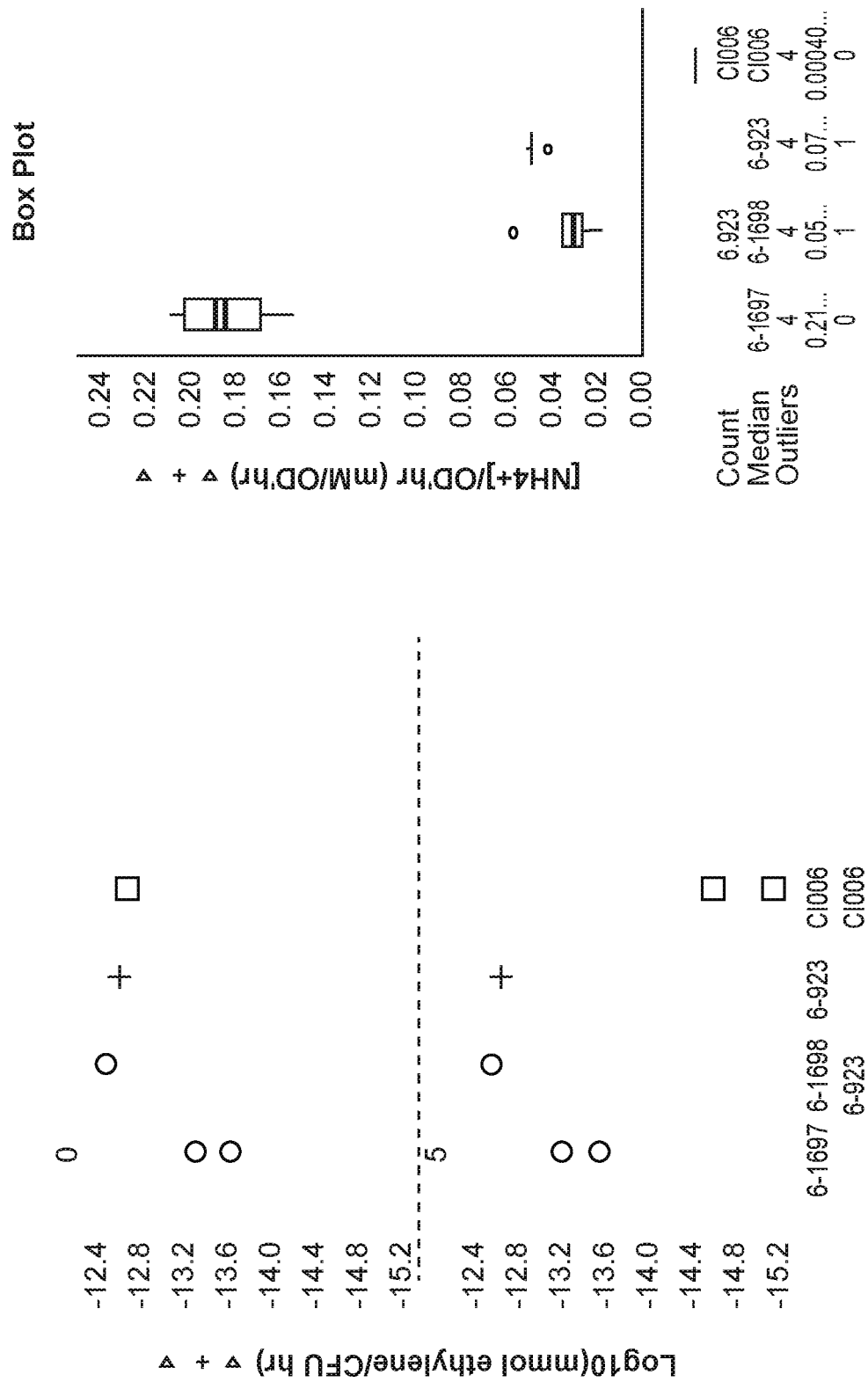
FIGS. 38 A and B depict increased nitrogenase activity and nitrogen excretion in mutants of K. sacchari strain CI006 with modifications in the expression of sulfate transport gene otsB created by inserting a promoter directly upstream of the gene compared with the parent strain.

A strain of nitrogen fixing bacteria was modified to increase expression of the otsB gene. An ARA assay was performed on the modified cells. Data is shown as the base 10 logarithm of the amount of ethylene formed per colony forming unit per hour, such that a higher amount of ethylene formation indicates more nitrogen fixation. The assay was performed with 0 mM (top panel) or 5 mM (bottom panel) ammonium phosphate provided as the nitrogen source. The modified strains are 6-1697 and 6-1698 (parent strain 6-923). CI006 was used as a negative control. Data is shown in FIG. 38A. Nitrogen fixing activity of the modified strain is increased compared with the parent. Thus, modifications of otsB can be performed without negatively affecting the nitrogen fixing activity of the cells.

An ammonium excretion assay was performed on the modified cells. Data is shown as the amount of NH4+ excreted (mM/OD) per hour, such that a higher value indicates greater nitrogen excretion. The data represents experiments conducted on different days. Data is shown in FIG. 38B. Nitrogen excreting activity was increased compared with the parent. Thus, modifications of otsB can be performed without negatively affecting the nitrogen fixing activity of the cells.

Example 20: cysZ Mutation Increases Nitrogen Fixation

Figure 39B:
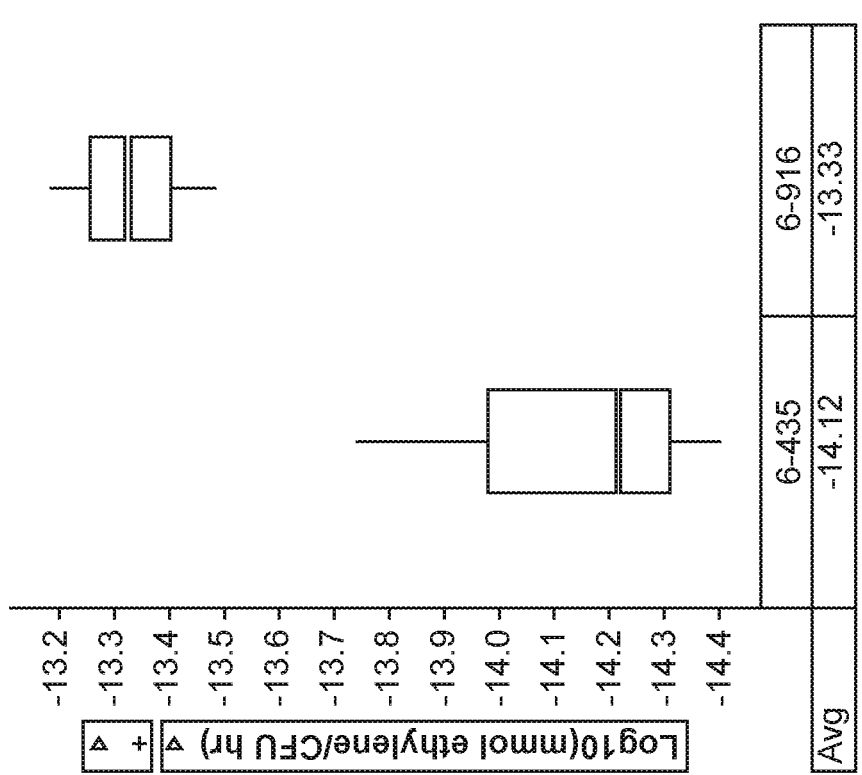
FIGS. 39 A and 39B depicts increased nitrogenase activity in mutants of K. sacchari strain CI006 with modifications in the expression of sulfate transport gene cysZ created by inserting a promoter directly upstream of the gene compared with parent strain.
Figure 39A:
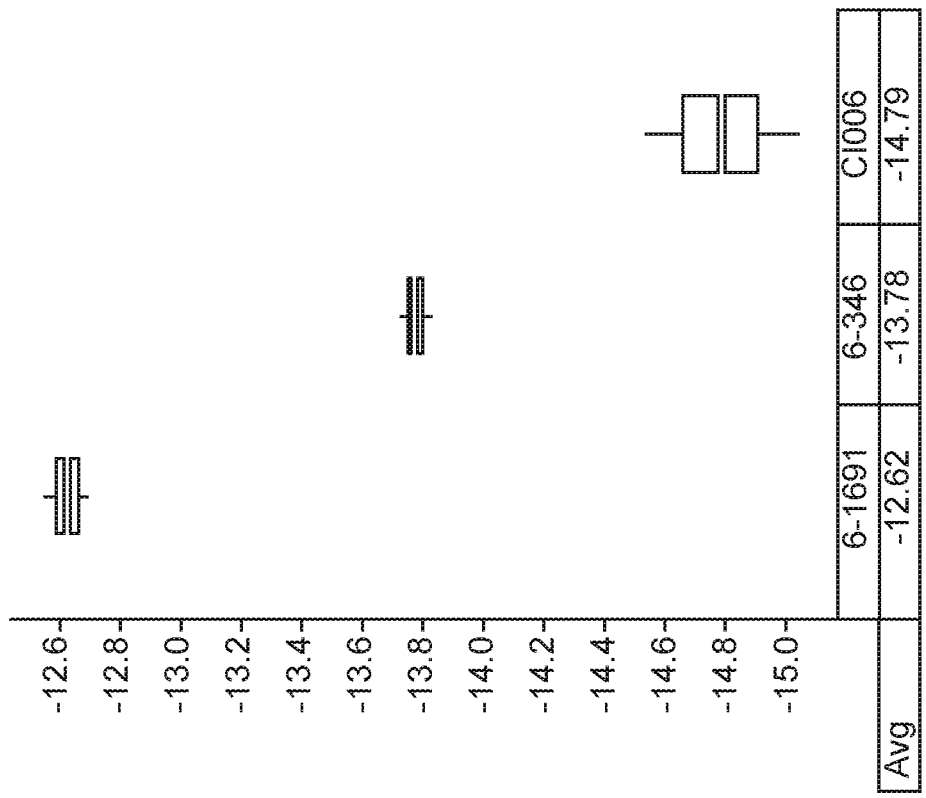

CysZ mediates sulfate uptake, providing sulfur subsequently utilized for the synthesis of sulfur-containing compounds in bacterial cells, including cofactors required for nitrogenase activity. Increasing the expression of a sulfur transport gene such as cysZ may increase the amount of functional nitrogenase complexes. To this end, two *Kosakonia sacchari* strains were created with cysZ modifications, which are notated as 6-1691 and 6-916. Acetylene reduction assays (ARA) were performed, and data was compared with the parent strain with no mutations in cysZ (strains 6-346 and 6-435 were parents for 6-1691 and 6-916, respectively). The strain CI006 was used as a negative control, and ARA assays were performed identically for both strains except that 6-1691 and its parent were assayed in 5 mM ammonium phosphate (FIG. 39A), while 6-916 and its parent were assayed in 5 mM glutamine (FIG. 39B). Both strains exhibit increased nitrogenase activity over the WT and parent strains. The increase displayed by 6-1691 was about 14 fold, while strain 6-916 had a nitrogen fixing activity about 6 times higher than that of its parent.

Example 21: Biofilm Formation

Biofilm formation can influence the amount of nitrogen being provided to an associated plant. An increase in biofilm formation on the root of a plant can increase the amount of nitrogen provided to the plant.

Some genes can regulate biofilm formation. For example, smZ can be a negative regulator of biofilm regulation. Mutation of smZ such that smZ has reduced or eliminated function can increase biofilm formation in bacteria. Mutagenesis can be performed to mutate smZ in strains with increased nitrogen excretion and fixation activity to create an smZ mutant library of bacteria.

Some proteins can promote biofilm formation. For example, large adhesion proteins including lapA can promote biofilm formation. One or more promoters regulating the expression of lapA may be upregulated, such that more lapA is produced, as detected by western blot.

Strains with smZ mutations and lapA upregulation may be generated to generate a smZ/lapA library of strains for testing. smZ/LapA strains can have increased biofilm formation, and can have biofilm formation ability which is higher than strains with an smZ mutation or lapA mutation alone.

Strains may be grown in lysogeny buffer (LB) and inoculated into soil with a seedling. The seedling, soil, and bacterial strain can be in a pot, in a field, indoors, or outdoors. The seedling can be planted in spring, summer, fall, or winter. The air can have about 0%, 10%, 20%, 30%, 40%, 50%, 60%, 70%, 80%, 90%, or 100% humidity. It may be raining, foggy, cloudy, or sunny. The temperature can be about 4° C., 10° C., 15° C., 20° C., 25° C., 30° C., 35° C., 40° C., or 45° C. The seedling can be planted at dawn, morning, midday, afternoon, dusk, evening, or night. The seedling can be left to grow for about 1, 2, 3, 4, 5, 6, 7, 8, 9, 10, 20, or 30 days. After the time has elapsed, the plant can be dug up and the amount of biofilm on the roots can be measured.

Example 22: Oxygen Sensitivity

Oxygen sensitivity of nitrogenase enzymes can affect nitrogen fixation, nitrogen excretion, or both. Decreasing the oxygen sensitivity of a nitrogenase enzyme can increase the nitrogen fixing activity, increase the nitrogen excreting activity, or both. A strain of bacteria comprising one or more nitrogenase enzymes with decreased oxygen may be created such that that strain displays increased nitrogen fixing activity or increased nitrogen excreting activity.

Genetic modifications can be performed in bacterial cells with wild type or genetically improved nitrogen fixing activity, nitrogen excreting activity, or both. Genetic modifications can be introduced to the cells such that one or more nitrogenase enzyme genes is muted by a mutagenesis protocol, and a library of such strains can be created.

Each strain in the library can be subjected to an oxygen sensitivity assay. To do this, AMM and ARA assays can be performed under conditions with varying oxygen concentrations. Oxygen concentrations can range from 1 µM to 6 µM. Data can be analyzed to determine whether the strains display decreased nitrogen excretion or nitrogen fixation activity as a function of oxygen concentration. Some strains with modified nitrogenase enzymes may display little or no reduction in nitrogen excretion or nitrogen fixation activity as the oxygen concentration increases.

Example 23:Altering modA, modB, modE

The molybdenum uptake pathway can refer to metabolic pathway in bacteria which enables the uptake of molybdenum into the cell. Molybdenum can act as a cofactor in nitrogen fixation. Increasing the molybdenum uptake of cells may increase nitrogen fixation, nitrogen excretion, or both.

Key enzymes in the molybdenum transport pathway can include modA, modB, and modE. Modification or upregulation of any one, two, or three of these genes in a bacterial strain may increase molybdenum uptake in the cells, and may increase the nitrogen fixation, nitrogen excretion, or both in the cells.

Genetic modifications can be performed on these genes in bacterial cells such that the modifications result in an increased molybdenum transport. To identify such modifications, mutagenesis may be performed in and around the active sites of the genes that code for modA, modB, or modC. A library of mutants may be constructed for each gene. These libraries can be then screened for increased molybdenum uptake activity. These libraries can be created from wild type cells, or from cells which have already been modified to display increased nitrogen fixation, increased nitrogen excretion, or both.

Genetic modifications can be performed in these cells such that one or more genes in the molybdenum uptake pathway is upregulated. A library of variants may also be constructed such that promoter activity for one or more genes in the molybdenum uptake pathway is increased. For example, the modABC promoter can be genetically tuned to increase the transcription. Western blotting can be used to determine which strains have increased expression of one or more molybdenum uptake genes, and these strains can be variants of interest.

To screen for increased molybdenum uptake activity, each mutant or variant of interest as well as the unmutated parent strain for each strain can be inoculated into and grown in three wells of a 96 well plate in LB medium. Once the cells reach OD=0.8, one of the wells of each mutant can be harvested, such that the cells are pelleted, excess LB is washed away, and cells are resuspended, lysed, and prepared for spectroscopy in a 96 well plate. Molybdenum content can be measured using spectroscopy to establish the baseline molybdenum content in the samples. The remaining samples can be spiked with molybdenum as tetraoxyanion molybdate in LB or LB alone, such that the amount added is 10% or less of the total volume in each well. The final concentration of molybdenum in each well in the assay can be one of 10 pM, 100 pM, 1 nM, 10 nM, or 100 nM, and more than one concentration can be tested. The assay can be conducted over one or more of 1 second, 10 seconds, 30 seconds, 1 minute, 2 minutes, 3 minutes, 4 minutes, 5 minutes, 10 minutes, 20 minutes, 30 minutes, and 60 minutes.

First, for each concentration, the amount of molybdenum transported into each cell as a function of time can be plotted to determine an optimal duration for the assay. The optimal duration can be a time interval wherein steady state has not been reached, and the reaction rate still linear. Then, for the optimal duration, the amount of molybdenum transported into each cell as a function of concentration can be plotted, and a Michaelis-Menten analysis can be performed. Mutant strains or variants of interest which show a significant increase ($p<0.05$) in molybdenum transport over the unmutated and unmodified parent strain as determined by Km comparison can be selected for further assays.

Next, each strain selected for further assays can be subjected to an AMM assay as well as an ARA assay as described herein to measure nitrogen excretion and fixation, respectively. One or more of these mutations or variants may increase the AMM, ARA, or both of one or more of these bacterial strains.

Example 24: Increasing Iron Transport May Increase Nitrogen Fixation

The iron uptake pathway can refer to metabolic pathway in bacteria which enables the uptake of iron into the cell. Iron can act as a cofactor to promote nitrogen fixation. Increasing the iron uptake of cells may increase nitrogen fixation, nitrogen excretion, or both.

Key enzymes in the iron transport pathway can include exbA, exbB, and tonB. Modification or upregulation of any one, two, or three of these genes in a bacterial strain may increase iron uptake in the cells, and may increase the nitrogen fixation, nitrogen excretion, or both in the cells.

Genetic modifications can be performed on these genes in bacterial cells such that the modifications result in an increased iron transport. To identify such modifications, mutagenesis may be performed in and around the active sites of the genes that code for exbA, exbB, or tonB. A library of mutants may be constructed for each gene. These libraries can be then screened for increased iron uptake activity. These libraries can be created from wild type cells, or from cells which have already been modified to display increased nitrogen fixation, increased nitrogen excretion, or both.

Genetic modifications can be performed in these cells such that one or more genes in the iron uptake pathway is upregulated. A library of variants may also be constructed such that promoter activity for one or more genes in the iron uptake pathway is increased. Western blotting can be used to determine which strains have increased expression of one or more iron uptake genes, and these strains can be variants of interest.

To screen for increased iron uptake activity, each mutant or variant of interest as well as the unmutated parent strain for each strain can be inoculated into and grown in three wells of a 96 well plate in LB medium. Once the cells reach OD=0.8, one of the wells of each mutant can be harvested, such that the cells are pelleted, excess LB is washed away, and cells are resuspended, lysed, and prepared for spectroscopy in a 96 well plate. Iron content can be measured using spectroscopy to establish the baseline iron content in the samples. The remaining samples can be spiked with iron as FeSO4 in LB or LB alone, such that the amount added is 10% or less of the total volume in each well. 0.1 mM of acetic acid (final concentration) may be included to aid in the solubility of the iron. The final concentration of iron in each well in the assay can be one of 10 pM, 100 pM, 1 nM, 10 nM, 100 nM, 1 µM, 10 µM, or 100 µM, and more than one concentration can be tested. The assay can be conducted over one or more of 1 second, 10 seconds, 30 seconds, 1 minute, 2 minutes, 3 minutes, 4 minutes, 5 minutes, 10 minutes, 20 minutes, 30 minutes, and 60 minutes.

First, for each concentration, the amount of iron transported into each cell as a function of time can be plotted to determine an optimal duration for the assay. The optimal duration can be a time interval wherein steady state has not been reached, and the reaction rate still linear. Then, for the optimal duration, the amount of iron transported into each cell as a function of concentration can be plotted, and a Michaelis-Menten analysis can be performed. Mutant strains or variants of interest which show a significant increase ($p<0.05$) in iron transport over the unmutated and unmodified parent strain as determined by Km comparison can be selected for further assays.

Next, each strain selected for further assays can be subjected to an AMM assay as well as an ARA assay as described herein to measure nitrogen excretion and fixation, respectively. One or more of these mutations or variants may increase the AMM, ARA, or both of one or more of these bacterial strains.

Example 25: Increasing Siderophore Biosynthesis Genes May Increase Nitrogen Fixation yhf siderophores, or iron chelating molecules may influence the uptake of iron in bacteria. Increasing the production of yhf siderophores can increase iron uptake in bacteria. Modifications in siderophore genes, including yhfA, yusV, sbnA, yfiZ, fiu, and fur, may increase the production of yhf siderophores, which may in turn increase iron uptake in cells. These modifications may lead to increased nitrogen fixation or excretion.

Genetic modifications can be performed on these genes in bacterial cells such that the modifications result in an increased siderophore production. To identify such modifications, mutagenesis may be performed in and around the active sites of the genes that code for yhfA, yusV, sbnA, yfiZ, fiu, or fur. A library of mutants may be constructed for each gene. These libraries can be then screened for increased siderophore production. These libraries can be created from wild type cells, or from cells which have already been modified to display increased nitrogen fixation, increased nitrogen excretion, or both. To screen for increased siderophore production, each mutant can be grown to OD=0.8 and then spiked with an excess but not toxic amount of siderophore precursors and incubated for 30 minutes or 60 minutes. The amount of siderophores produced after the allotted time period can be normalized, and strains which display increased siderophore production may be screened for increased iron transport.

To screen for increased iron uptake activity, each mutant or variant of interest as well as the unmutated parent strain for each strain can be inoculated into and grown in three wells of a 96 well plate in LB medium. Once the cells reach OD=0.8, one of the wells of each mutant can be harvested, such that the cells are pelleted, excess LB is washed away, and cells are resuspended, lysed, and prepared for spectroscopy in a 96 well plate. Iron content can be measured using spectroscopy to establish the baseline iron content in the samples. The remaining samples can be spiked with iron as FeSO4 in LB or LB alone, such that the amount added is 10% or less of the total volume in each well. 0.1 mM of acetic acid (final concentration) may be included to aid in the solubility of the iron. The final concentration of iron in each well in the assay can be one of 10 pM, 100 pM, 1 nM, 10 nM, 100 nM, 1 μM, 10 μM, or 100 μM, and more than one concentration can be tested. The assay can be conducted over one or more of 1 second, 10 seconds, 30 seconds, 1 minute, 2 minutes, 3 minutes, 4 minutes, 5 minutes, 10 minutes, 20 minutes, 30 minutes, and 60 minutes.

First, for each concentration, the amount of iron transported into each cell as a function of time can be plotted to determine an optimal duration for the assay. The optimal duration can be a time interval wherein steady state has not been reached, and the reaction rate still linear. Then, for the optimal duration, the amount of iron transported into each cell as a function of concentration can be plotted, and a Michaelis-Menten analysis can be performed. Mutant strains or variants of interest which show a significant increase ($p<0.05$) in iron transport over the unmutated and unmodified parent strain as determined by Km comparison can be selected for further assays.

Next, each strain selected for further assays can be subjected to an AMM assay as well as an ARA assay as described herein to measure nitrogen excretion and fixation, respectively. One or more of these mutations or variants may increase the AMM, ARA, or both of one or more of these bacterial strains.

Example 26: dctA1 and dctA2 dctA1 and dctA2 are responsible for the aerobic transport of the dicarboxylates fumarate, L- and D-malate and to a lesser extent succinate, from the periplasm across the inner membrane. Modifications to these genes may influence colonization of microbes.

Modifications to dctA1 (strain 137-1861) and dctA2 (strain 137-1905) were created in a strain with high nitrogen excretion as measured by an AMM assay. The parent strain was indicated as 137-1905.

Figure 40A:
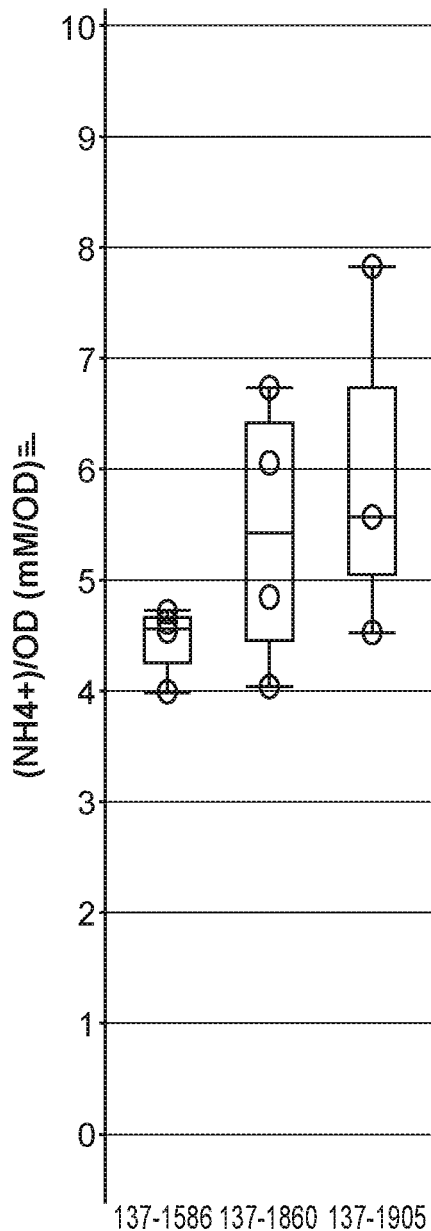
FIGS. 40A and 40B depict increased ammonium excretion in mutants of K. variicola strain CI137 with modifications in dctA1 and dctA2.

An AMM assay was performed on the cells to determine whether the modifications negatively affected the nitrogen excretion activity of the cells. The modifications did not reduce the nitrogen excretion activity of the cells (FIG. 40A). Thus dctA1 and dctA2 can be modified without reducing nitrogen excretion.

Figure 40B:
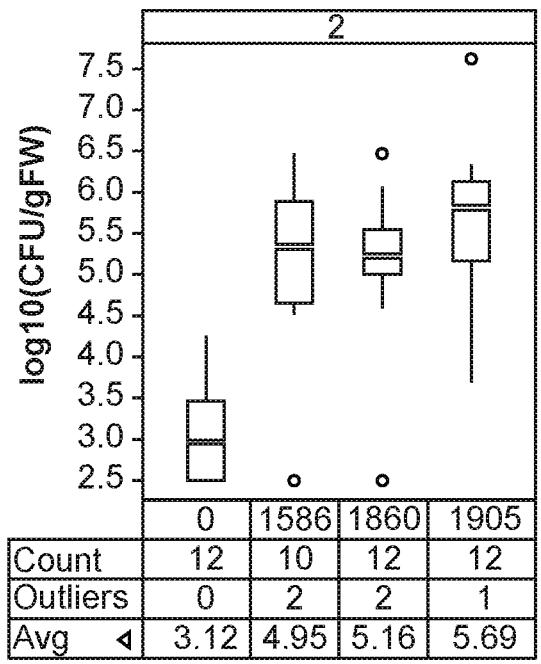

A colony formation assay was performed on the cells using qPCR to determine whether the modifications affected the colony forming properties of the cells. Briefly, plants were innoculated with about 109 cells after germination, and allowed to grow for 4 weeks, at which point they were harvested. Samples of combined seminal root and first node were taken from about 1-2 inches below the crown of the plant. After collection, samples were lysed and qPCR was performed to determine CFU/gfw. Data is shown in FIG. 40B. Both strains displayed increased colonization. Thus modifications of dctA1 and dctA2 can increase the colonization in cells.

Example 27: Increasing Dessication Tolerance

Improving desiccation tolerance may increase colonization of a strain used in a seed coating, or other dry application to a plant or field. A genetically engineered microbe will be created comprising an arabinose promoter operably linked to an rpoE gene. The genetically engineered microbe, and the non-engineered parental control, will be cultured in media supplemented with arabinose for 48 hours before being desiccated. After desiccation a portion of each of the engineered and non-engineered strains will be revived in media which does not contain arabinose, and the number of microbes in the media after 24 hours will be assayed. The media containing the engineered strain will contain more microbes than the media containing the non-engineered parental strain.

Desiccated microbes will be applied to corn seeds and planted in soil, lacking arabinose, in a greenhouse under conditions suitable for the germination of the corn seeds. After 4 weeks the seedlings will be harvested and the number of colony forming units of both the engineered and non-engineered microbes on the roots of the plants will be assessed. The plants exposed to the engineered microbes will be associated with more microbes than the plants exposed to the non-engineered parental strain.

Example 28: Altering nifA RBSs Increases nifH Transcription

Promoter-RBS sequences inserted upstream of nifA lead to increased ratios of nifH:nifA transcription, indicating an increase in the amount of active NifA protein due to the increased strength of the inserted RBS leading to higher translate initiation rates of NifA.

Figure 41A:
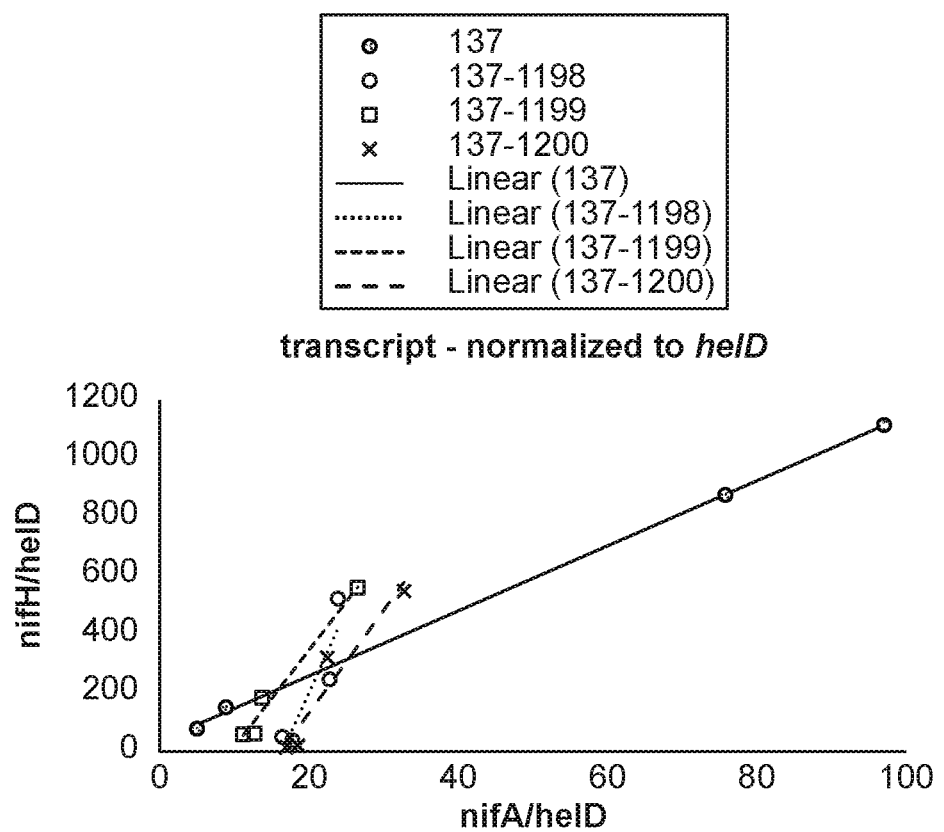
FIGS. 41A and 41B illustrate the ratio of nifH transcript to nifA transcript in several strains with different promoters and RBS sequences inserted upstream of nifA.
Figure 41B:
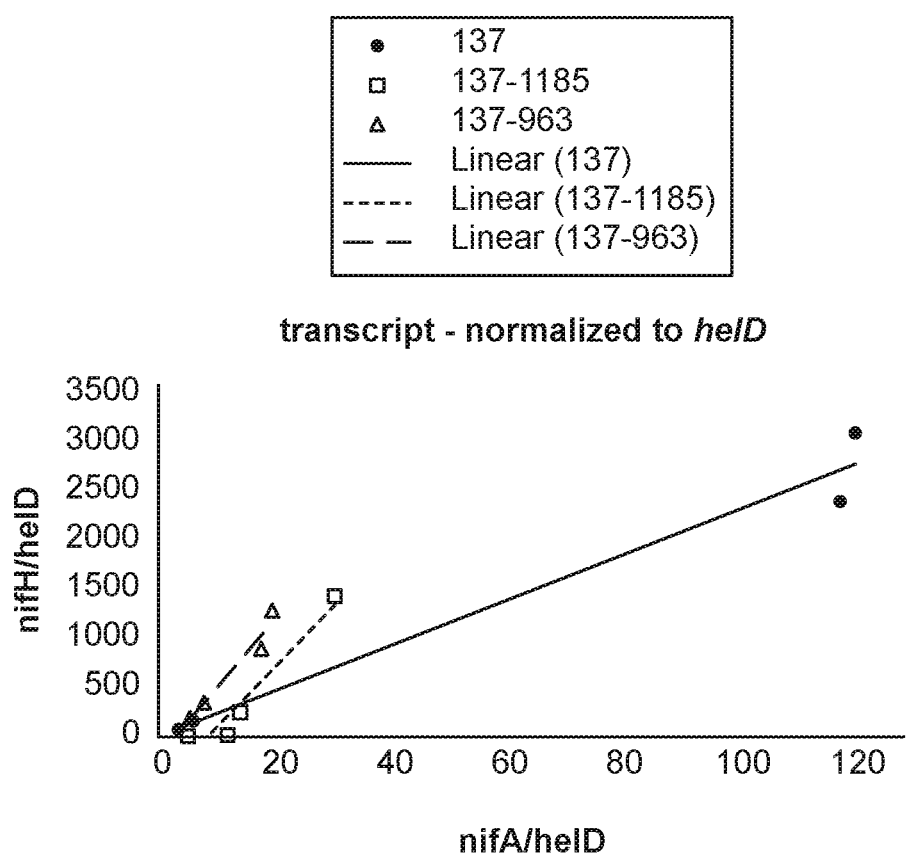

Strains were generated by deleting the nifL gene and inserting a sequence upstream of nifA which contained both the promoter and the ribosome binding site (RBS) of a gene found elsewhere in the host's genome. Two biological replicates were grown overnight in rich medium, then subcultured into minimal medium supplemented with 10 mM glutamine. The resulting culture was split and used to inoculate an anaerobic culture in ARA medium with either no fixed nitrogen source or 10 mM glutamine. After five hours of anaerobic culture, a sample of each culture was taken, and RNA extracted, subjected to reverse transcription to generate cDNA, and analyzed by qPCR to measure transcription of nifA and nifH. Transcripts of the genes of interest were normalized to housekeeping gene helD, which shows consistent transcription in different nitrogen conditions. The resulting normalized data for the four samples were plotted to show the relationship between nifA transcription and nifH transcription in each strain. The remodeled strains in FIGS. 41A and 41B show an increased slope in a linear best-fit line plotting nifH over nifA transcription, indicating that each nifA transcript results in a greater number of nifH transcripts in these strains due to an increase translation initiation rate of NifA.

TABLE 8

Strains described herein

Figure 4A:
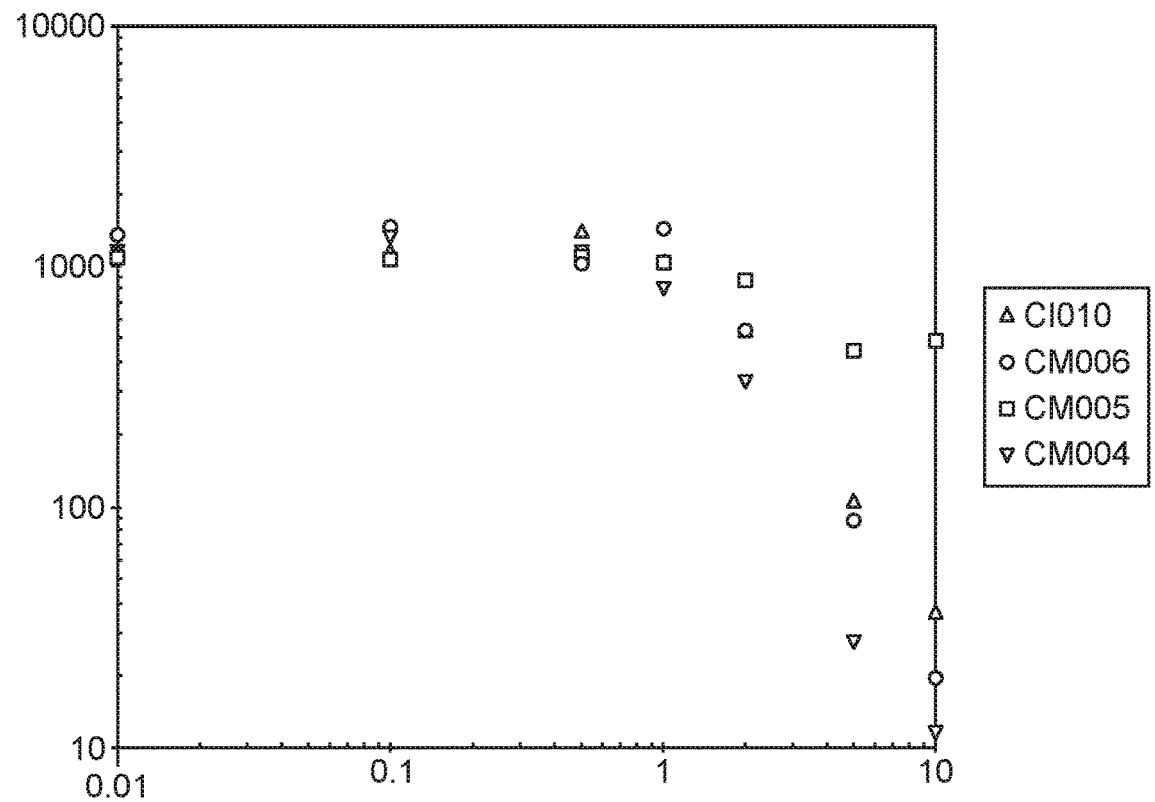
FIGS. 4A-D depict in vitro phenotypes of various strains. The Acetylene Reduction Assay (ARA) activities of mutants of strain CI010 (FIG. 4A) and mutants of strain CI006 (FIG. 4B) grown in nitrogen fixation media supplemented with 0 to 10 mM glutamine. ARA activities of additional strains are shown in FIG. 4C, and the ammonium excretion profile across time of two strains is shown in FIG. 4D.
Figure 4B:
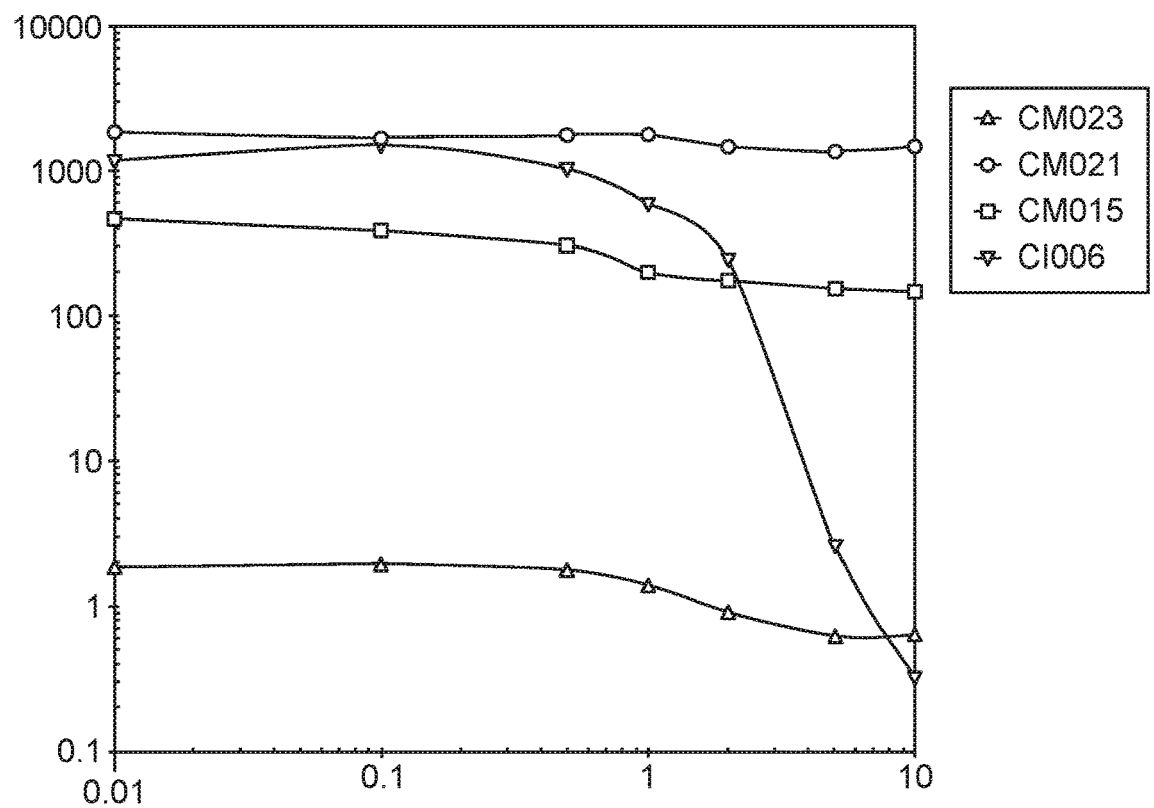
Figure 4C:
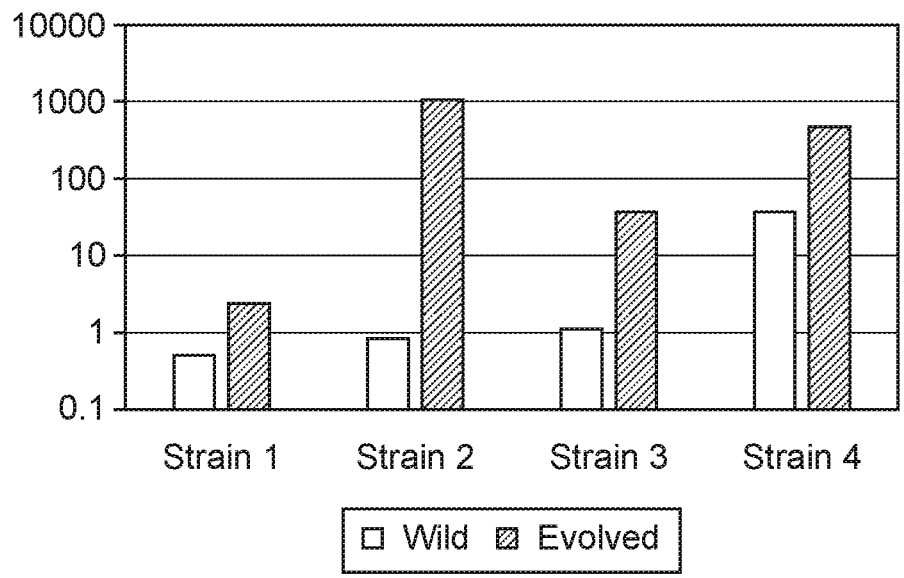
Figure 4D:
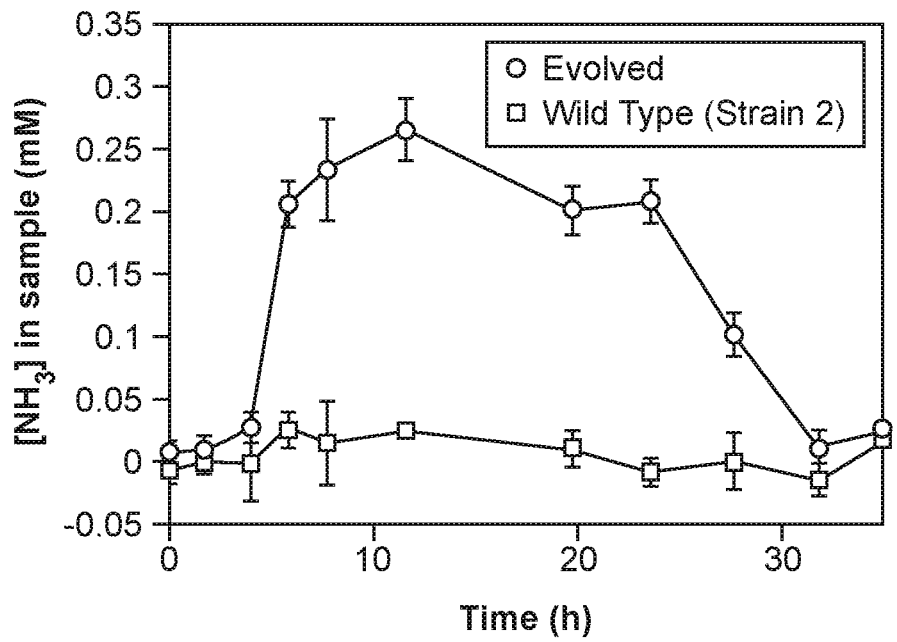
Figure 10A:
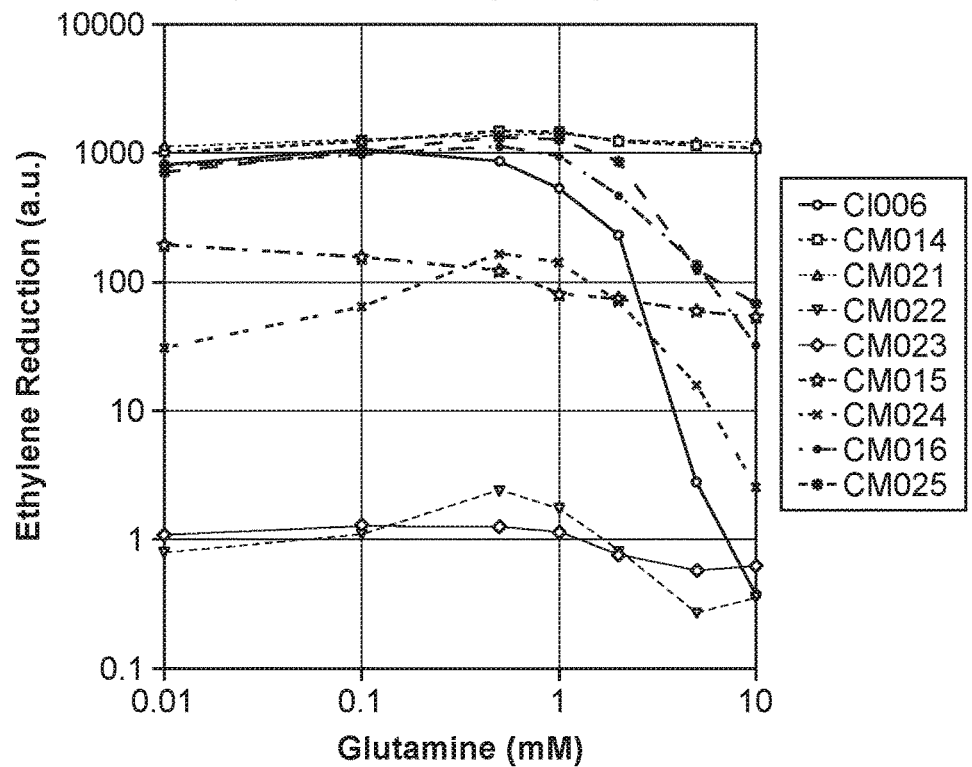
FIGS. 10A-C depicts additional results for ARA activities of candidate microbes and counterpart candidate mutants grown in nitrogen fixation media supplemented with 0 to 10 mM glutamine.

| Sort | First Reference | Current Name | Universal Name | Lineage | Mutagenic DNA Description | Genotype |
|---|---|---|---|---|---|---|
| 1 | Application text | CI006 | CI006 | Isolated strain from *Enterobacter* genera | None | WT |
| 2 | Application text | CI008 | CI008 | Isolated strain from *Burkholderia* genera | None | WT |
| 3 | Application text | CI010 | CI010 | Isolated strain from *Klebsiella* genera | None | WT |
| 4 | Application text | CI019 | CI019 | Isolated strain from *Rahnella* genera | None | WT |
| 5 | Application text | CI028 | CI028 | Isolated strain from *Enterobacter* genera | None | WT |
| 6 | Application text | CI050 | CI050 | Isolated strain from *Klebsiella* genera | None | WT |
| 7 | Application text | CM002 | CM002 | Mutant of CI050 | Disruption of nifL gene with a kanamycin resistance expression cassette (KanR) encoding the aminoglycoside O-phosphotransferase gene aph1 inserted. | ΔnifL::KanR |
| 8 | Application text | CM011 | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR |
| 9 | Application text | CM013 | CM013 | Mutant of CI006 | Disruption of nifL gene with a kanamycin resistance expression cassette (KanR) encoding the aminoglycoside O-phosphotransferase gene aph1 inserted. | ΔnifL::KanR |
| 10 | FIG. 4A | CM004 | CM004 | Mutant of CI010 | Disruption of amtB gene with a kanamycin resistance expression cassette (KanR) encoding the aminoglycoside O-phosphotransferase gene aph1 inserted. | ΔamtB::KanR |
| 11 | FIG. 4A | CM005 | CM005 | Mutant of CI010 | Disruption of nifL gene with a kanamycin resistance expression cassette (KanR) encoding the aminoglycoside O-phosphotransferase gene aph1 inserted. | ΔnifL::KanR |
| 12 | FIG. 4B | CM015 | CM015 | Mutant of CI006 | Disruption of nifL gene with a fragment of the region upstream of the ompX gene inserted (Prm5). | ΔnifL::Prm5 |
| 13 | FIG. 4B | CM021 | CM021 | Mutant of CI006 | Disruption of nifL gene with a fragment of the region upstream of an unanotated gene and the first 73 bp of that gene inserted (Prm2). | ΔnifL::Prm2 |
| 14 | FIG. 4B | CM023 | CM023 | Mutant of CI006 | Disruption of nifL gene with a fragment of the region upstream of the acpP gene and the first 121 bp of the acpP gene inserted (Prm4). | ΔnifL::Prm4 |
| 15 | FIG. 10A | CM014 | CM014 | Mutant of CI006 | Disruption of nifL gene with a fragment of the region upstream of the 1 pp gene and the first 29 bp of the 1 pp gene inserted (Prm1). | ΔnifL::Prm1 |
| 16 | FIG. 10A | CM016 | CM016 | Mutant of CI006 | Disruption of nifL gene with a fragment of the region upstream of the lexA 3 gene and the first 21 bp of the lexA 3 gene inserted (Prm9). | ΔnifL::Prm9 |
| 17 | FIG. 10A | CM022 | CM022 | Mutant of CI006 | Disruption of nifL gene with a fragment of the region upstream of the mntP 1 gene and the first 53 bp of the mntP 1 gene inserted (Prm3). | ΔnifL::Prm3 |
| 18 | FIG. 10A | CM024 | CM024 | Mutant of CI006 | Disruption of nifL gene with a fragment of the region upstream of the sspA gene inserted (Prm7). | ΔnifL::Prm7 |

TABLE 8-continued

Strains described herein

Figure 10B:
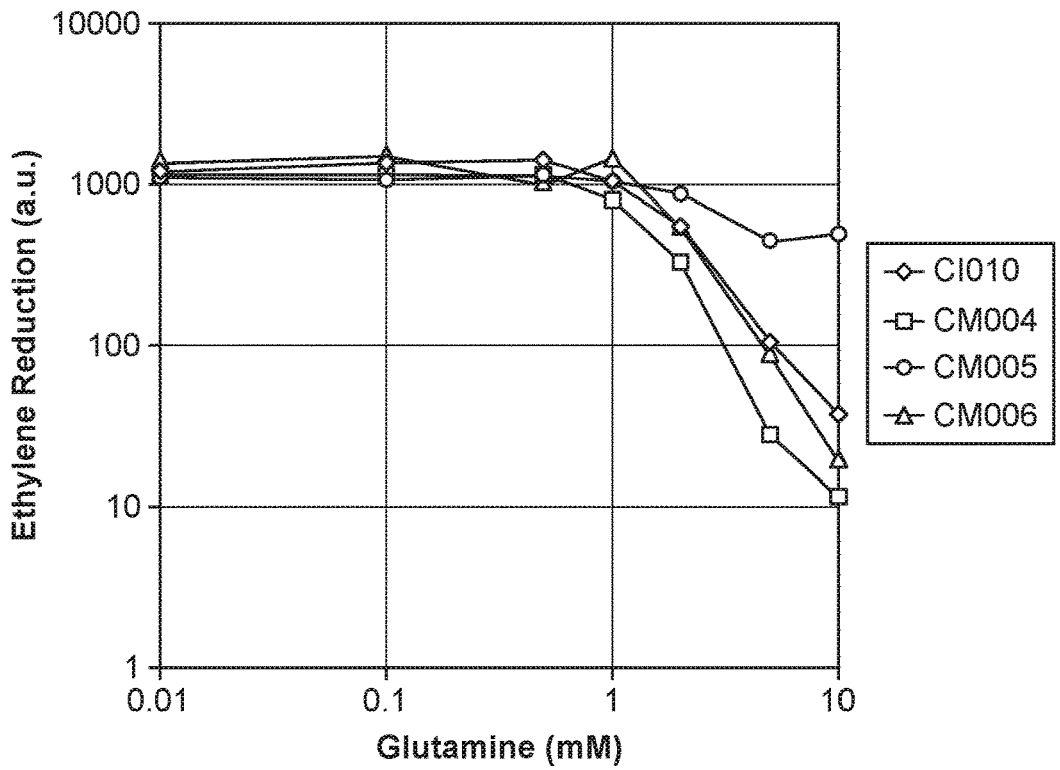
Figure 10C:
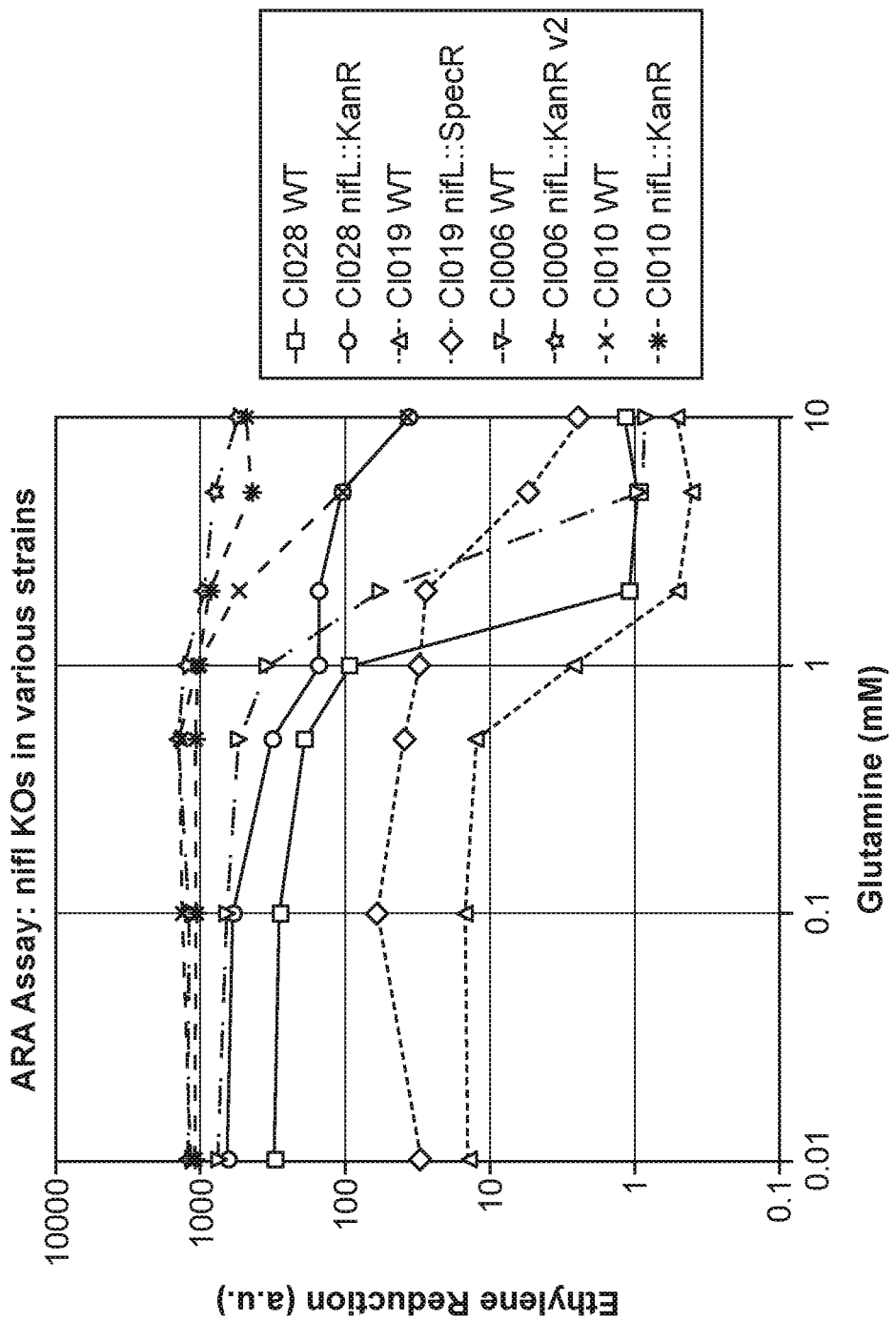

| Sort | First Reference | Current Name | Universal Name | Lineage | Mutagenic DNA Description | Genotype |
|---|---|---|---|---|---|---|
| 19 | FIG. 10A | CM025 | CM025 | Mutant of CI006 | Disruption of nifL gene with a fragment of the region upstream of the hisS gene and the first 52 bp of the hisS gene inserted (Prm10). | ΔnifL::Prm10 |
| 20 | FIG. 10B | CM006 | CM006 | Mutant of CI010 | Disruption of glnB gene with a kanamycin resistance expression cassette (KanR) encoding the aminoglycoside O-phosphotransferase gene aph1 inserted. | ΔglnB::KanR |
| 21 | FIG. 10C | CI028 nifL:KanR | CM017 | Mutant of CI028 | Disruption of nifL gene with a kanamycin resistance expression cassette (KanR) encoding the aminoglycoside O-phosphotransferase gene aph1 inserted. | ΔnifL::KanR |
| 22 | FIG. 10C | CI019 nifL:SpecR | CM011 | Mutant of CI019 | Disruption of nifL gene with a spectinomycin resistance expression cassette (SpecR) encoding the streptomycin 3''-O-adenylyltransferase gene aadA inserted. | ΔnifL::SpecR |
| 23 | FIG. 10C | CI006 nifL:KanR | CM013 | Mutant of CI006 | Disruption of nifL gene with a kanamycin resistance expression cassette (KanR) encoding the aminoglycoside O-phosphotransferase gene aph1 inserted. | ΔnifL::KanR |
| 24 | FIG. 10C | CI010 nifL:KanR | CM005 | Mutant of CI010 | Disruption of nifL gene with a kanamycin resistance expression cassette (KanR) encoding the aminoglycoside O-phosphotransferase gene aph1 inserted. | ΔnifL::KanR |
| 25 | FIG. 4C | Strain 2 | CI006 | Isolated strain from Enterobacter genera | None | WT |
| 26 | FIG. 4C | Strain 4 | CI010 | Isolated strain from Klebsiella genera | None | WT |
| 27 | FIG. 4C | Strain 1 | CI019 | Isolated strain from Rahnella genera | None | WT |
| 28 | FIG. 4C | Strain 3 | CI028 | Isolated strain from Enterobacter genera | None | WT |
| 29 | FIG. 4B | Strain 2 | CI006 | Isolated strain from Enterobacter genera | None | WT |
| 30 | FIG. 4B | High | CM014 | Mutant of CI006 | Disruption of nifL gene with a fragment of the region upstream of the 1 pp gene and the first 29 bp of the 1 pp gene inserted (Prm1). | ΔnifL::Prm1 |
| 31 | FIG. 4B | Med | CM015 | Mutant of CI006 | Disruption of nifL gene with a fragment of the region upstream of the ompX gene inserted (Prm5). | ΔnifL::Prm5 |
| 32 | FIG. 4B | Low | CM023 | Mutant of CI006 | Disruption of nifL gene with a fragment of the region upstream of the acpP gene and the first 121 bp of the acpP gene inserted (Prm4). | ΔnifL::Prm4 |
| 33 | FIG. 4D | Strain 2 | CI006 | Isolated strain from Enterobacter genera | None | WT |
| 34 | FIG. 4D | Evolved | CM029 | Mutant of CI006 | Disruption of nifL gene with a fragment of the region upstream of the ompX gene inserted (Prm5) and deletion of the 1287 bp after the start codon of the glnE gene containing the adenylyl-removing domain of glutamate-ammonia-ligase adenylyltransferase (ΔglnE-AR_KO1). | ΔnifL::Prm5 ΔglnE-AR_KO1 |
| 35 | FIG. 14C | Wild | CI006 | Isolated strain from Enterobacter genera | None | WT |

TABLE 8-continued

Strains described herein

Figure 15A:
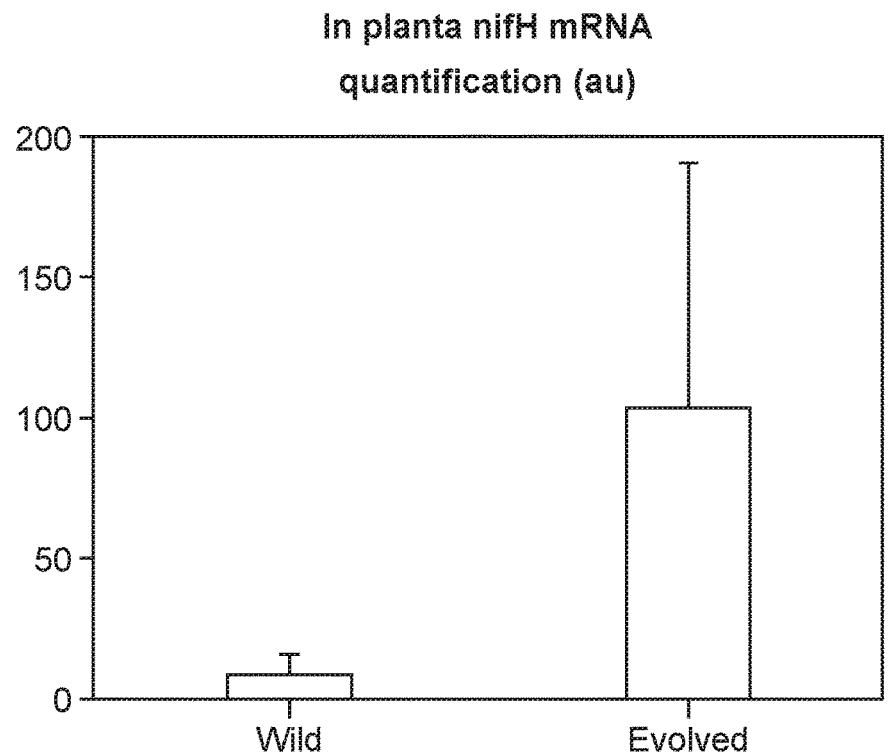
FIG. 15A depicts evolved strains that show significantly higher nifH production in the root tissue, as measured by in planta transcriptomic study.
Figure 15B:
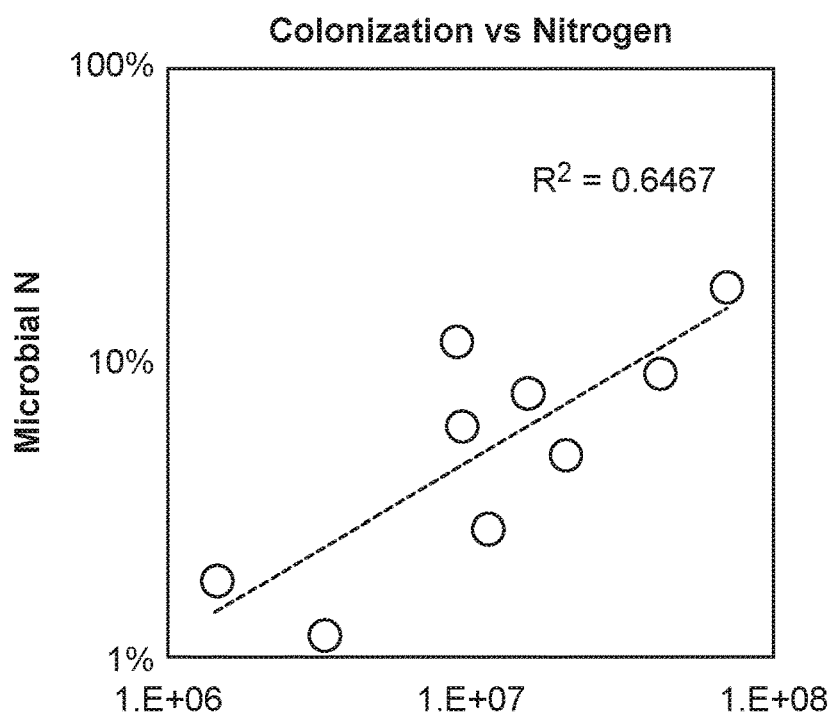
FIG. 15B depicts that rate of fixed nitrogen found in plant tissue is correlated with the rate in which that particular plant is colonized by HoME optimized strain.

| Sort | First Reference | Current Name | Universal Name | Lineage | Mutagenic DNA Description | Genotype |
|---|---|---|---|---|---|---|
| 36 | FIG. 14C | Evolved | CM014 | Mutant of CI006 | Disruption of nifL gene with a fragment of the region upstream of the 1 pp gene and the first 29 bp of the 1 pp gene inserted (Prm1). | ΔnifL::Prm1 |
| 37 | FIG. 14B | Wild | CI019 | Isolated strain from *Rahnella* genera | None | WT |
| 38 | FIG. 14B | Evolved | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR |
| 39 | FIG. 14A | Evolved | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR |
| 40 | FIG. 15A | Wild | CI006 | Isolated strain from *Enterobacter* genera | None | WT |
| 41 | FIG. 15A | Evolved | CM013 | Mutant of CI006 | Disruption of nifL gene with a kanamycin resistance expression cassette (KanR) encoding the aminoglycoside O-phosphotransferase gene aph1 inserted. | ΔnifL::KanR |
| 42 | FIG. 15B | No name | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR |
| 43 | FIG. 16B | Strain 5 | CI008 | Isolated strain from *Burkholderia* genera | None | WT |
| 44 | FIG. 16B | Strain 1 | CM011 | Mutant of CI019 | Disruption of nifL gene with a spectinomycin resistance expression cassette (SpecR) encoding the streptomycin 3"-O-adenylyltransferase gene aadA inserted. | ΔnifL::SpecR |
| 34 | FIG. 4D | Evolved | CM029 | Mutant of CI006 | Disruption of nifL gene with a fragment of the region upstream of the ompX gene inserted (Prm5) and deletion of the 1287 bp after the start codon of the glnE gene containing the adenylyl-removing domain of glutamate-ammonia-ligase adenylyltransferase (ΔglnE-AR_KO1). | ΔnifL::Prm5 ΔglnE-AR_KO1 |

TABLE 9

Further strains described herein

| Strain ID | Lineage | Mutagenic DNA Description | Chromosomal Genotype | Curing Status |
|---|---|---|---|---|
| CI006 | CI006 | Wildtype parent *Kosakonia saccari* | WT | N/A |
| CI137 | CI137 | Wildtype parent *K. variicola* | WT | N/A |
| CI137-1036 | Mutant of CI137 | Disruption of nifL gene with a fragment of the region upstream of the infC gene inserted (PinfC) upstream of nifA. Deletion of the 1647 bp after the start codon of the glnE gene containing the adenylyl-removing domain of glutamate-ammonia-ligase adenylyltransferase (ΔglnE-AR_KO2). | ΔnifL::PinfC | uncured |

TABLE 9-continued

Further strains described herein

| Strain ID | Lineage | Mutagenic DNA Description | Chromosomal Genotype | Curing Status |
|---|---|---|---|---|
| 6-412 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). | ΔnifL::Prm5 ΔglnE-AR_KO1 | Cured |
| 6-435 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. | ΔnifL::Prm1 ΔglnE-AR_KO1, ΔamtB | |
| 6-1691 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of 150 bp upstream of the cysZ gene and insertion of Prm1 directly upstream of cysZ. | ΔnifL::Prm, 1 ΔglnE-AR_KO1, cysZ::Prm1 | Uncured |
| 6-346 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). | ΔnifL::Prm1, ΔglnE-AR_KO1 | Uncured |
| 6-923 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. Deletion of the native treZ promoter and insertion of a fragment (Prm2), from the region upstream of PROKKA_04751 (a hypothetical protein), directly upstream of treZ. | ΔnifL::Prm1 ΔglnE-AR_KO1, ΔamtB, treZ::Prm2 | Uncured |
| 6-1694 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire glgA CDS. | ΔnifL::Prm5 ΔglnE-AR_KO1, ΔglgA | Uncured |
| 6-342 | Mutant of CI006 | Disruption of nifL gene with a fragment of the region upstream of the ompX gene inserted (Prm5) and deletion of the 1287 bp after the start codon of the glnE gene containing the adenylyl-removing domain of glutamate-ammonia-ligase adenylyltransferase (ΔglnE-AR_KO1). | ΔnifL::Prm5 ΔglnE-AR_KO1 | Uncured |

TABLE 9-continued

Further strains described herein

| Strain ID | Lineage | Mutagenic DNA Description | Chromosomal Genotype | Curing Status |
|---|---|---|---|---|
| 6-1681 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire glgA CDS. | ΔnifL::Prm1 ΔglnE-AR_KO1, ΔglgA | Uncured |
| 6-404 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). | ΔnifL::Prm1 ΔglnE-AR_KO1 | Cured |
| 6-921 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. Deletion of the native otsB promoter and insertion of Prm1 directly upstream of ostB. | ΔnifL::Prm1 ΔglnE-AR_KO1, ΔamtB, otsB::Prm1 | Uncured |
| 6-922 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. Deletion of the native otsB promoter and insertion of a fragment (Prm2), from the region upstream of PROKKA_04751 (a hypothetical protein), directly upstream of otsB. | ΔnifL::Prm1 ΔglnE-AR_KO1, ΔamtB, otsB::Prm2 | Uncured |
| 6-1744 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. Deletion of the entire glgA CDS. Deletion of the native treZ promoter and insertion of a fragment (Prm2), from the region upstream of PROKKA_04751 (a hypothetical protein), directly upstream of treZ. | ΔnifL::Prm1 ΔglnE-AR_KO1, ΔamtB, ΔglgA, treZ::Prm2 | uncured |
| 6-322 | Mutant of CI006 | Disruption of nifL gene with a fragment of the region upstream of the 1 pp gene inserted (Prm1) upstream of nifA. | ΔnifL::Prm1 | uncured |
| 6-400 | Mutant of CI006 | Disruption of nifL gene with a fragment of the region upstream of the 1 pp gene inserted (Prm1) upstream of nifA. | ΔnifL::Prm1 | cured |
| 6-848 | Mutant of CI006 | Disruption of nifL gene with a fragment of the region upstream of the 1 pp gene inserted (Prm1) upstream of nifA. Deletion of the 1647 bp after the start codon of the | ΔnifL::Prm1, ΔglnE-AR_KO2, ΔamtB | Cured |

TABLE 9-continued

Further strains described herein

| Strain ID | Lineage | Mutagenic DNA Description | Chromosomal Genotype | Curing Status |
|---|---|---|---|---|
| | | glnE gene containing the adenylyl-removing domain of glutamate-ammonia-ligase adenylyltransferase (ΔglnE-AR_KO2). Deletion of entire amtB CDS. | | |
| 137-2084 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). | ΔnifL::Prm1.2 ΔglnE-AR_KO2 | cured |
| 137-2251 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native rpoN promoter and insertion of a fragment (Prm8.2), found 77 bp after the start codon of nlpI to 376 bp after the start codon of nlpI, directly upstream of rpoN. | ΔnifL::Prm1.2 ΔglnE-AR_KO2, rpoN::Prm8.2 | cured |
| 137-2285 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native rpoN promoter and insertion of a fragment (Prm1.2) directly upstream of the rpoN CDS. | ΔnifL::Prm1.2 ΔglnE-AR_KO2, rpoN::Prm1.2 | cured |
| 137-2225 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of entire glnK CDS | ΔnifL::Prm1.2 ΔglnE-AR_KO2, ΔglnK | cured |
| 137-1586 | Mutant of CI137 | Disruption of nifL gene with a fragment of the region upstream of the infC gene inserted (PinfC) upstream of nifA. Deletion of the 1647 bp after the start codon of the glnE gene containing the adenylyl-removing domain of glutamate-ammonia-ligase adenylyltransferase (ΔglnE-AR_KO2). | ΔnifL::PinfC, ΔglnE-AR_KO2 | cured |
| 137-1860 | Mutant of CI137 | Disruption of nifL gene with a fragment of the region upstream of the infC gene inserted (PinfC) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native dctA1 promoter and insertion of a fragment (Prm8.2), found 77 bp after the start codon of nlpI to 376 bp after the start codon of nlpI, directly upstream of dctA1. The native start codon of dctA1 was also changed from GTG to ATG. | ΔnifL::PinfC, ΔglnE-AR_KO2, dctA1::Prm8.2 ATG-start | cured |

TABLE 9-continued

Further strains described herein

| Strain ID | Lineage | Mutagenic DNA Description | Chromosomal Genotype | Curing Status |
|---|---|---|---|---|
| 137-1905 | Mutant of CI137 | Disruption of nifL gene with a fragment of the region upstream of the infC gene inserted (PinfC) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native dctA1 promoter and insertion of a fragment (Prm1.2) directly upstream of dctA1. The native start codon of dctA1 was also changed from GTG to ATG. | ΔnifL::PinfC, ΔglnE-AR_KO2, dctA1::Prm1.2 ATG-start | uncured |
| 6-1697 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. Deletion of the native treZ promoter and insertion of a fragment (Prm2), from the region upstream of PROKKA_04751 (a hypothetical protein), directly upstream of treZ. Deletion of the native otsB promoter and insertion of Prm1 directly upstream of ostB. | ΔnifL::Prm1 ΔglnE-AR_KO1, ΔamtB, treZ::Prm2, otsB::Prm1 | Uncured |
| 137-1901 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native phoB1 promoter and insertion of a fragment (Prm1.2) directly upstream of the phoB1 CDS. | ΔnifL::Prm1.2 ΔglnE-AR_KO2, phoB1::Prm1.2 | Cured |
| 6-1779 | Mutant of CI006 | Disruption of nifL gene with a fragment of the region upstream of the 1 pp gene inserted (Prm1) upstream of nifA. Deletion of the 1647 bp after the start codon of the glnE gene containing the adenylyl-removing domain of glutamate-ammonia-ligase adenylyltransferase (ΔglnE-AR_KO2). Deletion of entire amtB CDS. Deletion of the native bcsII promoter and insertion of a fragment (Prm2), from the region upstream of PROKKA_04751 (a hypothetical protein), directly upstream of bcsII. Deletion of the native yjbE2 promoter and insertion of Prm1 directly upstream of yjbE2. | ΔnifL::Prm1, ΔglnE-AR_KO2, ΔamtB, bcsII::Prm2, yjbE2::Prm1 | Uncured |
| 6-1782 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deletion of the native glnA promoter and insertion of a fragment (PrmglnB) from the region upstream of the gene, glnB, directly upstream of glnA. | ΔnifL::Prm5 ΔglnE-AR_KO1, glnA::PrmglnB_ATG-start | Uncured |

TABLE 9-continued

Further strains described herein

| Strain ID | Lineage | Mutagenic DNA Description | Chromosomal Genotype | Curing Status |
|---|---|---|---|---|
| 6-1783 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deletion of the native glnA promoter and insertion of a fragment (PrmglnB) from the region upstream of the gene, glnB, directly upstream of glnA. The native start codon of glnA was also changed from ATG to GTG. | ΔnifL::Prm5 ΔglnE-AR_KO1, glnA::PrmglnB_GTG-start | Uncured |
| 6-1906 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the native glnA promoter and insertion of a fragment (PrmglnB) from the region upstream of the gene, glnB, directly upstream of glnA. The native start codon of glnA was also changed from ATG to GTG. | ΔnifL::Prm1 ΔglnE-AR_KO1, glnA::PrmglnB_GTG-start | Uncured |
| 6-1907 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the native glnA promoter and insertion of a fragment (PrmglnE) from the region upstream of the gene, glnE, directly upstream of glnA. | ΔnifL::Prm1 ΔglnE-AR_KO1, glnA::PrmglnE_ATG-start | Uncured |
| 6-1908 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the native glnA promoter and insertion of a fragment (PrmglnE) from the region upstream of the gene, glnE, directly upstream of glnA. The native start codon of glnA was also changed from ATG to GTG. | ΔnifL::Prm1 ΔglnE-AR_KO1, glnA::PrmglnE_GTG-start | Uncured |
| 6-1912 | Mutant of CI006 | Disruption of nifL gene with a fragment of the region upstream of the 1 pp gene inserted (Prm1) upstream of nifA. Deletion of the native glnA promoter and insertion of a fragment (PrmglnE) from the region upstream of the gene, glnE, directly upstream of glnA. | ΔnifL::Prm1, glnA::PrmglnE_ATG-start | Uncured |
| 137-2656 | Mutant of CI137 | Disruption of nifL gene with a fragment of the region upstream of the cspE gene inserted (Prm1.2) upstream of nifA. Deletion of the native glnA promoter and insertion of a fragment (PrmglnB) from the region upstream of the gene, glnB, directly upstream of glnA. | ΔnifL::Prm1.2, glnA::PrmglnB_ATG-start | Cured |

TABLE 9-continued

Further strains described herein

| Strain ID | Lineage | Mutagenic DNA Description | Chromosomal Genotype | Curing Status |
|---|---|---|---|---|
| 137-2657 | Mutant of CI137 | Disruption of nifL gene with a fragment of the region upstream of the cspE gene inserted (Prm1.2) upstream of nifA. Deletion of the native glnA promoter and insertion of a fragment (PrmglnB) from the region upstream of the gene, glnB, directly upstream of glnA. The native start codon of glnA was also changed from ATG to GTG. | ΔnifL::Prm1.2, glnA::PrmglnB_GTG-start | Cured |
| 137-2658 | Mutant of CI137 | Disruption of nifL gene with a fragment of the region upstream of the cspE gene inserted (Prm1.2) upstream of nifA. Deletion of the native glnA promoter and insertion of a fragment (PrmglnD) from the region upstream of the gene, glnD, directly upstream of glnA. | ΔnifL::Prm1.2, glnA::PrmglnD_ATG-start | Cured |
| 137-2659 | Mutant of CI137 | Disruption of nifL gene with a fragment of the region upstream of the cspE gene inserted (Prm1.2) upstream of nifA. Deletion of the native glnA promoter and insertion of a fragment (PrmglnD) from the region upstream of the gene, glnD, directly upstream of glnA. The native start codon of glnA was also changed from ATG to GTG. | ΔnifL::Prm1.2, glnA::PrmglnD_GTG-start | Cured |
| 137-2660 | Mutant of CI137 | Disruption of nifL gene with a fragment of the region upstream of the cspE gene inserted (Prm1.2) upstream of nifA. Deletion of the native glnA promoter and insertion of a fragment (PrmglnE) from the region upstream of the gene, glnE, directly upstream of glnA. | ΔnifL::Prm1.2, glnA::PrmglnE_ATG-start | Cured |
| 137-2661 | Mutant of CI137 | Disruption of nifL gene with a fragment of the region upstream of the cspE gene inserted (Prm1.2) upstream of nifA. Deletion of the native glnA promoter and insertion of a fragment (PrmglnE) from the region upstream of the gene, glnE, directly upstream of glnA. The native start codon of glnA was also changed from ATG to GTG. | ΔnifL::Prm1.2, glnA::PrmglnE GTG-start | Cured |
| 137-2257 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glnA promoter and insertion of a fragment (PrmglnB) from the region upstream of the gene, glnB, directly upstream of glnA. | ΔnifL::Prm1.2 ΔglnE-AR_KO2, glnA::PrmglnB_ATG-start | Cured |
| 137-2259 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glnA promoter and insertion of a fragment (PrmglnB) from the region upstream of the gene, glnB, directly upstream of glnA. The native start codon of glnA was also changed from ATG to GTG. | ΔnifL::Prm1.2 ΔglnE-AR_KO2, glnA::PrmglnB_GTG-start | Cured |

TABLE 9-continued

Further strains described herein

| Strain ID | Lineage | Mutagenic DNA Description | Chromosomal Genotype | Curing Status |
|---|---|---|---|---|
| 137-2261 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glnA promoter and insertion of a fragment (PrmglnD) from the region upstream of the gene, glnD, directly upstream of glnA. | ΔnifL::Prm1.2 ΔglnE-AR_KO2, glnA::PrmglnD_ATG-start | Cured |
| 137-2263 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glnA promoter and insertion of a fragment (PrmglnD) from the region upstream of the gene, glnD, directly upstream of glnA. The native start codon of glnA was also changed from ATG to GTG. | ΔnifL::Prm1.2 ΔglnE-AR_KO2, glnA::PrmglnD_GTG-start | Cured |
| 137-2281 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glnA promoter and insertion of a fragment (PrmglnE) from the region upstream of the gene, glnE, directly upstream of glnA. | ΔnifL::Prm1.2 ΔglnE-AR_KO2, glnA::PrmglnE_ATG-start | Cured |
| 137-2219 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the 546 bp before the stop codon of the glnD gene containing the ACT1/2 domain of the bifunctional uridylyltransferase/uridylyl-removing enzyme (ΔglnD-ACT12_truncation) | ΔnifL::Prm1.2 ΔglnE-AR_KO2, ΔglnD_ACT12_truncation | Cured |
| 137-2221 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the 975 bp after the start codon of the glnD gene containing the uridylyltransferase (UT) domain of the bifunctional uridylyltransferase/uridylyl-removing enzyme (ΔglnD-UT_truncation) | ΔnifL::Prm1.2 ΔglnE-AR_KO2, ΔglnD_UT_truncation | Cured |

TABLE 9-continued

Further strains described herein

| Strain ID | Lineage | Mutagenic DNA Description | Chromosomal Genotype | Curing Status |
|---|---|---|---|---|
| 137-2223 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the entire glnD CDS. | ΔnifL::Prm1.2 ΔglnE-AR_KO2, ΔglnD | Cured |
| 137-2245 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of 66 bp starting from bp 1519 to bp 1586 of the glnD gene containing the uridylylremoving (UR) domain of the bifunctional uridylyltransferase/uridylyl-removing enzyme (ΔglnD-UR_truncation) | ΔnifL::Prm1.2 ΔglnE-AR_KO2, ΔglnD_UR_truncation | Cured |
| 137-2227 | Mutant of CI137 | Disruption of nifL gene with a fragment of the region upstream of the infC gene inserted (PinfC) upstream of nifA. Deletion of the 546 bp before the stop codon of the glnD gene containing the ACT1/2 domain of the bifunctional uridylyltransferase/uridylyl-removing enzyme (ΔglnD-ACT12_truncation) | ΔnifL::PinfC, ΔglnD_ACT12_truncation | Cured |
| 137-2229 | Mutant of CI137 | Disruption of nifL gene with a fragment of the region upstream of the infC gene inserted (PinfC) upstream of nifA. Deletion of the entire glnD CDS. | ΔnifL::PinfC, ΔglnD | Cured |
| 137-2253 | Mutant of CI137 | Disruption of nifL gene with a fragment of the region upstream of the infC gene inserted (PinfC) upstream of nifA. Deletion of the 975 bp after the start codon of the glnD gene containing the uridylyltransferase (UT) domain of the bifunctional uridylyltransferase/uridylyl-removing enzyme (ΔglnD-UT_truncation) | ΔnifL::PinfC, ΔglnD_UT_truncation | Cured |
| 137-2283 | Mutant of CI137 | Disruption of nifL gene with a fragment of the region upstream of the infC gene inserted (PinfC) upstream of nifA. Deactivation of the uridylyltransferase (UT) domain of the bifunctional uridylyltransferase/uridylyl-removing enzyme, glnD, by mutating amino acid residues 90 and 91 from GG to DV as well as residue 104 from D to A. | ΔnifL::PinfC, ΔglnD_UT_deactivation | Cured |
| 137-2237 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glsA2 promoter and insertion of a fragment (Prm1.2) directly upstream of the glsA2 CDS. | ΔnifL::Prm1.2, ΔglnE-AR_KO2, glsaA2::Prm1.2 | Cured |

TABLE 9-continued

Further strains described herein

| Strain ID | Lineage | Mutagenic DNA Description | Chromosomal Genotype | Curing Status |
|---|---|---|---|---|
| 6-2552 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the 549 bp before the stop codon of the glnD gene containing the ACT1/2 domain of the bifunctional uridylyltransferase/uridylyl-removing enzyme (ΔglnD-ACT12_truncation) | ΔnifL::Prm1, ΔglnE-AR_KO1, ΔglnD-ACT12_truncation | Cured |
| 6-2597 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the 987 bp after the start codon of the glnD gene containing the uridylyltransferase (UT) domain of the bifunctional uridylyltransferase/uridylyl-removing enzyme (ΔglnD-UT_truncation) | ΔnifL::Prm1, ΔglnE-AR_KO1, ΔglnD_UT_truncation | Cured |
| 6-2587 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR-KO1). Deletion of the entire glnD CDS. | ΔnifL::Prm1, ΔglnE-AR_KO1, ΔglnD | Cured |
| 6-2636 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deactivation of the uridylyltransferase (UT) domain of the bifunctional uridylyltransferase/uridylyl-removing enzyme, glnD, by mutating amino acid residues 90 and 91 from GG to DV as well as residue 104 from D to A. | ΔnifL::Prm1, ΔglnE-AR_KO1, ΔglnD_UT_deactivation | Cured |
| 6-2090 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deletion of the 549 bp before the stop codon of the glnD gene containing the ACT1/2 domain of the bifunctional uridylyltransferase/uridylyl-removing enzyme (ΔglnD-ACT12_truncation) | ΔnifL::Prm5, ΔglnE-AR_KO1, ΔglnD-ACT12_truncation | Cured |

TABLE 9-continued

Further strains described herein

| Strain ID | Lineage | Mutagenic DNA Description | Chromosomal Genotype | Curing Status |
|---|---|---|---|---|
| 6-2122 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire glnD CDS. | ΔnifL::Prm5, ΔglnE-AR_KO1, ΔglnD | Cured |
| 6-2411 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deletion of the 987 bp after the start codon of the glnD gene containing the uridylyltransferase (UT) domain of the bifunctional uridylyltransferase/uridylyl-removing enzyme (ΔglnD-UT_truncation) | ΔnifL::Prm5, ΔglnE-AR_KO1, ΔglnD_UT_truncation | Cured |
| 6-2615 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deactivation of the uridylyltransferase (UT) domain of the bifunctional uridylyltransferase/uridylyl-removing enzyme, glnD, by mutating amino acid residues 90 and 91 from GG to DV as well as residue 104 from D to A. | ΔnifL::Prm5, ΔglnE-AR_KO1, ΔglnD_UT_deactivation | Cured |
| 6-2627 | Mutant of CI006 | Disruption of nifL gene with a fragment of the region upstream of the ompX gene inserted (Prm5) upstream of nifA. Deletion of the 1287 bp after the start codon of the glnE gene containing the adenylyl-removing domain of glutamate-ammonia-ligase adenylyltransferase (ΔglnE-AR_KO1). Deactivation of the uridylyl-removing (UR) domain of the bifunctional uridylyltransferase/uridylyl-removing enzyme, glnD, by mutating amino acid residues 515 and 516 from HD to AA. | ΔnifL::Prm5, ΔglnE-AR_KO1, ΔglnD_UR_deactivation | Cured |
| 6-916 | Mutant of CI006 | Disruption of nifL gene with a fragment of the region upstream of the 1 pp gene inserted (Prm1) upstream of nifA. Deletion of the 1287 bp after the start codon of the glnE gene containing the adenylyl-removing domain of glutamate-ammonia-ligase adenylyltransferase (ΔglnE-AR_KO1). Deletion of the entire amtB CDS. Deletion of the native cysZ promoter and insertion of Prm1 directly upstream of cysZ. | ΔnifL::Prm1 ΔglnE-AR_KO1, ΔamtB, cysZ::Prm1 | cured |
| 137-1893 | Mutant of CI137 | Disruption of nifL gene with a fragment of the region upstream of the infC gene inserted (PinfC) upstream of nifA. Deletion of the 1647 bp after the start codon of the glnE gene containing the adenylyl- | ΔnifL::PinfC, ΔglnE-AR_KO2, ΔglgA | cured |

TABLE 9-continued

Further strains described herein

| Strain ID | Lineage | Mutagenic DNA Description | Chromosomal Genotype | Curing Status |
|---|---|---|---|---|
| | | removing domain of glutamate-ammonia-ligase adenylyltransferase (ΔglnE-AR_KO2). Deletion of the entire glgA CDS. | | |
| 6-2118 | Mutant of CI006 | Disruption of nifL gene with a fragment of the region upstream of the 1 pp gene inserted (Prm1) upstream of nifA. Deletion of the native glsA2 promoter and insertion of Prm1 directly upstream of glsA2. | ΔnifL::Prm1, glsA2::Prm1 | cured |
| 137-2502 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of 1011 bp before the stop codon of the asnB gene coding for asparagine synthetase B. | ΔnifL::Prm1.2 ΔglnE-AR_KO2, ΔasnB-truncation | cured |
| 137-2504 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native asnB promoter and insertion of a fragment (Prm1.2) directly upstream of the asnB CDS. | ΔnifL::Prm1.2, ΔglnE-AR_KO2, asnB::Prm1.2 | cured |
| 137-2215 | Mutant of CI137 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native gltBD operon promoter and insertion of a fragment (PrmglnD) from the region upstream of the gene, glnD, directly upstream of the gltBD operon. | ΔnifL::Prm1.2 ΔglnE-AR_KO2, gltBD::PrmglnD_ATG-start | cured |

Notwithstanding the appended claims, the disclosure set forth herein is also defined by the following clauses:

1. A microbial strain with improved desiccation tolerance.
2. A microbial strain, wherein rpoE expression is regulated by a switchable promoter.
3. The microbial strain of clause 2, wherein said switchable promoter is an arabinose promoter.
4. The microbial strain of clause 2, wherein an rseA gene is downregulated.
5. The microbial strain of clause 2, wherein said switchable promoter is a promoter which may be activated with a chemical.
6. The microbial strain of clause 2, wherein said switchable promoter is a promoter which may be activated with a sugar.
7. The microbial strain of clause 2, wherein said switchable promoter is a promoter which may be activated with arabinose.
8. A method of increasing desiccation tolerance of a microbe, the method comprising engineering said microbe to contain an rpoE gene operably linked to a switchable promoter, activating said switchable promoter during the log phase of biomass growth, thus increasing desiccation tolerance of said microbe.
9. A method of increasing desiccation tolerance of a microbe during seed coating, the method comprising engineering said microbe to contain an rpoE gene operably linked to a switchable promoter, activating said switchable promoter prior to desiccation, thus increasing desiccation tolerance of said microbe.
10. The method of clause 9, wherein said switchable promoter is a promoter which may be activated with a chemical.
11. The method of clause 9, wherein said switchable promoter is a promoter which may be activated with a sugar.
12. The method of clause 9, wherein said switchable promoter is a promoter which may be activated with arabinose.
13. The method of clause 9, wherein said switchable promoter is activated during the log phase of biomass growth.
14. The method of clause 9, wherein said switchable promoter is activated during seed coating.
15. The method of clause 9, wherein said microbe is also engineered to decrease expression of rseA.

16. A genetically engineered bacterium comprising a heterologous regulatory element operably linked to cysP.
17. The genetically engineered bacterium of clause 16, wherein said heterologous regulatory element is a promoter.
18. The genetically engineered bacterium of clause 16, wherein said heterologous regulatory element is native to said genetically engineered bacterium.
19. A genetically engineered bacterium comprising a genetic variation that results in increased expression of a protein which catalyzes the transport of components of nitrogenase cofactors into the cell.
20. The genetically engineered bacterium of clause 19, wherein said protein which catalyzes the transport of components of nitrogenase cofactors into the cell is a sulfur transporter gene.
21. The genetically engineered bacterium of clause 20, wherein said sulfur transporter gene is cysZ.
22. The genetically engineered bacterium of clause 20, wherein said sulfur transporter gene is cysK.
23. The genetically engineered bacterium of clause 20, wherein said sulfur transporter gene is cysT.
24. The genetically engineered bacterium of clause 20, wherein said sulfur transporter gene is cysW.
25. The genetically engineered bacterium of clause 20, wherein said sulfur transporter gene is cysA.
26. The genetically engineered bacterium of clause 20, wherein said sulfur transporter gene is sbp.
27. The genetically engineered bacterium of clause 19, wherein said genetic variation results in increased expression of a cysZK operon.
28. The genetically engineered bacterium of clause 19, wherein said genetic variation results in increased expression of a cysPTWA operon.
29. The genetically engineered bacterium of clause 19, wherein said protein which catalyzes the transport of components of nitrogenase cofactors into the cell is a molybdenum transporter gene.
30. The genetically engineered bacterium of clause 29, wherein said molybdenum transporter gene is modE.
31. The genetically engineered bacterium of clause 29, wherein said molybdenum transporter gene is modB.
32. The genetically engineered bacterium of clause 29, wherein said molybdenum transporter gene is modA.
33. The genetically engineered bacterium of clause 19, wherein said genetic variation results in increased expression of a modEB operon.
34. The genetically engineered bacterium of clause 19, wherein said genetic variation results in increased expression of a modEBA operon.
35. The genetically engineered bacterium of clause 19, wherein said protein which catalyzes the transport of components of nitrogenase cofactors into the cell is an iron transporter gene.
36. The genetically engineered bacterium of clause 35, wherein said iron transporter gene is exbA.
37. The genetically engineered bacterium of clause 35, wherein said iron transporter gene is exbB.
38. The genetically engineered bacterium of clause 35, wherein said iron transporter gene is tonB.
39. The genetically engineered bacterium of clause 19, wherein said genetic variation results in increased expression of an exbAB operon.
40. The genetically engineered bacterium of any one of clauses 19-39, wherein said genetic variation comprises insertion of a promoter.
41. A genetically engineered bacterium, wherein said genetically engineered bacterium comprises altered expression of a siderophore biosynthesis gene.
42. The genetically engineered bacterium of clause 41, wherein said siderophore biosynthesis gene isyhfA.
43. The genetically engineered bacterium of clause 41, wherein said siderophore biosynthesis gene is yusV.
44. The genetically engineered bacterium of clause 41, wherein said siderophore biosynthesis gene is sbnA.
45. The genetically engineered bacterium of clause 41, wherein said siderophore biosynthesis gene is yfiZ.
46. The genetically engineered bacterium of clause 41, wherein said siderophore biosynthesis gene is flu.
47. The genetically engineered bacterium of clause 41, wherein said siderophore biosynthesis gene is fur.
48. A genetically engineered bacterium comprising a genetic variation in glgA; wherein said genetically engineered bacterium has increased nitrogen fixation activity as compared to a bacterium of the same species without said genetic variation in glgA.
49. The genetically engineered bacterium of clause 47, wherein said genetic variation results in decreased expression of glgA.
50. A genetically engineered bacterium comprising a non-native ribosome binding site which results in increased translation of NifA.
51. A genetically engineered bacterium comprising at least two copies of the NifA gene.
52. The genetically engineered bacterium of clause 51, wherein said genetically engineered bacterium comprises at least three copies of the NifA gene.
53. The genetically engineered bacterium of clause 51, wherein said genetically engineered bacterium comprises at least four copies of the NifA gene.
54. The genetically engineered bacterium of clause 51, wherein said genetically engineered bacterium comprises at least five copies of the NifA gene.
55. The genetically engineered bacterium of clause 51, wherein said genetically engineered bacterium comprises at least six copies of the NifA gene.
56. The genetically engineered bacterium of clause 51, wherein said genetically engineered bacterium comprises at least seven copies of the NifA gene.
57. The genetically engineered bacterium of clause 51, wherein said genetically engineered bacterium comprises greater than ten copies of the NifA gene.
58. A genetically engineered bacterium comprising a heterologous promoter operably linked to at least one gene selected from the group consisting of nifH, nifD, and nifK; wherein said heterologous promoter is derived from the host microbe's genetic material.
59. A genetically engineered bacterium comprising a genetic variant in a reactive oxygen species scavenging gene.
60. The genetically engineered bacterium of clause 59, wherein said reactive oxygen species scavenging gene is grxA.
61. The genetically engineered bacterium of clause 59, wherein said reactive oxygen species scavenging gene is grxB.
62. The genetically engineered bacterium of clause 59, wherein said reactive oxygen species scavenging gene is grxC.
63. The genetically engineered bacterium of clause 59, wherein said reactive oxygen species scavenging gene is grxD.

64. The genetically engineered bacterium of clause 59, wherein said reactive oxygen species scavenging gene is trxA.
65. The genetically engineered bacterium of clause 59, wherein said reactive oxygen species scavenging gene is trxC.
66. The genetically engineered bacterium of clause 59, wherein said reactive oxygen species scavenging gene is tpx.
67. A genetically engineered bacterium comprising a genetic which results in altered expression of a grxABCD operon.
68. A genetically engineered bacterium comprising a genetic variant which results results in an increased level of nitrogenase activity under conditions of at least 0.05% oxygen than in a non-engineered diazotrophic bacterium of the same species.
69. The genetically engineered bacterium of clause 68, wherein said genetic variant results in an increased level of nitrogenase activity under conditions of at least 0.1% oxygen than in a non-engineered diazotrophic bacterium of the same species.
70. The genetically engineered bacterium of clause 68, wherein said genetic variant results in an increased level of nitrogenase activity under conditions of at least 0.5% oxygen than in a non-engineered diazotrophic bacterium of the same species.
71. The genetically engineered bacterium of clause 68, wherein said genetic variant results in an increased level of nitrogenase activity under conditions of at least 1% oxygen than in a non-engineered diazotrophic bacterium of the same species.
72. The genetically engineered bacterium of clause 68, wherein said genetic variant results in altered expression of a cydABX operon.
73. The genetically engineered bacterium of clause 68, wherein said genetic variant results in altered expression of a cydAB operon.
74. The genetically engineered bacterium of clause 68, wherein said genetic variant results in altered expression of a cydX gene.
75. The genetically engineered bacterium of clause 68, wherein said genetic variant results in altered expression of a cydA gene.
76. The genetically engineered bacterium of clause 68, wherein said genetic variant results in altered expression of a cydB gene.
77. The genetically engineered bacterium of clause 68, wherein said genetic variant results in altered expression of a glbN gene.
78. The genetically engineered bacterium of clause 68, wherein said genetic variant results in altered expression of a fixNOPQ operon.
79. The genetically engineered bacterium of clause 68, wherein said genetic variant results in altered expression of a fixN gene.
80. The genetically engineered bacterium of clause 68, wherein said genetic variant results in altered expression of a fixO gene.
81. The genetically engineered bacterium of clause 68, wherein said genetic variant results in altered expression of a fixP gene.
82. The genetically engineered bacterium of clause 68, wherein said genetic variant results in altered expression of a fixQ gene.
83. A genetically engineered bacterium comprising a modification in asnB.
84. A genetically engineered bacterium comprising a modification in a gene selected from the group consisting of: asnB, asnA, glnL, uridylyl-transferase amtB, and GDH.
85. The genetically engineered bacterium of clause 84, wherein said genetic variant results in altered expression of an asnB gene.
86. The genetically engineered bacterium of clause 84, wherein said genetic variant results in altered expression of an asnA gene.
87. The genetically engineered bacterium of clause 84, wherein said genetic variant results in altered expression of a glnL gene.
88. The genetically engineered bacterium of clause 84, wherein said genetic variant results in altered expression of an uridylyl-transferase gene.
89. The genetically engineered bacterium of clause 84, wherein said genetic variant results in altered expression of a GDH gene.
90. A genetically engineered bacterium comprising a modification in glnK, wherein said modification is selected from the group consisting of: deletion of the entire gene, deletion of substantially the entire gene, deletion of an ACT domain, deletion of more than 50% of an ACT domain, deactivation of an ACT domain, and deactivation of an UTase domain.
91. A genetically engineered bacterium comprising a modification in glnD, wherein said modification is selected from the group consisting of: deletion of the entire gene, deletion of substantially the entire gene, deletion of an ACT domain, deletion of more than 50% of an ACT domain, deactivation of an ACT domain, and deactivation of an UTase domain.
92. A genetically engineered bacterium with improved survival in a rhizosphere compared to a non-engineered bacterium of the same species, the bacterium comprising a genetic variation resulting in increased expression of a sugar transporter.
93. The genetically engineered bacterium of clause 92, wherein said sugar transporter is dctA.
94. A genetically engineered bacterium comprising a genetic variation resulting in increased expression of a sugar transporter.
95. The genetically engineered bacterium of clause 94, wherein said sugar transporter is dctA.
96. A genetically engineered bacterium with improved survival in a rhizosphere compared to a non-engineered bacterium of the same species, the bacterium comprising a genetic variation resulting in altered quorum signaling.
97. The genetically engineered bacterium of clause 96, wherein said genetic variation resulting in altered quorum signaling results in altered quorum quenching.
98. The genetically engineered bacterium of clause 96, wherein said genetic variation resulting in altered quorum signaling results in altered Y2-aiiA expression.
99. The genetically engineered bacterium of clause 96, wherein said genetic variation resulting in altered quorum signaling results in altered ytnP expression.
100. A genetically engineered bacterium with improved survival in a rhizosphere compared to a non-engineered bacterium of the same species, the bacterium comprising a genetic variation resulting in increased root attachment.
101. The genetically engineered bacterium of clause 100, wherein said genetic variation resulting in increased root attachment comprises a genetic variation which results in altered phenazine biosynthesis.
102. The genetically engineered bacterium of clause 100, wherein said genetic variation resulting in increased root attachment comprises a genetic variation which results in altered cyclic lipopeptide biosynthesis.

103. The genetically engineered bacterium of clause 100, wherein said genetic variation resulting in increased root attachment comprises a genetic variation which results in altered expression of aglutanins.

104. The genetically engineered bacterium of clause 100, wherein said genetic variation resulting in increased root attachment comprises a genetic variation which results in altered expression of fhaB.

105. The genetically engineered bacterium of clause 100, wherein said genetic variation resulting in increased root attachment comprises a genetic variation which results in altered expression of fhaC.

106. The genetically engineered bacterium of clause 100, wherein said genetic variation resulting in increased root attachment comprises a genetic variation which results in altered expression of yjbE.

107. The genetically engineered bacterium of clause 100, wherein said genetic variation resulting in increased root attachment comprises a genetic variation which results in altered expression of pssM.

108. The genetically engineered bacterium of clause 100, wherein said genetic variation resulting in increased root attachment comprises a genetic variation which results in altered expression of acs genes.

109. The genetically engineered bacterium of clause 100, wherein said genetic variation resulting in increased root attachment comprises a genetic variation which results in altered expression of otsA.

110. The genetically engineered bacterium of clause 100, wherein said genetic variation resulting in increased root attachment comprises a genetic variation which results in altered expression of an operon comprising otsA.

111. The genetically engineered bacterium of clause 100, wherein said genetic variation resulting in increased root attachment comprises a genetic variation which results in altered expression of treY.

112. The genetically engineered bacterium of clause 100, wherein said genetic variation resulting in increased root attachment comprises a genetic variation which results in altered expression of an operon comprising treY.

113. A genetically engineered bacterium comprising a genetic variation resulting in increased biofilm formation.

114. The genetically engineered bacterium of clause 113, wherein said genetic variation resulting in increased biofilm formation comprises a genetic variation which results in altered expression of smZ.

115. The genetically engineered bacterium of clause 113, wherein said genetic variation resulting in increased biofilm formation comprises a genetic variation which results in altered expression of lapA.

116. The genetically engineered bacterium of clause 113, wherein said genetic variation resulting in increased biofilm formation comprises a genetic variation which results in altered expression of AHL biosynthesis genes.

117. The genetically engineered bacterium of clause 113, wherein said genetic variation resulting in increased biofilm formation comprises a genetic variation which results in altered expression of phoB.

118. The genetically engineered bacterium of clause 113, wherein said genetic variation resulting in increased biofilm formation comprises a genetic variation which results in altered expression of phoR.

119. The genetically engineered bacterium of clause 113, wherein said genetic variation resulting in increased biofilm formation comprises a genetic variation which results in altered expression of MucA.

120. A genetically engineered bacterium with improved survival in a rhizosphere compared to a non-engineered bacterium of the same species, the bacterium comprising a genetic variation resulting in increased expression of a cell-wall degrading enzyme.

121. The genetically engineered bacterium of clause 120, wherein said cell-wall degrading enzyme comprises a polygalacturonase.

122. The genetically engineered bacterium of clause 120, wherein said cell-wall degrading enzyme comprises a cellulase.

123. The genetically engineered bacterium of clause 120, wherein said cell-wall degrading enzyme comprises pehA.

124. The genetically engineered bacterium of any one of clauses 19-123, wherein said genetically engineered bacterium is a genetically engineered diazotrophic bacterium.

125. The genetically engineered bacterium of any one of clauses 19-123, wherein said genetically engineered bacterium is non-intergeneric.

126. The genetically engineered bacterium of any one of clauses 19-123, wherein said genetically engineered bacterium is intergeneric.

127. The genetically engineered bacterium of any one of clauses 19-123, wherein said genetically engineered bacterium is able to fix atmospheric nitrogen in the presence of exogenous nitrogen.

128. The genetically engineered bacterium of any one of clauses 19-123, wherein said genetically engineered bacterium comprises a modification in a nitrogen fixation genetic network.

129. The genetically engineered bacterium of any one of clauses 19-123, wherein said genetically engineered bacterium comprises a modification in NifA.

130. The genetically engineered bacterium of any one of clauses 19-123, wherein said genetically engineered bacterium comprises a modification which results in increased expression of NifA.

131. The genetically engineered bacterium of any one of clauses 19-123, wherein said genetically engineered bacterium comprises a modification in NifL.

132. The genetically engineered bacterium of any one of clauses 19-123, wherein said genetically engineered bacterium comprises a modification which results in decreased expression of NifL.

133. The genetically engineered bacterium of any one of clauses 19-123, wherein said genetically engineered bacterium comprises a modification in NifH.

134. The genetically engineered bacterium of any one of clauses 19-123, wherein said genetically engineered bacterium comprises a modification which results in increased expression of NifH.

135. The genetically engineered bacterium of any one of clauses 19-123, wherein said genetically engineered bacterium comprises a modification which results in increased expression of Nif cluster genes.

136. The genetically engineered bacterium of any one of clauses 19-123, wherein said genetically engineered bacterium comprises a modification in a nitrogen assimilation genetic network.

137. The genetically engineered bacterium of any one of clauses 19-123, wherein said genetically engineered bacterium comprises a modification in GlnE.

138. The genetically engineered bacterium of any one of clauses 19-123, wherein said genetically engineered bacterium comprises a modification which results in decreased activity of GlnE.

139. The genetically engineered bacterium of any one of clauses 19-123, wherein said genetically engineered bacterium comprises a modification which results in decreased activity of amtB.

140. A method of increasing the amount of atmospheric derived nitrogen in a plant, comprising contacting said plant with a plurality of said genetically engineered bacterium of any one of clauses 19-139.

141. The method of clause 140, wherein said genetically engineered bacterium is applied to a seed of said plant.

142. The method of clause 140, wherein said genetically engineered bacterium is applied to a seedling of said plant.

143. The method of clause 140, wherein said genetically engineered bacterium is applied to said plant in a liquid formulation.

144. The method of clause 140, wherein said genetically engineered bacterium is applied to said plant after planting but before harvest of said plant.

145. The method of clause 140, wherein said genetically engineered bacterium is applied to said plant as a side dressing.

146. The method of clause 140, wherein said genetically engineered bacterium is applied to said plant between one month and eight months after germination.

147. The method of clause 140, wherein said genetically engineered bacterium is applied to said plant between two months and eight months after germination.

148. The method of clause 140, wherein said genetically engineered bacterium is applied to said plant between one month and three months after germination.

149. The method of clause 140, wherein said genetically engineered bacterium is applied to said plant between three months and six months after germination.

150. The method of clause 140, wherein said plant is a cereal plant.

151. The method of clause 140, wherein said plant is a corn plant.

152. The method of clause 140, wherein said plant is a rice plant.

153. The method of clause 140, wherein said plant is a wheat plant.

154. The method of clause 140, wherein said plant is a soy plant.

155. A composition comprising a seed, and a seed coating; wherein the seed coating comprises a plurality of said genetically engineered bacterium of any one of clauses 19-39.

156. The composition of clause 155, wherein said seed is a cereal seed.

157. The composition of clause 155, wherein said seed is selected from the group consisting of: a corn seed, a wheat seed, a rice seed, a soy seed, a rye seed and a *sorghum* seed.

158. A composition comprising a plant and a plurality of said genetically engineered bacterium of any one of clauses 19-39.

159. The composition of clause 158, wherein said plant is a seedling.

160. The composition of clause 158, wherein said seed is a cereal seed.

161. The composition of clause 158, wherein said seed is selected from the group consisting corn, rice, wheat, soy, rye, and *sorghum*.

162. A method of increasing nitrogen fixation in a microbe, the method comprising introducing a genetic modification that results in altered activity of a sulfur transporter.

163. A method of increasing nitrogen fixation in a microbe, the method comprising introducing a genetic modification that results in altered expression of a sulfur transport gene.

164. A method of increasing nitrogen fixation in a microbe, the method comprising introducing a genetic modification that results in altered activity of a molybdenum transporter.

165. A method of increasing nitrogen fixation in a microbe, the method comprising introducing a genetic modification that results in altered expression of a molybdenum transport gene.

166. A method of increasing nitrogen fixation in a microbe, the method comprising introducing a genetic modification that results in altered activity of an iron transporter.

167. A method of increasing nitrogen fixation in a microbe, the method comprising introducing a genetic modification that results in altered expression of an iron transport gene.

168. A method of increasing nitrogen fixation in a microbe, the method comprising introducing a genetic modification that results in altered siderophore biosynthesis.

169. A method of increasing nitrogen fixation in a microbe, the method comprising introducing a genetic modification that results in altered expression of gene controlling siderophore biosynthesis.

170. A method of increasing nitrogen fixation in a microbe, the method comprising introducing a genetic modification that results in altered activity of a reactive oxygen species scavenger.

171. A method of increasing nitrogen fixation in a microbe, the method comprising introducing a genetic modification that results in altered expression of a reactive oxygen species scavenging gene.

172. A method of increasing nitrogen fixation in a microbe, the method comprising introducing a genetic modification resulting in altered activity of a protein involved in quorum signaling.

173. A method of increasing nitrogen fixation in a microbe, the method comprising introducing a genetic modification that results in altered expression of a quorum signaling gene.

174. A method of increasing nitrogen fixation in a microbe, the method comprising introducing a genetic modification that results in altered activity of aglutanins.

175. A method of increasing nitrogen fixation in a microbe, the method comprising introducing a genetic modification that results in altered expression of aglutanins.

176. A method of increasing nitrogen fixation in a microbe, the method comprising introducing a genetic modification that results in altered activity of a protein involved in biofilm formation 177. A method of increasing nitrogen fixation in a microbe, the method comprising introducing a genetic modification that results in altered expression of a biofilm formation gene.

178. A method of increasing nitrogen fixation in a microbe, the method comprising introducing a genetic modification that results in altered activity of an AHL biosynthesis protein.

179. A method of increasing nitrogen fixation in a microbe, the method comprising introducing a genetic modification that results in altered expression of an AHL biosynthesis gene.

180. A method of increasing nitrogen fixation in a microbe, the method comprising introducing a genetic modification that results in altered activity of a cell wall degrading enzyme.

181. A method of increasing nitrogen fixation in a microbe, the method comprising introducing a genetic modification that results in altered expression of a gene for a cell wall degrading enzyme.

182. A method of increasing nitrogen fixation in a microbe, the method comprising introducing a genetic modification that results in altered nitrogen fixation genetic network.

183. A method of increasing nitrogen fixation in a microbe, the method comprising introducing a genetic modification that results in altered nitrogen assimilation genetic network.

184. A method of increasing nitrogen fixation by a microbe, the method comprising introducing a genetic modification to a gene in the group consisting of rpoE, rseA, cysP, cysZ, cysK, cysT, cysW, cysA, sbp, a cysZK operon, a cysPTWA operon, modE, modB, modA, a modEB operon, a modEBA operon, exbA, exbB, tonB, an exbAB operon, isyhfA, yusV, sbnA, yfiZ, fiu, fur, glgA, NifA, nifH, nifD, nifK, grxA, grxB, grxC, grxD, trxA, trxC, tpx, a grxABCD operon, a cydABX operon, a cydAB operon cydX, cydA, cyddB, glbN, fixNOPQ, fixN, fixO, foxP, fixQ, asnB, asnA, glnL, uridylyl-transferase, amtB, glnK, GDH, and glnD.

186. A method of increasing ammonium excretion by a microbe, the method comprising introducing a genetic modification that results in altered activity of a sulfur transporter.

187. A method of increasing ammonium excretion by a microbe, the method comprising introducing a genetic modification that results in altered expression of a sulfur transport gene.

188. A method of increasing ammonium excretion by a microbe, the method comprising introducing a genetic modification that results in altered activity of a molybdenum transporter.

189. A method of increasing ammonium excretion by a microbe, the method comprising introducing a genetic modification that results in altered expression of molybdenum transport gene.

190. A method of increasing ammonium excretion by a microbe, the method comprising introducing a genetic modification that results in altered activity of an iron transporter.

191. A method of increasing ammonium excretion by a microbe, the method comprising introducing a genetic modification that results in altered expression of an iron transport gene.

192. A method of increasing ammonium excretion by a microbe, the method comprising introducing a genetic modification that results in altered siderophore biosynthesis.

193. A method of increasing ammonium excretion by a microbe, the method comprising introducing a genetic modification that results in altered expression of a gene controlling siderophore biosynthesis.

194. A method of increasing ammonium excretion by a microbe, the method comprising introducing a genetic modification that results in altered activity of a reactive oxygen species scavenger.

195. A method of increasing ammonium excretion by a microbe, the method comprising introducing a genetic modification that results in altered expression of a reactive oxygen species scavenging gene.

196. A method of increasing ammonium excretion by a microbe, the method comprising introducing a genetic modification that results in altered activity of a protein involved in quorum signaling.

197. A method of increasing ammonium excretion by a microbe, the method comprising introducing a genetic modification that results in altered expression of a quorum signaling gene.

198. A method of increasing ammonium excretion by a microbe, the method comprising introducing a genetic modification that results in altered activity of aglutanins.

199. A method of increasing ammonium excretion by a microbe, the method comprising introducing a genetic modification that results in altered expression of aglutanins.

200. A method of increasing ammonium excretion by a microbe, the method comprising introducing a genetic modification that results in altered activity of a protein involved in biofilm formation.

201. A method of increasing ammonium excretion by a microbe, the method comprising introducing a genetic modification that results in altered expression of a biofilm formation gene.

202. A method of increasing ammonium excretion by a microbe, the method comprising introducing a genetic modification that results in altered activity of an AHL biosynthesis protein.

203. A method of increasing ammonium excretion by a microbe, the method comprising introducing a genetic modification that results in altered expression of an AHL biosynthesis gene.

204. A method of increasing ammonium excretion by a microbe, the method comprising introducing a genetic modification that results in altered activity of a cell wall degrading enzyme.

205. A method of increasing ammonium excretion by a microbe, the method comprising introducing a genetic modification that results in altered expression of a gene for a cell wall degrading enzyme.

206. A method of increasing ammonium excretion by a microbe, the method comprising introducing a genetic modification that results in altered nitrogen fixation genetic network.

207. A method of increasing ammonium excretion by a microbe, the method comprising introducing a genetic modification that results in altered nitrogen assimilation genetic network.

208. A method of increasing ammonium excretion by a microbe, the method comprising introducing a genetic modification to a gene in the group consisting of rpoE, rseA, cysP, cysZ, cysK, cysT, cysW, cysA, sbp, a cysZK operon, a cysPTWA operon, modE, modB, modA, a modEB operon, a modEBA operon, exbA, exbB, tonB, an exbAB operon, isyhfA, yusV, sbnA, yfiZ, fiu, fur, glgA, NifA, nifH, nifD, nifK, grxA, grxB, grxC, grxD, trxA, trxC, tpx, a grxABCD operon, a cydABX operon, a cydAB operon cydX, cydA, cyddB, glbN, fixNOPQ, fixN, fixO, foxP, fixQ, asnB, asnA, glnL, uridylyl-transferase, amtB, glnK, GDH, and glnD.

209. A method of increasing survival of a microbe in a rhizosphere, the method comprising introducing a genetic modification that results in altered activity of a protein involved in root attachment.

210. A method of increasing survival of a microbe in a rhizosphere, the method comprising introducing a genetic modification that results in altered expression of a gene for a protein involved in root attachment.

211. A method of increasing survival of a microbe in a rhizosphere, the method comprising introducing a genetic modification that results in altered activity of a molybdenum transporter.

212. A method of increasing survival of a microbe in a rhizosphere, the method comprising introducing a genetic modification that results in altered expression of a molybdenum transport gene.

213. A method of increasing survival of a microbe in a rhizosphere, the method comprising introducing a genetic modification that results in altered activity of an iron transporter.

214. A method of increasing survival of a microbe in a rhizosphere, the method comprising introducing a genetic modification that results in altered expression of an iron transport gene.
215. A method of increasing survival of a microbe in a rhizosphere, the method comprising introducing a genetic modification that results in altered siderophore biosynthesis.
216. A method of increasing survival of a microbe in a rhizosphere, the method comprising introducing a genetic modification that results in altered expression of a gene controlling siderophore biosynthesis.
217. A method of increasing survival of a microbe in a rhizosphere, the method comprising introducing a genetic modification that results in altered activity of a reactive oxygen species scavenger.
218. A method of increasing survival of a microbe in a rhizosphere, the method comprising introducing a genetic modification that results in altered expression of a reactive oxygen species scavenging gene.
219. A method of increasing survival of a microbe in a rhizosphere, the method comprising introducing a genetic modification resulting in altered activity of a protein involved in quorum signaling.
220. A method of increasing survival of a microbe in a rhizosphere, the method comprising introducing a genetic modification that results in altered expression of a quorum signaling gene.
221. A method of increasing survival of a microbe in a rhizosphere, the method comprising introducing a genetic modification that results in altered activity of aglutanins.
222. A method of increasing survival of a microbe in a rhizosphere, the method comprising introducing a genetic modification that results in altered expression of aglutanins.
223. A method of increasing survival of a microbe in a rhizosphere, the method comprising introducing a genetic modification that results in altered activity of a protein involved in biofilm formation
224. A method of increasing survival of a microbe in a rhizosphere, the method comprising introducing a genetic modification that results in altered expression of a biofilm formation gene.
225. A method of increasing survival of a microbe in a rhizosphere, the method comprising introducing a genetic modification that results in altered activity of an AHL biosynthesis protein.
226. A method of increasing survival of a microbe in a rhizosphere, the method comprising introducing a genetic modification that results in altered expression of an AHL biosynthesis gene.
227. A method of increasing survival of a microbe in a rhizosphere, the method comprising introducing a genetic modification that results in altered activity of a cell wall degrading enzyme.
228. A method of increasing survival of a microbe in a rhizosphere, the method comprising introducing a genetic modification that results in altered expression of a gene for a cell wall degrading enzyme.
229. A method of increasing survival of a microbe in a rhizosphere, the method comprising introducing a genetic modification that results in altered nitrogen fixation genetic network.
230. A method of increasing survival of a microbe in a rhizosphere, the method comprising introducing a genetic modification that results in altered nitrogen assimilation genetic network.
231. A method of increasing survival of a microbe in a rhizosphere, the method comprising introducing a genetic modification to a gene in the group consisting of fhaB, fhaC, yjbE, pssM, otsA, treY, smZ, lapA, phoB, phoR, MucA, and pehA.

---

What is claimed is:

1. A genetically engineered diazotrophic bacterium having increased expression of rpoN, wherein:
   rpoN expression is increased by deleting the native rpoN promoter and replacing it with a strong intrageneric constitutive promoter; and
   the genetically engineered diazotrophic bacterium is capable of increasing the amount of atmospheric derived nitrogen in a plant.

2. The genetically engineered diazotrophic bacterium of claim 1, wherein said genetically engineered diazotrophic bacterium further comprises a modification in a nitrogen fixation genetic network.

3. The genetically engineered diazotrophic bacterium of claim 1, wherein said genetically engineered diazotrophic bacterium further comprises a genetic modification which results in increased expression of Nif cluster genes.

4. A method of increasing the amount of atmospheric derived nitrogen in a plant, comprising contacting said plant with a plurality of said genetically engineered diazotrophic bacterium of claim 1.

5. A composition comprising a seed, and a seed coating; wherein the seed coating comprises a plurality of said genetically engineered diazotrophic bacterium of claim 1.

6. A composition comprising a plant and a plurality of said genetically engineered diazotrophic bacterium of claim 1.

7. The method of claim 4, wherein said genetically engineered diazotrophic bacterium is applied to a seed of said plant.

8. The method of claim 4, wherein said genetically engineered diazotrophic bacterium is applied to a seedling of said plant.

9. The method of claim 4, wherein said plant is a cereal plant.

10. The method of claim 4, wherein said plant is a corn plant.

11. The method of claim 4, wherein said plant is a rice plant.

12. The method of claim 4, wherein said plant is a wheat plant.

13. The method of claim 4, wherein said plant is a soy plant.

14. The composition of claim 5, wherein said seed is a cereal seed.

15. The composition of claim 5, wherein said seed is selected from the group consisting of: a corn seed, a wheat seed, a rice seed, a soy seed, a rye seed and a *sorghum* seed.

16. The composition of claim 6, wherein said plant is a seedling.

17. The genetically engineered diazotrophic bacterium of claim 1, wherein said genetically engineered diazotrophic bacterium is from a genus selected from the group consisting of: *Clostridium, Agrobacterium, Bacillus, Bradyrhizobium, Brevibacillus, Delftia, Lysobacter, Paenibacillus, Pantoea, Pectobacterium, Pseudomonas, Serratia, Streptomyces, Xanthomonas, Xenorhabdus, Azotobacter, Methanosarcina, Klebsiella, Rhodobacter, Rhizobium, Rahnella, Kosakonia, Azospirillum, Enterobacter, Burkholderia, Sinorhizobium* and *Chlorobium*.

18. The genetically engineered diazotrophic bacterium of claim 17, wherein said genetically engineered diazotrophic bacterium is from the genus of *Klebsiella*.

19. The genetically engineered diazotrophic bacterium of claim 18, wherein said genetically engineered diazotrophic bacterium is *Klebsiella variicola*.

20. The genetically engineered diazotrophic bacterium of claim 19, wherein said genetically engineered diazotrophic bacterium is *Klebsiella variicola* strain CI137.

21. A genetically engineered diazotrophic bacterium having increased expression of rpoN, wherein:
   rpoN expression is increased by deleting the native rpoN promoter and replacing it with a strong constitutive promoter; and
   the genetically engineered diazotrophic bacterium is *Klebsiella variicola* and is capable of increasing the amount of atmospheric derived nitrogen in a plant.

* * * * *